(12) United States Patent
Teller et al.

(10) Patent No.: US 10,519,154 B2
(45) Date of Patent: Dec. 31, 2019

(54) 7-SUBSTITUTED 1-PYRIDYL-NAPHTHYRIDINE-3-CARBOXYLIC ACID AMIDES AND USE THEREOF

(71) Applicants: Bayer Pharma Aktiengesellschaft, Berlin (DE); Bayer Aktiengesellschaft, Leverkusen (DE)

(72) Inventors: Henrik Teller, Schwaan (DE); Melissa Boultadakis Arapinis, Düsseldorf (DE); Alexandros Vakalopoulos, Hilden (DE); Anne-Sophie Rebstock, Champagne au Mont d'Or (FR); Alexander Straub, Wuppertal (DE); Hanna Tinel, Wuppertal (DE); Markus Brechmann, San Francisco, CA (US); Matthias Beat Wittwer, Riehen (CH); Maximillian Andreas Kullmann, Leichlingen (DE); Klaus Münter, Wülfrath (DE); Thomas Mondritzki, Essen (DE); Tobias Marquardt, Wuppertal (DE)

(73) Assignees: Bayer Pharma Aktiengesellschaft, Berlin (DE); Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 16/317,322

(22) PCT Filed: Jul. 4, 2017

(86) PCT No.: PCT/EP2017/066632
§ 371 (c)(1),
(2) Date: Jan. 11, 2019

(87) PCT Pub. No.: WO2018/011017
PCT Pub. Date: Jan. 18, 2018

(65) Prior Publication Data
US 2019/0241562 A1    Aug. 8, 2019

(30) Foreign Application Priority Data

Jul. 11, 2016 (EP) .................................. 16178835
Dec. 6, 2016 (EP) .................................. 16202510

(51) Int. Cl.
| C07D 471/04 | (2006.01) |
| A61P 9/06 | (2006.01) |
| A61P 13/12 | (2006.01) |
| A61P 9/04 | (2006.01) |

(52) U.S. Cl.
CPC ............. *C07D 471/04* (2013.01); *A61P 9/04* (2018.01); *A61P 9/06* (2018.01); *A61P 13/12* (2018.01)

(58) Field of Classification Search
CPC .................................................... C07D 471/04

USPC ....................................................... 546/122
See application file for complete search history.

(56) References Cited

U.S. PATENT DOCUMENTS

| 4,990,517 | A | 2/1991 | Petersen |
| 5,496,947 | A | 3/1996 | Yoon |
| 2018/0297994 | A1 | 10/2018 | Teller |

FOREIGN PATENT DOCUMENTS

| CA | 3030204 A1 | 1/2018 |
| CL | 200701360 | 11/2007 |
| CL | 201201605 | 6/2012 |
| CL | 201703138 | 6/2018 |
| CL | 201703147 | 6/2018 |
| EP | 0350733 A2 | 1/1990 |
| EP | 1650192 A1 | 4/2006 |
| EP | 3312177 A2 | 4/2018 |
| JP | 2005012561 A | 1/2005 |
| WO | WO02085886 A2 | 10/2002 |
| WO | WO03050107 A1 | 6/2003 |
| WO | WO2005009971 A1 | 2/2005 |
| WO | WO2005026145 A2 | 3/2005 |
| WO | WO2005026165 A1 | 3/2005 |
| WO | WO2005028451 A1 | 3/2005 |
| WO | WO2005049602 A1 | 6/2005 |
| WO | WO2005056552 A1 | 6/2005 |
| WO | WO2010093341 A1 | 8/2010 |
| WO | WO2011084368 A1 | 7/2011 |
| WO | WO2015189560 A1 | 12/2015 |
| WO | WO2016071212 A1 | 5/2016 |
| WO | WO2016198342 A1 | 12/2016 |
| WO | WO2016200851 A1 | 12/2016 |
| WO | WO2018011017 A1 | 1/2018 |
| WO | WO2018050510 A1 | 3/2018 |

OTHER PUBLICATIONS

Bouzard, D. et al., (1992). "Fluoronaphthyridines as Antibacterial Agents," Med. Chem. 35(3): 518-252.
Chen, P-S. et al. (2014). "Role of the Autonomic Nervous System in Atrial Fibrillation," Circulation Research 114: 1500-1515.
Christopoulos, A. (Nov. 2014). "Advances in G Protein-Coupled Receptor Allostery: From Function to Structure," Mol Pharmacol 86: 436-478.
Chu, D.T.W. et al. (1992). "Synthesis and antibacterial activity of novel 6-fluoro-7-(gem-disubstituted piperazin-1-yl)-quinolines," Circ. Res. 114(9), 1500-1515.
Clark, A.L. et al. (1976). "The Inhibitory Effect of Gallamine on Muscarinic Receptors," Br. J. Pharmac. 58: 323-331.

(Continued)

*Primary Examiner* — Taofiq A Solola
(74) *Attorney, Agent, or Firm* — Morrison & Foerster LLP

(57) ABSTRACT

The present application relates to novel 7-substituted 1-pyridylnaphthyridine-3-carboxamides, to processes for their preparation, to their use, alone or in combinations, for the treatment and/or prevention of diseases, and to their use for the production of medicaments for the treatment and/or prevention of diseases, in particular for the treatment and/or prevention of cardiovascular disorders and/or renal disorders.

14 Claims, No Drawings

(56) References Cited

OTHER PUBLICATIONS

Conn, P.J. et al. (Jan. 2009). "Allosteric modulators of GPCRs: a novel approach for the treatment of CNS disorders," Nat Rev Drug Discov 8(1): 41-54.
Conn, P.J. et al. (Sep. 2014). "Opportunities and challenges in the discovery of allosteric modulators of GPCRs for treating CNS disorders," Nat Rev Drug Discov 13(9): 692-708.
Cooper, C.S. et al. (1992). "Preparation and in Vitro and in Vivo Evaluation of Quinolones with Selective Activity against Gram-Positive Organisms," J. Med. Chem. 35: 1392-1396.
Croy, C.H. et al. (Jul. 2014). "Characterization of the Novel Positive Allosteric Modulator, LY2119620, at the Muscarinic M2 and M4 Receptors," Molecular Pharmacology 86: 106-115.
Davie, B.J. (2013). "Development of M1 mAChR allosteric and Bitopic Ligands: Prospective Therapeutics for the Treatment of Cognitive Deficits," ACS Chem. Neurosci. 4: 1026-1048.
Deferrari, G.M. (2014). "Vagal Stimulation in Heart Failure," J. of Cardiovasc. Trans. Res. 7: 310-320.
Deferrari, G.M. et al. (2011). "Chronic vagus nerve stimulation: a new and promising therapeutic approach for chronic heart failure," European Heart Journal 32: 847-855.
European Search Report dated Oct. 31, 2016 for EP Application No. 16188728.6 filed on Sep. 14, 2016, 1 page. (Not in English).
Gold, M.R. et al. (2016). "Vagus Nerve Stimulation for the Treatment of Heart Failure," Journal of the American College of Cardiology 68(2): 149-158.
Gregory, K.J. et al. (2007). "Allosteric Modulation of Muscarinic Acetylcholine Receptors," current Neuropharmacology 5: 157-167.
Halaris, A. (2013). "Co-Morbidity between Cardiovascular Pathology and Depression: Role of Inflammation," Mod Trends Pharmacopsychiatry 28: 144-161.
Hauptmann, P.J. et al. (2012). "Rationale and study design of the INcrease of Vagal TonE in Heart Failure study: INOVATE-HF," Am Heart J 163: 954-962.
He, X. et al. (2015). "Novel strategies and underlying protective mechanisms of modulation of vagal activity in cardiovascular diseases," British Journal of Pharmacology DOI: 10.1111/bph.13010.
International Preliminary Report on Patentability dated Jan. 24, 2019, for PCT Application No. PCT/EP2017/066632, filed on Jul. 4, 2017, 21 pages. German with English Translation.
International Search Report and Written Opinion dated Aug. 22, 2016, for PCT Application No. PCT/EP2016/062737, filed on Jun. 6, 2016, 11 pages.
International Search Report and Written Opinion dated Sep. 22, 2017, for PCT Application No. PCT/EP2017/066632, filed on Jul. 4, 2017, 18 pages.
Klopman, G. et al. (Nov. 1996). "N-1-tert-Butyl-Substituted Quinolones: In Vitro Anti-*Mycobacterium avium* Activities and Structure-Activity Relationship Studies," Antimicrobial Agents and Chemotherapy 40(11): 2637-2643.
Kruse, A. et al. (Dec. 2013). "Activation and allosteric modulation of a muscarinic acetylcholine receptor," Nature 504: 101-106.
Kruse, A. et al. (Oct. 2013). "Muscarinic Receptors as Model Targets and Antitargets for Structure-Based Ligand Discovery," Mol Pharmacol 84: 528-540.
Leong-Sit, P. et al. (2015). "Atrial fibrillation and heart failure: a bad combination," Curr Opin Cardiol 30: 1-7.
Lewalter, T. et al. (2011). "Pathophysiologie, Klinik und Therapieoptionen bei Vorhofflimmern," Fortbildungstelegramm Pharmazie 5(4): 106-127. (English Abstract).
Maisel, W.H. et al. (2003). "Atrial Fibrillation in Heart Failure: Epidemiology, Pathophysiology, and Rationale for Therapy," The American Journal of Cardiology 91(6A): 2d-8d.
Miao Y. et al. (2016). "Accelerated structure-based design of chemically diverse allosteric modulators of a muscarinic G protein-coupled receptor," PNAS Early Edition, 113(38): E5675-E5684.
Mistry, S.N. (2013). "Synthesis and Pharmacological Profiling of Analogues of Benzyl Quinolone Carboxylic Acid (BQCA) as Allosteric Modulators of the M1 Muscarinic Receptor," J. Med. Chem. 56: 5151-5172.
Neubig, R.R. (2003). "International Union of Pharmacology Committee on Receptor Nomenclature and Drug Classification. XXV-VIII. Update on Terms and Symbols in Quantitative Pharmacology," Pharmacol Rev 55: 597-606.
Premchand, R.K. (2014). "Autonomic Regulation Therapy via Left or Right Cervical Vagus Nerve Stimulation in Patients with Chronic Heart Failure: Results of the ANTHEM-HF Trial," Journal of Cardiac Failure 20(11): 808-816.
Ranpuria, R. (Nov. 2007). "Heart rate variability (HRV) in kidney failure: measurement and consequences of reduced HRV," Nephrol Dial Transplant 23: 444-449.
Rash, J.A. (2012). "Attention-deficit hyperactivity disorder and cardiac vagal control: a systematic review," ADHD Atten Def Hyp Disord 4: 167-177.
Rosman, K. et al. (1998). "Isotopic Compositions of the Elements 1997," Pure & Appl. Chem., 70(1):217-235.
Schober, D.A. (Jul. 2014). "Development of a Radioligand, [3H]LY2119620, to Probe the Human M2 and M4 Muscarinic Receptor Allosteric Binding Sites," Mol Pharmacol 86: 116-123.
Schrage, R. (2014). "New insight into active muscarinic receptors with the novel radioagonist [3H]iperoxo," Biochemical Pharmacology 90: 307-319.
Sykora, M. (Dec. 2009). "Baroreflex: A New Therapeutic Target in Human Stroke?" Stroke 40: 678-682.
U.S. Appl. No. 16/333,079, filed Mar. 13, 2019, for Teller et al. (U.S. Patent Application is not submitted herewith pursuant to the waiver of 37C.F.R. § 1.98(a)(2)(iii) issued by the Office dated Sep. 21, 2004.).
Wang, L. (2009). "Allosteric Modulators of G Protein-Coupled Receptors: Future Therapeutics for Complex Physiological Disorders," The Journal of Pharmacology and Experimental Therapeutics 331(2): 340-348.
Zannad, F. et al. (Aug. 2014). "Chronic vagal stimulation for the treatment of low ejection fraction heart failure: results of the neural cardiac therapy for heart failure (NECTAR-HF) randomized controlled trial," European Heart Journal 425-433.
Zhang, T. et al. (2015). "Synthesis, antimycobacterial and antibacterial activity of fluroquinolone derivatives containing an 3-alkoxyimino-4-(cyclopropylanimo)methylpyrrolidine moiety," European Journal of Medicinal Chemistry 104: 73-85.

7-SUBSTITUTED 1-PYRIDYL-NAPHTHYRIDINE-3-CARBOXYLIC ACID AMIDES AND USE THEREOF

CROSS REFERENCE TO RELATED APPLICATIONS

This application is the national stage application under 35 U.S.C. § 371 of International Application No. PCT/EP2017/066632, filed internationally on Jul. 4, 2017, which claims the benefit of European Application Nos. 16178835.1, filed Jul. 11, 2016 and 16202510.0, filed Dec. 6, 2016.

The present application relates to novel 7-substituted 1-pyridylnaphthyridine-3-carboxamides, to processes for their preparation, to their use, alone or in combinations, for the treatment and/or prevention of diseases, and to their use for the production of medicaments for the treatment and/or prevention of diseases, in particular for the treatment and/or prevention of cardiovascular disorders and/or renal disorders.

Muscarinergic receptors are receptors which are positioned on the membrane and, as endogenous ligands, can bind the acetylcholine (ACh) neurotransmitter (acetylcholine receptors), but also be activated by muscarine. There are five subtypes of these G protein-coupled receptors (M1-M5) which are expressed in almost all kinds of tissue in the human organism. They are encountered both in the central and in the peripheral nervous system, and in many organs of the vegetative nervous system.

The M2 type (M2R) is expressed predominantly in the heart. At the cellular level, M2R stimulation by the acetylcholine agonist brings about inhibition of adenylcyclase and activation of the inwardly rectifying potassium channel (IKACh channel, GIRK: G protein activated inwardly rectifying K+ channel; also Kir3.x). This increases potassium conductivity, which leads to hyperpolarization of the muscle cells. Accordingly, the cells become more difficult to depolarize, which leads to an adverse chronotropic and dromotropic effect, and so the heart rate drops. M2R is the main mediator of the parasympathetic control of heart function, which is controlled by the vagus nerve. The right vagus nerve reduces the heart rate via the sinus node; the left vagus nerve predominantly increases the atrioventricular conduction time via the atrioventricular node (AV node). Overall, the influence of the vagus nerve on the resting heart rate is predominant compared to the sympathetic nerve. The effects of stimulation of M2R are thus opposed to those of beta-adrenergic stimulation.

The activation of the M2 receptor by the endogenous acetylcholine agonist, but also by synthetic analogs such as carbachol, oxotremorin-M or iperoxo (Schrage et al., Biochem. Pharmacol. 2014, 90(3), 307-319), is effected by binding of the agonist to what is called the orthosteric binding site of the receptor and a resultant change in conformation of the receptor or stabilization of the active receptor conformation. The conventional naturally occurring muscarine receptor agonists include, as well as the endogenous acetylcholine (ACh) agonist, various plant alkaloids such as arecoline, muscarine, and also pilocarpine (Neubig et al., Pharmacol Rev., 2003, 55, 597-606). The orthosteric binding site of all muscarinic acetylcholine receptors is highly evolutionarily conserved and has a high sequence and structural homology between the various subtypes. Therefore, many of the known agonists are unselective with respect to the various subtypes of the muscarinic acetylcholine receptors (Kruse et al., Mol Pharmacol., 2013, 84(4), 528-540). M2R has, as well as an orthosteric binding site, an allosteric binding site as well (Gregory et al., Current Neuropharmacol., 2007, 5(3), 157-167). The oldest known allosteric modulator is gallamine (Clark and Mitchelson, Br. J. Pharmac., 1976, 58, 323-331).

Allosteric modulators have distinct differences from conventional orthosteric ligands. The allosteric modulator itself has no direct influence on receptor activation. The allosteric binding instead results in modulation of the binding affinity and/or effectiveness of the orthosteric agonist. The effect of an allosteric modulator can thus be displayed only in the presence of the endogenous ligand. This results in specificity in terms of space and time in the allosteric effect (Conn et al., Nat. Rev. Drug Disc., 2009, 8, 41-54; Conn et al, Nat. Rev. Drug. Disc., 2014, 13, 692-708). Furthermore, the effect of an allosteric modulator is self-limiting when it stabilizes the binding of the agonist in high concentrations. This in turn results, in principle, in a more favorable pharmacological safety profile compared to agonists, since toxic effects caused by receptor overactivation are limited (Christopoulos, Mol. Pharmacol., 2014, 86, 463-478).

The mutual influencing of allosteric and orthosteric ligands in terms of affinity and intrinsic activity, which is referred to as cooperativity, is determined by both ligands. In the case of a positive allosteric modulator of M2R, the effects of ACh (orthosteric ligand) are enhanced (positive cooperativity). Because of their ability to modulate receptor conformations in the presence of an orthosteric ligand, allosteric ligands can bring about fine adjustment of pharmacological effects (Wang et al., J. Pharmacol. Exp. Therap., 2009, 331, 340-348). In the case of the positive allosteric modulator of M2R, this suggests an advantageous effect profile, a reduced risk of side effects and a starting point for the development of more subtype-selective ligands compared to a full agonist.

The crystal structure of the positive allosteric M4R and M2R ligand LY2119620 (3-amino-5-chloro-N-cyclopropyl-4-methyl-6-[2-(4-methylpiperazin-1-yl)-2-oxoethoxy]thieno[2,3-b]pyridine-2-carboxamide) in the complex with M2R has been published. The allosteric binding site of M2R is spatially adjacent to but clearly delimited from the orthosteric binding site and, compared to the other muscarinic receptor subtypes, exhibits lower conservation, i.e. has greater differences in sequence (Kruse et al., Nature, 2013, 504, 101-106). LY2119620 was described as an unselective M2R/M4R positive allosteric modulator (Croy et al., Molecular Pharmacology, July 2014 86, 1, 106-115; Schober et al., Molecular Pharmacology, July 2014 86, 1, 116-123).

M2R as a constituent of the autonomic nervous system plays an important role in the pathogenesis and progression of cardiovascular disorders. Autonomic imbalance characterized by vagal (parasympathetic) weakening and dominance of the sympathetic nervous system is closely correlated to increased morbidity and mortality. The clinical and prognostic significance of autonomic imbalance is well documented in various cardiovascular disorders, including heart failure (HF), heart rhythm disorders, ischemia/reperfusion (I/R), hypertension (He et al., Br. J. Pharmacol. 2014, Epub) and chronic kidney disease (Ranpuria et al., Nephrol Dial Transplant 2008, 23(2), 444-4499). Particularly in the case of patients having comorbidities such as diabetes, autonomic imbalance can contribute to increased morbidity and mortality (Vinik et al., Diabet Med., 2011, 28(6), 643-651). Baroreceptor reflex dysfunctions, such as hypertensive crises or variability in high blood pressure, as signs of a dysfunctional autonomic nervous system, often accompany the acute phase of ischemic or hemorrhagic stroke (Sykora et al., *Stroke,* 2009, 40(12), 678-682).

The frequent observation of comorbidity between cardiovascular and psychological disorders, such as between heart failure and depression, is probably based on common pathomechanisms that accompany the autonomic imbalance (Halaris et al., *Mod Trends Pharmacopsychiatri.,* 2013, 28, 144-161). Chronic stress shifts the homeostatic equilibrium of the autonomic nervous system. Reduced vagal tone contributes to pro-inflammatory status, with impairment of neurotransmitter regulation, especially serotonergic transmission. Other psychological disorders have also been connected to autonomic dysregulation, for example attention deficit/hyperactivity disorder (ADHD), which is characterized by loss of inhibition, lack of emotional self-control, inattentiveness and hyperactivity (Rash and Aguirre-Camacho, *Atten Defic Hyperact Disord.,* 2012, 4(4), 167-177).

Boosting parasympathetic activity by means of a positive allosteric modulator, including expected anti-inflammatory effects, elevation of nitrogen monoxide (NO), regulation of redox state, improvement of mitochondrial function and of calcium regulation, could therefore constitute a novel therapeutic principle, especially in the case of cardiovascular disorders. There are numerous pointers that the modulation of parasympathetic activity can be considered as a potential therapy target in the event of chronic heart failure. Vagal nerve stimulation in dogs that have recovered from myocardial infarction significantly lowered the incidence of sudden cardiac death, and mortality in rats suffering from chronic heart failure (De Ferrari, *J. Cardiovasc. Transl. Res.,* 2014, 7(3), 310-320). In a dog model with heart failure (LVEF 35%) and an implanted vagal stimulator, it was shown that, in the treatment group compared to the sham group, a significant improvement in the left-ventricular ejection fraction (LVEF) and reduction in the end-systolic and -diastolic volumes (LVESV, LVEDV) occurred, as did a significant reduction in heart rate within 3 months. The described effect of the VNS was additive to beta-blocker administration (De Ferrari, *J. Cardiovasc. Transl. Res.,* 2014, 7(3), 310-320). The plasma level for TNF-α and IL-6 and the myocardial protein expression thereof was lowered by vagal stimulation in this animal model, which suggests that boosting of the parasympathetic nervous system, as well as the effects on LV remodeling, also has positive effects on pro-inflammatory cytokines.

Based on experimental preclinical data, the first clinical studies on vagal stimulation in patients having chronic heart failure have now been done, as already established in the treatment of epilepsy and depression. The effect of boosting the parasympathetic system via direct vagal nerve stimulation (VNS) was assessed in a non-randomized observation study with 32 patients having left-ventricular (LV) systolic dysfunction, and the results suggest that vagal stimulation has a favorable effect on quality of life, stamina and LV remodeling (De Ferrari G M et al., *Eur. Heart J.,* 2011, 32, 847-855). In the multi-center open-label feasibility study ANTHEN-HF, the safety, compatibility and efficacy of vagal stimulation in patients having chronic stable symptomatic heart failure with reduced ejection fraction (HFrEF) were examined in addition to the standard treatment (Premchand R K et al., *J. Card. Fail.,* 2014, 20(11), 808-816). The continuous vagal nerve stimulation employed in this study led to an improvement in the ejection fraction, variability of heart rate, NYHA class and quality of life. The first placebo-controlled clinical study NECTAR-HF, in contrast, did not show any significant effect of vagal nerve stimulation on the heart function of HF patients after 6 months (Zannad et al., *Eur. Heart J.,* 2015, 36(7), 425-433). The only improvement was in quality of life. The INOVATE-HF study with 650 HF patients was unable to show any effects of this treatment in relation to mortality and hospitalization. (Gold et al., *J Am Coll Cardiol.,* 2016, Mar 29. pii: S0735-1097(16)32404-4. doi: 10.1016/j.jacc.2016.03.525). Quality of life and walking distance were significantly improved.

As well as the infection risk and the potential risks of a surgical intervention, treatment by means of electrical stimulation of the vagal nerve is limited by side effects such as dysphonia, coughing and oropharyngeal pain (Premchand R K et al., *J. Card. Fail.,* 2014, 20(11), 808-816). Medication-assisted boosting of the parasympathetic nervous system by a direct effect on M2R could constitute a novel therapy option.

Atrial fibrillation is the most common persistent heart rhythm disorder, and the prevalence thereof increases with age (Chen et al., *Circ. Res.,* 2014, 114(9), 1500-1515). Atrial fibrillation and heart failure often occur together in a mutually beneficial relationship. Thus, the prevalence of atrial fibrillation increases with the clinical severity of heart failure (Maisel and Stevenson, *Am. J. Cardiol.,* 2003, 91, (suppl) 2D-8D). Clinical data suggest that patients where heart failure is accompanied by atrial fibrillation have a poor prognosis. Both lethality (total lethality, sudden death and pump failure) and morbidity (hospitalization) were found to be significantly increased in this group of patients.

In the treatment of atrial fibrillation, there are two distinct treatment strategies: what is called rate control with adjustment and if at all possible normalization of ventricular frequency, and what is called rhythm control, comprising measures intended to establish or maintain a sinusoidal rhythm. An effective treatment consists of a combination of non-medication-assisted and medication-assisted or intervention measures (Levalter T, *Fortbildungsprogramm Pharmazie,* 2011, 5, 106-127).

For medication-assisted rhythm control after cardioversion, beta-blockers, class I and class III antiarrhythmics are used according to the underlying cardiac disorder and the extent of left-ventricular pumping function impairment. In patients having permanent atrial fibrillation and in oligosymptomatic (frequently older) patients having persistent or paroxysmal atrial fibrillation, simple rate control with retention and allowance of the atrial fibrillation is often the therapy of choice. Primarily medicaments that affect the refractory period or the conduction capacity of the AV node are used. In principle, this effect can be achieved by stimulation of the M2R, which plays the key physiological role at this point, for example with the aid of a positive allosteric modulator. The drugs available to date are beta-blockers, digitalis, calcium antagonists and, in individual cases, amiodarone, which are used with consideration of the lifestyle, underlying cardiac disorder and any secondary disorders. Especially in patients having reduced left ventricular pumping function and severe heart failure, however, the options for medication-assisted therapy are inadequate. Calcium antagonists are contraindicated in this group of patients. As the most recent studies have shown, treatment with digoxin leads to increased mortality of patients having atrial fibrillation (Leong-Sit and Tang, *Curr. Opin. Cardiol.,* 2015, Epub). For beta-blockers, a lack of effectiveness in patients having atrial fibrillation and heart failure was shown in a meta analysis (Leong-Sit and Tang, *Curr. Opin. Cardiol.,* 2015, Epub). The medical demand for novel efficient and safe treatments for rate control is correspondingly high. This could be achieved by medication-assisted stimulation of M2R.

The problem addressed by the present invention is that of identifying and providing novel substances which constitute potent, positive allosteric modulators of the muscarinic M2 receptor and as such are suitable for treatment and/or prevention particularly of cardiovascular disorders and/or renal disorders.

1-Benzyl-substituted 4-oxo-1,4-dihydroquinoline-3-carboxylic acids have been described as allosteric modulators of the M1 muscarine receptor for treatment of neurodegenerative disorders such as Alzheimer's and schizophrenia (Scammells et al., *ACS Chem. Neurosci.*, 2013, 4 (7), 1026-1048; Mistry et al., *J. Med. Chem.* 2013, 56, 5151-5172). Among other documents, EP 0945435 B1 discloses pyridonecarboxylic acid derivatives having antibacterial activity. WO 2002/085886-A2, WO 2003/050107-A1 and WO 2005/026145-A2 claim 7-piperidino-substituted quinolonecarboxylic acid derivatives, and WO 2005/026165-A1 and WO 2005/049602-A1 various 7-pyrrolidino-substituted quinolonecarboxylic acid derivatives, and EP 1650192-A1 specific 7-azetidinylquinolonecarboxylic acid derivatives having antimicrobial/antibacterial activity. WO 2005/009971-A1 and JP 2005012561 disclose quinolone derivatives which can be used as platelet aggregation inhibitors. WO 2015/189560-A1 discloses 1,4-dihydroquinoline derivatives as NPRC agonists for treatment of cardiovascular disorders. Quinolonecarboxylic acid derivatives as MCT modulators are described in WO 2016/081464-A1, in particular for the treatment of tumor disorders and inflammatory processes.

The present invention relates to compounds of the general formula (I)

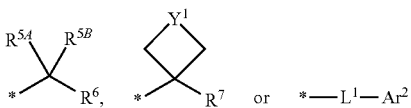

(I)

in which
$R^1$ represents $NR^3R^4$,
  in which
    $R^3$ represents hydrogen, methyl, $(C_2-C_4)$-alkyl or $(C_3-C_6)$-cycloalkyl,
      where $(C_2-C_4)$-alkyl may be substituted by hydroxy or up to trisubstituted by fluorine and
    $R^4$ represents $(C_1-C_6)$-alkyl, $(C_3-C_6)$-cycloalkyl, 3- to 6-membered saturated heterocyclyl or $(C_1-C_4)$-alkylsulfonyl,
      where $(C_1-C_6)$-alkyl, $(C_3-C_6)$-cycloalkyl and 3- to 6-membered saturated heterocyclyl may be up to trisubstituted by identical or different substituents from the group consisting of methyl, difluoromethyl, trifluoromethyl, hydroxy, hydroxycarbonyl, oxo, methoxy, difluoromethoxy, trifluoromethoxy and cyano and furthermore up to tetrasubstituted by fluorine,
    or
    $R^3$ and $R^4$ together with the nitrogen atom to which they are attached form a saturated or partially unsaturated 3- to 6-membered monocyclic or 6- to 10-membered bicyclic heterocycle which may contain one or two further identical or different heteroatoms from the group consisting of N, O, S, SO and $SO_2$ as ring members,
      where the 3- to 6-membered monocyclic and the 6- to 10-membered bicyclic heterocycle may each be substituted by 1 to 5 substituents independently selected from the group of $(C_1-C_4)$-alkyl, difluoromethyl, trifluoromethyl, hydroxy, hydroxycarbonyl, oxo, $(C_1-C_3)$-alkoxy, difluoromethoxy, trifluoromethoxy, cyano, $(C_1-C_3)$-alkoxycarbonyl, aminocarbonyl, mono-$(C_1-C_3)$-alkylaminocarbonyloxy, —NHC(=O)$R^{14A}$ and —CH$_2$NHC(=O)$R^{14B}$, and additionally up to tetrasubstituted by fluorine, in which
        $R^{14A}$ and $R^{14B}$ independently represent $(C_1-C_3)$-alkyl or cyclopropyl, and
      where $(C_1-C_4)$-alkyl may be mono- or disubstituted by identical or different substituents from the group consisting of hydroxy and $(C_1-C_3)$-alkoxy, and up to tetrasubstituted by fluorine,
$R^2$ represents a group of the formula

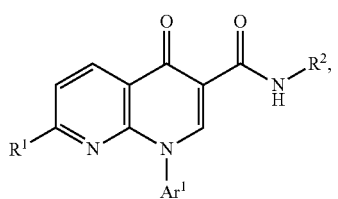

in which
* marks the point of attachment to the nitrogen atom of the amide moiety,
$R^{5A}$ represents hydrogen or $(C_1-C_4)$-alkyl,
$R^{5B}$ represents hydrogen, $(C_1-C_4)$-alkyl, cyclopropyl, monofluoromethyl, difluoromethyl, trifluoromethyl, pentafluoroethyl, methoxymethyl or trifluoromethoxymethyl,
$R^6$ represents $(C_1-C_4)$-alkyl which is up to pentasubstituted by fluorine, or $(C_3-C_5)$-cycloalkyl which is up to tetrasubstituted by fluorine,
$Y^1$ represents —(CH$_2$)$_k$—, —CF$_2$—, —O—CH$_2$—, —CH$_2$—O— or —CH$_2$—O—CH$_2$—,
  in which
  k represents 0, 1, 2 or 3,
$R^7$ represents hydrogen, $(C_1-C_2)$-alkyl which is up to pentasubstituted by fluorine, or trifluoromethoxymethyl,
$L^1$ represents a bond or a group of the formula —C($R^{8A}R^{8B}$)—(C($R^{9A}R^{9B}$))$_m$—,
  in which
  m represents 0 or 1,
  $R^{8A}$ represents hydrogen or methyl,
  $R^{8B}$ represents hydrogen, methyl, trifluoromethyl, pentafluoroethyl or trifluoromethoxymethyl,
  $R^{9A}$ and $R^{9B}$ independently represent hydrogen or methyl,
$Ar^2$ represents phenyl,
  where phenyl may be mono- to trisubstituted by identical or different substituents from the group consisting of fluorine, chlorine, $(C_1-C_3)$-alkyl, difluoromethoxymethyl, trifluoromethoxymethyl and trifluoromethyl,
or
represents a 5- to 10-membered bicyclic or tricyclic carbocycle,
where the 5- to 10-membered bicyclic or tricyclic carbocycle may be up to trisubstituted, identically or differently, by (C$_1$-C$_3$)-alkyl and trifluoromethyl, and additionally up to tetrasubstituted by fluorine,
represents a pyridine ring which is attached via a ring carbon atom,
where the pyridine ring may be mono- or disubstituted by fluorine, chlorine, cyano, methyl or trifluoromethyl,
and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Compounds according to the invention are likewise N-oxides of the compounds of the formula (I) and the salts, solvates and solvates of the salts thereof.

Preferred salts in the context of the present invention are physiologically acceptable salts of the compounds according to the invention. Also encompassed are salts which are not themselves suitable for pharmaceutical applications but can be used, for example, for the isolation, purification or storage of the compounds of the invention.

A suitable pharmaceutically acceptable salt of the compounds of the present invention may be, for example, an acid-addition salt of a compound of the present invention bearing a sufficiently basic nitrogen atom in a chain or in a ring, such as an acid-addition salt with an inorganic acid, or "mineral acid", such as hydrochloric acid, hydrobromic acid, hydroiodic acid, sulfuric acid, sulfamic acid, bisulfuric acid, phosphoric acid or nitric acid, for example, or with an organic acid such as formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, 3-phenylpropionic acid, pivalic acid, 2-hydroxyethanesulfonic acid, itaconic acid, trifluoromethanesulfonic acid, dodecylsulfuric acid, ethanesulfonic acid, benzenesulfonic acid, paratoluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid or thiocyanic acid, for example.

Further, another suitable pharmaceutically acceptable salt of a sufficiently acidic compound of the present invention is an alkali metal salt, for example a sodium or potassium salt, an alkaline earth metal salt, for example a calcium, magnesium or strontium salt, or an aluminum or zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methylglucamine, N,N-dimethylglucamine, N-ethylglucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognize that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown. Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of this salt not being specified. This applies analogously to cases in which synthesis intermediates or example compounds or salts thereof have been obtained as solvates, for example hydrates, by the preparation and/or purification processes described.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. It is possible to isolate the stereoisomerically homogeneous constituents from such mixtures of enantiomers and/or diastereomers in a known manner. Preference is given to employing chromatographic methods for this purpose, especially HPLC chromatography on achiral or chiral separation phases. In the case of carboxylic acids as intermediates or end products, separation is alternatively also possible via diastereomeric salts using chiral amine bases.

In the context of the present invention, the term "enantiomerically pure" is understood to the effect that the compound in question with respect to the absolute configuration of the chiral centers is present in an enantiomeric excess of more than 95%, preferably more than 98%. The enantiomeric excess, ee, is calculated here by evaluating an HPLC analysis chromatogram on a chiral phase using the formula below:

$$ee = \frac{\text{Enantiomer 1 (area percent)} - \text{Enantiomer 2 (area percent)}}{\text{Enantiomer 1 (area percent)} + \text{Enantiomer 2 (area percent)}} \times 100\%.$$

If the compounds of the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature ("unnatural fraction"). The expression "unnatural fraction" is understood to mean a fraction of such an isotope higher than its natural frequency. The natural frequencies of isotopes to be employed in this connection can be found in "Isotopic Compositions of the Elements 1997", Pure Appl. Chem., 70(1), 217-235, 1998. Examples of isotopes which can be incorporated into a compound according to the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labeled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. With regard to the treatment and/or prophylaxis of the disorders specified here, the isotopic variant(s) of the compounds of the general formula (I) preferably contain deuterium ("deuterium-containing compounds of the general formula (I)"). Isotopic variants of the compounds of the general formula (I) into which one or more radioactive isotopes such as $^3$H or $^{14}$C have been incorporated are beneficial, for example, in medicament and/or substrate tissue distribution studies. Because of their easy incorporability and detectability, these isotopes are particularly preferred. It is possible to incorporate positron-emitting isotopes such as $^{18}$F or $^{11}$C into a compound of the general formula (I). These isotopic variants of the compounds of the general formula (I) are suitable for use in in vivo imaging applications. Deuterium-containing and $^{13}$C-containing compounds of the general formula (I) can be used within the scope of preclinical or clinical studies in mass spectrometry analyses (H. J. Leis et al., Curr. Org. Chem., 1998, 2, 131). Isotopic variants of the compounds of the invention can be prepared by commonly used processes known to those skilled in the art, for example by the methods described further down and the procedures described in the working examples, by using corresponding isotopic modifications of the respective reagents and/or starting compounds.

Isotopic variants of the compounds of the general formula (I) can in general be prepared by processes known to those skilled in the art as described in the schemes and/or examples described here, by replacing a reagent with an isotopic variant of the reagent, preferably a deuterium-containing reagent. According to the deuteration sites desired, it is possible in some cases to incorporate deuterium from D$_2$O either directly into the compounds or into reagents which can be used for the synthesis of such compounds (Esaki et al., Tetrahedron, 2006, 62, 10954; Esaki et al., Chem. Eur. J., 2007, 13, 4052). Another useful reagent for incorporation of deuterium into molecules is deuterium gas. A rapid route for incorporation of deuterium is the catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865). For direct exchange of hydrogen for deuterium in hydrocarbons containing functional groups, it is also possible to use metal catalysts (i.e. Pd, Pt and Rh) in the presence of deuterium gas (J. G. Atkinson et al., U.S. Pat. No. 3,966,781). Various deuterated reagents and synthesis units are commercially available from companies like, for example, C/D/N Isotopes, Quebec, Canada; Cambridge Isotope Laboratories Inc., Andover, Mass., USA; and CombiPhos Catalysts, Inc., Princeton, N.J., USA. Further information relating to the prior art with regard to deuterium-hydrogen exchange can be found, for example, in Hanzlik et al., J. Org. Chem., 1990, 55, 3992-3997; R. P. Hanzlik et al., Biochem. Biophys. Res. Commun., 1989, 160, 844; P. J. Reider et al., J. Org. Chem., 1987, 52, 3326-3334; M. Jarman et al., Carcinogenesis, 1993, 16(4), 683-688; J. Atzrodt et al., Angew. Chem., Int. Ed. 2007, 46, 7744; K. Matoishi et al., 2000, J. Chem. Soc, Chem. Commun., 1519-1520; K. Kassahun et al., WO 2012/112363.

The term "deuterium-containing compound of the general formula (I)" is defined as a compound of the general formula (I) in which one or more hydrogen atoms have been replaced by one or more deuterium atoms and in which the frequency of deuterium in every deuterated position in the compound of the general formula (I) is higher than the natural frequency of deuterium, which is about 0.015%. More particularly, in a deuterium-containing compound of the general formula (I), the frequency of deuterium in every deuterated position in the compound of the general formula (I) is higher than 10%, 20%, 30%, 40%, 50%, 60%, 70% or 80%, preferably higher than 90%, 95%, 96% or 97%, even further preferably higher than 98% or 99%, in this position or these positions. It will be apparent that the frequency of deuterium in every deuterated position is independent of the frequency of deuterium in other deuterated positions.

The selective incorporation of one or more deuterium atoms into a compound of the general formula (I) can alter the physicochemical properties (for example acidity [A. Streitwieser et al., J. Am. Chem. Soc., 1963, 85, 2759; C. L. Perrin et al., J. Am. Chem. Soc., 2007, 129, 4490], basicity [C. L. Perrin, et al., J. Am. Chem. Soc., 2003, 125, 15008; C. L. Perrin in Advances in Physical Organic Chemistry, 44, 144; C. L. Perrin et al., J. Am. Chem. Soc., 2005, 127, 9641], lipophilicity [B. Testa et al., Int. J. Pharm., 1984, 19(3), 271]) and/or the metabolic profile of the molecule, and cause changes in the ratio of parent compound to metabolites or the amounts of metabolites formed. Such changes may lead to particular therapeutic benefits and therefore be preferable under particular circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent compound and metabolites can have important consequences with respect to the pharmacodynamics, tolerability and efficacy of a deuterium-containing compound of the general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Uetrecht et al., Chemical Research in Toxicology, 2008, 21, 9, 1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Indiplon (A. J. Morales et al., Abstract 285, The 15$^{th}$ North American Meeting of the International Society of Xenobiotics, San Diego, Calif., Oct. 12-16, 2008), ML-337 (C. J. Wenthur et al., J. Med. Chem., 2013, 56, 5208), and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In the context of the present invention, unless specified otherwise, the substituents are defined as follows:

Alkyl per se and "Alk" and "alkyl" in alkoxy, alkylsulfonyl, alkylaminocarbonyloxy and alkoxycarbonyl are a linear or branched alkyl radical having generally 1 to 6 and preferably 1 to 4 or 1 to 3 carbon atoms, by way of example and with preference methyl, ethyl, n-propyl, isopropyl, tert-butyl, isobutyl (2-methylprop-1-yl), n-pentyl and n-hexyl.

Alkoxy is, by way of example and with preference, methoxy, ethoxy, n-propoxy, isopropoxy, tert-butoxy, n-pentoxy and n-hexoxy.

Alkylaminocarbonyloxy is an alkylaminocarbonyloxy radical having one or two (independently chosen) alkyl substituents. ($C_1$-$C_3$)-Alkylaminocarbonyloxy is, for example, a monoalkylaminocarbonyloxy radical having 1 to 3 carbon atoms or a dialkylaminocarbonyloxy radical having 1 to 3 carbon atoms in each alkyl substituent. Preferred examples include: methylaminocarbonyloxy, ethylaminocarbonyloxy, n-propylaminocarbonyloxy, isopropylaminocarbonyloxy, tert-butylaminocarbonyloxy, n-pentylaminocarbonyloxy, n-hexylaminocarbonyloxy, N,N-dimethylaminocarbonyloxy, N,N-diethylaminocarbonyloxy, N-ethyl-N-methylaminocarbonyloxy, N-methyl-N-n-propylaminocarbonyloxy, N-isopropyl-N-n-propylaminocarbonyloxy, N-tert-butyl-N-methylaminocarbonyl, N-ethyl-N-n-pentylaminocarbonyl and N-n-hexyl-N-methylaminocarbonyloxy.

Alkylsulfonyl in the context of the invention is a straight-chain or branched alkyl radical which has 1 to 4 carbon atoms and is attached via a sulfonyl group. Preferred examples include: methylsulfonyl, ethylsulfonyl, n-propylsulfonyl, isopropylsulfonyl, n-butylsulfonyl and tert-butylsulfonyl.

Alkoxycarbonyl is, by way of example and with preference, methoxycarbonyl, ethoxycarbonyl, n-propoxycarbonyl, isopropoxycarbonyl, tert-butoxycarbonyl, n-pentoxycarbonyl and n-hexoxycarbonyl.

Carbocycle in the context of the invention is a mono-, poly- or spirocyclic, preferably mono- or bicyclic, saturated carbocycle having a total of 3 to 6 ring atoms. A monocyclic saturated carbocycle is referred to synonymously as cycloalkyl. Examples include: cyclopropyl, cyclobutyl, cyclopentyl, cyclohexyl, cycloheptyl, cyclopentenyl, cyclohexenyl, cyclohexadienyl, cycloheptenyl, cycloheptadienyl, spiro[2.3]hexyl, spiro[2.4]heptyl, spiro[2.5]octyl, bicyclo[1.1.1]pentyl, bicyclo[2.2.1]heptyl, bicyclo[2.2.2]octyl, tricyclo[3.3.1.13,7]decyl. Monocyclic cycloalkyl having 3 to 5 carbon atoms is preferred. Preferred examples include: cyclopropyl, cyclobutyl, cyclopentyl and bicyclo[1.1.1]pent-1-yl.

Heterocyclyl is a mono-, poly- or spirocyclic, preferably mono-, bi- or spirocyclic, nonaromatic heterocyclic radical having generally 3 to 10 ring atoms and up to 3, preferably up to 2, heteroatoms and/or hetero groups from the group consisting of N, O, S, SO and $SO_2$. The heterocyclyl radicals can be saturated or partially unsaturated. Preference is given to 4- to 6-membered monocyclic saturated heterocyclyl radicals having one nitrogen atom and to those having a further heteroatom from the group consisting of N and O, and also to 6- to 7-membered bi- or spirocyclic saturated heterocyclyl radicals having one nitrogen atom. Preferred examples include: azetidinyl, pyrrolidinyl, piperidinyl, piperazinyl, oxazolidinyl, imidazolidinyl, morpholinyl, tetrahydropyrimidine, azaspiro[2.4]heptyl and azabicyclo[3.1.0]hexyl.

Halogen represents fluorine, chlorine, bromine and iodine, preferably chlorine.

In the formula of the group that $R^1$, $R^2$, $Ar^1$, $Ar^2$, $Y^1$ or $Y^2$ may represent, the end point of the line marked by the symbol #$^1$, #$^2$, #$^3$; *,  and * does not represent a carbon atom or a $CH_2$ group but is part of the bond to the respective atom to which $R^1$, $R^2$, $Ar^1$, $Ar^2$, $Y^1$ and $Y^2$, respectively, is attached.

When radicals in the compounds of the invention are substituted, the radicals may be mono- or polysubstituted, unless specified otherwise. In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given in the context of the present invention to compounds of the formula (I) in which
$R^1$ represents $NR^3R^4$,
in which
$R^3$ represents hydrogen, methyl or $(C_2-C_4)$-alkyl, and
$R^4$ represents $(C_1-C_6)$-alkyl which is up to tetrasubstituted by fluorine,
where $(C_1-C_6)$-alkyl may be substituted by oxo,
or
$R^3$ and $R^4$ together with the nitrogen atom to which they are attached form a saturated 4- to 6-membered monocyclic or 6- to 9-membered bicyclic heterocycle which may contain one or two further identical or different heteroatoms from the group consisting of N and O as ring members,
where the 4- to 6-membered monocyclic and 6- to 9-membered bicyclic heterocycle may each be substituted by 1 to 5 substituents independently selected from the group of $(C_1-C_4)$-alkyl, difluoromethyl, trifluoromethyl, hydroxy, oxo, $(C_1-C_3)$-alkoxy, difluoromethoxy, trifluoromethoxy, and furthermore up to tetrasubstituted by fluorine,
where $(C_1-C_4)$-alkyl may be mono- or disubstituted by identical or different substituents from the group consisting of hydroxy and $(C_1-C_3)$-alkoxy, and up to tetrasubstituted by fluorine,
$R^2$ represents a group of the formula

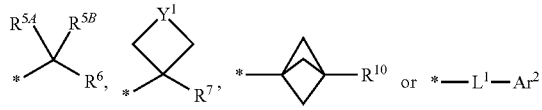

in which
\* marks the point of attachment to the nitrogen atom of the amide moiety,
$R^{5A}$ represents hydrogen or $(C_1-C_4)$-alkyl,
$R^{5B}$ represents methyl, monofluoromethyl, difluoromethyl, trifluoromethyl, pentafluoroethyl or trifluoromethoxymethyl, and
$R^6$ represents $(C_1-C_4)$-alkyl which is up to pentasubstituted by fluorine, or $(C_3-C_5)$-cycloalkyl which is up to tetrasubstituted by fluorine,
$Y^1$ represents $—(CH_2)_k—$,
in which
k represents 1 or 2,
$R^7$ represents $(C_1-C_2)$-alkyl which is up to pentasubstituted by fluorine,
$R^{10}$ represents hydrogen, fluorine or trifluoromethyl,
$L^1$ represents a bond or a group of the formula $—CR^{8A}R^{8B}—$,
in which
$R^{8A}$ represents hydrogen,
$R^{8B}$ represents methyl, trifluoromethyl, pentafluoroethyl or trifluoromethoxymethyl, $Ar^2$ represents phenyl,
where phenyl may be mono- to trisubstituted by identical or different substituents from the group consisting of fluorine, chlorine, $(C_1-C_3)$-alkyl and trifluoromethyl,
$Ar^1$ represents a pyridine ring which is attached via a ring carbon atom,
where the pyridine ring may be mono- or disubstituted by fluorine, chlorine, cyano, methyl or trifluoromethyl,
and the salts, solvates and solvates of the salts thereof.

Preference is given in the context of the present invention to compounds of the formula (I) in which
in which
$R^1$ represents $NR^3R^4$,
in which
$R^3$ represents hydrogen or methyl, and
$R^4$ represents methyl or 2-fluoroethyl,
or
represents a heterocycle, attached via a nitrogen atom, of the formula

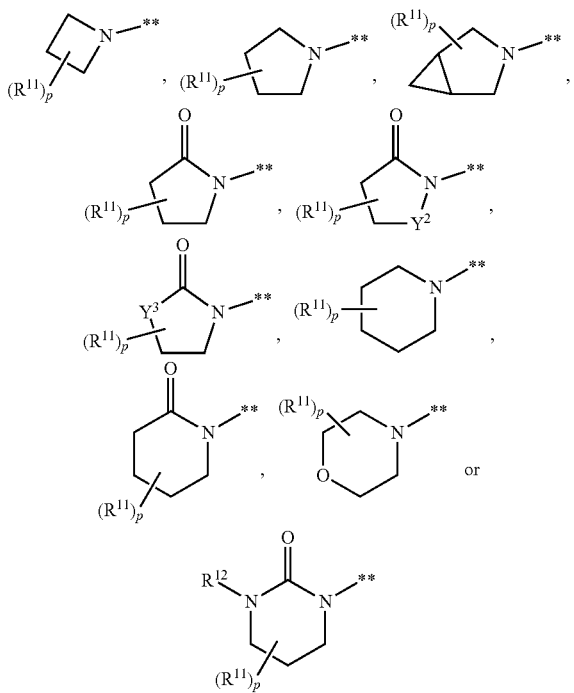

in which
\*\* marks the point of attachment to the remainder of the molecule,
$Y^2$ represents a group of the formula

in which
$\#^1$ marks the point of attachment to the nitrogen atom of the pyrrolidinone ring, and
$\#^2$ marks the point of attachment to the carbon atom of the pyrrolidinone ring, and $Y^3$ represents —$N(R^{12})$— or a group of the formula

in which
$\#^1$ and $\#^2$ each mark the point of attachment to the carbon atom of the pyrrolidinone ring,
$R^{11}$ represents fluorine, $(C_1-C_4)$-alkyl, difluoromethyl, trifluoromethyl, hydroxy, hydroxymethyl, methoxy, difluoromethoxy or trifluoromethoxy,
p represents the number 0, 1, 2, 3 or 4,
  where, in the case that the substituents $R^{11}$ occur more than once, their meanings may in each case be identical or different,
$R^{12}$ represents hydrogen or 2-hydroxyethyl,
$R^2$ represents a group of the formula

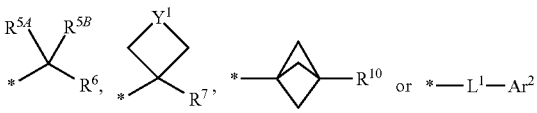

in which
* marks the point of attachment to the nitrogen atom of the amide moiety,
$R^{5A}$ represents hydrogen or methyl,
$R^{5B}$ represents methyl, monofluoromethyl, difluoromethyl, trifluoromethyl, pentafluoroethyl or trifluoromethoxymethyl, and
$R^6$ represents methyl, ethyl, trifluoromethyl, 2,2,2-trifluoroethyl, tert-butyl, isobutyl or cyclopropyl,
$Y^1$ represents —$(CH_2)_k$—,
  in which
  k represents 1 or 2,
$R^7$ represents trifluoromethyl,
$R^{10}$ represents hydrogen, fluorine or trifluoromethyl,
$L^1$ represents a bond or a group of the formula —$CR^{8A}R^{8B}$—,
  in which
  $R^{8A}$ represents hydrogen,
  $R^{8B}$ represents trifluoromethyl,
$Ar^2$ represents phenyl,
  where phenyl may be mono- or disubstituted by identical or different substituents from the group consisting of fluorine and chlorine,
$Ar^1$ represents a group of the formula

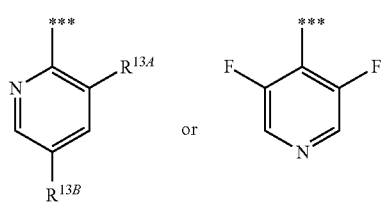

in which
*** marks the point of attachment to the nitrogen atom,
$R^{13A}$ represents fluorine or chlorine,
$R^{13B}$ represents fluorine or hydrogen,
and the salts, solvates and solvates of the salts thereof.

In the context of the present invention, particular preference is given to compounds of the formula (I) in which
in which
$R^1$ represents a heterocycle, attached via a nitrogen atom, of the formula

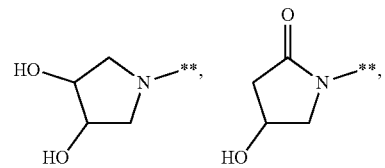

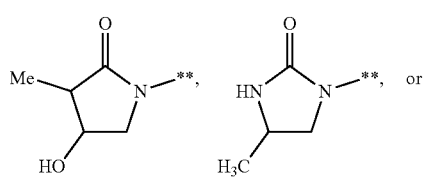

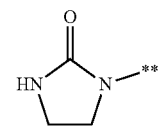

in which
** marks the point of attachment to the remainder of the molecule,
$R^2$ represents a group of the formula

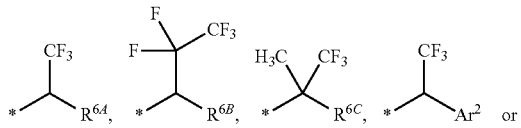

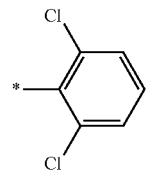

in which
* marks the point of attachment to the nitrogen atom of the amide moiety,
$R^{6A}$ represents trifluoromethyl, ethyl, tert-butyl, isobutyl or cyclopropyl,
$R^{6B}$ represents methyl or ethyl,
$R^{6C}$ represents trifluoromethyl or cyclopropyl,
$Ar^2$ represents a group of the formula

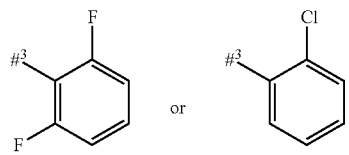

in which

³ in each case marks the bonding site

Ar¹ represents a group of the formula

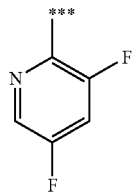

in which

*** marks the point of attachment to the nitrogen atom, and the salts, solvates and solvates of the salts thereof.

A further particular embodiment of the present invention encompasses compounds of the formula (I) in which $R^1$ represents a heterocycle, attached via a nitrogen atom, of the formula

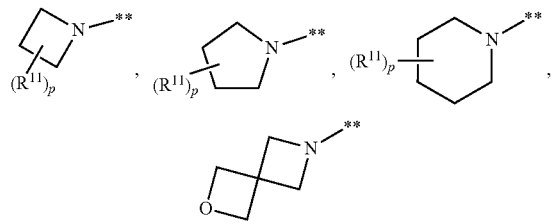

in which
- ** marks the point of attachment to the remainder of the molecule,
- $R^{11}$ represents fluorine, $(C_1-C_4)$-alkyl, difluoromethyl, trifluoromethyl, hydroxy, hydroxymethyl, methoxy, difluoromethoxy or trifluoromethoxy,
- p represents the number 0, 1, 2, 3 or 4,
  where, in the case that the substituents $R^{11}$ occur more than once, their meanings may in each case be identical or different,
- $R^2$ represents a group of the formula

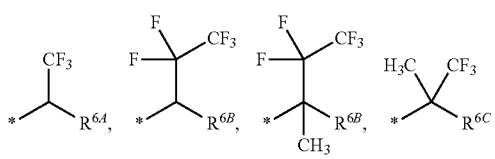

in which
- * marks the point of attachment to the nitrogen atom of the amide moiety,
- $R^{6A}$ represents trifluoromethyl, ethyl, tert-butyl, isobutyl or cyclopropyl,
- $R^{6B}$ represents methyl, ethyl, tert-butyl or cyclopropyl,
- $R^{6C}$ represents trifluoromethyl or cyclopropyl, Ar¹ represents a group of the formula

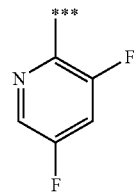

in which

*** marks the point of attachment to the nitrogen atom, and the salts, solvates and solvates of the salts thereof.

A further particular embodiment of the present invention encompasses compounds of the formula (I) in which $R^1$ represents a heterocycle, attached via a nitrogen atom, of the formula

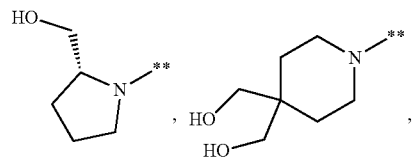

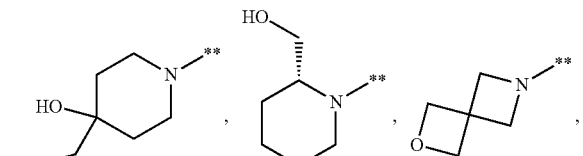

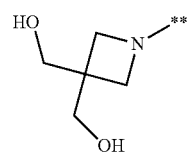

in which
- ** marks the point of attachment to the remainder of the molecule,
- $R^2$ represents a group of the formula

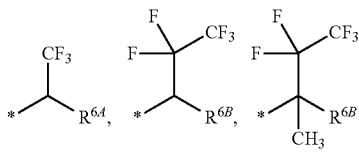

in which
- * marks the point of attachment to the nitrogen atom of the amide moiety,
- $R^{6A}$ represents trifluoromethyl,
- $R^{6B}$ represents methyl, $Ar^1$ represents a group of the formula

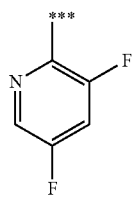

in which
\*\*\* marks the point of attachment to the nitrogen atom,
and the salts, solvates and solvates of the salts thereof.

A further particular embodiment of the present invention encompasses compounds of the formula (I) in which
$R^1$ represents a heterocycle, attached via a nitrogen atom, of the formula

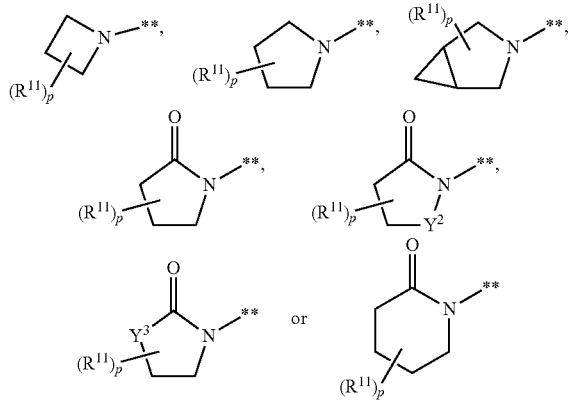

in which
\*\* marks the point of attachment to the remainder of the molecule,
$Y^2$ represents a group of the formula

in which
$\#^1$ marks the point of attachment to the nitrogen atom of the pyrrolidinone ring, and
$\#^2$ marks the point of attachment to the carbon atom of the pyrrolidinone ring, and
$Y^3$ represents —$N(R^{12})$— or a group of the formula

in which
$\#^1$ and $\#^2$ each mark the point of attachment to the carbon atom of the pyrrolidinone ring,
$R^{11}$ represents fluorine, $(C_1-C_4)$-alkyl, difluoromethyl, trifluoromethyl, hydroxy, hydroxymethyl, methoxy, difluoromethoxy or trifluoromethoxy,
p represents the number 0, 1, 2, 3 or 4,
where, in the case that the substituents $R^{11}$ occur more than once, their meanings may in each case be identical or different,
and the N-oxides, salts, solvates, salts of the N-oxides and solvates of the N-oxides or salts thereof.

A further particular embodiment of the present invention encompasses compounds of the formula (I) in which
$R^1$ represents a heterocycle, attached via a nitrogen atom, of the formula

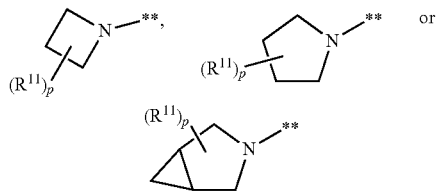

in which
\*\* marks the point of attachment to the remainder of the molecule,
$R^{11}$ represents fluorine, $(C_1-C_4)$-alkyl, difluoromethyl, trifluoromethyl, hydroxy, hydroxymethyl, methoxy, difluoromethoxy or trifluoromethoxy,
p represents the number 0, 1, 2, 3 or 4,
where, in the case that the substituents $R^{11}$ occur more than once, their meanings may in each case be identical or different,
and the N-oxides, salts, solvates, salts of the N-oxides and solvates of the N-oxides or salts thereof.

A further particular embodiment of the present invention encompasses compounds of the formula (I) in which
$R^1$ represents a heterocycle, attached via a nitrogen atom, of the formula

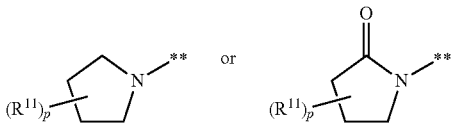

in which
\*\* marks the point of attachment to the remainder of the molecule,
$R^{11}$ represents fluorine, $(C_1-C_4)$-alkyl, difluoromethyl, trifluoromethyl, hydroxy, hydroxymethyl, methoxy, difluoromethoxy or trifluoromethoxy,
p represents the number 0, 1, 2, 3 or 4,
where, in the case that the substituents $R^{11}$ occur more than once, their meanings may in each case be identical or different,
and the N-oxides, salts, solvates, salts of the N-oxides and solvates of the N-oxides or salts thereof.

A further particular embodiment of the present invention encompasses compounds of the formula (I) in which
$R^1$ represents a heterocycle, attached via a nitrogen atom, of the formula

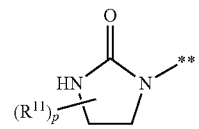

in which
\*\* marks the point of attachment to the remainder of the molecule, $R^{11}$ represents fluorine, $(C_1-C_4)$-alkyl, difluoromethyl, trifluoromethyl, hydroxy, hydroxymethyl, methoxy, difluoromethoxy or trifluoromethoxy, p represents the number 0, 1, 2, 3 or 4,
where, in the case that the substituents $R^9$ occur more than once, their meanings may in each case be identical or different, and the N-oxides, salts, solvates, salts of the N-oxides and solvates of the N-oxides or salts thereof.

A further particular embodiment of the present invention encompasses compounds of the formula (I) in which
$R^1$ represents a heterocycle, attached via a nitrogen atom, of the formula

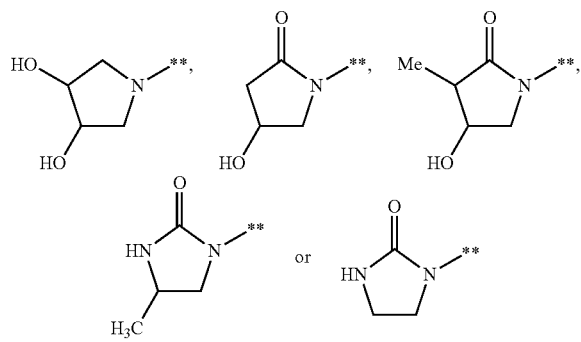

in which
** marks the point of attachment to the remainder of the molecule, and the N-oxides, salts, solvates, salts of the N-oxides and solvates of the N-oxides or salts thereof.

A further particular embodiment of the present invention encompasses compounds of the formula (I) in which
$R^1$ represents a heterocycle, attached via a nitrogen atom, of the formula

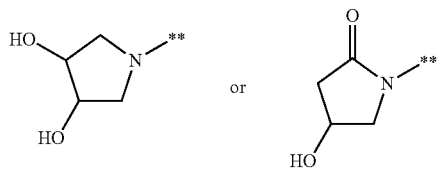

in which
** marks the point of attachment to the remainder of the molecule, and the N-oxides, salts, solvates, salts of the N-oxides and solvates of the N-oxides or salts thereof.

A further particular embodiment of the present invention encompasses compounds of the formula (I) in which
$R^1$ represents a heterocycle, attached via a nitrogen atom, of the formula

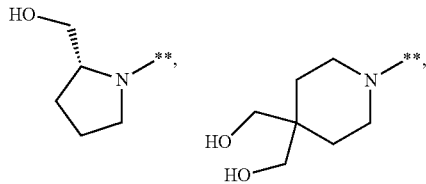

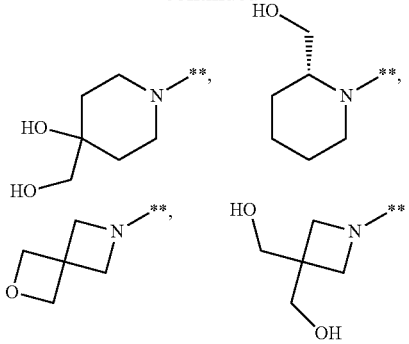

in which
** marks the point of attachment to the remainder of the molecule, and the N-oxides, salts, solvates, salts of the N-oxides and solvates of the N-oxides or salts thereof.

A further particular embodiment of the present invention encompasses compounds of the formula (I) in which
$R^2$ represents a group of the formula

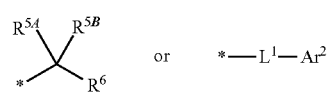

in which
* marks the point of attachment to the nitrogen atom of the amide moiety,
$R^{5A}$ represents hydrogen or methyl,
$R^{5B}$ represents methyl, monofluoromethyl, difluoromethyl, trifluoromethyl, pentafluoroethyl or trifluoromethoxymethyl, and
$R^6$ represents methyl, ethyl, trifluoromethyl, 2,2,2-trifluoroethyl, tert-butyl, isobutyl or cyclopropyl,
$L^1$ represents a bond or a group of the formula $-CR^{8A}R^{8B}-$,
in which
$R^{8A}$ represents hydrogen,
$R^{8B}$ represents trifluoromethyl,
$Ar^2$ represents phenyl,
where phenyl may be mono- or disubstituted by identical or different substituents from the group consisting of fluorine and chlorine, and the N-oxides, salts, solvates, salts of the N-oxides and solvates of the N-oxides or salts thereof.

A further particular embodiment of the present invention encompasses compounds of the formula (I) in which
$R^2$ represents a group of the formula

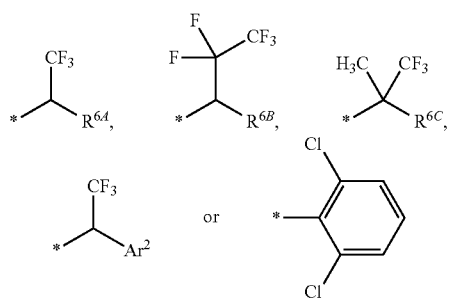

in which
* marks the point of attachment to the nitrogen atom of the amide moiety,
$R^{6A}$ represents trifluoromethyl, ethyl, tert-butyl, isobutyl or cyclopropyl,
$R^{6B}$ represents methyl or ethyl,
$R^{6C}$ represents trifluoromethyl or cyclopropyl,
$Ar^2$ represents a group of the formula

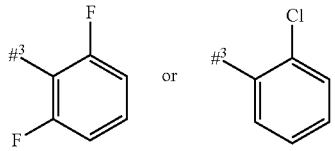

in which
³ in each case marks the bonding site
and the N-oxides, salts, solvates, salts of the N-oxides and solvates of the N-oxides or salts thereof.

A further particular embodiment of the present invention encompasses compounds of the formula (I) in which
$R^2$ represents a group of the formula

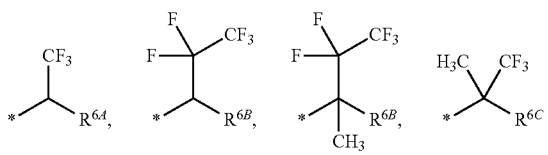

in which
* marks the point of attachment to the nitrogen atom of the amide moiety,
$R^{6A}$ represents trifluoromethyl, ethyl, tert-butyl, isobutyl or cyclopropyl,
$R^{6B}$ represents methyl, ethyl, tert-butyl or cyclopropyl,
$R^{6C}$ represents trifluoromethyl or cyclopropyl,
and the N-oxides, salts, solvates, salts of the N-oxides and solvates of the N-oxides or salts thereof.

A further particular embodiment of the present invention encompasses compounds of the formula (I) in which
$R^2$ represents a group of the formula

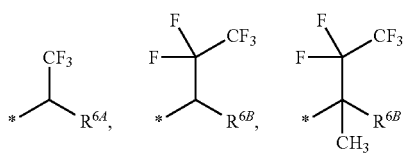

in which
* marks the point of attachment to the nitrogen atom of the amide moiety,
$R^{6A}$ represents trifluoromethyl,
$R^{6B}$ represents methyl,
and the N-oxides, salts, solvates, salts of the N-oxides and solvates of the N-oxides or salts thereof.

A further particular embodiment of the present invention encompasses compounds of the formula (I) in which
$R^2$ represents a group of the formula

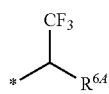

in which
* marks the point of attachment to the nitrogen atom of the amide moiety,
$R^{6A}$ represents trifluoromethyl, ethyl, tert-butyl, isobutyl or cyclopropyl,
and the N-oxides, salts, solvates, salts of the N-oxides and solvates of the N-oxides or salts thereof.

A further particular embodiment of the present invention encompasses compounds of the formula (I) in which
$R^2$ represents a group of the formula

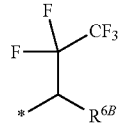

in which
* marks the point of attachment to the nitrogen atom of the amide moiety,
$R^{6B}$ represents methyl or ethyl,
and the N-oxides, salts, solvates, salts of the N-oxides and solvates of the N-oxides or salts thereof.

A further particular embodiment of the present invention encompasses compounds of the formula (I) in which
$R^2$ represents a group of the formula

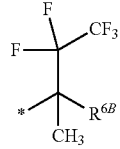

in which
* marks the point of attachment to the nitrogen atom of the amide moiety,
$R^{6B}$ represents methyl,
and the N-oxides, salts, solvates, salts of the N-oxides and solvates of the N-oxides or salts thereof.

A further particular embodiment of the present invention encompasses compounds of the formula (I) in which
$Ar^1$ represents a group of the formula

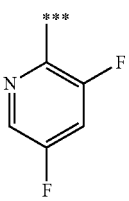

in which
* * * marks the point of attachment to the nitrogen atom,
and the N-oxides, salts, solvates, salts of the N-oxides and solvates of the N-oxides or salts thereof.

The individual radical definitions specified in the respective combinations or preferred combinations of radicals are, independently of the respective combinations of the radicals specified, also replaced as desired by radical definitions of other combinations.

Very particular preference is given to combinations of two or more of the abovementioned preferred ranges and embodiments.

The radical definitions specified as preferred, particularly preferred and very particularly preferred apply both to the compounds of the formula (I) and correspondingly toward all intermediates.

The invention further provides a process for preparing compounds of the formula (I) according to the invention, characterized in that

[A] a compound of the formula (II)

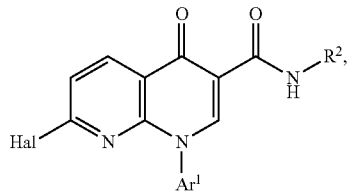

in which R² and Ar¹ have the definitions given above, and

Hal represents fluorine, chlorine, bromine or iodine, preferably chlorine, is reacted with a compound of the formula (III)

in which R¹ has the meaning given above,
to give the carboxamide of the formula (I) according to the invention

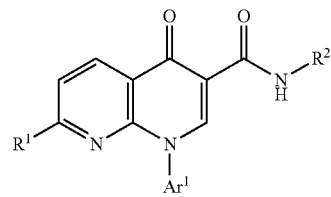

in which R¹, R² and Ar¹ have the definitions given above, or

[B] a compound of the formula (IV)

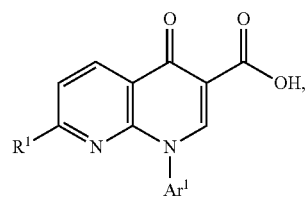

in which R¹ and Ar¹ have the definitions given above, is reacted with a compound of the formula (V)

in which R² has the meaning given above,
to give the carboxamide of the formula (I) according to the invention

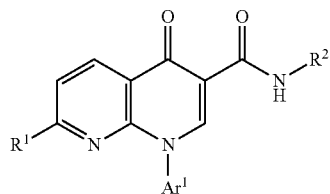

in which R¹, R² and Ar¹ have the definitions given above, and, if appropriate, the compounds of the formula (I) thus obtained are separated into their enantiomers and/or diastereomers and/or converted with the appropriate (i) solvents and/or (ii) bases or acids to their solvates, salts and/or solvates of the salts.

The reaction (II)+(III)→(I) can be effected via a nucleophilic substitution reaction or via a transition metal-mediated coupling reaction.

The nucleophilic substitution reaction is preferably carried out in the presence of a base. Suitable bases for the process step (II)+(III)→(I) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate or cesium carbonate, alkali metal alkoxides such as lithium tert-butoxide, sodium tert-butoxide or potassium tert-butoxide, alkali metal hydrides such as sodium hydride or potassium hydride, or organic amines such as N,N-diisopropylethylamine (DIPEA), 1,5-diazabicyclo[4.3.0]non-5-ene (DBN) and 1,8-diazabicyclo[5.4.0] undec-7-ene (DBU). Preference is given to using N,N-diisopropylethylamine (DIPEA). The reaction is conducted generally within a temperature range from 0° C. to +100° C., preferably at +23° C. to +80° C.

Inert solvents for the process step (II)+(III)→(I) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide (DMF), N,N'-dimethylpropyleneurea (DMPU) or N-methylpyrrolidone (NMP). It is likewise possible to use mixtures of the solvents mentioned. Preference is given to using dimethylformamide (DMF) or N-methylpyrrolidone (NMP).

The transition metal-mediated coupling reaction for the process step (II)+(III)→(I), in a preferred embodiment, is conducted in the presence of a palladium catalyst. Suitable palladium catalysts are, for example, palladium(II) acetate, palladium(II) chloride, bis(triphenylphosphine)palladium (II) chloride, bis(acetonitrile)palladium(II) chloride, tetrakis (triphenylphosphine)palladium(0), bis(dibenzylideneacetone)palladium(0), tris(dibenzylideneacetone)palladium(0) or [1,1'-bis(diphenylphosphino)ferrocene]palladium(II) chloride, optionally in combination with a suitable phosphine ligand, for example triphenylphosphine, tri-tert-butylphosphine, 2-dicyclohexylphosphino-2',4',6'-triisopropylbiphenyl (X-Phos), 2-dicyclohexylphosphino-2',6'- dimethoxybiphenyl (S-Phos), 1,2,3,4,5pentaphenyl-1'-(di-tert-butylphosphino)ferrocene (Q-Phos), 4,5-bis(diphenylphosphino)-9,9-dimethylxanthene (Xantphos), 2,2'-bis(diphenylphosphino)-1,1'-binaphthyl (BINAP), 2dicyclohexylphosphino-2'-(N,N-dimethylamino)biphenyl or 2-di-tert-butylphosphino-2'-(N,N-dimethylamino)biphenyl.

The palladium-catalyzed coupling reaction (II)+(III)→(I) is generally conducted in the presence of a base. Suitable bases are especially alkali metal carbonates such as sodium carbonate, potassium carbonate or cesium carbonate, alkali metal phosphates such as sodium phosphate or potassium phosphate, alkali metal fluorides such as potassium fluoride or cesium fluoride, or alkali metal tert-butoxides such as sodium tert-butoxide or potassium tert-butoxide. The reaction is carried out in an inert solvent, for example toluene, 1,2-dimethoxyethane, tetrahydrofuran, 1,4-dioxane, dimethyl sulfoxide (DMSO), N,N-dimethylformamide (DMF), N,N-dimethylacetamide (DMA) or mixtures thereof, within a temperature range from +80° C. to +200° C., preferably at +80° C. to +150° C., where heating by means of a microwave apparatus may be advantageous.

Preference is given to using, for this coupling reaction, a catalyst/ligand/base system consisting of palladium(II) acetate, 4,5-bis(diphenylphosphino)-9,9-dimethylxanthene (Xantphos) and cesium carbonate or potassium carbonate, and 1,4-dioxane as solvent.

The coupling reaction (II)+(III)→(I) may, in a further preferred embodiment, also be conducted with the aid of a copper(I) catalyst, such as copper(I) oxide, bromide or iodide, in the presence of a copper ligand such as trans-N,N'-dimethyl-1,2-cyclohexanediamine, 8-hydroxyquinoline or 1,10-phenanthroline, and of an inorganic or organic carbonate base, such as potassium carbonate, cesium carbonate or bis(tetraethylammonium) carbonate. Suitable inert solvents for this reaction are in particular toluene, xylene, 1,4-dioxane, acetonitrile, dimethyl sulfoxide (DMSO), N,N-dimethylformamide (DMF) or mixtures thereof, optionally with addition of water. Preference is given to using a system consisting of copper(I) iodide, trans-N,N'-dimethyl-1,2-cyclohexanediamine and potassium carbonate in dimethylformamide. The reaction is conducted generally within a temperature range from +50° C. to +200° C., preferably at +60° C. to +150° C.

The coupling reaction (IV)+(V)→(I) [amide formation] can be effected either by a direct route with the aid of a condensing or activating agent or via the intermediate stage of a carbonyl chloride, carboxylic ester or carbonyl imidazolide obtainable from (IV).

Suitable for use as condensing agents or activating agents are, for example, carbodiimides such as N,N'-diethyl-, N,N'-dipropyl-, N,N'-diisopropyl-, N,N'-dicyclohexylcarbodiimide (DCC) or N-(3dimethylaminopropyl)-N'-ethylcarbodiimide hydrochloride (EDC), phosgene derivatives such as N,N'-carbonyldiimidazole (CDI), isopropyl chloroformate or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, α-chlorenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (T3P, PPACA), diethyl cyanophosphonate, diphenylphosphoryl azide (DPPA), bis(2-oxo-3oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), O-(1H-6-chlorobenzotriazol-1-yl)-1,1,3,3-tetramethyluronium tetrafluoroborate (TCTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate, or tertiary amine bases such as triethylamine, N-methylmorpholine (NMM), N-methylpiperidine (NMP), N,N-diisopropylethylamine (DIPEA), pyridine or 4-N,N-dimethylaminopyridine (DMAP). Condensing or activating agents used with preference are O-(7-azabenzotriazol-1-yl)-N,N,N',N'-tetramethyluronium hexafluorophosphate (HATU) in combination with N,N-diisopropylethylamine (DIPEA), and also n-propanephosphonic anhydride (T3P, PPACA) in combination with N,N-diisopropylethylamine (DIPEA).

The compounds of the formula (II) can be prepared by reacting a carboxylic acid compound of the formula (VI)

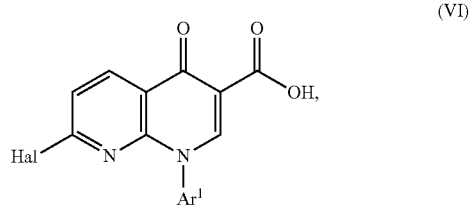

(VI)

in which Hal and Ar¹ have the definitions given above is reacted with a compound of the formula (V)

(V)

in which R² has the meaning given above, to give the inventive carboxamide of the formula (II)

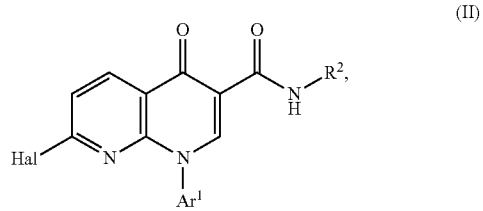

(II)

in which Hal, R¹, R² and Ar¹ have the definitions given above.

The coupling reaction (VI)+(V)→(II) [amide formation] can be effected either by a direct route with the aid of a condensing or activating agent or via the intermediate stage of a carbonyl chloride, carboxylic ester or carbonyl imidazolide obtainable from (VI), analogously to the conditions and reagents already described for the reaction (IV)+(V)→(I).

If HATU is used as activating agent in the coupling reaction to give (II), it is possible that either an individual defined product of the general formula (II) is obtained, or else a mixture with a "HATU adduct". A "HATU adduct" in the present context refers to a pseudohalide compound where the Hal substituent in the general formula (II) is replaced by the 3H-[1,2,3]triazolo[4,5-b]pyridin-3-ol group, also referred to as 1-hydroxy-7-azabenzotriazole. Such a mixture of a halogen compound of the general formula (II) and a "HATU adduct" can likewise be used, analogously to the reaction described, as reactant for the further reaction (after (I) or (VIII)).

In the case of a two-stage reaction regime via the carbonyl chlorides or carbonyl imidazolides obtainable from (VI), the coupling with the amine component (V) is carried out in the presence of a customary base, for example sodium carbonate or potassium carbonate, triethylamine, DIPEA, N-methylmorpholine (NMM), N-methylpiperidine (NMP), pyridine, 2,6-dimethylpyridine, 4-N,N-dimethylaminopyridine (DMAP), 1,8-diazabicyclo[5.4.0]undec-7-ene (DBU), 1,5-diazabicyclo[4.3.0]non-5-ene (DBN), sodium methoxide or potassium methoxide, sodium ethoxide or potassium ethoxide, sodium tert-butoxide or potassium tert-butoxide, or sodium hydride or potassium hydride.

The carbonyl imidazolides themselves are obtainable by known methods by reaction of (VI) with N,N'-carbonyldiimidazole (CDI) at elevated temperature (+60° C. to +150° C.) in a correspondingly relatively high-boiling solvent such as N,N-dimethylformamide (DMF). The preparation of the carbonyl chlorides is accomplished in a customary manner by treating (VI) with thionyl chloride or oxalyl chloride in an inert solvent such as dichloromethane or THF.

Inert solvents for the coupling reactions mentioned are—according to the method used—for example ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP). It is also possible to use mixtures of such solvents. Preference is given to using N,N-dimethylformamide (DMF) and dichloromethane (DCM) in combination with triethylamine. The couplings are generally conducted within a temperature range from 0° C. to +130° C., preferably at +20° C. to +30° C.

Depending on their respective substitution pattern, the compounds of the formula (IV) can be prepared by reacting either

[C] a compound of the formula (VII)

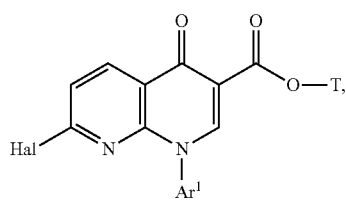

(VII)

in which Hal and Ar¹ have the definitions given above and
T represents (C₁-C₄)-alkyl or benzyl in a first step with a compound of the formula (III)

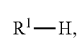

(III)

in which R¹ has the meaning given above,
to give a compound of the formula (VIII)

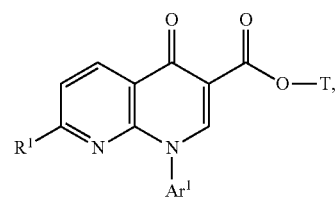

(VIII)

in which T, R¹ and Ar¹ have the definitions given above, and optionally, in a second step, detaching the ester radical T to give the inventive carboxylic acid of the formula (IV)

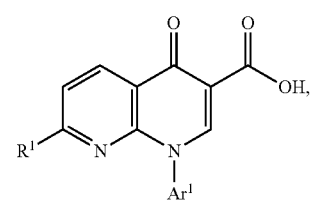

(IV)

in which R¹ and Ar¹ have the definitions given above,
or
[D] a compound of the formula (VI)

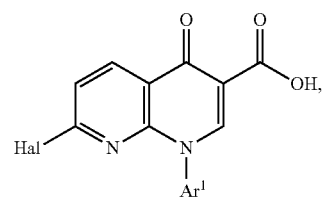

(VI)

in which Hal and Ar¹ have the definitions given above
with a compound of the formula (III)

(III)

in which R¹ has the meaning given above,
to give the inventive carboxylic acid of the formula (IV)

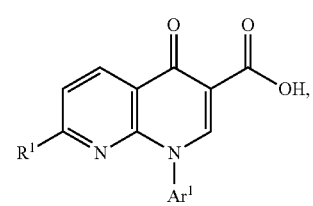

(IV)

in which R¹ and Ar¹ have the definitions given above.
The reaction (VII)+(III)→(VIII) [route C] or the reaction (VI)+(III)→(IV) [route D] can be effected via a nucleophilic substitution reaction or a transition metal-mediated coupling reaction analogously to the conditions already described for the reaction (II)+(III)→(I).

In a preferred embodiment, the reaction is conducted according to route C as a nucleophilic substitution reaction in the presence of a base, preference being given to using N,N-diisopropylethylamine (DIPEA). Preference is given to using dimethylformamide (DMF), N-methylpyrrolidone (NMP) or acetonitrile as solvent.

In a preferred embodiment, the reaction is conducted according to route D as a transition metal-mediated coupling reaction in the presence of a suitable palladium catalyst. Preference is given to using a system of palladium(II) acetate in combination with 4,5-bis(diphenylphosphino)-9,9-dimethylxanthene (xantphos), cesium carbonate or potassium carbonate and 1,4-dioxane as solvent.

The detachment of the ester group T in process step (VIII)→(IV) is conducted by customary methods, by treating the ester in an inert solvent with an acid or a base, with conversion of the salt of the carboxylic acid initially formed in the latter variant to the free carboxylic acid by subsequent treatment with acid. In the case of the tert-butyl esters, the ester cleavage is preferably effected with an acid. Benzyl esters can alternatively also be cleaved by hydrogenation (hydrogenolysis) in the presence of a suitable catalyst, for example palladium on activated carbon.

Suitable solvents for these reactions are water and the organic solvents customary for ester cleavage. These include in particular alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetonitrile, N,N-dimethylformamide or dimethyl sulfoxide. It is equally possible to use mixtures of these solvents. In the case of a basic ester hydrolysis, preference is given to using mixtures of water with tetrahydrofuran.

Suitable bases for a hydrolysis reaction are the customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to using aqueous hydrochloric acid (18 percent) in a water/tetrahydrofuran mixture.

The ester cleavage is generally conducted within a temperature range from −20° C. to +100° C., preferably at 23° C. to +120° C.

Depending on the particular substitution pattern, the compounds of the formula (VI) and of the formula (VIII) can be prepared by, in analogy to known processes (see, for example, EP 0607825 A1, p. 25-26), reacting a 2,6-dichloronicotinoylacrylate derivative of the formula (IX)

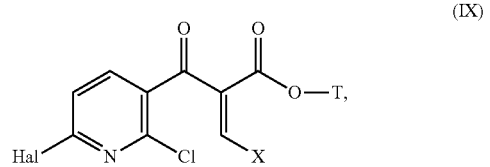

in which Hal and T have the definitions given above and
X represents a leaving group such as dimethylamino, methoxy or ethoxy, and in a first stage, preferably in the presence of a suitable base, with an aminopyridine compound of the formula (X)

in which Ar¹ has the meanings given above,
and then, in a second step, reacting this in the presence of a suitable base to give the ester compound of the formula (VII)

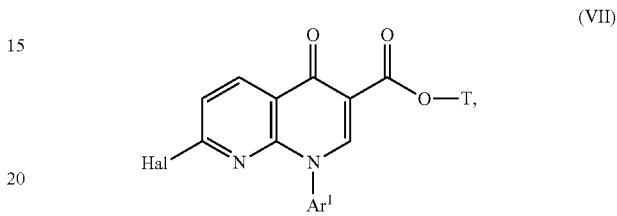

in which Hal, Ar¹ and T have the definition given above,
and then optionally converting the ester compound (VII) under hydrolysis conditions in a further step to the carboxylic acid compound (VI)

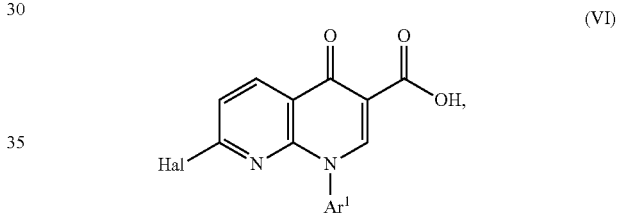

in which Hal and Ar¹ have the definitions given above under the reaction conditions known in the literature.

The compounds of the formula (IX) are known from the literature (see, for example, EP 0607825 A1) or can be prepared in analogy to processes known from the literature.

The compounds of the formulae (III), (V) and (X) are commercially available or described as such in the literature, or they can be prepared in a way obvious to the person skilled in the art, in analogy to methods published in the literature. Numerous detailed methods and literature data for preparation of the respective starting materials can also be found in the Experimental Part in the section relating to the preparation of the starting compounds and intermediates.

The separation of stereoisomers (enantiomers and/or diastereomers) of the inventive compounds of the formula (I) can be achieved by customary methods familiar to those skilled in the art. Preference is given to employing chromatographic methods on achiral or chiral separation phases for this purpose.

Separation of the compounds of the invention into the corresponding enantiomers and/or diastereomers can, if appropriate, also be conducted at the early stage of the intermediates (II), (IV) or (VIII), which are then reacted further in separated form in accordance with the reaction sequence described above. For such a separation of the stereoisomers of intermediates, preference is likewise given to employing chromatographic methods on achiral or chiral separation phases. Alternatively, separation can also be effected via diastereomeric salts of the carboxylic acids of the formula (IV) with chiral amine bases.
The preparation of the compounds of the invention can be illustrated by way of example by the following reaction schemes:
Scheme 1
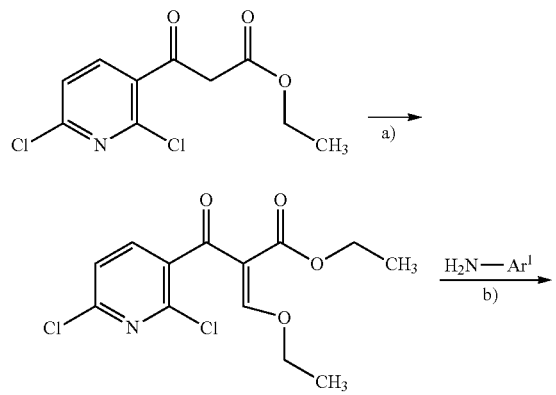
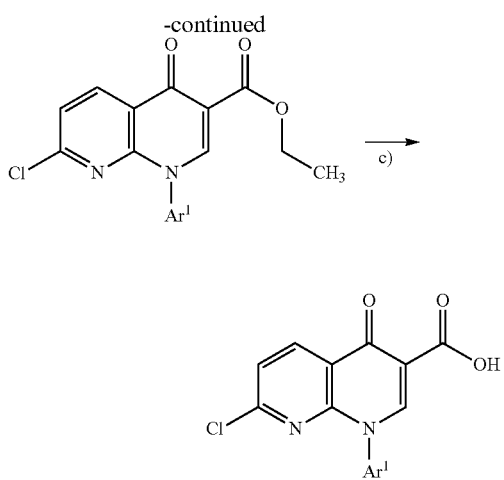
[a]: triethyl orthoformate, acetic anhydride; b): DIPEA, DCM, then $K_2CO_3$; c): 18% strength hydrochloric acid, THF, water].
Scheme 2
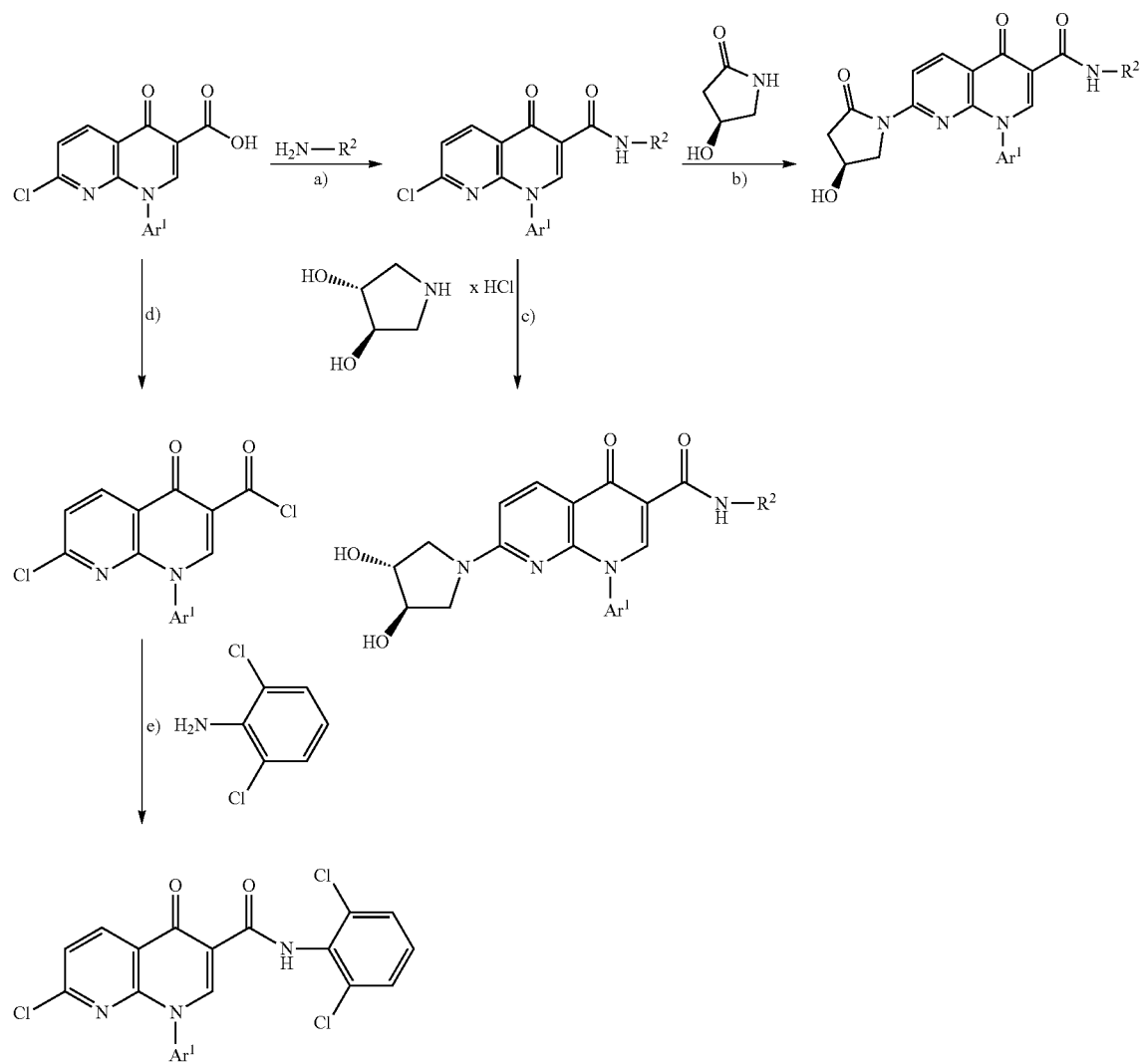

[a]: HATU, DIPEA, DMF or T3P, DIPEA, EtOAc; b): Pd(OAc)$_2$, xantphos, K$_2$CO$_3$, 1,4-dioxane; c): DIPEA, DMF; d): (COCl)$_2$, cat. DMF, THF; e): NaH, DMF or triethylamine, DCM].

Scheme 3

[a]: DIPEA, DMF; b): aq. LiOH, THF or 18% strength hydrochloric acid, THF, water; c): HATU, DIPEA, DMF, RT.]

Scheme 4

[a): Pd(OAc)$_2$, xantphos, K$_2$CO$_3$, 1,4-dioxane; b) HATU, DIPEA, DMF; c) DIPEA, DMF].

Further compounds of the formula (I) according to the invention can, if expedient, also be prepared by transformations of functional groups of individual radicals or substituents, in particular those listed under R$^1$ and R$^2$, proceeding from other compounds of the formula (I) or precursors thereof obtained by the above processes. These transformations are conducted by customary methods familiar to the person skilled in the art and include, for example, reactions such as nucleophilic or electrophilic substitution reactions, transition-metal-mediated coupling reactions, preparation and addition reactions of metal organyls (e.g. Grignard compounds or lithium organyls), oxidation and reduction reactions, hydrogenation, halogenation (e.g. fluorination, bromination), dehalogenation, amination, alkylation and acylation, the formation of carboxylic esters, carboxamides and sulfonamides, ester cleavage and hydrolysis, and the introduction and removal of temporary protecting groups.

The invention relates, in a further aspect, to intermediates of the general formula (II)

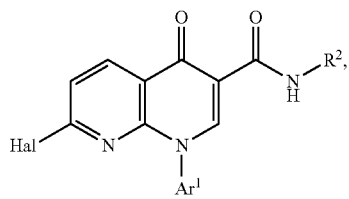

in which R$^2$ and Ar$^1$ have the definitions given above for compounds of the formula (I)
and
Hal represents fluorine, chlorine, bromine or iodine, preferably chlorine.

The invention relates, in a further aspect, to intermediates of the general formula (IV)

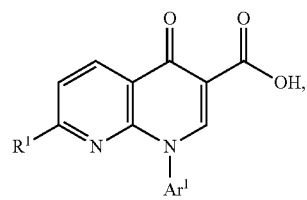

in which R$^1$ and Ar$^1$ have the definitions given above for compounds of the formula (I).

The invention relates, in a further aspect, to the use of a compound of the general formula (II)

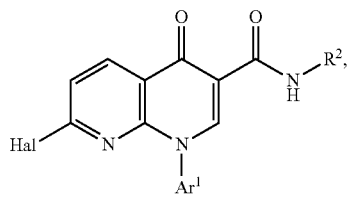

in which R$^2$ and Ar$^1$ have the definitions given above for compounds of the formula (I)
and
Hal represents fluorine, chlorine, bromine or iodine, preferably chlorine.

or
a compound of the general formula (IV)

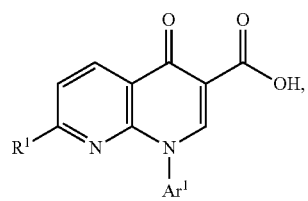

in which R$^1$ and Ar$^1$ have the definitions given above for compounds of the formula (I)
for preparation of a compound of the general formula (I) as defined above.

The compounds according to the invention have an unforeseeable useful spectrum of pharmacological and pharmacokinetic activity.

They are therefore suitable for use as medicaments for treatment and/or prophylaxis of diseases in humans and animals The compounds of the invention have valuable pharmacological properties and can be used for treatment and/or prophylaxis of disorders in humans and animals.

The compounds according to the invention are positive allosteric modulators of the muscarinic M2 receptor and are therefore suitable for treatment and/or prevention of disorders and pathological processes, especially cardiovascular disorders and/or renal disorders, wherein the M2 receptor is involved in dysregulation of the autonomic nervous system or an imbalance between the activity of the sympathetic and parasympathetic portion of the autonomic nervous system.

The present invention provides positive allosteric modulators of the muscarinic M2 receptor. Allosteric modulators have distinct differences from conventional orthosteric ligands. The effect of an allosteric modulator is self-limiting when it stabilizes the binding of the agonist in high concentrations. Furthermore, the effect of an allosteric modulator can be displayed only in the presence of the endogenous ligand. The allosteric modulator itself has no direct influence on receptor activation. This gives rise to specificity of the allosteric effect in terms of space and time. The mutual influencing of allosteric and orthosteric ligands in terms of affinity and intrinsic activity, which is referred to as cooperativity, is determined by the two ligands. In the case of a positive allosteric modulator, the effects of the orthosteric ligand are enhanced (positive cooperativity). Because of its ability to modulate receptor conformations in the presence of an orthosteric ligand, allosteric ligands can bring about fine adjustment of pharmacological effects.

In the context of the present invention, disorders of the cardiovascular system or cardiovascular disorders are understood to mean, for example, the following disorders: acute and chronic heart failure, arterial hypertension, coronary heart disease, stable and unstable angina pectoris, myocardial ischemia, myocardial infarction, shock, atherosclerosis, cardiac hypertrophy, cardiac fibrosis, atrial and ventricular arrhythmias, tachycardia, transitory and ischemic attacks, stroke, pre-eclampsia, inflammatory cardiovascular disorders, peripheral and cardiac vascular disorders, peripheral perfusion disorders, arterial pulmonary hypertension, spasms of the coronary arteries and peripheral arteries, thromboses, thromboembolic disorders, edema development, for example pulmonary edema, cerebral edema, renal edema or heart failure-related edema, and restenoses such as after thrombolysis treatments, percutaneous transluminal angioplasty (PTA), transluminal coronary angioplasty (PTCA), heart transplants and bypass operations, and micro- and macrovascular damage (vasculitis), reperfusion damage, arterial and venous thromboses, microalbuminuria, myocardial insufficiency, endothelial dysfunction, peripheral and cardiac vascular disorders, peripheral perfusion disorders, heart failure-related edema, elevated levels of fibrinogen and of low-density LDL and elevated concentrations of plasminogen activator/inhibitor 1 (PAI 1).

In the context of the present invention, the term "heart failure" also includes more specific or related types of disease, such as acutely decompensated heart failure, right heart failure, left heart failure, global failure, ischemic cardiomyopathy, dilated cardiomyopathy, congenital heart defects, heart valve defects, heart failure associated with heart valve defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, heart failure with preserved ejection fraction (HFpEF), diastolic heart failure and heart failure with reduced ejection fraction (HfrEF), systolic heart failure.

In the context of the present invention, the term atrial and ventricular arrhythmias also includes more specific or related types of disease, such as: atrial fibrillation, paroxysmal atrial fibrillation, intermittierent atrial fibrillation, permanent atrial fibrillation, atrial flutter, sinusoidal arrhythmia, sinusoidal tachycardia, passive heterotopia, active heterotopia, escape systoles, extrasystoles, impulse conduction disorders, sick sinus syndrome, hypersensitive carotid sinus, tachycardias, AV node reentry tachycardia, atriventricular reentry tachycardia, WPW syndrome (Wolff-Parkinson-White), Mahaim tachycardia, hidden accessory conduction pathway, permanent junctional reentry tachycardia, focal atrial tachycardia, junctional ectopic tachycardia, atrial reentry tachycardia, ventricular tachycardia, ventricular flutter, ventricular fibrillation, sudden cardiac death.

In the context of the present invention, the term coronary heart disease also encompasses more specific or related types of disease, such as: ischemic heart disease, stable angina pectoris, acute coronary syndrome, unstable angina pectoris, NSTEMI (non-ST elevation myocardial infarction), STEMI (ST elevation myocardial infarction), ischemic heart muscle damage, heart rhythm dysfunctions and myocardial infarction.

The compounds according to the invention are further suitable for the prophylaxis and/or treatment of polycystic kidney disease (PCKD) and of the syndrome of inappropriate ADH secretion (SIADH).

The compounds of the invention are also suitable for the treatment and/or prophylaxis of kidney disorders, in particular of acute and chronic renal insufficiency and acute and chronic renal failure.

In the context of the present invention, the term "acute renal insufficiency" encompasses acute manifestations of kidney disease, of kidney failure and/or renal insufficiency with and without the need for dialysis, and also underlying or related renal disorders such as renal hypoperfusion, intradialytic hypotension, volume deficiency (e.g. dehydration, blood loss), shock, acute glomerulonephritis, hemolytic-uremic syndrome (HUS), vascular catastrophe (arterial or venous thrombosis or embolism), cholesterol embolism, acute Bence-Jones kidney in the event of plasmacytoma, acute supravesicular or subvesicular efflux obstructions, immunological renal disorders such as kidney transplant rejection, immune complex-induced renal disorders, tubular dilatation, hyperphosphatemia and/or acute renal disorders which can be characterized by the need for dialysis, including in the case of partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematosus, renal artery thrombosis, renal vein thrombosis, analgesic nephropathy and renal-tubular acidosis, and x-ray contrast agent- and medicament-induced acute interstitial renal disorders.

In the context of the present invention, the term "chronic renal insufficiency" encompasses chronic manifestations of kidney disease, of kidney failure and/or renal insufficiency with and without the need for dialysis, and also underlying or related renal disorders such as renal hypoperfusion, intradialytic hypotension, obstructive uropathy, glomerulopathy, glomerular and tubular proteinuria, renal edema, hematuria, primary, secondary and chronic glomerulonephritis, membranous and membranoproliferative glomerulonephritis, Alport syndrome, glomerulosclerosis, tubulointerstitial disorders, nephropathic disorders such as primary and congenital kidney disease, renal inflammation, immunological renal disorders such as kidney transplant rejection, immune complex-induced renal disorders, diabetic and nondiabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, glomerular and arteriolar lesions, tubular dilatation, hyperphosphatemia and/or the need for dialysis, and also for renal cell carcinomas, after partial resections of the kidney, dehydration through forced diuresis, uncontrolled blood pressure increase with malignant hypertension, urinary tract obstruction and infection and amyloidosis and systemic disorders with glomerular factors, such as rheumatological-immunological systemic disorders, for example lupus erythematosus, and renal artery stenosis, renal artery thrombosis, renal vein thrombosis, analgesic nephropathy and renal-tubular acidosis. In addition, X-ray contrast agent- and medicament-induced chronic interstitial renal disorders, metabolic syndrome and dyslipidemia. The present invention also encompasses the use of the compounds according to the invention for treatment and/or prophylaxis of sequelae of renal insufficiency, for example pulmonary edema, heart failure, uremia, anemia, electrolyte disorders (for example hyperkalemia, hyponatremia) and disorders in bone and carbohydrate metabolism.

In addition, the compounds according to the invention are also suitable for treatment and/or prophylaxis of pulmonary arterial hypertension (PAH) and other forms of pulmonary hypertension (PH), of chronic obstructive pulmonary disease (COPD), of acute respiratory distress syndrome (ARDS), of acute lung injury (ALI), of alpha-1-antitrypsin deficiency (AATD), of pulmonary fibrosis, of pulmonary emphysema (for example pulmonary emphysema caused by cigarette smoke), of cystic fibrosis (CF), of acute coronary syndrome (ACS), heart muscle inflammations (myocarditis) and other autoimmune cardiac disorders (pericarditis, endocarditis, valvolitis, aortitis, cardiomyopathies), cardiogenic shock, aneurysms, sepsis (SIRS), multiple organ failure (MODS, MOF), inflammatory disorders of the kidney, chronic intestinal disorders (IBD, Crohn's Disease, UC), pancreatitis, peritonitis, rheumatoid disorders, inflammatory skin disorders and inflammatory eye disorders.

The compounds according to the invention can also be used for treatment and/or prophylaxis of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of Bronchiolitis obliterans, bronchiectasis, pneumonia, idiopathic interstitial pneumonia, farmer's lung and related diseases, of coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds described in the present invention are also active compounds for control of central nervous system disorders characterized by disturbances of the NO/cGMP system. In particular, they are suitable for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prevention of central nervous system disorders such as states of anxiety, tension and depression, bipolar disorder, CNS-related sexual dysfunctions and sleep disturbances, and for controlling pathological disturbances of the intake of food, stimulants and addictive substances.

Furthermore, the compounds according to the invention are also suitable for the treatment and/or prophylaxis of urological disorders such as: urine incontinence, in particular stress incontinence, urge incontinence, reflex incontinence and overflow incontinence, detrusor hyperactivity, neurogenic detrusor hyperactivity, idiopathic detrusor hyperactivity, benign prostate hyperplasia (BPH syndrome), lower urinary tract symptoms (LUTS).

The compounds according to the invention are furthermore suitable for the treatment and/or prevention of gastroenterological disorders such as esophagus disorders, emesis, achalasia, gastroesophageal reflux disease, stomach disorders such as gastritis, disorders of the intestine such as diarrhea, constipation, malassimilation syndrome, bile acid loss syndrome, Crohn's disease, ulcerative colitis, microscopic colitis and irritable bowel syndrome.

The compounds according to the invention are further suitable for the treatment and/or prevention of states of pain such as menstruation disorders, dysmenorrhea, endometriosis, premature birth, tocolysis.

Because of their profile of biochemical and pharmacological properties, the compounds according to the invention are also especially suitable for treatment and/or prevention of heart failure, coronary heart disease, atrial and ventricular arrhythmia, kidney failure and nephropathy.

The compounds of the invention can additionally be used for the treatment and/or prophylaxis of primary and secondary Raynaud's phenomenon, of microcirculation impairments, claudication, peripheral and autonomic neuropathies, diabetic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds of the invention are additionally suitable for treatment and/or prevention of ophthalmologic disorders, for example glaucoma, age-related macular degeneration (AMD), of dry (non-exudative) AMD, wet (exudative, neovascular) AMD, choroidal neovascularization (CNV), diabetic retinopathy, atrophic changes to the retinal pigment epithelium (RPE), hypertrophic changes to the retinal pigment epithelium, macular edema, diabetic macular edema, retinal vein occlusion, choroidal retinal vein occlusion, macular edema due to retinal vein occlusion, angiogenesis at the front of the eye, for example corneal angiogenesis, for example following keratitis, cornea transplant or keratoplasty, corneal angiogenesis due to hypoxia (as a result of extensive wearing of contact lenses), pterygium conjunctiva, subretinal edema and intraretinal edema. In addition, the compounds of the invention are suitable for treatment and/or prevention of elevated and high intraocular pressure as a result of traumatic hyphema, periorbital edema, postoperative viscoelastic retention or intraocular inflammation.

Moreover, the compounds according to the invention are suitable for the treatment and/or prophylaxis of hepatitis, neoplasms, osteoporosis, glaucoma and gastroparesis.

In addition, the compounds of the invention are also suitable for controlling cerebral blood flow and are effective agents for controlling migraine. They are also suitable for the prophylaxis and control of sequelae of cerebral infarct (Apoplexia cerebri) such as stroke, cerebral ischemias and craniocerebral trauma. The compounds of the invention can also be used for controlling pain, neuralgias and tinnitus.

The aforementioned well-characterized diseases in humans can also occur with comparable etiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The present invention further provides the compounds according to the invention for use in a method of treatment and/or prevention of disorders, especially of the aforementioned disorders.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders. Preferred examples of combination active ingredients suitable for this purpose include:

active hypotensive ingredients, by way of example and with preference from the group of calcium antagonists, angiotensin AII antagonists, ACE inhibitors, NEP inhibitors, vasopeptidase inhibitors, endothelin antagonists, renin inhibitors, alpha-receptor blockers, beta-receptor blockers, mineralocorticoid receptor antagonists, and rho kinase inhibitors and the diuretics;

antiarrhythmics, by way of example and with preference sodium channel blockers, beta receptor blockers, potassium channel blockers, calcium antagonists, If channel blockers, digitalis, parasympatholytics (vagolytics), sympathomimetics and other antiarrhythmics such as adenosine, adenosine receptor agonists and vernakalant;

compounds having a positive inotropic effect, for example cardiac glycosides (digoxin), beta-adrenergic and dopaminergic agonists such as isoprenaline, adrenaline, noradrenaline, dopamine or dobutamine;

vasopressin receptor antagonists, by way of example and with preference conivaptan, tolvaptan, lixivaptan, mozavaptan, satavaptan, SR-121463, RWJ 676070 or BAY 86-8050, and also the compounds described in WO 2010/105770, WO2011/104322 and WO 2016/071212;

natriuretic peptides, for example atrial natriuretic peptide (ANP), natriuretic peptide type B (BNP, nesiritide) natriuretic peptide type C (CNP) or urodilatin;

activators of cardial myosins, for example omecamtiv mecarbil (CK-1827452);

calcium sensitizers, for example levosimendan;

compounds which modulate the energy metabolism of the heart, by way of example and with preference etomoxir, dichloroacetate, ranolazine or trimetazidine, full or partial adenosine A1 receptor agonists such as GS□9667 (known beforehand as CVT□3619), capadenoson, neladenoson and BAY 1067197;

compounds which modulate the heart rate, for example ivabradine compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil, udenafil, desantafil, avanafil, mirodenafil, lodenafil or PF-00489791;

antithrombotic agents, by way of example and with preference from the group of the platelet aggregation inhibitors, the anticoagulants or the profibrinolytic substances;

bronchodilatory agents, by way of example and with preference from the group of the beta-adrenergic receptor agonists, such as especially albuterol, isoproterenol, metaproterenol, terbutalin, formoterol or salmeterol, or from the group of the anticholinergics, such as especially ipratropium bromide;

anti-inflammatory agents, by way of example and with preference from the group of the glucocorticoids, such as especially prednisone, prednisolone, methylprednisolone, triamcinolone, dexamethasone, beclomethasone, betamethasone, flunisolide, budesonide or fluticasone and also non-steroidal anti-inflammatory drugs (NSAIDs) such as, in particular, acetylsalicylic acid (aspirin), ibuprofen and naproxen, 5-aminosalicylic acid derivatives, leukotriene antagonists, TNF-alpha inhibitors and chemokine receptor antagonists such as CCR1, 2 and/or 5 inhibitors;

active compounds which modulate lipid metabolism, by way of example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-6 agonists, cholesterol absorption inhibitors, lipase inhibitors, polymeric bile acid adsorbents, bile acid reabsorption inhibitors and lipoprotein(a) antagonists.

compounds which inhibit the signal transduction cascade, by way of example and with preference from the group of the kinase inhibitors, especially from the group of the tyrosine kinase and/or serine/threonine kinase inhibitors;

compounds which inhibit the degradation and alteration of the extracellular matrix, by way of example and with preference inhibitors of the matrix metalloproteases (MMPs), especially inhibitors of chymase, stromelysin, collagenases, gelatinases and aggrecanases (in this context particularly of MMP-1, MMP-3, MMP-8, MMP-9, MMP-10, MMP-11 and MMP-13) and of metalloelastase (MMP-12) and neutrophile elastase (HNE), such as sivelestat or DX-890;

compounds which block the binding of serotonin to its receptor by way of example and with preference antagonists of the 5-HT$_{2b}$ receptor;

organic nitrates and NO donors, for example sodium nitroprusside, nitroglycerin, isosorbide mononitrate, isosorbide dinitrate, molsidomine or SIN-1, and inhaled NO;

NO-independent but heme.-dependent stimulators of soluble guanylate cyclase, such as in particular the compounds described in WO 00/06568, WO 00/06569, WO 02/42301, WO 03/095451, WO 2011/147809, WO 2012/004258, WO 2012/028647 and WO 2012/059549;

NO- and heme-independent activators of soluble guanylate cyclase, such as especially the compounds described in WO 01/19355, WO 01/19776, WO 01/19778, WO 01/19780, WO 02/070462 and WO 02/070510;

compounds which increase the synthesis of cGMP, for example sGC modulators such as, by way of example and with preference, riociguat, cinaciguat, vericiguat or BAY 1101042 prostacyclin analogs, by way of example and with preference iloprost, beraprost, treprostinil or epoprostenol;

compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

active compounds which modulate glucose metabolism, for example insulins, biguanides, thiazolidinediones, sulfonylureas, acarbose, DPP4 inhibitors, GLP-1 analogs or SGLT-1 inhibitors.

In a preferred embodiment of the invention, the compounds according to the invention are used in combination with a kinase inhibitor, by way of example and with preference bortezomib, canertinib, erlotinib, gefitinib, imatinib, lapatinib, lestaurtinib, lonafarnib, nintedanib, dasatinib, nilotinib, bosutinib, axitinib, telatinib, imatinib, brivanib, pazopanib, pegaptinib, pelitinib, semaxanib, sorafenib, regorafenib, sunitinib, tandutinib, tipifarnib, vatalanib, fasudil, lonidamine, leflunomide, BMS-3354825 or Y-27632.

In a preferred embodiment of the invention, the compounds according to the invention are used in combination with a serotonin receptor antagonist, by way of example and with preference PRX-08066.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds according to the invention are administered in combination with a thrombin inhibitor, by way of example and with preference dabigatran, ximelagatran, melagatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban, edoxaban (DU-176b), apixaban, otamixaban, fidexaban, razaxaban, fondaparinux, idraparinux, PMD-3112, YN-150, KFA-1982, EMD-503982, MCN-17, mLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, rho kinase inhibitors, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1 receptor blocker, by way of example and with preference prazosin.

In a preferred embodiment of the invention, the compounds of the invention are administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embursatan, irbesartan, olmesartan, eprosartan or azilsartan or a dual angiotensin AII antagonist/NEP inhibitor, for example and with preference Entresto (LCZ696, valsartan/sacubitril).

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan, avosentan, macitentan, atrasentan or sitaxsentan.

In a preferred embodiment of the invention, the compounds according to the invention are administered in combination with a TGFbeta antagonist, by way of example and with preference pirfenidone or fresolimumab.

In a preferred embodiment of the invention, the compounds according to the invention are administered in combination with a TNFalpha antagonist, by way of example and with preference adalimumab.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with HIF-PH inhibitors, by way of example and with preference molidustat or roxadustat.

In a preferred embodiment of the invention, the compounds of the invention are administered in combination with a mineralocorticoid receptor antagonist, by way of example and with preference spironolactone or eplerenone, finerenone.

In a preferred embodiment of the invention, the compounds according to the invention are administered in combination with a rho kinase inhibitor, by way of example and with preference fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic, by way of example and with preference furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-δ agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), anacetrapib, HT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds according to the invention are administered in combination with a PPAR-δ agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

In a preferred embodiment of the invention, the compounds according to the invention are administered in combination with sGC modulators, by way of example and with preference riociguat, cinaciguat, vericiguat or BAY 1101042.

In a preferred embodiment of the invention, the compounds according to the invention are administered in combination with an active ingredient which modulates glucose metabolism, by way of example and with preference insulin, a sulfonylurea, acarbose, DPP4 inhibitors, GLP-1 analogs or SGLT-1 inhibitor.

Particular preference is given to combinations of the compounds according to the invention with one or more further active ingredients selected from the group consisting of active hypotensive ingredients, active antiarrhythmic ingredients, vasopressin receptor antagonists, PDE 5 inhibitors, platelet aggregation inhibitors, sGC activators and sGC stimulators.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally) Administration forms suitable for parenteral administration include inter alia preparations for injection and infusion in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral, intravenous and intrapulmonary (inhalative) administration.

The compounds according to the invention can be converted to the administration forms mentioned. This can be accomplished in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavor and/or odor correctors.

In general, it has been found to be advantageous in the case of parenteral administration to administer amounts of about 0.001 to 1 mg/kg, preferably about 0.01 to 0.5 mg/kg body weight to achieve effective results. In the case of oral administration the dosage is about 0.01 to 100 mg/kg, preferably about 0.01 to 20 mg/kg and most preferably 0.1 to 10 mg/kg body weight.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

| Abbreviations and acronyms: | |
|---|---|
| GP | General Procedure |
| abs. | absolute |
| aq. | aqueous, aqueous solution |
| br. | broad (in NMR signal) |
| Ex. | Example |
| Bu | butyl |
| c | concentration |
| ca. | circa, about |
| cat. | catalytic |
| CDI | carbonyldiimidazole |
| CI | chemical ionization (in MS) |
| d | doublet (in NMR) |
| d | day(s) |
| DCM | dichloromethane |
| dd | doublet of doublets (in NMR) |
| de | diastereomeric excess |
| DEA | diethylamine |
| dist. | distilled |

-continued

| Abbreviations and acronyms: | |
|---|---|
| DIPEA | N,N-diisopropylethylamine |
| DMAP | 4-N,N-dimethylaminopyridine |
| DMF | N,N-dimethylformamide |
| DMSO | dimethyl sulfoxide |
| dt | doublet of triplets (in NMR) |
| ee | enantiomeric excess |
| EI | electron impact ionization (in MS) |
| ent | enantiomerically pure, enantiomer |
| eq. | equivalent(s) |
| ESI | electrospray ionization (in MS) |
| Et | ethyl |
| GC | gas chromatography |
| GC/MS | gas chromatography-coupled mass spectrometry |
| h | hour(s) |
| HATU | O-(7-azabenzotriazol-1-yl)-N,N,N',N'-tetramethyluronium hexafluorophosphate |
| HPLC | high-pressure, high-performance liquid chromatography |
| conc. | concentrated (in the case of a solution) |
| LC | liquid chromatography |
| LC/MS | liquid chromatography-coupled mass spectrometry |
| lit. | literature (reference) |
| m | multiplet (in NMR) |
| M | molar (in solution) |
| Me | methyl |
| min | minute(s) |
| MS | mass spectrometry |
| NMR | nuclear magnetic resonance spectrometry |
| q (or quart) | quartet (in NMR) |
| qd | quartet of doublets (in NMR) |
| quant. | quantitative (in chemical yield) |
| quintt | quintet (in NMR) |
| rac | racemic, racemate |
| RP | reverse phase (in HPLC) |
| RT | room temperature |
| Rt | retention time (in HPLC, LC/MS) |
| s | singlet (in NMR) |
| sept | septet (in NMR) |
| SFC | supercritical liquid chromatography |
| t | triplet (in NMR) |
| tBu | tert-butyl |
| td | triplet of doublets (in NMR) |
| THF | tetrahydrofuran |
| TFA | trifluoroacetic acid |
| UV | ultraviolet spectrometry |
| cf. | see |
| v/v | volume to volume ratio (of a solution) |
| xantphos | 9,9-dimethyl-4,5-bis(diphenylphosphino)xanthene |
| tog. | together |

HPLC and LC/MS Methods

Method 1:
Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2:
MS instrument type: Thermo Scientific FT-MS; instrument type UHPLC+: Thermo Scientific UltiMate 3000; column: Waters, HSST3, 2.1×75 mm, C18 1.8 µm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method 3:
Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 4:

Instrument: Thermo DFS, Trace GC Ultra; column: Restek RTX-35, 15 m×200 μm×0.33 μm; constant helium flow rate: 1.20 ml/min; oven: 60° C.; inlet: 220° C.; gradient: 60° C., 30° C/min→300° C. (maintain for 3.33 min).

Method 5:

MS instrument: Waters (Micromass) Quattro Micro; instrument Waters UPLC Acquity; column: Waters BEH C18 1.7μ 50×2.1 mm; mobile phase A: 1 l of water+0.01 mol of ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm.

Further Details

The percentages in the example and test descriptions which follow are, unless indicated otherwise, percentages by weight; parts are parts by weight. Solvent ratios, dilution ratios and concentration data for liquid/liquid solutions are based in each case on volume.

In the case of purifications of compounds of the invention by preparative HPLC by the described methods in which the mobile phases contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Purity figures are generally based on corresponding peak integrations in the LC/MS chromatogram, but may additionally also have been determined with the aid of the 1H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of 1H NMR signals that follow have in some cases been taken directly from the suggestions of the ACD SpecManager (ACD/Labs Release 12.00, Product version 12.5) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the center of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

Melting points and melting ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

General Procedures

GP1

N,N-Diisopropylethylamine (1.4-1.5 eq., or 2.4-3.0 eq. when the amine was used in hydrochloride form) and HATU (1.0-1.65 eq.) were added to a solution of the corresponding carboxylic acid (1 eq.) in DMF (0.08-0.12M), and the mixture was stirred at RT for 30 min. Subsequently, the appropriate amine (1.04-1.5 eq.) was added and the mixture was stirred at room temperature for a further 0.15-2 h. The reaction was then terminated by the addition of water and 1 M aqueous hydrochloric acid. The precipitate was filtered off, taken up in DCM, dried over magnesium sulfate and filtered, and the solvent was removed under reduced pressure. Alternatively, the acidification was followed by extraction with ethyl acetate, drying of the combined organic phases over magnesium sulfate or sodium sulfate, filtration and removal of the solvent under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient). Alternatively, the reaction mixture was diluted with a little acetonitrile, water and formic acid and the crude solution was purified by RP-HPLC (water/acetonitrile gradient).

GP2

Potassium carbonate or cesium carbonate (1.5-2.5 eq.) was baked in a reaction vessel under reduced pressure. The vessel was cooled to RT and flooded with argon. Palladium acetate (0.1-0.36 eq.), 9,9-dimethyl-4,5-bis(diphenylphosphino)xanthene (Xantphos, 0.18-0.36 eq.) and dioxane (0.04-0.12M) were added, and the suspension was degassed in an argon stream at room temperature for 10 min. Subsequently, the appropriate amide (1.0-10 eq.) and the appropriate 7-chloro-4-oxo-1,4-dihydro-1,8-naphthyridine (1.0 eq.) were added. The mixture was stirred at 80-110° C. for 1 h (or until conversion was complete by analytical HPLC or thin-layer chromatography with appropriate mobile phase mixtures). The mixture was cooled to RT and all volatile components were removed under reduced pressure, or alternatively the reaction mixture was poured into water, the pH was adjusted to pH 1 with 1M aqueous hydrochloric acid, the mixture was extracted with ethyl acetate, the combined organic phases were washed with saturated aqueous sodium chloride solution, dried over magnesium sulfate and filtered, and the solvent was removed under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient). Alternatively, the reaction mixture was diluted with a little acetonitrile, water and formic acid and the crude solution was purified by RP-HPLC (water/acetonitrile gradient).

GP3

To a solution of the appropriate 7-chloro-4-oxo-1,4-dihydro-1,8-naphthyridine in DMF (0.10-0.22 M) were successively added the appropriate amine (1.2 eq.) and DIPEA (1.5-3.5 eq.). The reaction solution was stirred at RT overnight. The crude product was subsequently, after aqueous work-up and extraction with the appropriate organic solvent, purified either by normal-phase chromatography (mobile phase: cyclohexane/ethyl acetate mixtures or dichloromethane/methanol mixtures) or by preparative RP-HPLC (water/acetonitrile gradient). Alternatively, the reaction mixture was diluted with a little acetonitrile, water and formic acid and the crude solution was purified by RP-HPLC (water/acetonitrile gradient).

STARTING COMPOUNDS AND INTERMEDIATES

Example 1A

Ethyl 3-(1-{[(benzyloxy)carbonyl]amino}cyclopropyl)-3-oxopropanoate

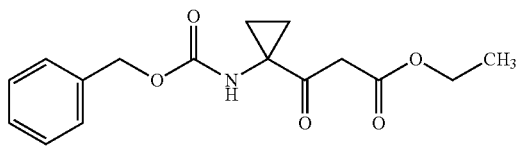 [SMILES: CCOC(=O)CC(=O)C1(NC(=O)OCc2ccccc2)CC1]

5.48 g (33.8 mmol) of carbonyldiimidazole (CDI) were added to a solution of 10.0 g (42.5 mmol) of 1-{[(benzyloxy)carbonyl]amino}cyclopropanecarboxylic acid in 316 ml of THF, and the mixture was stirred at RT for 2.5 h. Subsequently, while cooling with an ice bath, 5.79 g (34.0 mmol) of potassium 3-ethoxy-3-oxopropanoate and 2.93 g (30.8 mmol) of magnesium chloride were added. On completion of addition, stirring was continued at 50° C. overnight. The solvent was removed under reduced pressure, the residue was taken up in ethyl acetate and saturated aqueous ammonium chloride solution, and the phases were separated. The organic phase was washed with saturated aqueous sodium chloride solution, dried over magnesium sulfate and filtered, and the solvent was removed under reduced pressure. The residue was purified by normal phase chromatography (ethyl acetate/cyclohexane gradient), giving 7.38 g (57% of theory; purity 100%) of the title compound.

LC-MS (Methode 1): Rt=0.86 min; MS (ESIpos): m/z=306 [M+H]+.

$^1$H-NMR (400 MHz, DMSO-d6): δ [ppm]=8.16 (s, 1H), 7.31-7.40 (m, 5H), 5.06 (s, 2H), 4.07 (q, 2H), 3.60 (s, 2H), 1.36-1.47 (m, 2H), 1.12-1.20 (m, 5H).

Example 1B

Ethyl 3-(1-{[(benzyloxy)carbonyl]amino}cyclopropyl)-2,2-dimethyl-3-oxopropanoate

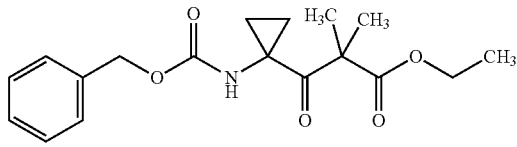 [SMILES: CCOC(=O)C(C)(C)C(=O)C1(NC(=O)OCc2ccccc2)CC1]

The total amount was divided into two microwave vials. A suspension of 1.50 g (4.91 mmol) of ethyl 3-(1-{[(benzyloxy)carbonyl]amino}cyclopropyl)-3-oxopropanoate, 917 µl (14.7 mmol) of iodomethane and 1.36 g (9.83 mmol) of potassium carbonate in 21 ml of acetone was reacted in a microwave at 60° C. for 16 h. A further 459 µl (7.37 mmol) of iodomethane were then added, and the mixture was reacted in the microwave at 60° C. for 1 h and at 120° C. for 3 h. The reaction mixture was poured into water and extracted three times with ethyl acetate. The combined organic phases were washed with saturated aqueous sodium chloride solution, dried over sodium sulfate and filtered, and the solvent was removed under reduced pressure. The residue was dissolved in a little acetonitrile, filtered through a Millipore filter and separated in five runs by preparative HPLC (column: Chromatorex C18, 10 µm, 125*40 mm, solvent: acetonitrile, water, 0.1% formic acid). This gave 471 mg (27% of theory, purity 94%) of the title compound.

LC-MS (Methode 2): Rt=1.91 min; MS (ESIpos): m/z=334 [M+H]+.

$^1$H-NMR (500 MHz, DMSO-d6): δ [ppm]=7.89 (s, 1H), 7.29-7.42 (m, 5H), 5.00 (s, 2H), 3.99 (q, 2H), 1.37 (q, 2H), 1.25 (s, 6H), 1.08-1.15 (m, 5H).

Example 1C

Ethyl 3-(1-{[(benzyloxy)carbonyl]amino}cyclopropyl)-3-hydroxypivaloate (racemate)

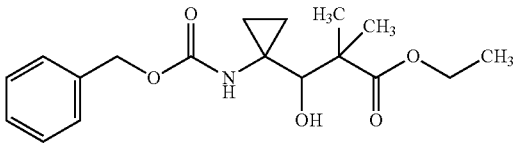 [SMILES: CCOC(=O)C(C)(C)C(O)C1(NC(=O)OCc2ccccc2)CC1]

At −30° C., 73.9 mg (1.95 mmol) of sodium borohydride were added to a solution of 465 mg (1.40 mmol) of ethyl 3-(1-{[(benzyloxy)carbonyl]amino}cyclopropyl)-2,2-dimethyl-3-oxopropanoate in 7.3 ml of methanol. The mixture was stirred at −30° C. for 2 h and then warmed to RT and stirred for a further hour. The reaction solution was poured into saturated aqueous ammonium chloride solution and extracted three times with ethyl acetate. The combined organic phases were washed with saturated aqueous sodium chloride solution, dried over sodium sulfate and filtered, and the solvent was removed under reduced pressure. The residue was taken up in a little acetonitrile, filtered through a Millipore filter and purified in two runs by preparative HPLC (column: Chromatorex C18, 10 µm, 125*40 mm, solvent: acetonitrile, water, 0.1% formic acid). This gave 330 mg (71% of theory, purity 100%) of the title compound.

LC-MS (Methode 1): Rt=0.94 min; MS (ESIpos): m/z=336 [M+H]+.

$^1$H-NMR (400 MHz, DMSO-d6): δ [ppm]=7.25-7.45 (m, 6H), 4.84-5.06 (m, 3H), 3.80-4.06 (m, 3H), 1.05-1.16 (m, 9H), 0.78-0.87 (m, 2H), 0.54-0.62 (m, 1H), 0.27-0.41 (m, 1H).

Example 1D

7-Hydroxy-6,6-dimethyl-4-azaspiro[2.4]heptan-5-one (racemate)

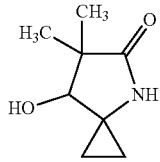

To a solution of 325 mg (969 μmol) of ethyl 3-(1-{[(benzyloxy)carbonyl]amino}cyclopropyl)-3-hydroxypivaloate in 4.9 ml of methanol were added 24.3 mg of palladium on charcoal (10%), and hydrogenation was effected at standard pressure and room temperature for 6 h. The reaction mixture was then filtered through a Millipore filter and the solvent was removed under reduced pressure. This gave 150 mg (99% of theory, purity 95%) of the title compound.

$^1$H-NMR (400 MHz, DMSO-d6): δ [ppm]=7.53 (br s, 1H), 5.03 (d, 1H), 3.66 (d, 1H), 1.04 (s, 3H), 0.94 (s, 3H), 0.84-0.91 (m, 1H), 0.56-0.69 (m, 2H), 0.43-0.51 (m, 1H).

Example 2A

Ethyl 4-{[(benzyloxy)carbonyl]amino}-3-oxobutanoate

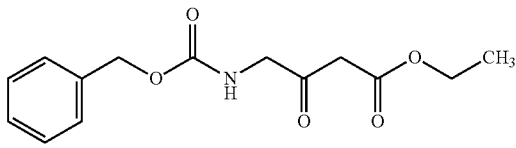 [SMILES: CCOC(=O)CC(=O)CNC(=O)OCc1ccccc1]

To a solution of 15.0 g (71.7 mmol) of N-[(benzyloxy)carbonyl]glycine in 534 ml of THF were added 9.24 g (57.0 mmol) of carbonyldiimidazole (CDI), and the mixture was stirred at RT for 2.5 h. Subsequently, while cooling with an ice bath, 9.76 g (57.4 mmol) of potassium 3-ethoxy-3-oxopropanoate and 4.95 g (52.0 mmol) of magnesium chloride were added. On completion of addition, stirring was continued at 50° C. for a further 48 h. The solvent was removed under reduced pressure, the residue was taken up with ethyl acetate and saturated aqueous ammonium chloride solution, and the phases were separated. The organic phase was washed with saturated aqueous sodium chloride solution, dried over sodium sulfate and filtered, and the solvent was removed under reduced pressure. The residue was purified by normal phase chromatography (ethyl acetate-cyclohexane gradient), giving 12.7 g (60% of theory; 95% purity) of the title compound.

LC-MS (Methode 1): Rt=0.83 min; MS (ESIneg): m/z=278 [M–H]–.

$^1$H-NMR (400 MHz, DMSO-d6): δ [ppm]=7.56 (br t, 1H), 7.25-7.41 (m, 5H), 5.04 (s, 2H), 4.09 (q, 2H), 3.97 (d, 2H), 3.60 (s, 2H), 1.19 (t, 3H).

Example 2B

Ethyl 4-{[(benzyloxy)carbonyl]amino}-2-methyl-3-oxobutanoate (racemate)

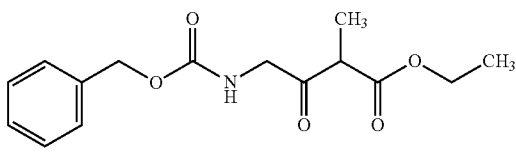 [SMILES: CCOC(=O)C(C)C(=O)CNC(=O)OCc1ccccc1]

A suspension of 1.00 g (3.58 mmol) of ethyl 4-{[(benzyloxy)carbonyl]amino}-3-oxobutanoate, 669 μl (10.7 mmol) of iodomethane and 990 mg (7.16 mmol) of potassium carbonate in 15 ml of acetone was reacted in a microwave at 50° C. for 2 h. Microwave irradiation was continued, while monitoring the reaction, at 45° C. for a further 2 h. The reaction mixture was poured into water and extracted three times with ethyl acetate. The combined organic phases were washed with saturated aqueous sodium chloride solution, dried over sodium sulfate and filtered, and the solvent was removed under reduced pressure. The residue was dissolved in a little acetonitrile, filtered through a Millipore filter and separated in two runs by preparative HPLC (column: Chromatorex C18, 10 μm, 125*40 mm, solvent: acetonitrile, water, 0.1% formic acid). This gave 536 mg (51% of theory, purity 100%) of the title compound.

LC-MS (Methode 1): Rt=0.87 min; MS (ESIneg): m/z=292 [M–H]–.

$^1$H-NMR (400 MHz, DMSO-d6): δ [ppm]=7.57 (br t, 1H), 7.24-7.40 (m, 5H), 5.04 (s, 2H), 4.09 (q, 2H), 4.03 (d, 2H), 3.80 (q, 1H), 1.22-1.09 (m, 6H).

Example 2C

Ethyl 4-{[(benzyloxy)carbonyl]amino}-3-hydroxy-2-methylbutanoate (diastereomer mixture)

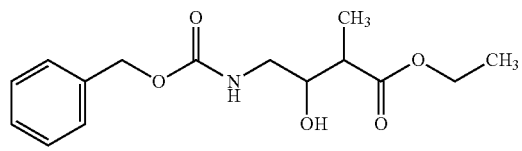 [SMILES: CCOC(=O)C(C)C(O)CNC(=O)OCc1ccccc1]

To a solution of 533 mg (1.82 mmol) of ethyl 4-{[(benzyloxy)carbonyl]amino}-2-methyl-3-oxobutanoate in 9.2 ml of methanol were added, at –78° C., 96.2 mg (2.54 mmol) of sodium borohydride. The mixture was warmed gradually to –15° C. while monitoring the reaction. At –15° C., the reaction was ended by adding saturated aqueous ammonium chloride solution. The mixture was extracted three times with ethyl acetate. The combined organic phases were washed with saturated aqueous sodium chloride solution, dried over sodium sulfate and filtered, and the solvent was removed under reduced pressure. The residue was taken up in a little acetonitrile and purified in two runs by preparative HPLC (column: Chromatorex C18, 10 μm, 125*40 mm, solvent: acetonitrile, water, 0.1% formic acid). This gave 398 mg (74% of theory, purity 100%) of the title compound.

LC-MS (Methode 1): Rt=0.80 min; MS (ESIpos): m/z=296 [M+H]+.

$^1$H-NMR (400 MHz, DMSO-d6): δ [ppm]=7.26-7.45 (m, 5H), 7.20-7.25 (m, 0.3H), 7.11 (br t, 0.7H), 5.01 (s, 2H), 4.90-4.97 (m, 1H), 3.98-4.08 (m, 2H), 3.81-3.88 (m, 0.3H), 3.63-3.71 (m, 0.7H), 3.11-3.20 (m, 0.7H), 2.93-3.07 (m, 1.3H), 2.40-2.49 (m, 1H), 1.17 (t, 3H), 1.00-1.05 (m, 3H).

Example 2D

4-Hydroxy-3-methylpyrrolidin-2-one (diastereomer mixture)

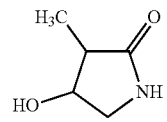

To a solution of 397 mg (1.34 mmol) of ethyl 4-{[(benzyloxy)carbonyl]amino}-3-hydroxy-2-methylbutanoate in 7.2 ml of methanol were added 40 mg of palladium on charcoal (10%), and hydrogenation was effected at standard pressure and room temperature for 6 h. The reaction mixture was then filtered through a Millipore filter and the solvent was removed under reduced pressure. 211 mg (quantitative) of the title compound were obtained, which were used without further purification in the next step.

Example 3A

Ethyl 2-dibenzylaminopropanoate (racemate)

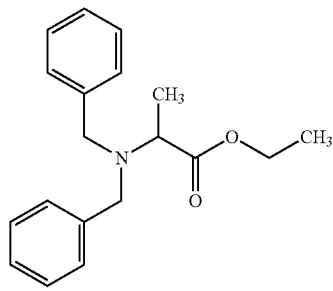 [SMILES: CCOC(=O)C(C)N(Cc1ccccc1)Cc1ccccc1]

14.4 g (72.9 mmol) of dibenzylamine were added to a solution of 12.0 g (66.3 mmol) of ethyl 2-bromopropanoate in 17.5 ml of ethanol, and the mixture was heated under reflux overnight. Subsequently, the solvent was removed under reduced pressure, and 1M aqueous sodium hydroxide solution was added to the residue. The mixture was extracted three times with dichloromethane and the combined organic phases were washed with saturated aqueous sodium chloride solution. The organic phases were dried over sodium sulfate and filtered and the solvent was removed under reduced pressure. The residue was purified by normal phase chromatography (ethyl acetate/cyclohexane gradient). This gave 10 g (50% of theory, 97% purity) of the title compound.

LC-MS (Methode 1): Rt=1.28 min; MS (ESIpos): m/z=298 [M+H]+.

$^1$H-NMR (400 MHz, DMSO-d6): δ [ppm]=7.20-7.37 (m, 10H), 4.06-4.20 (m, 2H), 3.74 (d, 2H), 3.58 (d, 2H), 3.32-3.40 (m, 1H), 1.22-1.28 (m, 6H).

Example 3B

Ethyl 4-(dibenzylamino)-3-oxopentanoate (racemate)

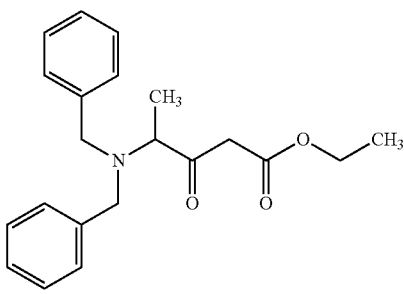 [SMILES: CCOC(=O)CC(=O)C(C)N(Cc1ccccc1)Cc1ccccc1]

A solution of 168 ml (168 mmol, 1M in THF) of bis(trimethylsilyl)lithium amide, diluted with 75 ml of THF, was cooled to −78° C., and 6.91 ml (70.6 mmol) of ethyl acetate were added. The mixture was stirred at −78° C. for a further 30 min. A solution of 10.0 g (33.6 mmol) of ethyl 2-dibenzylaminopropanoate in 37 ml of THF was then slowly added dropwise. The mixture was stirred at −78° C. for 2 h and at 0° C. for 1 h. The reaction was ended by adding saturated aqueous ammonium chloride solution. The mixture was extracted three times with ethyl acetate. The combined organic phases were washed with saturated aqueous sodium chloride solution, dried over sodium sulfate and filtered, and the solvent was removed under reduced pressure. The residue was purified by normal phase chromatography (ethyl acetate/cyclohexane gradient). This gave 9.89 g (87% of theory, purity 100%) of the title compound.

LC-MS (Methode 2): Rt=2.42 min; MS (ESIpos): m/z=340 [M+H]+.

$^1$H-NMR (400 MHz, DMSO-d6): δ [ppm]=7.24-7.40 (m, 10H), 3.99 (q, 2H), 3.68-3.77 (m, 1H), 3.53-3.64 (m, 3H), 3.37-3.49 (m, 3H), 1.07-1.13 (m, 6H).

Example 3C

Ethyl 1-[2-(dibenzylamino)propanoyl]cyclopropanecarboxylate (racemate)

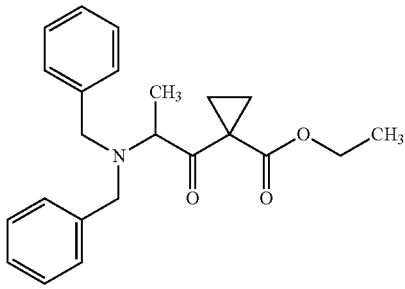 [SMILES: CCOC(=O)C1(C(=O)C(C)N(Cc2ccccc2)Cc2ccccc2)CC1]

A suspension of 2.00 g (5.89 mmol) of ethyl 4-(dibenzylamino)-3-oxopentanoate, 1.12 ml (12.9 mmol) of 1,2-dibromoethane and 1.63 g (11.8 mmol) of potassium carbonate in 6 ml of acetone was heated at reflux overnight. A further 0.56 ml (1.1 eq.) of 1,2-dibromoethane and 814 mg of potassium carbonate were then added and the mixture was heated under reflux for 48 h. The reaction mixture was poured into water and extracted three times with ethyl acetate. The combined organic phases were washed with saturated aqueous sodium chloride solution, dried over sodium sulfate and filtered, and the solvent was removed under reduced pressure. The residue was taken up in a little acetonitrile, filtered through a Millipore filter and purified in five runs by preparative HPLC (column: Chromatorex C18, 10 μm, 125*40 mm, solvent: acetonitrile, water, 0.1% formic acid). This gave 926 mg (41% of theory, purity 96%) of the title compound.

LC-MS (Methode 1): Rt=1.29 min; MS (ESIpos): m/z=366 [M+H]+.

$^1$H-NMR (400 MHz, DMSO-d6): δ [ppm]=7.22-7.36 (m, 10H), 4.24 (q, 1H), 3.92 (dq, 1H), 3.71 (dq, 1H), 3.51 (s, 4H), 1.50 (qd, 2H), 1.07-1.17 (m, 5H), 0.95 (t, 3H).

Example 3D

Ethyl 1-[2-(dibenzylamino)-1-hydroxypropyl]cyclopropanecarboxylate (diastereomer mixture)

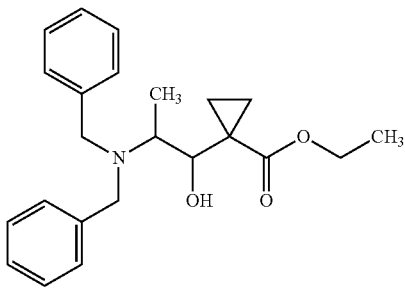 [SMILES: CCOC(=O)C1(C(O)C(C)N(Cc2ccccc2)Cc2ccccc2)CC1]

At −78° C., 134 mg (3.54 mmol) of sodium borohydride were added to a solution of 925 mg (2.53 mmol) of ethyl 1-[2-(dibenzylamino)propanoyl]cyclopropanecarboxylate in 13 ml of methanol. The mixture was warmed gradually to −15° C. while monitoring the reaction. At −15° C., the reaction was ended by adding saturated aqueous ammonium chloride solution. The mixture was extracted three times with ethyl acetate. The combined organic phases were washed with saturated aqueous sodium chloride solution, dried over sodium sulfate and filtered, and the solvent was removed under reduced pressure. The residue was taken up in a little acetonitrile and purified in three runs by preparative HPLC (column: Chromatorex C18, 10 μm, 125*40 mm, solvent: acetonitrile, water, 0.1% formic acid). This gave 628 mg (66% of theory, purity 98%) of the title compound.

LC-MS (Methode 1): Rt=0.70 min; MS (ESIpos): m/z=368 [M+H]+.

$^1$H-NMR (400 MHz, DMSO-d6): δ [ppm]=7.17-7.38 (m, 10H), 4.29 (d, 1H), 3.76-3.89 (m, 4H), 3.54 (br dd, 1H), 3.40 (d, 2H), 3.09 (quintt, 1H), 1.06-1.12 (m, 1H), 0.91-1.03 (m, 7H), 0.80-0.88 (m, 1H), 0.65-0.72 (m, 1H).

Example 3E

7-Hydroxy-6-methyl-5-azaspiro[2.4]heptan-4-one (diastereomer mixture)

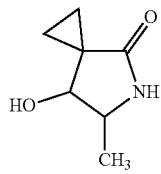

63.5 mg of palladium on carbon (10%) were added to a solution of 626 mg (1.70 mmol) of ethyl 1-[2-(dibenzylamino)-1-hydroxypropyl]cyclopropanecarboxylate in 12.7 ml of methanol, and the mixture was hydrogenated at standard pressure and room temperature for 6 h. The reaction mixture was then filtered through a Millipore filter and the solvent was removed under reduced pressure. This gave 243 mg (96% of theory, purity 95%) of the title compound.

LC-MS (Methode 5): Rt=0.49 min; MS (ESIpos): m/z=142 [M+H]+.

$^1$H-NMR (400 MHz, DMSO-d6): δ [ppm]=7.58 (br s, 1H), 4.86 (d, 1H), 3.91 (t, 1H), 3.69 (quintt, 1H), 1.07 (d, 3H), 0.86-0.93 (m, 1H), 0.67-0.79 (m, 3H).

Example 4A

Ethyl 7-chloro-1-(3,5-difluoropyridin-2-yl)-4-oxo-1,4-dihydro-1,8-naphthyridine-3-carboxylate

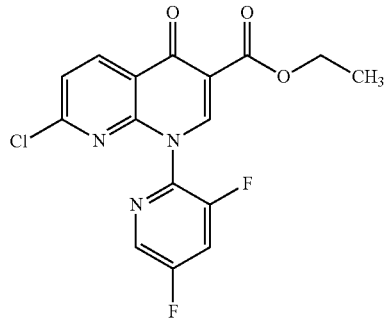

167 ml (961 mmol) of DIPEA were added to a solution of 43.7 g (137 mmol) of ethyl 2-[(2,6-dichloropyridin-3-yl)carbonyl]-3-ethoxyacrylate (CAS 157373-27-8) and 25.0 g (192 mmol) of 3,5-difluoropyridin-2-amine in 216 ml of DCM, and the mixture was stirred at RT for 4 h. 19.0 g (137 mmol) of potassium carbonate were then added, and the mixture was heated under reflux for 2 d. The mixture was diluted with DCM and washed three times with 1 M aqueous hydrochloric acid. The organic phase was dried over sodium sulfate and filtered, and the solvent was removed under reduced pressure. The mixture was diluted with ether and the precipitate was filtered off with suction. The procedure was repeated with the mother liquor and the solid obtained was combined with the main fraction. This gave 26.6 g (53% of theory, purity 100%) of the title compound.

LC-MS (Methode 2): Rt=1.67 min; MS (ESIpos): m/z=366 [M+H]+.

$^1$H-NMR (400 MHz, DMSO-d6): δ [ppm]=8.89 (s, 1H), 8.66 (d, 1H), 8.62 (d, 1H), 8.39 (ddd, 1H), 7.68 (d, 1H), 4.26 (q, 2H), 1.28 (t, 3H).

Example 4B

7-Chloro-1-(3,5-difluoropyridin-2-yl)-4-oxo-1,4-dihydro-1,8-naphthyridine-3-carboxylic acid

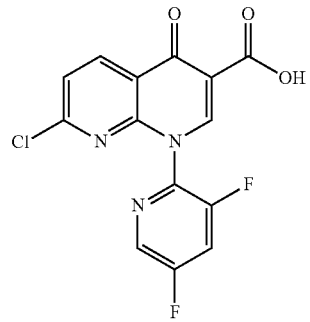 [SMILES: O=C(O)c1cn(-c2ncc(F)cc2F)c2nc(Cl)ccc2c1=O]

26.6 g (72.9 mmol) of ethyl 7-chloro-1-(3,5-difluoropyridin-2-yl)-4-oxo-1,4-dihydro-1,8-naphthyridine-3-carboxylate were initially charged in 218 ml of water, 218 ml of 36 percent strength aqueous hydrochloric acid and 218 ml of THF were added and the mixture was stirred at 120° C. for 3 h. The reaction mixture was cooled to RT and 1450 ml of water were added. The precipitate was filtered off with suction, washed with water and dried under high vacuum. This gave 24.3 g (97% of theory, 99% purity) of the title compound.

LC-MS (Methode 2): Rt=1.61 min; MS (ESIpos): m/z=338 [M+H]+.

$^1$H-NMR (400 MHz, DMSO-d6): δ [ppm]=13.86 (s, 1H), 9.18 (s, 1H), 8.78 (d, 1H), 8.67 (d, 1H), 8.42 (ddd, 1H), 7.82 (d, 1H).

Example 4C

7-Chloro-1-(3,5-difluoropyridin-2-yl)-4-oxo-N-[(2R)-1,1,1-trifluorobutan-2-yl]-1,4-dihydro-1,8-naphthyridine-3-carboxamide

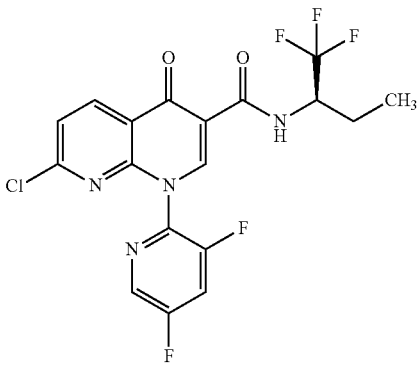

According to General Procedure 1, 200 mg (592 µmol) of 7-chloro-1-(3,5-difluoropyridin-2-yl)-4-oxo-1,4-dihydro-1,8-naphthyridine-3-carboxylic acid (Example 4B) were reacted with 145 mg (888 µmol) of (2R)-1,1,1-trifluorobutan-2-amine hydrochloride in the presence of 270 mg (711 µmol) of HATU and 413 µl (2.40 mmol) of DIPEA in 3 ml of DMF. The mixture was stirred for another 10 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 197 mg (74% of theory, purity 100%) of the title compound.

LC-MS (Methode 1): Rt=1.15 min; MS (ESIpos): m/z=447 [M+H]+.

$^1$H-NMR (400 MHz, DMSO-d6): δ [ppm]=9.89 (d, 1H), 9.10 (s, 1H), 8.75 (d, 1H), 8.67 (d, 1H), 8.40 (ddd, 1H), 7.78 (d, 1H), 4.71-4.85 (m, 1H), 1.83-1.96 (m, 1H), 1.60-1.74 (m, 1H), 0.98 (t, 3H).

Example 5A

7-Chloro-1-(3,5-difluoropyridin-2-yl)-4-oxo-N-[(2S)-1,1,1-trifluorobutan-2-yl]-1,4-dihydro-1,8-naphthyridine-3-carboxamide

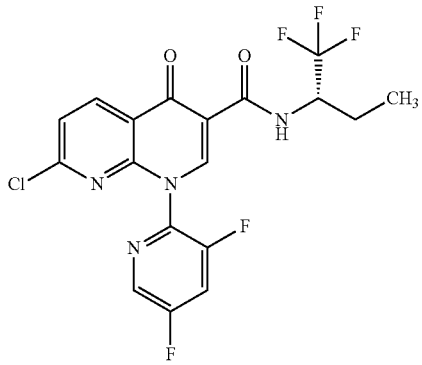 [SMILES: CC[C@H](NC(=O)c1cn(-c2ncc(F)cc2F)c2nc(Cl)ccc2c1=O)C(F)(F)F]

According to General Procedure 1, 400 mg (1.19 mmol) of 7-chloro-1-(3,5-difluoropyridin-2-yl)-4-oxo-1,4-dihydro-1,8-naphthyridine-3-carboxylic acid (Example 4B) were reacted with 290 mg (1.78 mmol) of (2S)-1,1,1-trifluorobutan-2-amine in the presence of 540 mg (1.42 µmol) of HATU and 0.83 ml (4.7 mmol) of DIPEA in 6 ml of DMF. The mixture was then diluted with 20 ml of water and 30 ml of ethyl acetate. The phases were separated and the aqueous phase was extracted three times with 20 ml of ethyl acetate. The combined organic phases were washed with 20 ml of 1M aqueous hydrochloric acid/saturated aqueous sodium chloride solution (1:1) and three times with 15 ml of saturated aqueous sodium chloride solution. The organic phases were dried over sodium sulfate and filtered and the solvent was removed under reduced pressure. The crude product was dissolved in a little acetonitrile and purified in two runs by preparative HPLC (column: Chromatorex C18, 10 µm, 125*40 mm, solvent: acetonitrile, water, 0.1% formic acid), giving 367 mg (69% of theory, purity 100%) of the title compound.

LC-MS (Methode 2): Rt=2.19 min; MS (ESIpos): m/z=447 [M+H]+.

$^1$H-NMR (400 MHz, DMSO-d6): δ [ppm]=9.89 (d, 1H), 9.10 (s, 1H), 8.75 (d, 1H), 8.67 (d, 1H), 8.40 (ddd, 1H), 7.78 (d, 1H), 4.72-4.84 (m, 1H), 1.84-1.95 (m, 1H), 1.62-1.73 (m, 1H), 0.98 (br t, 3H).

Example 6A

7-Chloro-1-(3,5-difluoropyridin-2-yl)-4-oxo-N-[(2S)-1,1,1-trifluoropropan-2-yl]-1,4-dihydro-1,8-naphthyridine-3-carboxamide

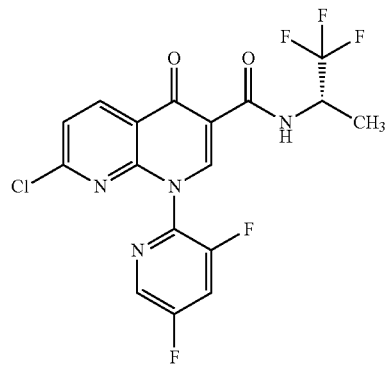 [SMILES: C[C@H](NC(=O)c1cn(-c2ncc(F)cc2F)c2nc(Cl)ccc2c1=O)C(F)(F)F]

According to General Procedure 1, 200 mg (592 µmol) of 7-chloro-1-(3,5-difluoropyridin-2-yl)-4-oxo-1,4-dihydro-1,8-naphthyridine-3-carboxylic acid (Example 4B) were reacted with 133 mg (888 µmol) of (2S)-1,1,1-trifluoropropan-2-amine hydrochloride in the presence of 270 mg (711 µmol) of HATU and 0.41 ml (2.4 mmol) of DIPEA in 3 ml of DMF. The mixture was stirred for another 10 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 180 mg (70% of theory, purity 100%) of the title compound.

LC-MS (Methode 1): Rt=1.15 min; MS (ESIpos): m/z=433 [M+H]+.

$^1$H-NMR (500 MHz, DMSO-d6): δ [ppm]=9.94 (d, 1H), 9.10 (s, 1H), 8.74 (d, 1H), 8.67 (d, 1H), 8.40 (ddd, 1H), 7.78 (d, 1H), 4.89-4.98 (m, 1H), 1.40 (d, 3H).

Example 7A

7-Chloro-N-[1-cyclopropyl-2,2,2-trifluoroethyl]-1-(3,5-difluoropyridin-2-yl)-4-oxo-1,4-dihydro-1,8-naphthyridine-3-carboxamide (racemate)

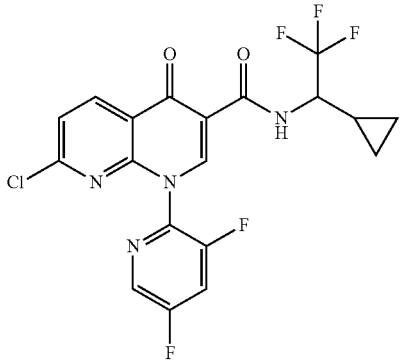 [SMILES: O=C(NC(C1CC1)C(F)(F)F)c1cn(-c2ncc(F)cc2F)c2nc(Cl)ccc2c1=O]

According to General Procedure 1, 100 mg (296 µmol) of 7-chloro-1-(3,5-difluoropyridin-2-yl)-4-oxo-1,4-dihydro-1,8-naphthyridine-3-carboxylic acid (Example 4B) were reacted with 67.6 mg (385 µmol) of 1-cyclopropyl-2,2,2-trifluoroethanamine hydrochloride (racemate) in the presence of 135 mg (355 µmol) of HATU and 206 µl (1.20 mmol) of DIPEA in 1.5 ml of DMF. The mixture was stirred for another 10 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 102 mg (75% of theory, purity 100%) of the title compound.

LC-MS (Methode 1): Rt=1.16 min; MS (ESIpos): m/z=459 [M+H]+.

$^1$H-NMR (400 MHz, DMSO-d6): δ [ppm]=10.04 (d, 1H), 9.09 (s, 1H), 8.75 (d, 1H), 8.67 (d, 1H), 8.40 (ddd, 1H), 7.78 (d, 1H), 4.34-4.48 (m, 1H), 1.18-1.30 (m, 1H), 0.50-0.72 (m, 3H), 0.33 (br. s., 1H).

Example 8A

7-Chloro-N-[(1R)-1-cyclopropyl-2,2,2-trifluoroethyl]-1-(3,5-difluoropyridin-2-yl)-4-oxo-1,4-dihydro-1,8-naphthyridine-3-carboxamide

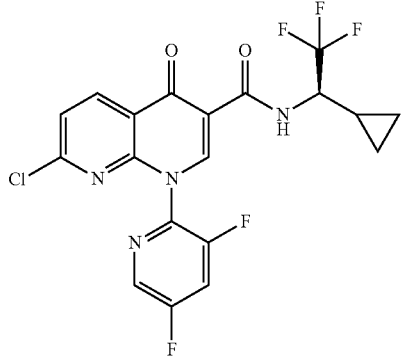 [SMILES: O=C(N[C@H](C1CC1)C(F)(F)F)c1cn(-c2ncc(F)cc2F)c2nc(Cl)ccc2c1=O]

According to General Procedure 1, 200 mg (592 µmol) of 7-chloro-1-(3,5-difluoropyridin-2-yl)-4-oxo-1,4-dihydro-1,8-naphthyridine-3-carboxylic acid (Example 4B) were reacted with 135 mg (770 µmol) of (1R)-1-cyclopropyl-2,2,2-trifluoroethanamine hydrochloride in the presence of 270 mg (711 µmol) of HATU and 0.41 ml (2.4 mmol) of DIPEA in 2.7 ml of DMF. The mixture was stirred for another 10 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 180 mg (66% of theory, purity 100%) of the title compound.

LC-MS (Methode 2): Rt=2.22 min; MS (ESIpos): m/z=459 [M+H]+.

$^1$H-NMR (400 MHz, DMSO-d6): δ [ppm]=10.04 (d, 1H), 9.09 (s, 1H), 8.75 (d, 1H), 8.67 (d, 1H), 8.40 (ddd, 1H), 7.78 (d, 1H), 4.34-4.47 (m, 1H), 1.19-1.31 (m, 1H), 0.52-0.71 (m, 3H), 0.33 (br. s., 1H).

Example 9A

7-Chloro-N-[(1S)-1-cyclopropyl-2,2,2-trifluoroethyl]-1-(3,5-difluoropyridin-2-yl)-4-oxo-1,4-dihydro-1,8-naphthyridine-3-carboxamide

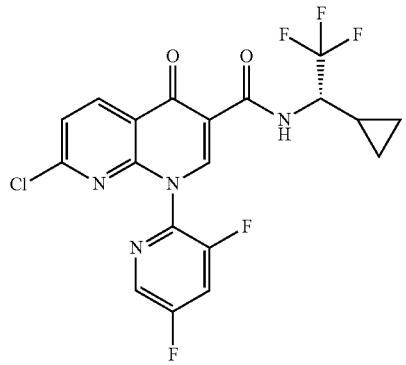 [SMILES: O=C(N[C@@H](C1CC1)C(F)(F)F)c1cn(-c2ncc(F)cc2F)c2nc(Cl)ccc2c1=O]

According to General Procedure 1, 600 mg (1.78 mmol) of 7-chloro-1-(3,5-difluoropyridin-2-yl)-4-oxo-1,4-dihydro-1,8-naphthyridine-3-carboxylic acid (Example 4B) were reacted with 468 mg (2.67 mmol) of (1S)-1-cyclopropyl-2,2,2-trifluoroethanamine hydrochloride in the presence of 675 mg (1.77 mmol) of HATU and 0.74 ml (4.3 mmol) of DIPEA in 18 ml of DMF. The mixture was then diluted with 20 ml of water and 30 ml of ethyl acetate. The phases were separated and the aqueous phase was extracted three times with 20 ml of ethyl acetate. The combined organic phases were washed with 20 ml of 1M aqueous hydrochloric acid/saturated aqueous sodium chloride solution (1:1) and three times with 15 ml of saturated aqueous sodium chloride solution, dried over sodium sulfate and filtered, and the solvent was removed under reduced pressure. The crude product was dissolved in a little dichloromethane and purified by normal phase chromatography (ethyl acetate/cyclohexane gradient), giving 384 mg (47% of theory, purity 100%) of the title compound.

LC-MS (Methode 1): Rt=1.21 min; MS (ESIpos): m/z=459 [M+H]+.

$^1$H-NMR (500 MHz, DMSO-d6): δ [ppm]=10.04 (br d, 1H), 9.09 (br s, 1H), 8.75 (d, 1H), 8.66 (d, 1H), 8.39 (ddd, 1H), 7.78 (d, 1H), 4.41 (sxt, 1H), 1.21-1.28 (m, 1H), 0.63-0.70 (m, 1H), 0.54-0.63 (m, 2H), 0.29-0.38 (m, 1H).

Example 10A

7-Chloro-1-(3,5-difluoropyridin-2-yl)-N-(1,1,1,3,3,3-hexafluoropropan-2-yl)-4-oxo-1,4-dihydro-1,8-naphthyridine-3-carboxamide

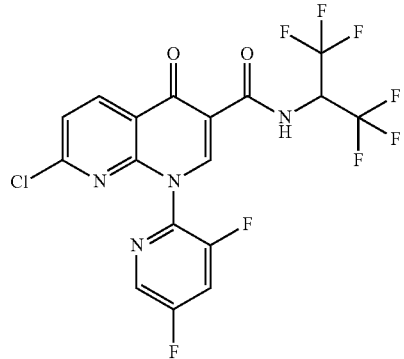 [SMILES: O=C(NC(C(F)(F)F)C(F)(F)F)c1cn(-c2ncc(F)cc2F)c2nc(Cl)ccc2c1=O]

4.15 ml (7.11 mmol) of 2,4,6-tripropyl-1,3,5,2,4,6-trioxatriphosphorinane 2,4,6-trioxide (T3P, 50% in DMF) were added dropwise to a solution of 800 mg (2.37 mmol) of 7-chloro-1-(3,5-difluoropyridin-2-yl)-4-oxo-1,4-dihydro-1,8-naphthyridine-3-carboxylic acid (Example 4B), 435 mg (2.61 mmol) of 1,1,1,3,3,3-hexafluoropropan-2-amine and 1.24 ml (7.11 mmol) of DIPEA in 21 ml of ethyl acetate. The mixture was stirred at 80° C. overnight. The reaction mixture was poured into water and ethyl acetate, and the phases were separated. The organic phase was washed three times with water and once with saturated aqueous sodium chloride solution, dried over sodium sulfate and filtered, and the solvent was removed under reduced pressure. The residue was dissolved in a little acetonitrile, filtered through a Millipore filter and purified in three runs by preparative HPLC (column: Chromatorex C18, 10 μm, 125*40 mm, solvent: acetonitrile, water, 0.1% formic acid). This gave 785 mg (68% of theory, purity 100%) of the title compound.

LC-MS (Methode 2): Rt=2.29 min; MS (ESIpos): m/z=487 [M+H]+.

$^1$H-NMR (400 MHz, DMSO-d6): δ [ppm]=10.77 (d, 1H), 9.19 (s, 1H), 8.78 (d, 1H), 8.68 (d, 1H), 8.41 (ddd, 1H), 7.81 (d, 1H), 6.35-6.50 (m, 1H).

Example 11A

7-Chloro-1-(3,5-difluoropyridin-2-yl)-4-oxo-1,4-dihydro-1,8-naphthyridine-3-carbonyl chloride

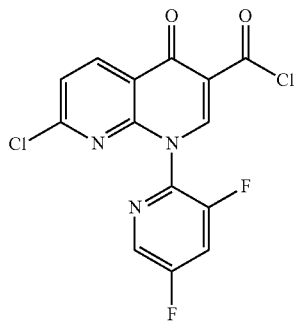 [SMILES: O=C(Cl)c1cn(-c2ncc(F)cc2F)c2nc(Cl)ccc2c1=O]

639 μl (8.77 mmol) of thionyl chloride were added to a solution of 1.00 g (2.96 mmol) of 7-chloro-1-(3,5-difluoropyridin-2-yl)-4-oxo-1,4-dihydro-1,8-naphthyridine-3-carboxylic acid (Example 4B) in 23.7 ml of THF, and the mixture was stirred at RT for one hour. The mixture was heated under reflux for one hour and all volatile components were then removed under reduced pressure. The crude product was used in the next step without further workup (conversion was assumed to be quantitative).

Example 11B

7-Chloro-N-(2,6-dichlorophenyl)-1-(3,5-difluoropyridin-2-yl)-4-oxo-1,4-dihydro-1,8-naphthyridine-3-carboxamide

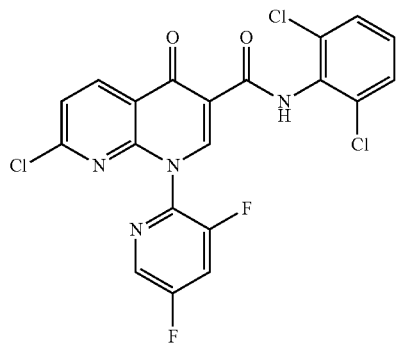 [SMILES: O=C(Nc1c(Cl)cccc1Cl)c1cn(-c2ncc(F)cc2F)c2nc(Cl)ccc2c1=O]

At RT, 1.23 ml (8.85 mmol) of triethylamine and 573 mg (3.54 mmol) of 2,6-dichloroaniline were added to a solution of 1.05 g (2.95 mmol) of 7-chloro-1-(3,5-difluoropyridin-2-yl)-4-oxo-1,4-dihydro-1,8-naphthyridine-3-carbonyl chloride in 62 ml of dichloromethane. The mixture was stirred at RT for 30 min and at 50° C. overnight. The reaction mixture was concentrated and taken up in dichloromethane, washed twice with 1 M aqueous hydrochloric acid, dried over magnesium sulfate and filtered, and the solvent was removed under reduced pressure. The crude product was purified by normal phase chromatography (ethyl acetate:cyclohexane/50:50). This gave 412 mg (29% of theory, purity 100%) of the title compound.

LC-MS (Methode 1): Rt=1.17 min; MS (ESIpos): m/z=481 [M+H]+.

$^1$H-NMR (400 MHz, DMSO-d6): δ [ppm]=11.34 (s, 1H), 9.17 (s, 1H), 8.81 (d, 1H), 8.67 (d, 1H), 8.40 (ddd, 1H), 7.80 (d, 1H), 7.60 (d, 2H), 7.40 (t, 1H).

Example 12A

7-Chloro-1-(3,5-difluoropyridin-2-yl)-4-oxo-N-[1-(trifluoromethoxy)butan-2-yl]-1,4-dihydro-1,8-naphthyridine-3-carboxamide (racemate)

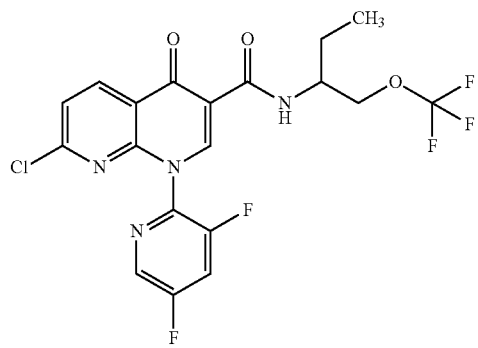 [SMILES: CCC(COC(F)(F)F)NC(=O)c1cn(-c2ncc(F)cc2F)c2nc(Cl)ccc2c1=O]

According to General Procedure 1, 200 mg (585 μmol) of 7-chloro-1-(3,5-difluoropyridin-2-yl)-4-oxo-1,4-dihydro-1,8-naphthyridine-3-carboxylic acid (Example 4B) were reacted with 170 mg (878 μmol) of 1-(trifluoromethoxy)butan-2-amine hydrochloride (racemate) in the presence of 267 mg (702 μmol) of HATU and 408 μl (2.34 mmol) of DIPEA in 2.5 ml of DMF. The mixture was stirred for 10 min. The crude solution was purified by preparative HPLC (column: Chromatorex C18, 10 μm, 125*40 mm, solvent: acetonitrile, water, 0.1% formic acid), giving 148 mg (52% of theory, purity 98%) of the title compound.

LC-MS (Methode 2): Rt=2.24 min; MS (ESIpos): m/z=477 [M+H]+.

$^1$H-NMR (500 MHz, DMSO-d6): δ [ppm]=9.61 (d, 1H), 9.05 (s, 1H), 8.74 (d, 1H), 8.66 (d, 1H), 8.39 (ddd, 1H), 7.75 (d, 1H), 4.15-4.27 (m, 3H), 1.55-1.74 (m, 2H), 0.94 (t, 3H).

Example 13A

7-Chloro-1-(3,5-difluoropyridin-2-yl)-4-oxo-N-[(2S)-1,1,1-trifluoro-3,3-dimethylbutan-2-yl]-1,4-dihydro-1,8-naphthyridine-3-carboxamide

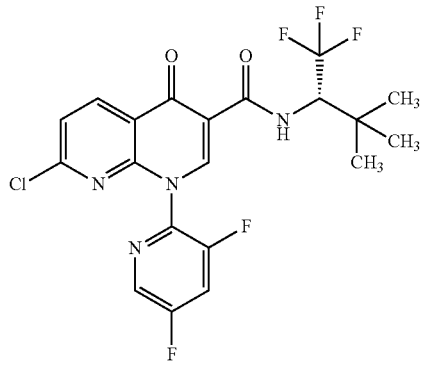 [SMILES: CC(C)(C)[C@H](NC(=O)c1cn(-c2ncc(F)cc2F)c2nc(Cl)ccc2c1=O)C(F)(F)F]

According to General Procedure 1, 600 mg (1.78 mmol) of 7-chloro-1-(3,5-difluoropyridin-2-yl)-4-oxo-1,4-dihydro-1,8-naphthyridine-3-carboxylic acid (Example 4B) were reacted with 331 mg (2.13 mmol) of (S)-2,2-dimethyl-1-trifluoromethylpropylamine in the presence of 811 mg (2.13 mmol) of HATU and 929 µl (5.33 mmol) of DIPEA in 6 ml of DMF. The mixture was stirred for another 5 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 719 mg (85% of theory, purity 100%) of the title compound.

LC-MS (Methode 2): Rt=2.38 min; MS (ESIpos): m/z=475 [M+H]+.

$^1$H-NMR (400 MHz, DMSO-d6): δ [ppm]=10.25 (d, 1H), 9.12 (s, 1H), 8.78 (d, 1H), 8.67 (d, 1H), 8.40 (ddd, 1H), 7.78 (d, 1H), 4.67 (quintt, 1H), 1.10 (s, 9H).

Example 14A

N-Benzyl-1,1,1,2,2-pentafluoropentan-3-amine (racemate)

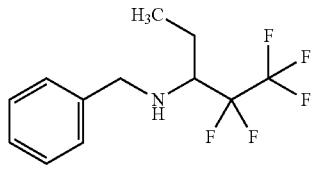 [SMILES: CCC(NCc1ccccc1)C(F)(F)C(F)(F)F]

To a solution of 2.00 g (11.4 mmol) of 1,1,1,2,2-pentafluoropentan-3-one in 10 ml of dichloromethane were added, at 0° C., 5.03 ml (17.0 mmol) of titanium tetraisopropoxide and 2.48 ml (22.7 mmol) of benzylamine. The mixture was stirred at RT for a further 90 min before being cooled down again to 0° C. Subsequently, 2.00 g (31.8 mmol) of sodium cyanoborohydride, 36 ml of methanol and 3 Å molecular sieve were added. The mixture was warmed to RT and stirred for a further 2 d. A little water and ethyl acetate were then added and the reaction solution was filtered. The filtrate was washed twice with saturated aqueous sodium bicarbonate solution and once with saturated aqueous sodium chloride solution. The organic phase was dried over sodium sulfate and filtered, and the solvent was removed under reduced pressure. The residue was purified by normal phase chromatography (ethyl acetate/cyclohexane 1/20), giving 989 mg (25% of theory; purity 76%) of the title compound.

LC-MS (Methode 1): Rt=1.27 min; MS (ESIpos): m/z=268 [M+H]+.

$^1$H-NMR (400 MHz, DMSO-d6): δ [ppm]=7.21-7.36 (m, 5H), 3.73-3.85 (m, 2H), 3.05-3.20 (m, 1H), 1.63-1.75 (m, 1H), 1.49-1.61 (m, 1H), 1.15-1.20 (m, 1H), 0.96 (t, 3H).

Example 14B 1,1,1,2,2-Pentafluoropentan-3-amine hydrochloride (racemate)

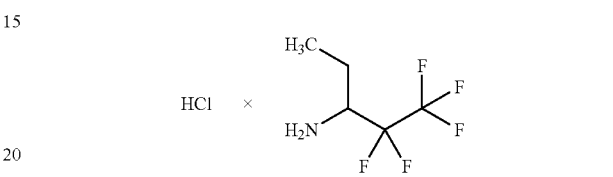

To a solution of 980 mg (2.75 mmol, purity 75%) of N-benzyl-1,1,1,2,2-pentafluoropentan-3-amine in 11.3 ml of methanol were added 75 mg of palladium on charcoal (10%), and hydrogenation was effected at standard pressure and room temperature for 6 h. The reaction mixture was then filtered through a Millipore filter and the solvent was removed under reduced pressure. The receiver containing the solvent distilled off was then transferred to a flask and admixed with 4 N hydrochloric acid in dioxane and concentrated again. The residue was stirred with ether and the precipitate was filtered off with suction and dried under high vacuum. This gave 379 mg (65% of theory, purity 100%) of the title compound.

$^1$H-NMR (400 MHz, DMSO-d6): δ [ppm]=8.97 (br. s, 3H), 4.16-4.28 (m, 1H), 1.67-1.94 (m, 2H), 1.05 (t, 3H).

Example 15A

7-Chloro-1-(3,5-difluoropyridin-2-yl)-4-oxo-N-[1,1,1,2,2-pentafluoropentan-3-yl]-1,4-dihydro-1,8-naphthyridine-3-carboxamide (racemate)

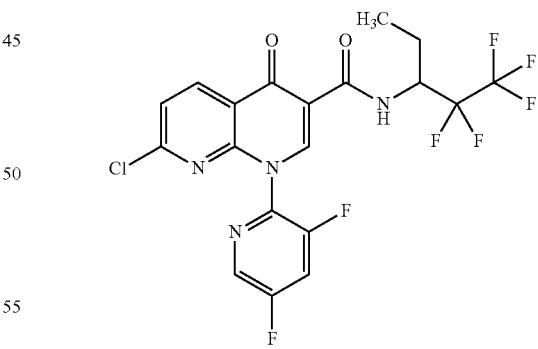

According to General Procedure 1, 200 mg (592 µmol) of 7-chloro-1-(3,5-difluoropyridin-2-yl)-4-oxo-1,4-dihydro-1,8-naphthyridine-3-carboxylic acid (Example 4B) were reacted with 152 mg (711 µmol) of 1,1,1,2,2-pentafluoropentan-3-amine hydrochloride in the presence of 270 mg (711 µmol) of HATU and 413 µl (2.37 mmol) of DIPEA in 2 ml of DMF. The mixture was stirred for another 5 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 248 mg (84% of theory, purity 100%) of the title compound.

LC-MS (Methode 2): Rt=2.32 min; MS (ESIpos): m/z=497 [M+H]+.

¹H-NMR (400 MHz, DMSO-d6): δ [ppm]=9.93 (d, 1H), 9.11 (s, 1H), 8.75 (d, 1H), 8.66 (d, 1H), 8.40 (ddd, 1H), 7.78 (d, 1H), 4.84-4.97 (m, 1H), 1.88-1.99 (m, 1H), 1.63-1.75 (m, 1H), 0.97 (t, 3H).

Example 16A

Ethyl 7-chloro-1-(3-chloro-5-fluoropyridin-2-yl)-4-oxo-1,4-dihydro-1,8-naphthyridine-3-carboxylate

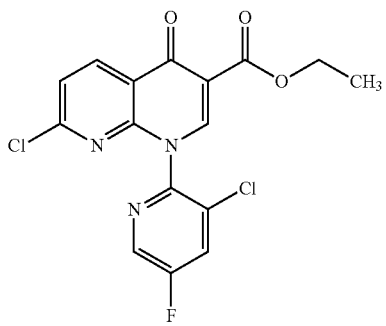 [SMILES: CCOC(=O)c1cn(-c2ncc(F)cc2Cl)c2nc(Cl)ccc2c1=O]

5.94 ml (34.1 mmol) of DIPEA were added to a solution of 1.55 g (4.87 mmol) of ethyl 2-[(2,6-dichloropyridin-3-yl)carbonyl]-3-ethoxyacrylate (CAS 157373-27-8) and 1.00 g (6.82 mmol) of 3-chloro-5-fluoropyridin-2-amine in 7.7 ml of DCM, and the mixture was stirred at RT for 4 h. 674 mg (4.87 mmol) of potassium carbonate were then added, and the mixture was heated under reflux for 72 h. The mixture was diluted with dichloromethane and washed twice with 1 M aqueous hydrochloric acid and once with saturated aqueous sodium chloride solution. The organic phase was dried over sodium sulfate and filtered, and the solvent was removed under reduced pressure. The residue was purified by normal phase chromatography (dichloromethane/ethyl acetate gradient), giving 698 mg (37% of theory, purity 100%) of the title compound.

LC-MS (Methode 1): Rt=0.91 min; MS (ESIpos): m/z=382 [M+H]+.

¹H-NMR (400 MHz, DMSO-d6): δ [ppm]=8.93 (s, 1H), 8.76 (d, 1H), 8.63 (d, 1H), 8.54 (dd, 1H), 7.67 (d, 1H), 4.25 (q, 2H), 1.28 (t, 3H).

Example 16B

7-Chloro-1-(3-chloro-5-fluoropyridin-2-yl)-4-oxo-1,4-dihydro-1,8-naphthyridine-3-carboxylic acid

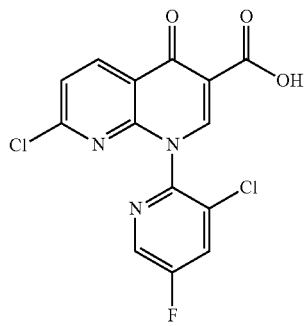 [SMILES: O=C(O)c1cn(-c2ncc(F)cc2Cl)c2nc(Cl)ccc2c1=O]

695 mg (1.82 mmol) of ethyl 7-chloro-1-(3-chloro-5-fluoropyridin-2-yl)-4-oxo-1,4-dihydro-1,8-naphthyridine-3-carboxylate were initially charged in 5.4 ml of water, 5.4 ml of 36 percent strength aqueous hydrochloric acid and 5.4 ml of THF were added and the mixture was stirred at 120° C. for 4 h. The reaction mixture was cooled to RT and 36 ml of water were added. The precipitate was filtered off with suction, washed with water and dried under high vacuum. This gave 614 mg (95% of theory, purity 100%) of the title compound.

LC-MS (Methode 1): Rt=0.96 min; MS (ESIpos): m/z=354 [M+H]+.

¹H-NMR (400 MHz, DMSO-d6): δ [ppm]=13.89 (s, 1H), 9.27 (s, 1H), 8.75-8.81 (m, 3H), 8.56 (dd, 1H), 7.81 (d, 1H).

Example 16C

7-Chloro-1-(3-chloro-5-fluoropyridin-2-yl)-4-oxo-N-[(2R)-1,1,1-trifluorobutan-2-yl]-1,4-dihydro-1,8-naphthyridine-3-carboxamide

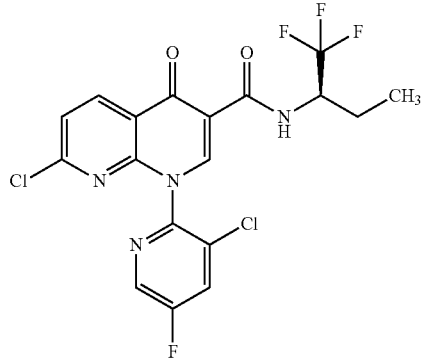 [SMILES: CC[C@@H](NC(=O)c1cn(-c2ncc(F)cc2Cl)c2nc(Cl)ccc2c1=O)C(F)(F)F]

According to General Procedure 1, 150 mg (424 μmol) of 7-chloro-1-(3-chloro-5-fluoropyridin-2-yl)-4-oxo-1,4-dihydro-1,8-naphthyridine-3-carboxylic acid (Example 16B) were reacted with 104 mg (635 μmol) of (2R)-1,1,1-trifluorobutan-2-amine hydrochloride in the presence of 193 mg (508 μmol) of HATU and 295 μl (1.69 mmol) of DIPEA in 2 ml of DMF. The mixture was stirred for another 10 min and diluted with water, acetonitrile and formic acid. The crude solution was filtered through a Millipore filter and purified by preparative HPLC (column: Chromatorex C18, 10 μm, 125*40 mm, solvents: acetonitrile, water 0.1% formic acid), giving 150 mg (77% of theory, purity 100%) of the title compound.

LC-MS (Methode 2): Rt=2.26 min; MS (ESIpos): m/z=463 [M+H]+.

¹H-NMR (400 MHz, DMSO-d6): δ [ppm]=9.90 (d, 1H), 9.14 (d, 1H), 8.72-8.80 (m, 2H), 8.54 (dd, 1H), 7.77 (d, 1H), 4.72-4.84 (m, 1H), 1.83-1.96 (m, 1H), 1.62-1.74 (m, 1H), 0.98 (t, 3H).

Example 17A

7-Chloro-1-(3-chloro-5-fluoropyridin-2-yl)-N-[(1R)-1-cyclopropyl-2,2,2-trifluoroethyl]-4-oxo-1,4-dihydro-1,8-naphthyridine-3-carboxamide

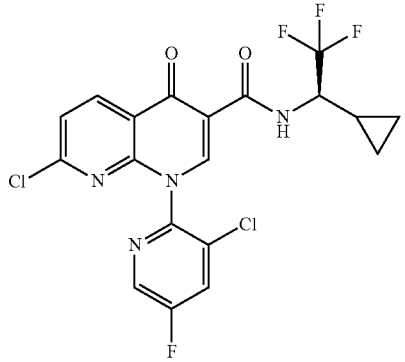 [SMILES: O=C(N[C@H](C1CC1)C(F)(F)F)c1cn(-c2ncc(F)cc2Cl)c2nc(Cl)ccc2c1=O]

According to General Procedure 1, 150 mg (424 µmol) of 7-chloro-1-(3-chloro-5-fluoropyridin-2-yl)-4-oxo-1,4-dihydro-1,8-naphthyridine-3-carboxylic acid (Example 16B) were reacted with 112 mg (635 µmol) of (1R)-1-cyclopropyl-2,2,2-trifluoroethanamine hydrochloride in the presence of 193 mg (508 µmol) of HATU and 295 µl (1.69 mmol) of DIPEA in 2 ml of DMF. The mixture was stirred for another 10 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 159 mg (79% of theory, purity 100%) of the title compound.

LC-MS (Methode 1): Rt=1.19 min; MS (ESIpos): m/z=475 [M+H]+.

$^1$H-NMR (400 MHz, DMSO-d6): δ [ppm]=10.06 (dd, 1H), 9.14 (d, 1H), 8.72-8.79 (m, 2H), 8.54 (ddd, 1H), 7.77 (d, 1H), 4.33-4.46 (m, 1H), 1.19-1.30 (m, 1H), 0.52-0.71 (m, 3H), 0.29-0.39 (m, 1H).

Example 18A

Ethyl 7-chloro-1-(3-chloropyridin-2-yl)-4-oxo-1,4-dihydro-1,8-naphthyridine-3-carboxylate

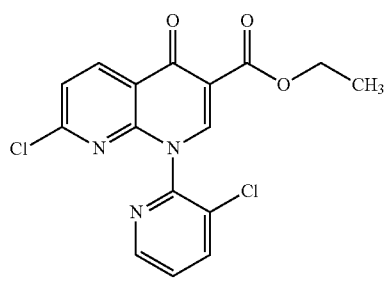 [SMILES: CCOC(=O)c1cn(-c2ncccc2Cl)c2nc(Cl)ccc2c1=O]

23.3 ml (134 mmol) of DIPEA were added to a solution of 6.07 g (19.1 mmol) of ethyl 2-[(2,6-dichloropyridin-3-yl)carbonyl]-3-ethoxyacrylate (CAS 157373-27-8) and 3.43 g (26.7 mmol) of 3-chloropyridin-2-amine in 30 ml of DCM, and the mixture was stirred at RT for 4 h. 2.64 g (19.1 mmol) of potassium carbonate were then added, and the mixture was heated under reflux for 3 d. The mixture was diluted with dichloromethane and washed twice with 1 M aqueous hydrochloric acid and once with saturated aqueous sodium chloride solution. The organic phase was dried over sodium sulfate and filtered, and the solvent was removed under reduced pressure. The residue was stirred with ether and the precipitate was filtered off with suction, washed with ether and dried under high vacuum. This gave 4.14 g (60% of theory, purity 100%) of the title compound.

LC-MS (Methode 2): Rt=1.63 min; MS (ESIpos): m/z=364 [M+H]+.

$^1$H-NMR (500 MHz, DMSO-d6): δ [ppm]=8.92 (s, 1H), 8.67 (dd, 1H), 8.63 (d, 1H), 8.33 (dd, 1H), 7.76 (dd, 1H), 7.67 (d, 1H), 4.25 (q, 2H), 1.28 (t, 3H).

Example 18B

7-Chloro-1-(3-chloropyridin-2-yl)-4-oxo-1,4-dihydro-1,8-naphthyridine-3-carboxylic acid

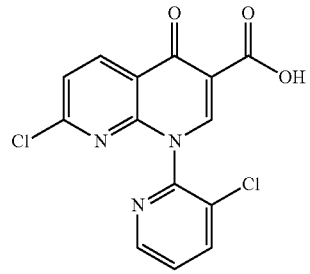 [SMILES: O=C(O)c1cn(-c2ncccc2Cl)c2nc(Cl)ccc2c1=O]

4.09 g (11.2 mmol) of ethyl 7-chloro-1-(3-chloropyridin-2-yl)-4-oxo-1,4-dihydro-1,8-naphthyridine-3-carboxylate were initially charged in 33 ml of water, 33 ml of 36 percent strength aqueous hydrochloric acid and 33 ml of THF were added and the mixture was stirred at 120° C. for 4 h. The reaction mixture was cooled to RT and 220 ml of water were added. The precipitate was filtered off with suction, washed with water and dried under high vacuum. This gave 3.53 g (92% of theory, 98% purity) of the title compound.

LC-MS (Methode 1): Rt=0.90 min; MS (ESIpos): m/z=336 [M+H]+.

$^1$H-NMR (400 MHz, DMSO-d6): δ [ppm]=13.92 (br. s., 1H), 9.26 (s, 1H), 8.79 (d, 1H), 8.68 (dd, 1H), 8.34 (dd, 1H), 7.76-7.83 (m, 2H).

Example 18C

7-Chloro-1-(3-chloropyridin-2-yl)-4-oxo-N-[(2R)-1,1,1-trifluorobutan-2-yl]-1,4-dihydro-1,8-naphthyridine-3-carboxamide

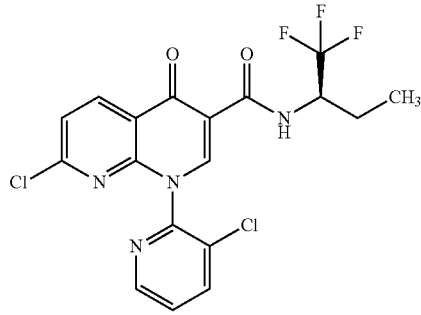

According to General Procedure 1, 800 mg (2.38 mmol) of 7-chloro-1-(3-chloropyridin-2-yl)-4-oxo-1,4-dihydro-1,8-naphthyridine-3-carboxylic acid (Example 18B) were reacted with 584 mg (3.57 mmol) of (2R)-1,1,1-trifluorobutan-2-amine hydrochloride in the presence of 1.09 g (2.86 µmol) of HATU and 1.24 ml (7.14 mmol) of DIPEA in 12 ml of DMF. The mixture was stirred for another 10 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 827 mg (78% of theory, purity 100%) of the title compound.

LC-MS (Methode 2): Rt=2.19 min; MS (ESIpos): m/z=445 [M+H]+.

$^1$H-NMR (400 MHz, DMSO-d6): δ [ppm]=9.92 (d, 1H), 9.11 (d, 1H), 8.76 (dd, 1H), 8.68 (dt, 1H), 8.34 (dd, 1H), 7.73-7.81 (m, 2H), 4.72-4.84 (m, 1H), 1.83-1.96 (m, 1H), 1.62-1.75 (m, 1H), 0.98 (t, 3H).

Example 19A

7-Chloro-1-(3-chloropyridin-2-yl)-N-[(1R)-1-cyclopropyl-2,2,2-trifluoroethyl]-4-oxo-1,4-dihydro-1,8-naphthyridine-3-carboxamide

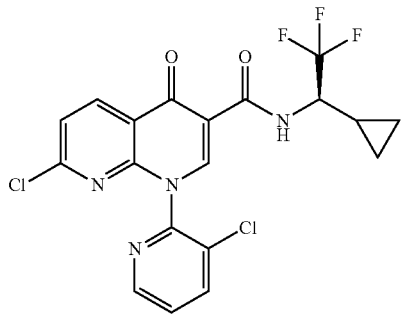

According to General Procedure 1, 150 mg (446 µmol) of 7-chloro-1-(3-chloropyridin-2-yl)-4-oxo-1,4-dihydro-1,8-naphthyridine-3-carboxylic acid (Example 18B) were reacted with 118 mg (669 µmol) of (1R)-1-cyclopropyl-2,2,2-trifluoroethanamine hydrochloride in the presence of 204 mg (535 µmol) of HATU and 311 µl (1.79 mmol) of DIPEA in DMF. The mixture was stirred for another 10 min and diluted with water, acetonitrile and formic acid. The crude solution was filtered through a Millipore filter and purified by preparative HPLC (column: Chromatorex C18, 10 µm, 125*40 mm, solvents: acetonitrile, water, 0.1% formic acid), giving 167 mg (82% of theory, purity 100%) of the title compound.

LC-MS (Methode 1): Rt=1.15 min; MS (ESIpos): m/z=457 [M+H]+.

$^1$H-NMR (400 MHz, DMSO-d6): δ [ppm]=10.07 (dd, 1H), 9.11 (d, 1H), 8.77 (d, 1H), 8.67 (dd, 1H), 8.33 (dt, 1H), 7.73-7.81 (m, 2H), 4.40 (quint, 1H), 1.19-1.31 (m, 1H), 0.52-0.72 (m, 3H), 0.29-0.39 (m, 1H).

Example 20A

Ethyl 7-chloro-1-(3-fluoropyridin-2-yl)-4-oxo-1,4-dihydro-1,8-naphthyridine-3-carboxylate

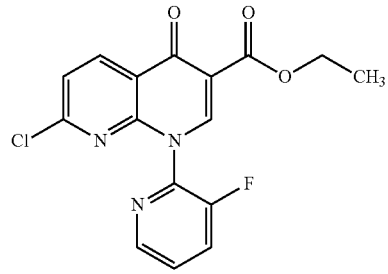 [SMILES: CCOC(=O)c1cn(-c2ncccc2F)c2nc(Cl)ccc2c1=O]

23.2 ml (133 mmol) of DIPEA were added to a solution of 6.05 g (19.0 mmol) of ethyl 2-[(2,6-dichloropyridin-3-yl)carbonyl]-3-ethoxyacrylate (CAS 157373-27-8) and 2.98 g (26.6 mmol, 1.4 eq.) of 3-fluoropyridin-2-amine in 30 ml of DCM, and the mixture was stirred at RT for 4 h. 2.63 g (19.0 mmol) of potassium carbonate were then added, and the mixture was heated under reflux overnight. The reaction mixture was diluted with 300 ml of DCM and washed twice with 75 ml of 1 M aqueous hydrochloric acid. The organic phase was dried over sodium sulfate and filtered, and the solvent was removed under reduced pressure. The suspension obtained was stirred with 40 ml of tert-butyl methyl ether, and the precipitate was filtered off with suction, washed with 10 ml of tert-butyl methyl ether and dried under high vacuum. This gave 4.51 g (63% of theory, 92% purity) of the title compound.

LC-MS (Methode 2): Rt=1.57 min; MS (ESIpos): m/z=348 [M+H]+.

$^1$H-NMR (400 MHz, DMSO-d6): δ [ppm]=8.90 (s, 1H), 8.63 (d, 1H), 8.55 (d, 1H), 8.16-8.10 (m, 1H), 7.84-7.78 (m, 1H), 7.68 (d, 1H), 4.26 (q, 2H), 1.28 (t, 3H).

Example 20B

7-Chloro-1-(3-fluoropyridin-2-yl)-4-oxo-1,4-dihydro-1,8-naphthyridine-3-carboxylic acid

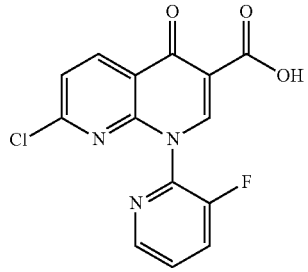 [SMILES: O=C(O)c1cn(-c2ncccc2F)c2nc(Cl)ccc2c1=O]

4.51 g (11.9 mmol, purity 92%) of ethyl 7-chloro-1-(3-fluoropyridin-2-yl)-4-oxo-1,4-dihydro-1,8-naphthyridine-3-carboxylate were initially charged in 36.6 ml of water, 36.6 ml of 36 percent strength aqueous hydrochloric acid and 36.6 ml of THF were added and the mixture was stirred at 120° C. for 4 h. The reaction mixture was cooled to RT and 100 ml of water were added. The precipitate was filtered off with suction and dried under high vacuum. This gave 3.84 g (98% of theory, 97% purity) of the title compound.

LC-MS (Methode 2): Rt=1.49 min; MS (ESIpos): m/z=320 [M+H]+.

¹H-NMR (400 MHz, DMSO-d6): δ [ppm]=13.9 (s, 1H), 9.18 (s, 1H), 8.79 (d, 1H), 8.56 (d, 1H), 8.19-8.12 (m, 1H), 7.87-7.79 (m, 2H).

Example 20C

7-Chloro-N-[(1R)-1-cyclopropyl-2,2,2-trifluoroethyl]-1-(3-fluoropyridin-2-yl)-4-oxo-1,4-dihydro-1,8-naphthyridine-3-carboxamide

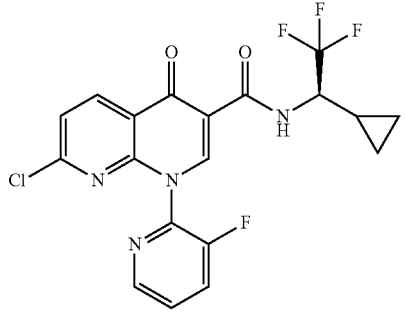 [SMILES: O=C(N[C@H](C1CC1)C(F)(F)F)c1cn(-c2ncccc2F)c2nc(Cl)ccc2c1=O]

According to General Procedure 1, 150 mg (457 μmol) of 7-chloro-1-(3-fluoropyridin-2-yl)-4-oxo-1,4-dihydro-1,8-naphthyridine-3-carboxylic acid (Example 20B) were reacted with 88.3 mg (503 μmol) of (1R)-1-cyclopropyl-2,2,2-trifluoroethanamine hydrochloride in the presence of 174 mg (457 μmol) of HATU and 239 μl (1.37 mmol) of DIPEA in 4.5 ml of DMF. After aqueous work-up, the crude product was purified by normal phase chromatography (ethyl acetate/cyclohexane gradient), giving 103 mg (51% of theory; purity 100%) of the title compound.

LC-MS (Methode 2): Rt=2.13 min; MS (ESIpos): m/z=441 [M+H]+.

¹H-NMR (400 MHz, DMSO-d6): δ [ppm]=10.06 (d, 1H), 9.09 (s, 1H), 8.76 (d, 1H), 8.56 (d, 1H), 8.17-8.10 (m, 1H), 7.85-7.76 (m, 2H), 4.47-4.35 (m, 1H), 1.29-1.21 (m, 1H), 0.71-0.53 (m, 3H), 0.39-0.30 (m, 1H).

Example 21A

7-Chloro-1-(3-fluoropyridin-2-yl)-4-oxo-N-[(2R)-1,1,1-trifluorobutan-2-yl]-1,4-dihydro-1,8-naphthyridine-3-carboxamide

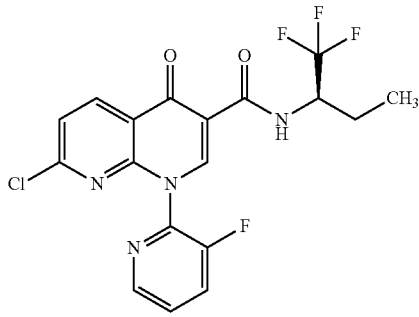 [SMILES: CC[C@@H](NC(=O)c1cn(-c2ncccc2F)c2nc(Cl)ccc2c1=O)C(F)(F)F]

According to General Procedure 1, 1.00 g (3.05 mmol) of 7-chloro-1-(3-fluoropyridin-2-yl)-4-oxo-1,4-dihydro-1,8-naphthyridine-3-carboxylic acid (Example 20B) were reacted with 648 mg (3.96 mmol) of (2R)-1,1,1-trifluorobutan-2-amine hydrochloride in the presence of 1.16 g (3.05 μmol) of HATU and 1.59 ml (9.14 mmol) of DIPEA in 30 ml of DMF. After aqueous work-up, the crude product was purified by normal phase chromatography (ethyl acetate/cyclohexane gradient), giving 670 mg (51% of theory; purity 100%) of the title compound.

LC-MS (Methode 2): Rt=2.13 min; MS (ESIpos): m/z=429 [M+H]+.

¹H-NMR (400 MHz, DMSO-d6): δ [ppm]=9.90 (d, 1H), 9.10 (s, 1H), 8.76 (d, 1H), 8.56 (d, 1H), 8.17-8.11 (m, 1H), 7.85-7.76 (m, 2H), 4.84-4.72 (m, 2H), 1.96-1.83 (m, 1H), 1.74-1.61 (m, 1H), 0.98 (t, 3H).

Example 22A

Ethyl 7-chloro-1-(3,5-difluoropyridin-4-yl)-4-oxo-1,4-dihydro-1,8-naphthyridine-3-carboxylate

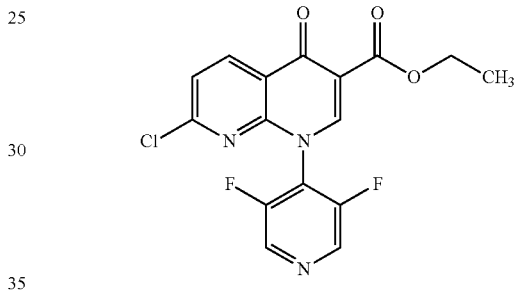

4.7 ml (26.7 mmol) of DIPEA were added to a solution of 1.22 g (3.82 mmol) of ethyl 2-[(2,6-dichloropyridin-3-yl)carbonyl]-3-ethoxyacrylate (CAS 157373-27-8) and 696 mg (5.35 mmol) of 3,5-difluoropyridin-4-amine in 10 ml of dichloromethane, and the mixture was stirred at RT for 4 h. 528 mg (3.82 mmol) of potassium carbonate were then added, and the mixture was heated under reflux overnight. The mixture was diluted with 100 ml of DCM and washed three times with 20 ml of 1 M aqueous hydrochloric acid and extracted once with saturated aqueous sodium chloride solution. The organic phase was dried over magnesium sulfate and filtered, and the solvent was removed under reduced pressure. The residue was purified in a silica gel cartridge (dichloromethane/methanol). The solvents were evaporated under reduced pressure and the residue was purified directly by preparative RP-HPLC (column: Reprosil 250×30; 10μ, flow rate: 50 ml/min, acetonitrile/water; 0.1% trifluoroacetic acid). The solvents were evaporated under reduced pressure and the residue was dried under high vacuum. This gave 203 mg (15% of theory, purity 100%) of the title compound.

LC-MS (Methode 2): Rt=1.55 min; MS (ESIpos): m/z=366 [M+H]+.

¹H-NMR (400 MHz, DMSO-d6): δ [ppm]=8.99 (s, 1H), 8.91 (s, 2H), 8.63 (d, 1H), 7.70 (d, 1H), 4.25 (q, 2H), 1.27 (t, 3H).

Example 22B

7-Chloro-1-(3,5-difluoropyridin-4-yl)-4-oxo-1,4-dihydro-1,8-naphthyridine-3-carboxylic acid

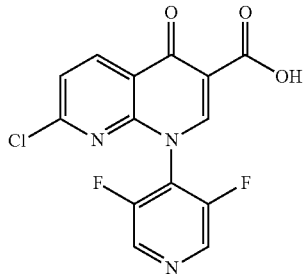 [SMILES: O=C(O)c1cn(-c2c(F)cncc2F)c2nc(Cl)ccc2c1=O]

203 mg (555 µmol) of ethyl 7-chloro-1-(3,5-difluoropyridin-4-yl)-4-oxo-1,4-dihydro-1,8-naphthyridine-3-carboxylate were initially charged in 2.5 ml of water, 2.5 ml of 36 percent strength aqueous hydrochloric acid and 2.5 ml of THF were added and the mixture was stirred at 120° C. for 2 h. The reaction mixture was cooled to RT and 10 ml of water were added. The precipitate was filtered off with suction, washed with water and dried under high vacuum. This gave 169 mg (90% of theory, purity 100%) of the title compound.

LC-MS (Methode 1): Rt=0.84 min; MS (ESIpos): m/z=338 [M+H]+.

$^1$H-NMR (400 MHz, DMSO-d6): δ [ppm]=13.72 (s, 1H), 9.30 (s, 1H), 8.93 (s, 2H), 8.78 (d, 1H), 7.83 (d, 1H).

Example 22C

7-Chloro-1-(3,5-difluoropyridin-4-yl)-4-oxo-N-[(2S)-1,1,1-trifluorobutan-2-yl]-1,4-dihydro-1,8-naphthyridine-3-carboxamide

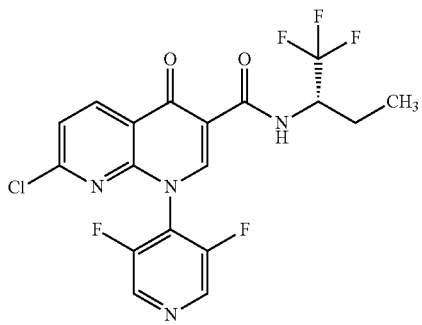 [SMILES: CC[C@H](NC(=O)c1cn(-c2c(F)cncc2F)c2nc(Cl)ccc2c1=O)C(F)(F)F]

According to General Procedure 1, 147 mg (434 µmol) of 7-chloro-1-(3,5-difluoropyridin-4-yl)-4-oxo-1,4-dihydro-1,8-naphthyridine-3-carboxylic acid (Example 22B) were reacted with 82.7 mg (651 µmol) of (2S)-1,1,1-trifluorobutan-2-amine in the presence of 165 mg (434 µmol) of HATU and 181 µl (1.04 mmol) of DIPEA in 6 ml of DMF. The reaction was diluted with water and acetonitrile and purified by preparative HPLC (column: Reprosil, 10 µm, 125*30 mm, solvents: water, acetonitrile, 0.1% trifluoroacetic acid), giving 111 mg (57% of theory, purity 100%) of the title compound.

LC-MS (Methode 2): Rt=2.11 min; MS (ESIpos): m/z=447 [M+H]+.

$^1$H-NMR (400 MHz, DMSO-d6): δ [ppm]=9.83 (d, 1H), 9.21 (s, 1H), 8.92 (s, 2H), 8.76 (d, 1H), 7.80 (d, 1H), 4.72-4.83 (m, 1H), 1.85-1.95 (m, 1H), 1.62-1.74 (m, 1H), 0.98 (t, 3H).

Example 23A

Ethyl 1-(3,5-difluoropyridin-2-yl)-7-[(3R,4R)-3,4-dihydroxypyrrolidin-1-yl]-4-oxo-1,4-dihydro-1,8-naphthyridine-3-carboxylate

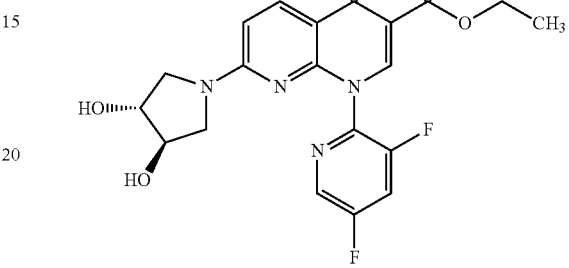

According to General Procedure 3, 1.00 g (2.73 mmol) of ethyl 7-chloro-1-(3,5-difluoropyridin-2-yl)-4-oxo-1,4-dihydro-1,8-naphthyridine-3-carboxylate (Example 7A) were reacted with 458 mg (3.28 mmol) of (3R,4R)-pyrrolidine-3,4-diol hydrochloride in the presence of 1.67 ml (9.57 mmol) of DIPEA in 12.3 ml of DMF. The reaction was terminated by addition of water, acetonitrile and formic acid, the mixture was filtered through a Millipore filter and the crude solution was purified by preparative HPLC (column: Chromatorex C18, 10 µm, 125*40 mm, solvents: acetonitrile, water, 0.1% formic acid), giving 580 mg (49% of theory, purity 100%) of the title compound.

LC-MS (Methode 2): Rt=1.10 min; MS (ESIpos): m/z=433 [M+H]+.

$^1$H-NMR (500 MHz, DMSO-d6): δ [ppm]=8.58-8.63 (m, 2H), 8.32 (td, 1H), 8.18 (d, 1H), 6.67 (d, 1H), 5.21-5.27 (m, 0.5H), 5.17 (d, 1H), 5.02-5.08 (m, 0.5H), 4.21 (q, 2H), 4.01-4.07 (m, 1H), 3.88-3.96 (m, 1H), 3.52-3.64 (m, 1H), 3.16-3.31 (m, 2H), 2.99-3.13 (m, 1H), 1.26 (t, 3H).

Example 23B 1-(3,5-Difluoropyridin-2-yl)-7-[(3R,4R)-3,4-dihydroxypyrrolidin-1-yl]-4-oxo-1,4-dihydro-1,8-naphthyridine-3-carboxylic acid

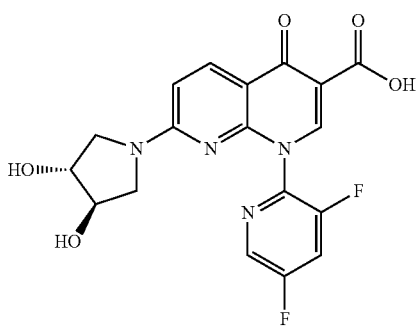 [SMILES: O=C(O)c1cn(-c2ncc(F)cc2F)c2nc(N3C[C@@H](O)[C@H](O)C3)ccc2c1=O]

Variant A: 500 mg (1.16 mmol) of ethyl 1-(3,5-difluoropyridin-2-yl)-7-[(3R,4R)-3,4-dihydroxypyrrolidin-1-yl]-4-oxo-1,4-dihydro-1,8-naphthyridine-3-carboxylate were initially charged in 3.50 ml of water, 3.50 ml of 36 percent strength aqueous hydrochloric acid and 3.50 ml of THF were added and the mixture was stirred at 120° C. for 3 h. The reaction mixture was cooled to RT and 10 ml of water were added. The precipitate was filtered off with suction, washed with water and dried under high vacuum. This gave 372 mg (80% of theory, purity 100%) of the title compound.

LC-MS (Methode 2): Rt=0.99 min; MS (ESIpos): m/z=405 [M+H]+.

$^{1}$H-NMR (500 MHz, DMSO-d6): δ [ppm]=15.23 (br s, 1H), 8.94 (br d, 1H), 8.63 (br t, 1H), 8.33-8.39 (m, 1H), 8.30 (d, 1H), 6.86 (d, 1H), 4.99-5.41 (m, 2H), 4.06 (br s, 1H), 3.94 (br s, 1H), 3.59-3.69 (m, 1H), 3.36-3.41 (m, 1H) ,3.24 (br. dd, 1H), 3.03-3.17 (m, 1H).

Variant B: Alternatively, the title compound can be prepared as follows. At RT, 1.81 ml (10.4 mmol) of DIPEA were added to a solution of 1.00 g (2.96 mmol) of 7-chloro-1-(3,5-difluoropyridin-2-yl)-4-oxo-1,4-dihydro-1,8-naphthyridine-3-carboxylic acid (Example 4B) and 496 mg (3.55 mmol) of (3R,4R)-pyrrolidine-3,4-diol hydrochloride in 14.2 ml of DMF. The mixture was stirred at RT overnight. The reaction mixture was added to water, aqueous 1N hydrochloric acid and ethyl acetate. The solid was filtered off with suction and dried under high vacuum. This gave 1.04 g (87% of theory, purity 100%) of the title compound.

Example 24A 1-(3,5-Difluoropyridin-2-yl)-7-[(4S)-4-hydroxy-2-oxopyrrolidin-1-yl]-4-oxo-1,4-dihydro-1,8-naphthyridine-3-carboxylic acid

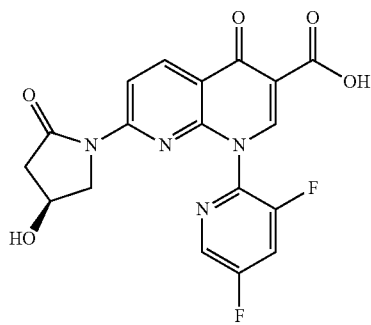 [SMILES: O=C(O)c1cn(-c2ncc(F)cc2F)c2nc(N3C[C@@H](O)CC3=O)ccc2c1=O]

According to General Procedure 2, 1.58 g (4.68 mmol) of 7-chloro-1-(3,5-difluoropyridin-2-yl)-4-oxo-1,4-dihydro-1,8-naphthyridine-3-carboxylic acid (Example 4B) were reacted with 568 mg (5.62 mmol) of (4S)-4-hydroxypyrrolidin-2-one in the presence of 970 mg (7.02 mmol) of potassium carbonate, 210 mg (0.94 mmol) of palladium acetate and 541 mg (0.94 mmol) of Xantphos in 31.6 ml of dioxane at 80° C. The reaction mixture was diluted with acetonitrile and filtered. The residue from the filter was stirred with warm acetonitrile and filtered again (the procedure was repeated four times). The filtrates were combined and concentrated almost completely. The precipitate was filtered off with suction and dried under high vacuum. This gave 1.36 g (72% of theory, purity 100%) of the title compound.

LC-MS (Methode 2): Rt=1.15 min; MS (ESIpos): m/z=403 [M+H]+.

$^{1}$H-NMR (400 MHz, DMSO-d6): δ [ppm]=14.42 (br. s., 1H), 9.15 (s, 1H), 8.75 (d, 1H), 8.68 (br. dd, 1H), 8.56-8.63 (m, 1H), 8.42 (td, 1H), 5.24-5.42 (m, 1H), 4.30 (br. s., 1H), 3.63-3.80 (m, 1H), 3.42-3.56 (m, 1H), 2.88-3.05 (m, 1H), 2.39 (br. dd, 1H).

Example 25A 1-(3,5-Difluoropyridin-2-yl)-7-[3-(2-hydroxyethyl)-2-oxoimidazolidin-1-yl]-4-oxo-1,4-dihydro-1,8-naphthyridine-3-carboxylic acid

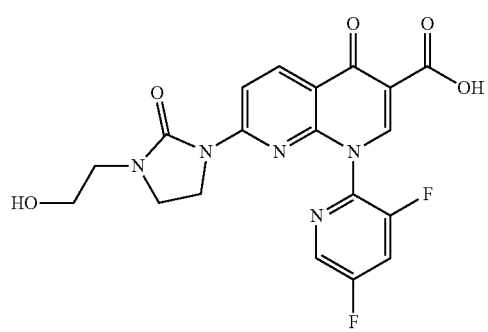 [SMILES: O=C(O)c1cn(-c2ncc(F)cc2F)c2nc(N3CCN(CCO)C3=O)ccc2c1=O]

According to General Procedure 2, 250 mg (740 μmol) of 7-chloro-1-(3,5-difluoropyridin-2-yl)-4-oxo-1,4-dihydro-1,8-naphthyridine-3-carboxylic acid (Example 4B) were reacted with 217 mg (888 μmol) of 1-(2-{[tert-butyl(dimethyl)silyl]oxy}ethyl)imidazolidin-2-one (EP 1721905 A1, Ex. 43) in the presence of 256 mg (1.85 mmol) of potassium carbonate, 33.2 mg (148 μmol) of palladium acetate and 85.7 mg (148 μmol) of Xantphos in 5 ml of dioxane at 90° C. for 90 min. 10 ml of dioxane and 10 ml of 1N aqueous HCl were added and the reaction mixture was stirred at 50° C. for about 60 min. The reaction mixture was filtered through a Millipore filter and added to ethyl acetate and water. The phases were separated and the aqueous phase was extracted three times with ethyl acetate. The combined organic phases were washed with saturated aqueous sodium chloride solution and dried over sodium sulfate and the solvent was removed under reduced pressure. The residue was crystallized from acetonitrile and the precipitate was filtered off with suction, washed with a little cold acetonitrile and dried under high vacuum. This gave 269 mg (84% of theory, purity 100%) of the title compound.

LC-MS (Methode 2): Rt=1.18 min; MS (ESIpos): m/z=432 [M+H]+.

$^{1}$H-NMR (400 MHz, DMSO-d6): δ [ppm]=14.67 (s, 1H), 9.10 (s, 1H), 8.65 (d, 1H), 8.61 (d, 1H), 8.51 (d, 1H), 8.35 (ddd, 1H), 4.75 (t, 1H), 3.43-3.63 (m, 6H), 3.22-3.30 (m, 2H).

Example 26A 1-(2-{[tert-Butyl(dimethyl)silyl]oxy}ethyl)tetrahydropyrimidin-2(1H)-one

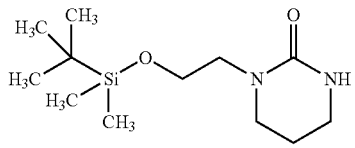 [SMILES: CC(C)(C)[Si](C)(C)OCCN1CCCNC1=O]

At 0° C., 340 mg (4.99 mmol) of imidazole were added to a solution of 600 mg (4.16 mmol) of 1-(2-hydroxyethyl)

tetrahydropyrimidin-2(1H)-one (DE 1121617, Chem. Abstr. 1962, 56, 11601g) and 690 mg (4.58 mmol) of tert-butyl (chloro)dimethylsilane in 4.2 ml DMF. The mixture was stirred at 0° C. for 30 min and at RT overnight. Subsequently, all volatile constituents were removed under reduced pressure and the residue was admixed with 10 ml of water and extracted three times with 20 ml of ethyl acetate. The combined organic phases were washed with 30 ml of saturated aqueous sodium chloride solution, dried with magnesium sulfate and filtered, and the solvent was removed under reduced pressure. This gave 732 mg (68% of theory, purity 100%) of the title compound.

LC-MS (Methode 2): Rt=1.83 min; MS (ESIpos): m/z=259 [M+H]+.

¹H-NMR (400 MHz, DMSO-d6): δ [ppm]=6.11 (s, 1H), 3.63 (t, 2H), 3.30-3.21 (m, 4H), 3.11-3.04 (m, 2H), 1.80-1.72 (m, 2H), 0.86 (s, 9H), 0.03 (s, 6H).

Example 26B 1-(3,5-Difluoropyridin-2-yl)-7-[3-(2-hydroxyethyl)-2-oxo-tetrahydropyrimidin-1(2H)-yl]-4-oxo-1,4-dihydro-1,8-naphthyridine-3-carboxylic acid

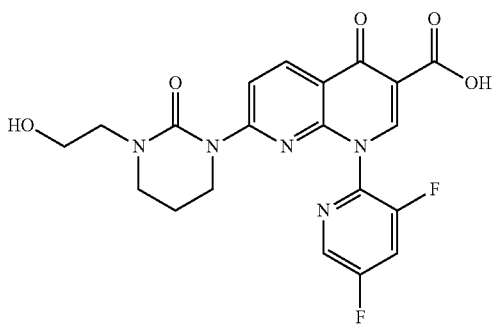 [SMILES: O=C(O)c1cn(-c2ncc(F)cc2F)c2nc(N3CCCN(CCO)C3=O)ccc2c1=O]

According to General Procedure 2, 250 mg (740 µmol) of 7-chloro-1-(3,5-difluoropyridin-2-yl)-4-oxo-1,4-dihydro-1,8-naphthyridine-3-carboxylic acid (Example 4B) were reacted with 230 mg (888 µmol) of 1-(2-{[tert-butyl(dimethyl)silyl]oxy}ethyl)tetrahydropyrimidin-2(1H)-one in the presence of 256 mg (1.85 mmol) of potassium carbonate, 33.2 mg (148 µmol) of palladium acetate and 85.7 mg (148 µmol) of Xantphos in 5 ml of dioxane at 90° C. for 90 min. 10 ml of dioxane and 10 ml of 1N aqueous HCl were added and the reaction mixture was stirred at 50° C. for about 60 min. The reaction mixture was filtered through a Millipore filter and added to ethyl acetate and water. The phases were separated and the aqueous phase was extracted three times with ethyl acetate. The combined organic phases were washed with saturated aqueous sodium chloride solution and dried over sodium sulfate and the solvent was removed under reduced pressure. The residue was crystallized from acetonitrile and the precipitate was filtered off with suction, washed with a little cold acetonitrile and dried under high vacuum. This gave 219 mg (57% of theory, purity 86%) of the title compound.

LC-MS (Methode 2): Rt=1.20 min; MS (ESIpos): m/z=446 [M+H]+.

¹H-NMR (400 MHz, DMSO-d6): δ [ppm]=14.62 (s, 1H), 9.12 (s, 1H), 8.66 (d, 1H), 8.54 (d, 1H), 8.34-8.42 (m, 1H), 8.24 (d, 1H), 4.72 (t, 1H), 3.48-3.58 (m, 4H), 3.39 (br t, 4H), 1.85-1.97 (m, 2H).

Example 27A 1-(3-Chloropyridin-2-yl)-7-[(4S)-4-hydroxy-2-oxopyrrolidin-1-yl]-4-oxo-1,4-dihydro-1,8-naphthyridine-3-carboxylic acid

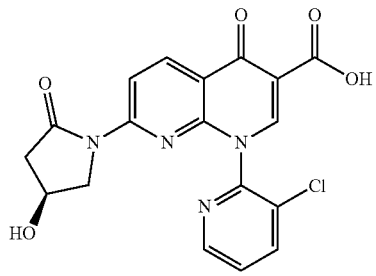 [SMILES: O=C(O)c1cn(-c2ncccc2Cl)c2nc(N3C[C@@H](O)CC3=O)ccc2c1=O]

According to General Procedure 2, 1.50 g (4.46 mmol) of 7-chloro-1-(3-chloropyridin-2-yl)-4-oxo-1,4-dihydro-1,8-naphthyridine-3-carboxylic acid (Example 18B) were reacted with 541 mg (5.36 mmol) of (4S)-4-hydroxypyrrolidin-2-one in the presence of 925 mg (6.69 mmol) of potassium carbonate, 200 mg (892 µmol) of palladium acetate and 516 mg (892 µmol) of Xantphos in 30 ml of dioxane at 80° C. for 3 h. 1N aqueous hydrochloric acid was added and the reaction mixture was thoroughly extracted with ethyl acetate. The combined organic phases were washed with saturated aqueous sodium chloride solution and dried over sodium sulfate and the solvent was removed under reduced pressure. The crude product was allowed to stand for 1 h in a little ethyl acetate and the precipitated solid was then filtered off with suction and dried under high vacuum. This gave 1.16 g (52% of theory, 80% purity) of the title compound.

LC-MS (Methode 1): Rt=0.63/0.65 min; MS (ESIpos): m/z=401 [M+H]+.

¹H-NMR (400 MHz, DMSO-d6): δ [ppm]=14.50 (br. s, 1H), 9.23 (br. d, 1H), 8.76 (d, 1H), 8.68 (ddd, 1H), 8.59 (dd, 1H), 8.35 (dt, 1H), 7.79 (ddd, 1H), 5.25-5.40 (m, 1H), 4.20-4.30 (m, 1H), 3.51-3.68 (m, 1H), 3.32-3.45 (m, 1H), 2.87-3.02 (m, 1H), 2.37 (dd, 1H).

Example 28A

N-Benzyl-1,1,1,2,2-pentafluorobutan-3-amine (racemate)

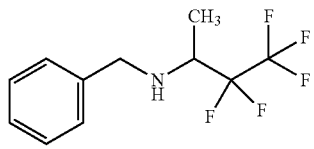 [SMILES: CC(NCc1ccccc1)C(F)(F)C(F)(F)F]

At 0° C., 5.40 ml (18.3 mmol) of titanium tetraisopropoxide and 2.66 ml (24.4 mmol) of benzylamine were added to a solution of 2.00 g (12.2 mmol) of 3,3,4,4,4-pentafluorobutan-2-one in 10 ml of dichloromethane. The mixture was stirred at RT for a further 90 min before being cooled down again to 0° C. Subsequently, 2.14 g (34.1 mmol) of sodium cyanoborohydride, 36 ml of methanol and 3 Å molecular sieve were added. The mixture was warmed to RT and stirred for a further 2 d. The reaction solution was admixed with a little water and ethyl acetate and filtered. The filtrate was washed twice with saturated aqueous sodium bicarbonate solution and once with saturated aqueous sodium chloride solution. The organic phase was dried over sodium sulfate and filtered, and the solvent was removed under reduced pressure. The residue was purified twice by normal phase chromatography (ethyl acetate/cyclohexane 1/20), giving 1.65 g (48% of theory; 91% purity) of the title compound.

LC-MS (Methode 5): Rt=2.17 min; MS (ESIpos): m/z=254 [M+H]+.

$^1$H-NMR (500 MHz, DMSO-d6): δ [ppm]=7.28-7.36 (m, 4H), 7.20-7.27 (m, 1H), 3.83 (dd, 1H), 3.72 (dd, 1H), 3.22-3.30 (m, 1H), 2.43-2.48 (m, 1H), 1.20 (d, 3H).

Example 28B 1,1,1,2,2-Pentafluorobutan-3-amine hydrochloride (racemate)

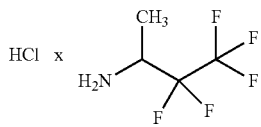

To a solution of 1.50 g (5.92 mmol) of N-benzyl-1,1,1,2,2-pentafluoropentan-3-amine in 27.4 ml of methanol were added 150 mg of palladium on charcoal (10%), and hydrogenation was effected at standard pressure and room temperature for 6 h. The reaction mixture was then filtered through a Millipore filter and the solvent was removed under reduced pressure. The receiver containing the solvent distilled off was then transferred to a flask and admixed with 4 N hydrochloric acid in dioxane and concentrated again. The residue was stirred with ether and the precipitate was filtered off with suction and dried under high vacuum. This gave 456 mg (39% of theory, purity 100%) of the title compound.

$^1$H-NMR (500 MHz, DMSO-d6): δ [ppm]=9.21 (br. s, 3H), 4.40-4.29 (m, 1H), 1.41 (d, 3H).

Example 29A

7-Chloro-1-(3,5-difluoropyridin-2-yl)-N-(1,1,1,3,3,3-hexafluoro-2-methylpropan-2-yl)-4-oxo-1,4-dihydro-1,8-naphthyridine-3-carboxamide

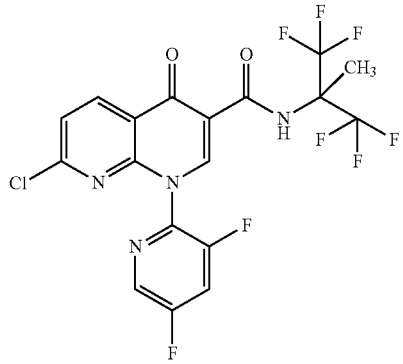 [SMILES: CC(NC(=O)c1cn(-c2ncc(F)cc2F)c2nc(Cl)ccc2c1=O)(C(F)(F)F)C(F)(F)F]

0.47 ml (0.80 mmol) of 2,4,6-tripropyl-1,3,5,2,4,6-trioxatriphosphorinane 2,4,6-trioxide (T3P, 50% in DMF) were added dropwise to a solution of 90.0 mg (267 µmol) of 7-chloro-1-(3,5-difluoropyridin-2-yl)-4-oxo-1,4-dihydro-1,8-naphthyridine-3-carboxylic acid (Example 7B), 58.1 mg (321 µmol) of 1,1,1,3,3,3-hexafluoro-2-methylpropan-2-amine and 0.14 ml (0.80 mmol) of DIPEA in 1 ml of ethyl acetate. The mixture was stirred at 80° C. over the weekend. The reaction solution was concentrated and the residue was dissolved in a little water, acetonitrile and formic acid, filtered through a Millipore filter and purified by preparative HPLC (acetonitrile/water/0.1% formic acid). This gave 23.1 mg (17% of theory, purity 100%) of the title compound.

LC-MS (Methode 2): R$_t$=2.35 min; MS (ESIpos): m/z=501 [M+H]+.

$^1$H NMR (400 MHz, DMSO-d6): δ [ppm]=10.97 (s, 1H), 9.13 (s, 1H), 8.79 (d, 1H), 8.67 (d, 1H), 8.44-8.37 (m, 1H), 7.79 (d, 1H), 2.08 (s, 1H).

Example 30A 1-(3,5-Difluoropyridin-2-yl)-4-oxo-7-(2-oxoimidazolidin-1-yl)-1,4-dihydro-1,8-naphthyridine-3-carboxylic acid

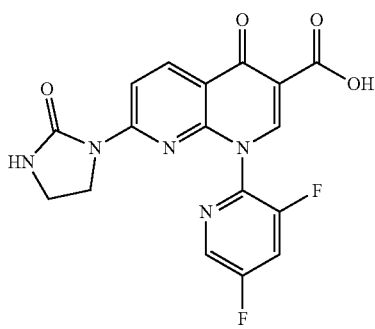 [SMILES: O=C(O)c1cn(-c2ncc(F)cc2F)c2nc(N3CCNC3=O)ccc2c1=O]

According to General Procedure 2, 800 mg (2.37 mmol) of 7-chloro-1-(3,5-difluoropyridin-2-yl)-4-oxo-1,4-dihydro-1,8-naphthyridine-3-carboxylic acid (Example 4B) were reacted with 2.04 g (23.7 mmol) of imidazolidin-2-one in the presence of 491 mg (3.55 mmol) of potassium carbonate, 106 mg (474 µmol) of palladium acetate and 274 mg (474 µmol) of Xantphos in 21.1 ml of dioxane at 80° C. overnight. The dioxane was then removed on a rotary evaporator and acetonitrile was added to the reaction solution. The mixture was filtered through a filter. The filtrate was kept and the filter residue was stirred with hot acetonitrile and filtered again. This procedure was repeated twice. This gave 805 mg (68% of theory, purity 78%) of the title compound.

LC-MS (Methode 2): Rt=1.21 min; MS (ESIpos): m/z=388 [M+H]+.

Example 31A

Ethyl 7-({(2R)-2-[(tert-butoxycarbonyl)amino]propyl}amino)-1-(3,5-difluoropyridin-2-yl)-4-oxo-1,4-dihydro-1,8-naphthyridine-3-carboxylate

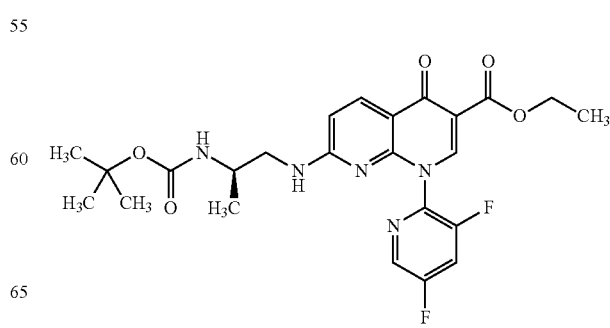

The compound from Example 4A (1.89 g, 5.17 mmol) was initially charged in 33 ml of DMF, tert-butyl [(2R)-1-aminopropan-2-yl]carbamate hydrochloride (1.31 g, 6.20 mmol) and N,N-diisopropylethylamine (3.2 ml, 18 mmol) were added and the mixture was stirred at 60° C. overnight. The reaction solution was added to about 300 ml of water and adjusted to pH=5 with 1 N hydrochloric acid. The precipitate was filtered off, washed with water and dried under high vacuum. The crude product was purified on silica gel (mobile phase: cyclohexane/ethyl acetate=2/1, then dichloromethane/methanol=20/1). This gave 1.58 g of the target compound (53% of theory, purity 93%).

LC-MS (Methode 2): $R_t$=1.70 min; MS (ESIpos): m/z=504 [M+H]+

Example 31B

Ethyl 7-{[(2R)-2-aminopropyl]amino}-1-(3,5-difluoropyridin-2-yl)-4-oxo-1,4-dihydro-1,8-naphthyridine-3-carboxylate trifluoroacetate

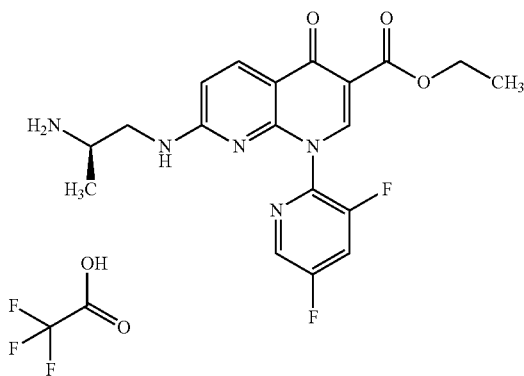 [SMILES: O=C(O)C(F)(F)F ; CCOC(=O)c1cn(-c2ncc(F)cc2F)c2nc(NC[C@@H](C)N)ccc2c1=O]

The compound from Example 31A (1.38 g, 2.74 mmol) was initially charged in dichloromethane (80 ml), trifluoroacetic acid (4.2 ml, 55 mmol) was added with ice cooling and the mixture was stirred at room temperature for 4.5 h. The reaction mixture was concentrated using a rotary evaporator, twice, toluene was added and the mixture was concentrated, and the residue was then dried under high vacuum. This gave 2.18 g of the target compound (88% of theory, purity 57%). The crude product was converted further without further purification.

LC-MS (Methode 2): $R_t$=0.80 min; MS (ESIpos): m/z=404 [M+H]+

Example 31C

Ethyl 1-(3,5-difluoropyridin-2-yl)-7-[(4R)-4-methyl-2-oxoimidazolidin-1-yl]-4-oxo-1,4-dihydro-1,8-naphthyridine-3-carboxylate

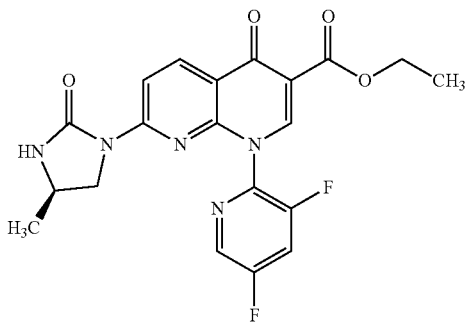 [SMILES: CCOC(=O)c1cn(-c2ncc(F)cc2F)c2nc(N3C[C@@H](C)NC3=O)ccc2c1=O]

Under argon, the compound from Example 31B (2.50 g, purity 57%, 2.75 mmol) was dissolved in DMF (61 ml), potassium carbonate (381 mg, 2.75 mmol) and 1,1'-carbonyldiimidazole (1.12 g, 6.89 mmol) were added and the mixture was stirred at room temperature for 1.5 h. The reaction solution was added to about 600 ml of water, acidified with 1 N hydrochloric acid and then extracted three times with ethyl acetate. The combined organic phases were washed once with water, then dried over sodium sulfate, filtered and concentrated on a rotary evaporator. This gave 960 mg of the target compound (70% of theory, purity 87%).

LC-MS (Methode 2): $R_t$=1.38 min; MS (ESIpos): m/z=430 [M+H]+

$^1$H-NMR (400 MHz, DMSO-$d_6$) δ [ppm]: 0.008 (1.58), 1.090 (1.23), 1.102 (1.26), 1.147 (1.29), 1.159 (1.19), 1.242 (0.90), 1.255 (3.35), 1.273 (6.25), 1.291 (2.93), 1.908 (0.48), 2.731 (13.52), 2.891 (16.00), 2.933 (0.66), 3.060 (0.42), 3.716 (0.82), 3.755 (0.71), 3.770 (0.60), 4.205 (0.65), 4.214 (1.15), 4.223 (0.87), 4.231 (2.82), 4.249 (2.63), 4.267 (0.80), 7.762 (1.77), 7.952 (2.11), 8.332 (1.63), 8.354 (2.25), 8.430 (2.46), 8.452 (1.55), 8.603 (0.53), 8.612 (0.92), 8.629 (1.49), 8.767 (2.11).

Example 31D 1-(3,5-Difluoroyridin-2-yl)-7-[(4R)-4-methyl-2-oxoimidazolidin-1-yl]-4-oxo-1,4-dihydro-1,8-naphthyridine-3-carboxylic acid

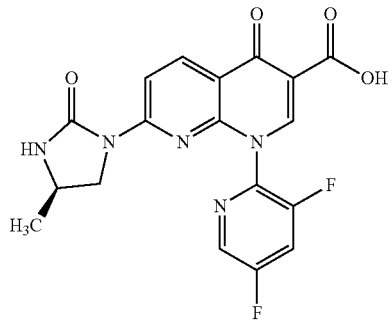 [SMILES: C[C@@H]1CN(c2ccc3c(=O)c(C(=O)O)cn(-c4ncc(F)cc4F)c3n2)C(=O)N1]

The compound from Example 31C (960 mg, purity 87%, 1.95 mmol) was suspended in 5.9 ml of THF. 5.9 ml of water and 18 ml of conc. hydrochloric acid were added and the mixture was stirred at a bath temperature of 110° C. for 3 h. After cooling, the solid obtained was filtered off, washed with water and dried under high vacuum. This gave 420 mg of the target compound (54% of theory, purity 100%).

LC-MS (Methode 1): $R_t$=0.73 min; MS (ESIpos): m/z=402 [M+H]+

$^1$H-NMR (500 MHz, DMSO-$d_6$) δ [ppm]: −0.007 (1.58), 0.006 (1.20), 1.104 (4.83), 1.114 (4.85), 1.160 (5.01), 1.170 (4.83), 1.232 (0.69), 2.516 (1.88), 2.520 (1.64), 2.524 (1.25), 3.090 (1.26), 3.101 (1.27), 3.122 (0.49), 3.149 (1.26), 3.160 (1.27), 3.706 (0.56), 3.723 (1.92), 3.735 (2.25), 3.785 (2.31), 3.799 (1.78), 7.906 (6.55), 8.337 (0.72), 8.354 (1.27), 8.374 (1.08), 8.395 (1.21), 8.411 (0.66), 8.493 (3.64), 8.511 (5.36), 8.582 (16.00), 8.600 (10.62), 8.654 (5.90), 9.089 (5.35), 9.095 (5.25), 14.664 (1.73).

Example 32A

7-Chloro-1-(3,5-difluoropyridin-2-yl)-4-oxo-N-(3,3,4,4,4-pentafluoro-2-methylbutan-2-yl)-1,4-dihydro-1,8-naphthyridine-3-carboxamide

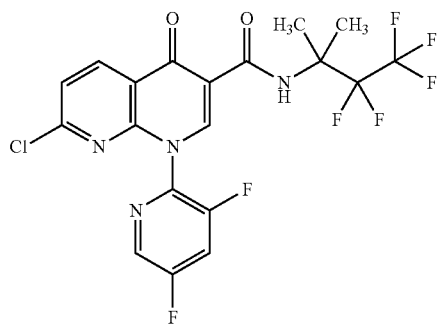 [SMILES: CC(C)(NC(=O)c1cn(-c2ncc(F)cc2F)c2nc(Cl)ccc2c1=O)C(F)(F)C(F)(F)F]

7-Chloro-1-(3,5-difluoropyridin-2-yl)-4-oxo-1,4-dihydro-1,8-naphthyridine-3-carboxylic acid (800 mg, purity 95%, 2.25 mmol), 3,3,4,4,4-pentafluoro-2-methylbutan-2-amine hydrochloride (1:1) (529 mg, 2.48 mmol) and N,N-diisopropylethylamine (1.6 ml, 9.0 mmol) were initially charged in 23 ml of ethyl acetate, T3P (50% in ethyl acetate, 2,4,6-tripropyl-1,3,5,2,4,6-trioxatriphosphorinane 2,4,6-trioxide solution) (5.3 ml, purity 50%, 9.0 mmol) was added and the mixture was stirred at 80° C. overnight. The reaction mixture was added to water and ethyl acetate. The phases were separated. The aqueous phase was extracted three more times with ethyl acetate. The combined organic phases were washed with saturated aqueous sodium chloride solution, dried over sodium sulfate, filtered and concentrated. The residue was purified by silica gel chromatography (mobile phase: cyclohexane/ethyl acetate 3:1). The product-containing fractions were combined and concentrated by evaporation. The residue was dried under high vacuum. This gave 1.1 g of the target compound (98% of theory, purity 100%).

LC-MS (Methode3): $R_t$=1.55 min; MS (ESIpos): m/z=497 [M+H]$^+$ $^1$H-NMR (400 MHz, DMSO-d6) δ [ppm]: −0.008 (1.91), 0.008 (1.83), 1.157 (0.54), 1.175 (1.10), 1.193 (0.56), 1.398 (0.53), 1.703 (16.00), 1.989 (2.02), 4.021 (0.48), 4.039 (0.48), 7.757 (4.23), 7.778 (4.44), 8.372 (0.78), 8.378 (0.89), 8.395 (1.19), 8.399 (1.29), 8.416 (0.80), 8.422 (0.89), 8.661 (3.86), 8.667 (3.65), 8.745 (4.39), 8.767 (4.21), 9.066 (7.38), 10.122 (4.04).

Example 33A 3,3,4,4,4-Pentafluoro-N-[(1S)-1-phenylethyl]butan-2-imine

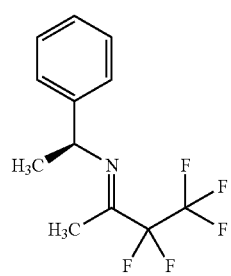 [SMILES: C/C(=N\[C@@H](C)c1ccccc1)C(F)(F)C(F)(F)F]

3,3,4,4,4-Pentafluorobutan-2-one (200 g, 1.23 mol) was initially charged in 6.4 l of diethyl ether and cooled to −40° C. (1S)-1-Phenylethanamine (160 ml 1.2 mol) and triethylamine (340 ml, 2.5 mol) were then added rapidly, and at an internal temperature of 0° C. titanium(IV) chloride (1 M in toluene, 620 ml, 620 mmol) was subsequently slowly added dropwise. The ice bath was then removed and the mixture was warmed to RT. The reaction mixture was then heated under reflux for 1 h and subsequently stirred at RT overnight. Celite was added, the reaction mixture was stirred for 1 h and then filtered through Celite, thoroughly rinsing with diethyl ether. The filtrate was concentrated at water bath temperature of 25° C. Cyclohexane was added to the residue and the residue was once more filtered off through Celite and washed with cyclohexane. The filtrate was concentrated at water bath temperature of 25° C. The crude product was used for the next step without further purification. This gave 289 g (88% of theory) of the title compound.

Example 34A 3,3,4,4,4-Pentafluoro-N-[(1S)-1-phenylethyl]butan-2-amine hydrochloride (enantiomerically pure)

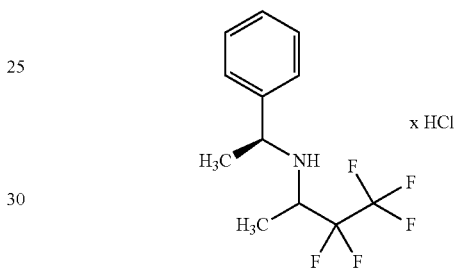

3,3,4,4,4-Pentafluoro-N-[(1S)-1-phenylethyl]butan-2-imine (239 g, 901 mmol) was initially charged in 1.9 l of dichloromethane, 420 ml of DMF and molecular sieve 3 Å were then added and the mixture was stirred at RT for 1 h. The reaction mixture was then cooled to −50° C., and trichlorosilane (270 ml, 2.7 mol) was slowly added dropwise. After 30 min and at an internal temperature of −70° C. to −50° C., the mixture was carefully quenched with semi-concentrated sodium hydroxide solution until a pH of 7 had been reached. Dichloromethane was added and the phases were separated. The organic phase was dried over sodium sulfate, 2.2 l of hydrogen chloride in diethyl ether (2 M solution) were then added and the crude product was concentrated under reduced pressure. This gave 192 g (70% of theory) of the title compound.

LC-MS (Methode 1): $R_t$=1.22 min; MS (ESIpos): m/z=268 [M-HCl+H]$^+$

Example 35A 3,3,4,4,4-Pentafluorobutan-2-amine hydrochloride (enantiomerically pure)

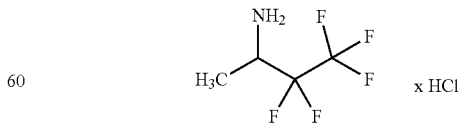

192 g (632 mmol) of 3,3,4,4,4-pentafluoro-N-[(1S)-1-phenylethyl]butan-2-amine hydrochloride (enantiomerically pure, from Example 34A) were dissolved in 1.2 l of ethanol, 19.2 g of palladium(II) hydroxide (20% on carbon) were

Example 36A

7-Chloro-1-(3,5-difluoropyridin-2-yl)-4-oxo-N-(3,3,4,4,4-pentafluorobutan-2-yl)-1,4-dihydro-1,8-naphthyridine-3-carboxamide (enantiomerically pure)

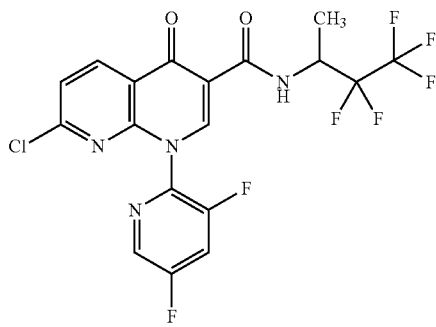 [SMILES: CC(NC(=O)c1cn(-c2ncc(F)cc2F)c2nc(Cl)ccc2c1=O)C(F)(F)C(F)(F)F]

7-Chloro-1-(3,5-difluoropyridin-2-yl)-4-oxo-1,4-dihydro-1,8-naphthyridine-3-carboxylic acid (800 mg, purity 95%, 2.25 mmol), 3,3,4,4,4-pentafluorobutan-2-amine hydrochloride (enantiomerically pure) and N,N-diisopropylethylamine (1.6 ml, 9.0 mmol) were initially charged in 22 ml of ethyl acetate, T3P (50% in ethyl acetate) 2,4,6-tripropyl-1,3,5,2,4,6-trioxatriphosphorinane 2,4,6-trioxide solution (5.3 ml, purity 50%, 9.0 mmol) was added and the mixture was stirred at 80° C. overnight. The reaction mixture was added to water and ethyl acetate. The phases were separated. The aqueous phase was extracted three more times with ethyl acetate. The combined organic phases were washed with saturated aqueous sodium chloride solution, dried over sodium sulfate, filtered and concentrated. The residue was purified by silica gel chromatography (mobile phase: cyclohexane/ethyl acetate 3:1). The product-containing fractions were combined and concentrated. The residue was dried under high vacuum. This gave 1.1 g of the target compound (100% of theory, purity 100%).

LC-MS (Methode 3): $R_t$=1.50 min; MS (ESIpos): m/z=483 [M+H]$^+$ $^1$H-NMR (400 MHz, DMSO-d6) δ [ppm]: −0.149 (0.75), −0.008 (9.15), 0.008 (5.98), 0.146 (0.74), 1.157 (1.80), 1.175 (3.54), 1.193 (1.86), 1.398 (4.14), 1.411 (12.90), 1.429 (12.48), 1.988 (6.38), 2.328 (0.75), 2.366 (0.74), 2.524 (3.41), 2.670 (0.83), 2.710 (0.77), 4.003 (0.52), 4.021 (1.51), 4.039 (1.49), 4.056 (0.50), 5.009 (0.77), 5.030 (1.24), 5.053 (1.49), 5.073 (1.45), 5.096 (1.20), 5.116 (0.66), 7.767 (11.03), 7.788 (11.45), 8.373 (1.93), 8.380 (2.11), 8.400 (3.33), 8.418 (1.88), 8.424 (1.93), 8.664 (9.19), 8.670 (8.42), 8.737 (12.44), 8.758 (11.90), 9.106 (16.00), 9.998 (5.24), 10.022 (4.95).

Example 37A

7-Chloro-1-(3,5-difluoropyridin-2-yl)-N-(1,1,1,3,3,3-hexafluoropropan-2-yl)-4-oxo-1,4-dihydro-1,8-naphthyridine-3-carboxamide

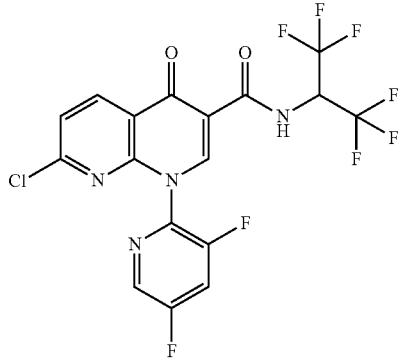 [SMILES: O=C(NC(C(F)(F)F)C(F)(F)F)c1cn(-c2ncc(F)cc2F)c2nc(Cl)ccc2c1=O]

7-Chloro-1-(3,5-difluoropyridin-2-yl)-4-oxo-1,4-dihydro-1,8-naphthyridine-3-carboxylic acid (800 mg, 2.37 mmol), 1,1,1,3,3,3-pentafluoropropan-2-amine (435 mg, 2.61 mmol) and N,N-diisopropylethylamine (1.2 ml, 7.1 mmol) were initially charged in 21 ml of ethyl acetate, T3P (50% in ethyl acetate) 2,4,6-tripropyl-1,3,5,2,4,6-trioxatriphosphorinane 2,4,6-trioxide solution (5.5 ml, purity 50%, 9.5 mmol) was added and the mixture was stirred at 80° C. overnight. More 1,1,1,3,3,3-hexafluoropropan-2-amine (79 mg, 475 µmol) was added and the mixture was stirred at 80° C. overnight. The reaction mixture was added to water and ethyl acetate. The phases were separated. The aqueous phase was extracted three more times with ethyl acetate. The combined organic phases were washed with saturated aqueous sodium chloride solution, dried over sodium sulfate, filtered and concentrated. The residue was purified by silica gel chromatography (mobile phase: cyclohexane/ethyl acetate 3:1). The product-containing fractions were combined and evaporated. The substance was recrystallized from acetonitrile, the solid was filtered off with suction, rinsed with acetonitrile and under high vacuum. This gave 495 mg of the target compound (43% of theory, purity 99%).

LC-MS (§MCW-FT-MS-M1): $R_t$=2.28 min; MS (ESIpos): m/z=487 [M+H]$^+$ $^1$H-NMR (400 MHz, DMSO-d6) δ [ppm]: −0.149 (0.46), −0.008 (4.04), 0.146 (0.49), 2.328 (0.57), 2.670 (0.62), 6.378 (0.45), 6.397 (1.11), 6.415 (1.54), 6.440 (1.62), 6.458 (1.07), 6.477 (0.41), 7.797 (9.34), 7.817 (9.78), 8.387 (1.78), 8.393 (2.08), 8.410 (2.89), 8.414 (3.15), 8.431 (1.88), 8.437 (2.04), 8.678 (8.72), 8.684 (8.40), 8.767 (9.84), 8.789 (9.45), 9.192 (16.00), 10.761 (4.75), 10.786 (4.59).

Example 38A 1-(3,5-Difluoropyridin-2-yl)-7-(2-oxa-6-azaspiro[3.3]hept-6-yl)-4-oxo-1,4-dihydro-1,8-naphthyridine-3-carboxylic acid

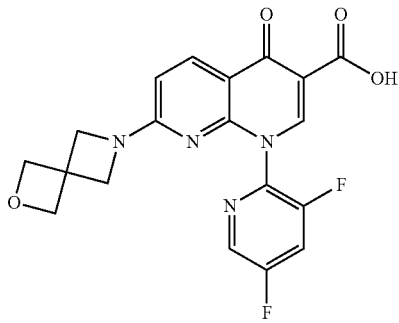 [SMILES: O=C(O)c1cn(-c2ncc(F)cc2F)c2nc(N3CC4(COC4)C3)ccc2c1=O]

7-Chloro-1-(3,5-difluoropyridin-2-yl)-4-oxo-1,4-dihydro-1,8-naphthyridine-3-carboxylic acid (300 mg, 888 µmol) was initially charged in 4.8 ml of DMF, and N,N-diisopropylethylamine (1.5 ml, 8.9 mmol) and ethanedioic acid 2-oxa-6-azaspiro[3.3]heptane (1:2) (192 mg, 666 µmol) were added at room temperature. The reaction solution was stirred at room temperature overnight. The reaction solution was added to water and acidified with 1N hydrochloric acid and the resulting precipitate was stirred briefly. The solid was filtered off and dried under high vacuum. This gave 302 mg of the target compound (83% of theory, purity 98%).

LC-MS (Methode 2): R$_t$=1.36 min; MS (ESIpos): m/z=401 [M+H]$^+$ $^1$H-NMR (400 MHz, DMSO-d6) δ [ppm]: −0.008 (2.52), 0.008 (2.29), 2.524 (1.17), 3.994 (0.50), 4.308 (0.49), 4.663 (16.00), 6.659 (5.39), 6.681 (5.50), 8.288 (5.50), 8.310 (5.36), 8.318 (1.21), 8.324 (1.28), 8.341 (1.71), 8.345 (1.82), 8.362 (1.12), 8.369 (1.22), 8.619 (5.31), 8.626 (5.15), 8.932 (9.50), 15.150 (9.52).

WORKING EXAMPLES:

Example 1

1-(3,5-Difluoropyridin-2-yl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

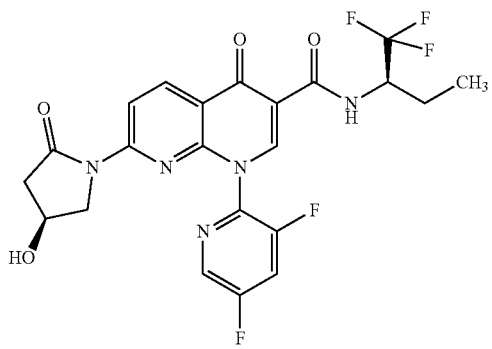

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 45.7 mg (280 µmol) of (2R)-1,1,1-trifluorobutan-2-amine hydrochloride in the presence of 85.1 mg (224 µmol) of HATU and 0.13 ml (0.75 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 66.5 mg (70% of theory, purity 100%) of the title compound.

LC-MS (Methode 2): Rt=1.74 min; MS (ESIpos): m/z=512 [M+H]+.

$^1$H-NMR (400 MHz, DMSO-d6): δ [ppm]=10.12 (d, 1H), 9.06 (s, 1H), 8.71 (d, 1H), 8.67 (br. s, 1H), 8.54 (br. t, 1H), 8.39 (td, 1H), 5.21-5.40 (m, 1H), 4.70-4.84 (m, 1H), 4.29 (br. s., 1H), 3.64-3.80 (m, 1H), 3.44-3.58 (m, 1H), 2.87-3.03 (m, 1H), 2.32-2.43 (m, 1H), 1.83-1.96 (m, 1H), 1.59-1.73 (m, 1H), 0.93-1.03 (m, 3H).

Example 2

1-(3,5-Difluoropyridin-2-yl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide

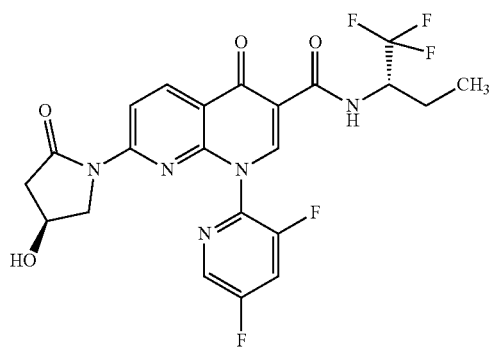

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 35.5 mg (280 µmol) of (2S)-1,1,1-trifluorobutan-2-amine in the presence of 85.1 mg (224 µmol) of HATU and 0.10 ml (0.56 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 77.2 mg (81% of theory, purity 100%) of the title compound.

LC-MS (Methode 1): Rt=0.93 min; MS (ESIpos): m/z=512 [M+H]+.

$^1$H-NMR (400 MHz, DMSO-d6): δ [ppm]=10.12 (d, 1H), 9.06 (s, 1H), 8.71 (d, 1H), 8.62-8.69 (m, 1H), 8.54 (br. t, 1H), 8.34-8.43 (m, 1H), 5.23-5.41 (m, 1H), 4.71-4.83 (m, 1H), 4.29 (br. s., 1H), 3.64-3.79 (m, 1H), 3.44-3.58 (m, 1H), 2.87-3.03 (m, 1H), 2.32-2.43 (m, 1H), 1.83-1.96 (m, 1H), 1.60-1.74 (m, 1H), 0.92-1.02 (m, 3H).

Example 3

1-(3,5-Difluoropyridin-2-yl)-7-[(4S)-4-hydroxy-2-oxopyrrolidin-1-yl]-4-oxo-N-[(2S)-1,1,1-trifluoropropan-2-yl]-1,4-dihydro-1,8-naphthyridine-3-carboxamide

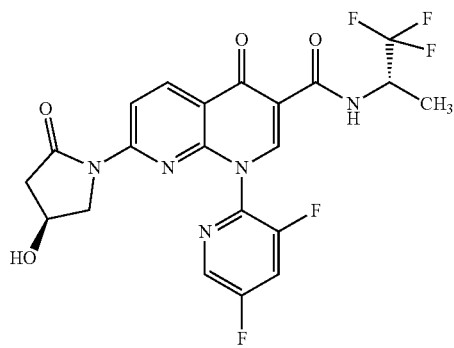 [SMILES: C[C@H](NC(=O)c1cn(-c2ncc(F)cc2F)c2nc(N3C[C@@H](O)CC3=O)ccc2c1=O)C(F)(F)F]

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 31.6 mg (280

µmol) of (2S)-1,1,1-trifluoropropan-2-amine in the presence of 85.1 mg (224 µmol) of HATU and 0.10 ml (0.56 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 67.9 mg (73% of theory, purity 100%) of the title compound.

LC-MS (Methode 2): Rt=1.62 min; MS (ESIpos): m/z=498 [M+H]+.

$^1$H-NMR (400 MHz, DMSO-d6): δ [ppm]=10.17 (d, 1H), 9.05 (s, 1H), 8.70 (d, 1H), 8.62-8.68 (m, 1H), 8.54 (br. t, 1H), 8.39 (ddd, 1H), 5.22-5.41 (m, 1H), 4.87-4.99 (m, 1H), 4.29 (br. s., 1H), 3.64-3.78 (m, 1H), 3.44-3.57 (m, 1H), 2.87-3.03 (m, 1H), 2.32-2.43 (m, 1H), 1.40 (d, 3H).

Example 4

N-[1-(2-Chlorophenyl)-2,2,2-trifluoroethyl]-1-(3,5-difluoropyridin-2-yl)-7-[(4S)-4-hydroxy-2-oxopyrrolidin-1-yl]-4-oxo-1,4-dihydro-1,8-naphthyridine-3-carboxamide (diastereomer mixture)

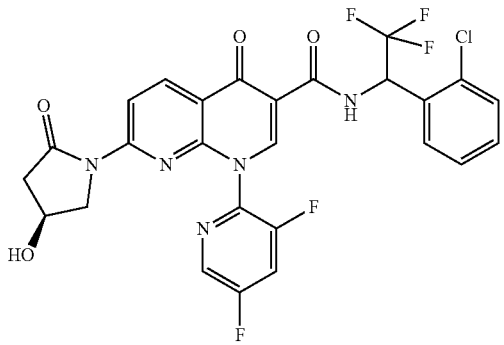 [SMILES: O=C(NC(c1ccccc1Cl)C(F)(F)F)c1cn(-c2ncc(F)cc2F)c2nc(N3C[C@@H](O)CC3=O)ccc2c1=O]

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 58.6 mg (280 µmol) of 1-(2-chlorophenyl)-2,2,2-trifluoroethanamine in the presence of 85.1 mg (224 µmol) of HATU and 0.10 ml (0.56 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 86.9 mg (78% of theory, purity 100%) of the title compound.

LC-MS (Methode 2): Rt=2.03 min; MS (ESIpos): m/z=594 [M+H]+.

$^1$H-NMR (400 MHz, DMSO-d6): δ [ppm]=11.22 (d, 1H), 9.06 (s, 1H), 8.75 (d, 1H), 8.62-8.71 (m, 1H), 8.51-8.60 (m, 1H), 8.39 (td, 1H), 7.44-7.70 (m, 4H), 6.47 (quintt, 1H), 5.20-5.42 (m, 1H), 4.29 (br. s, 1H), 3.61-3.80 (m, 1H), 3.42-3.58 (m, 1H), 2.85-3.05 (m, 1H), 2.29-2.45 (m, 1H).

67.0 mg of the title compound (diastereomer mixture) were separated into the diastereomers by chiral HPLC (preparative HPLC: column: Daicel Chiralpak AZ-H 5 µm 250×30 mm; mobile phase: 40% isohexane, 60% isopropanol; temperature: 23° C.; flow rate: 40 ml/min; UV detection: 220 nm).

This gave (in the sequence of elution from the column) 18.2 mg of diastereomer 1 (Example 5) (99% de), Rt=6.21 min and 24.0 mg of diastereomer 2 (99% de) Rt=10.47 min.

[Analytical HPLC: column: Daicel Chiralpak AZ-3 3 µm 50×4.6 mm; mobile phase: 50% isohexane, 50% isopropanol; flow rate: 1.0 ml/min; UV detection: 220 nm]

Diastereomer 2 was additionally purified by preparative HPLC (column: Chromatorex C18, 10 µm, 125*40 mm, solvent: acetonitrile, water, 0.1% formic acid), giving 11.4 mg (10% of theory, purity 100%) of the title compound from Example 6.

Example 5

N-[1-(2-Chlorophenyl)-2,2,2-trifluoroethyl]-1-(3,5-difluoropyridin-2-yl)-7-[(4S)-4-hydroxy-2-oxopyrrolidin-1-yl]-4-oxo-1,4-dihydro-1,8-naphthyridine-3-carboxamide (diastereomer 1)

LC-MS (Methode 2): Rt=2.03 min; MS (ESIpos): m/z=594 [M+H]+.

$^1$H-NMR (400 MHz, DMSO-d6): δ [ppm]=11.22 (d, 1H), 9.06 (br. s, 1H), 8.76 (d, 1H), 8.66 (br. s, 1H), 8.51-8.60 (m, 1H), 8.34-8.44 (m, 1H), 7.60-7.69 (m, 2H), 7.47-7.59 (m, 2H), 6.47 (quintt, 1H), 5.22-5.41 (m, 1H), 4.29 (br. s, 1H), 3.64-3.78 (m, 1H), 3.43-3.56 (m, 1H), 2.88-3.03 (m, 1H), 2.31-2.43 (m, 1H).

Example 6

N-[1-(2-Chlorophenyl)-2,2,2-trifluoroethyl]-1-(3,5-difluoropyridin-2-yl)-7-[(4S)-4-hydroxy-2-oxopyrrolidin-1-yl]-4-oxo-1,4-dihydro-1,8-naphthyridine-3-carboxamide (diastereomer 2)

LC-MS (Methode 2): Rt=2.02 min; MS (ESIpos): m/z=594 [M+H]+.

$^1$H-NMR (400 MHz, DMSO-d6): δ [ppm]=11.22 (d, 1H), 9.06 (s, 1H), 8.75 (d, 1H), 8.66 (dd, 1H), 8.56 (br. t, 1H), 8.39 (br. t, 1H), 7.59-7.69 (m, 2H), 7.47-7.59 (m, 2H), 6.47 (quint, 1H), 5.22-5.42 (m, 1H), 4.29 (br. s, 1H), 3.63-3.79 (m, 1H), 3.43-3.57 (m, 1H), 2.87-3.04 (m, 1H), 2.32-2.44 (m, 1H).

Example 7

N-[1-(3-Chlorophenyl)-2,2,2-trifluoroethyl]-1-(3,5-difluoropyridin-2-yl)-7-[(4S)-4-hydroxy-2-oxopyrrolidin-1-yl]-4-oxo-1,4-dihydro-1,8-naphthyridine-3-carboxamide (diastereomer mixture)

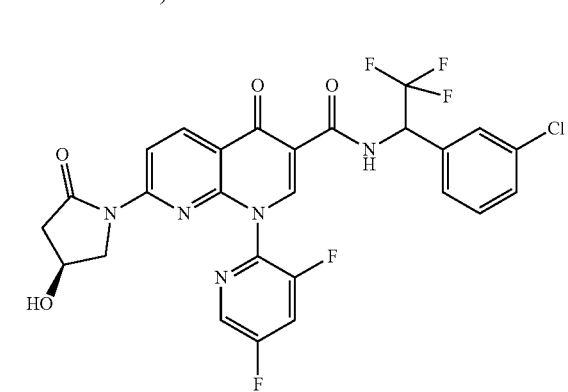

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 58.6 mg (280 µmol) of 1-(3-chlorophenyl)-2,2,2-trifluoroethanamine in the presence of 85.1 mg (224 µmol) of HATU and 0.10 ml (0.56 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 82.5 mg (75% of theory, purity 100%) of the title compound.

LC-MS (Methode 2): Rt=2.09 min; MS (ESIpos): m/z=594 [M+H]+.

¹H-NMR (400 MHz, DMSO-d6): δ [ppm]=11.11 (d, 1H), 9.06 (s, 1H), 8.77 (d, 1H), 8.62-8.71 (m, 1H), 8.56 (t, 1H), 8.39 (td, 1H), 7.69 (br. s, 1H), 7.47-7.61 (m, 3H), 6.21 (quint, 1H), 5.20-5.42 (m, 1H), 4.29 (br. s, 1H), 3.62-3.80 (m, 1H), 3.42-3.58 (m, 1H), 2.86-3.05 (m, 1H), 2.32-2.44 (m, 1H).

Example 8

N-[1-(4-Chlorophenyl)-2,2,2-trifluoroethyl]-1-(3,5-difluoropyridin-2-yl)-7-[(4S)-4-hydroxy-2-oxopyrrolidin-1-yl]-4-oxo-1,4-dihydro-1,8-naphthyridine-3-carboxamide (diastereomer mixture)

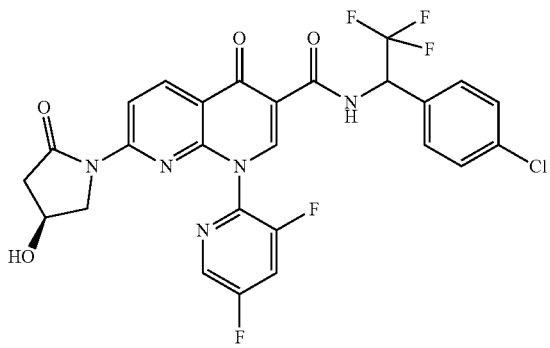 [SMILES: O=C(NC(c1ccc(Cl)cc1)C(F)(F)F)c1cn(-c2ncc(F)cc2F)c2nc(N3C[C@@H](O)CC3=O)ccc2c1=O]

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 58.6 mg (280 µmol) of 1-(4-chlorophenyl)-2,2,2-trifluoroethanamine in the presence of 85.1 mg (224 µmol) of HATU and 0.10 ml (0.56 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 91.4 mg (83% of theory, purity 100%) of the title compound.

LC-MS (Methode 1): Rt=1.16 min; MS (ESIpos): m/z=594 [M+H]+.

¹H-NMR (400 MHz, DMSO-d6): δ [ppm]=11.10 (d, 1H), 9.06 (s, 1H), 8.76 (d, 1H), 8.62-8.70 (m, 1H), 8.56 (t, 1H), 8.32-8.43 (m, 1H), 7.51-7.66 (m, 4H), 6.12-6.24 (m, 1H), 5.21-5.42 (m, 1H), 4.29 (br. s, 1H), 3.63-3.79 (m, 1H), 3.43-3.57 (m, 1H), 2.86-3.04 (m, 1H), 2.32-2.44 (m, 1H).

Example 9

N-[1-(2,6-Difluorophenyl)-2,2,2-trifluoroethyl]-1-(3,5-difluoropyridin-2-yl)-7-[(4S)-4-hydroxy-2-oxopyrrolidin-1-yl]-4-oxo-1,4-dihydro-1,8-naphthyridine-3-carboxamide (diastereomer mixture)

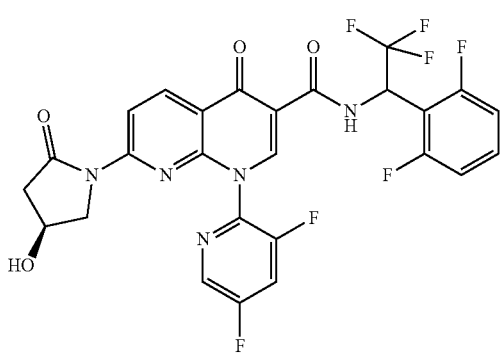 [SMILES: O=C(NC(c1c(F)cccc1F)C(F)(F)F)c1cn(-c2ncc(F)cc2F)c2nc(N3C[C@@H](O)CC3=O)ccc2c1=O]

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 59.0 mg (280 µmol) of 1-(2,6-difluorophenyl)-2,2,2-trifluoroethanamine in the presence of 85.1 mg (224 µmol) of HATU and 0.10 ml (0.56 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 89.0 mg (80% of theory, purity 100%) of the title compound.

LC-MS (Methode 1): Rt=1.10 min; MS (ESIpos): m/z=596 [M+H]+.

¹H-NMR (400 MHz, DMSO-d6): δ [ppm]=11.29 (d, 1H), 9.08 (s, 1H), 8.75 (d, 1H), 8.62-8.70 (m, 1H), 8.50-8.59 (m, 1H), 8.34-8.44 (m, 1H), 7.64 (quint, 1H), 7.32 (t, 2H), 6.44 (quint, 1H), 5.21-5.42 (m, 1H), 4.29 (br. s, 1H), 3.62-3.80 (m, 1H), 3.42-3.57 (m, 1H), 2.86-3.04 (m, 1H), 2.31-2.44 (m, 1H).

Example 10

1-(3,5-Difluoropyridin-2-yl)-7-[(4S)-4-hydroxy-2-oxopyrrolidin-1-yl]-4-oxo-N-[2,2,2-trifluoro-1-(3-fluorophenyl)ethyl]-1,4-dihydro-1,8-naphthyridine-3-carboxamide (diastereomer mixture)

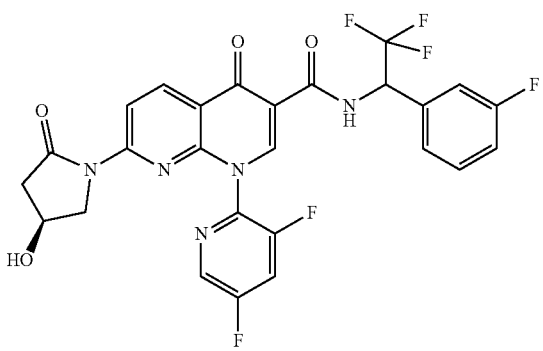 [SMILES: O=C(NC(c1cccc(F)c1)C(F)(F)F)c1cn(-c2ncc(F)cc2F)c2nc(N3C[C@@H](O)CC3=O)ccc2c1=O]

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 54.0 mg (280 µmol) of 2,2,2-trifluoro-1-(3-fluorophenyl)ethanamine in the presence of 85.1 mg (224 µmol) of HATU and 0.10 ml (0.56 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 80.5 mg (75% of theory, purity 100%) of the title compound.

LC-MS (Methode 2): Rt=1.97 min; MS (ESIpos): m/z=578 [M+H]+.

¹H-NMR (400 MHz, DMSO-d6): δ [ppm]=11.10 (d, 1H), 9.07 (s, 1H), 8.77 (d, 1H), 8.63-8.70 (m, 1H), 8.51-8.60 (m, 1H), 8.39 (td, 1H), 7.52-7.62 (m, 1H), 7.41-7.50 (m, 2H), 7.31 (br. t, 1H), 6.20 (quint, 1H), 5.21-5.42 (m, 1H), 4.29 (br. s, 1H), 3.63-3.80 (m, 1H), 3.43-3.58 (m, 1H), 2.86-3.04 (m, 1H), 2.31-2.45 (m, 1H).

Example 11

1-(3,5-Difluoropyridin-2-yl)-7-[(4S)-4-hydroxy-2-oxopyrrolidin-1-yl]-4-oxo-N-[2,2,2-trifluoro-1-(4-fluorophenyl)ethyl]-1,4-dihydro-1,8-naphthyridine-3-carboxamide (diastereomer mixture)

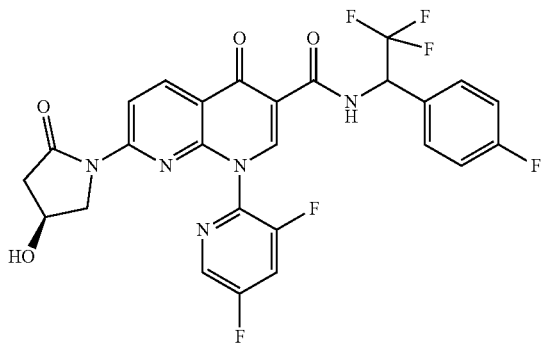 [SMILES: O=C(NC(c1ccc(F)cc1)C(F)(F)F)c1cn(-c2ncc(F)cc2F)c2nc(N3C[C@@H](O)CC3=O)ccc2c1=O]

According to General Procedure 1, 75.0 mg (186 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 54.0 mg (280 µmol) of 2,2,2-trifluoro-1-(4-fluorophenyl)ethanamine in the presence of 85.1 mg (224 µmol) of HATU and 0.10 ml (0.56 mmol) of DIPEA in 1.2 ml of DMF. The crude product was purified by preparative HPLC (column: Chromatorex C18, 10 µm, 125*40 mm, solvent: acetonitrile, water, 0.1% formic acid), giving 85.0 mg (79% of theory, purity 100%) of the title compound.

LC-MS (Methode 1): Rt=1.09 min; MS (ESIpos): m/z=578 [M+H]+.

$^1$H-NMR (400 MHz, DMSO-d6): δ [ppm]=11.09 (d, 1H), 9.06 (s, 1H), 8.76 (d, 1H), 8.62-8.70 (m, 1H), 8.51-8.60 (m, 1H), 8.39 (td, 1H), 7.61-7.69 (m, 2H), 7.30-7.39 (m, 2H), 6.16 (quint, 1H), 5.23-5.41 (m, 1H), 4.29 (br. s, 1H), 3.64-3.79 (m, 1H), 3.44-3.57 (m, 1H), 2.88-3.03 (m, 1H), 2.38 (dd, 1H).

71.0 mg of the title compound (diastereomer mixture) were separated into the diastereomers by chiral HPLC (preparative HPLC: column: Daicel Chiralpak OX-H 5 µm 250×20 mm; mobile phase: 25% n-heptane, 75% isopropanol; temperature: 50° C.; flow rate: 15 ml/min; UV detection: 220 nm).

This gave (in the sequence of elution from the column) 30.2 mg of diastereomer 1 (99% de) R$_t$=14.57 min and 30.2 mg of diastereomer 2 (99% de) R$_t$=19.05 min.

[Analytical HPLC: column: Daicel Chiralpak OX-H 5 µm 250×20 mm; mobile phase: 30% n-heptane, 70% isopropanol; temperature: 50° C.; flow rate: 15 ml/min; UV detection: 220 nm]

Diastereomer 1 was additionally obtained by preparative HPLC (acetonitrile/water/0.1% formic acid), giving 24.5 mg (23% of theory, purity 99%) of the title compound from Example 12.

Diastereomer 2 was additionally obtained by preparative HPLC (acetonitrile/water/0.1% formic acid), giving 24.6 mg (23% of theory, purity 100%) of the title compound from Example 13.

Example 12

1-(3,5-Difluoropyridin-2-yl)-7-[(4S)-4-hydroxy-2-oxopyrrolidin-1-yl]-4-oxo-N-[2,2,2-trifluoro-1-(4-fluorophenyl)ethyl]-1,4-dihydro-1,8-naphthyridine-3-carboxamide (diastereomer 1)

LC-MS (Methode 2): R$_t$=1.92 min; MS (ESIpos): m/z=578 [M+H]+.$^1$HNMR (400 MHz, DMSO-d6): δ [ppm]=11.09 (d, 1H), 9.06 (s, 1H), 8.76 (d, 1H), 8.63-8.69 (m, 1H), 8.56 (br t, 1H), 8.35-8.42 (m, 1H), 7.59-7.71 (m, 2H), 7.28-7.40 (m, 2H), 6.16 (quin, 1H), 5.23-5.41 (m, 1H), 4.23-4.34 (m, 1H), 3.63-3.78 (m, 1H), 3.44-3.57 (m, 1H), 2.88-3.03 (m, 1H), 2.34-2.46 (m, 1H).

Example 13

1-(3,5-Difluoropyridin-2-yl)-7-[(4S)-4-hydroxy-2-oxopyrrolidin-1-yl]-4-oxo-N-[2,2,2-trifluoro-1-(4-fluorophenyl)ethyl]-1,4-dihydro-1,8-naphthyridine-3-carboxamide (diastereomer 2)

LC-MS (Methode 2): R$_t$=1.90 min; MS (ESIpos): m/z=578 [M+H]+.$^1$H NMR (400 MHz, DMSO-d6): δ [ppm]=11.09 (d, 1H), 9.06 (d, 1H), 8.76 (d, 1H), 8.66 (d, 1H), 8.52-8.59 (m, 1H), 8.35-8.42 (m, 1H), 7.61-7.68 (m, 2H), 7.30-7.38 (m, 2H), 6.12-6.21 (m, 1H), 5.22-5.40 (m, 1H), 4.26-4.32 (m, 1H), 3.64-3.78 (m, 1H), 3.43-3.57 (m, 1H), 2.88-3.03 (m, 1H), 2.34-2.43 (m, 1H).

Example 14

N-[(1S)-1-Cyclopropyl-2,2,2-trifluoroethyl]-1-(3,5-difluoropyridin-2-yl)-7-[(4S)-4-hydroxy-2-oxopyrrolidin-1-yl]-4-oxo-1,4-dihydro-1,8-naphthyridine-3-carboxamide

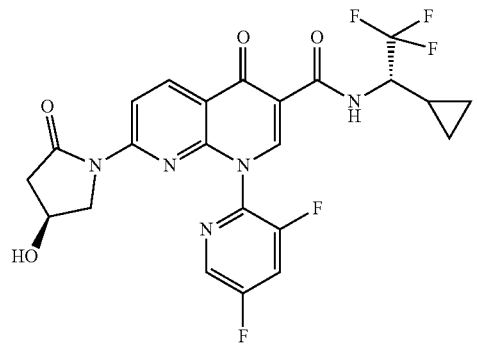 [SMILES: O=C(N[C@@H](C1CC1)C(F)(F)F)c1cn(-c2ncc(F)cc2F)c2nc(N3C[C@@H](O)CC3=O)ccc2c1=O]

According to General Procedure 2, 100 mg (218 µmol) of 7-chloro-N-[(1S)-1-cyclopropyl-2,2,2-trifluoroethyl]-1-(3,5-difluoropyridin-2-yl)-4-oxo-1,4-dihydro-1,8-naphthyridine-3-carboxamide (Example 9A) were reacted with 26.4 mg (262 µmol) of (4S)-4-hydroxypyrrolidin-2-one in the presence of 45.2 mg (327 µmol) of potassium carbonate, 9.80 mg (44.0 µmol) of palladium acetate and 25.2 mg (44.0 µmol) of Xantphos in 2.1 ml of dioxane at 80° C. The mixture was then cooled to RT, 100 mg of N-acetylcysteine were then added and the mixture for stirred for 15 min. The mixture was diluted with 15 ml of saturated aqueous sodium bicarbonate solution and 20 ml of ethyl acetate and the phases were separated. The aqueous phase was extracted three times with ethyl acetate. The combined organic phases were dried over magnesium sulfate and filtered, and the solvent was removed under reduced pressure. The crude product was dissolved in a little acetonitrile, water and formic acid, filtered through a Millipore filter and purified by preparative HPLC (column: Chromatorex C18, 10 µm, 125*40 mm, solvent: acetonitrile, water, 0.1% formic acid), giving 74.6 mg (65% of theory, purity 100%) of the title compound.

LC-MS (MCW_SQ-HSST3-Methode 1): Rt=0.94 min; MS (ESIpos): m/z=524 [M+H]+.

$^1$H-NMR (400 MHz, DMSO-d6): δ [ppm]=10.26 (d, 1H), 9.05 (s, 1H), 8.72 (d, 1H), 8.63-8.69 (m, 1H), 8.54 (t, 1H), 8.34-8.43 (m, 1H), 5.22-5.41 (m, 1H), 4.42 (sxt, 1H), 4.29 (br. s, 1H), 3.64-3.79 (m, 1H), 3.44-3.58 (m, 1H), 2.86-3.04 (m, 1H), 2.38 (dd, 1H), 1.18-1.29 (m, 1H), 0.50-0.72 (m, 3H), 0.29-0.40 (m, 1H).

Example 15

1-(3,5-Difluoropyridin-2-yl)-N-(1,1,1,3,3,3-hexafluoropropan-2-yl)-7-[(4S)-4-hydroxy-2-oxopyrrolidin-1-yl]-4-oxo-1,4-dihydro-1,8-naphthyridine-3-carboxamide

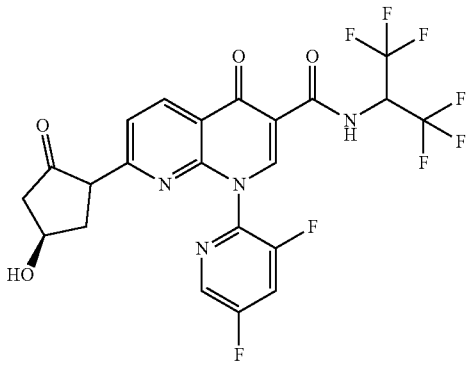 [SMILES: O=C(NC(C(F)(F)F)C(F)(F)F)c1cn(-c2ncc(F)cc2F)c2nc(C3C[C@@H](O)CC3=O)ccc2c1=O]

According to General Procedure 2, 18.6 g (38.2 mmol) of 7-chloro-1-(3,5-difluoropyridin-2-yl)-N-(1,1,1,3,3,3-hexafluoropropan-2-yl)-4-oxo-1,4-dihydro-1,8-naphthyridin-3-carboxamide (Example 10A) were reacted with 4.64 g (45.9 mmol) of (4S)-4-hydroxypyrrolidin-2-one in the presence of 7.92 g (57.3 mmol) of potassium carbonate, 1.72 g (7.64 mmol) of palladium acetate and 4.42 g (7.64 mmol) of Xantphos in 372 ml of dioxane at 80° C. The reaction mixture was pounred into water and stirred for 15 min and the precipitate was filtered off with suction, washed with water and dried under high vacuum. The solid was dissolved in acetonitrile and purified by normal phase chromatography (ethyl acetate/cyclohexane gradient). The solvent was removed under reduced pressure and the residue was recrystallized from a little acetonitrile. This gave 13.3 g (63% of theory, purity 100%) of the title compound.

LC-MS (Methode 2): Rt=1.88 min; MS (ESIpos): m/z=552 [M+H]+.

$^1$H-NMR (400 MHz, DMSO-d6): δ [ppm]=11.04 (d, 1H), 9.14 (s, 1H), 8.74 (d, 1H), 8.66-8.70 (m, 1H), 8.52-8.60 (m, 1H), 8.40 (td, 1H), 6.33-6.45 (m, 1H), 5.24-5.41 (m, 1H), 4.30 (br. s, 1H), 3.64-3.79 (m, 1H), 3.44-3.57 (m, 1H), 2.88-3.04 (m, 1H), 2.33-2.44 (m, 1H).

Example 16

N-(2,6-Dichlorophenyl)-1-(3,5-difluoropyridin-2-yl)-7-[(4S)-4-hydroxy-2-oxopyrrolidin-1-yl]-4-oxo-1,4-dihydro-1,8-naphthyridine-3-carboxamide

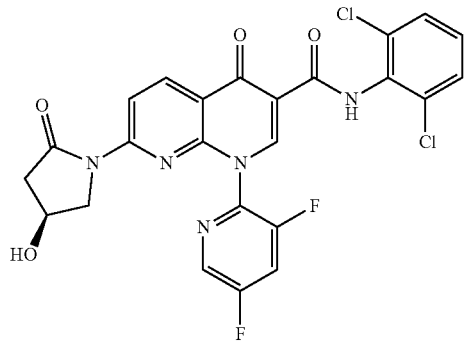 [SMILES: O=C(Nc1c(Cl)cccc1Cl)c1cn(-c2ncc(F)cc2F)c2nc(N3C[C@@H](O)CC3=O)ccc2c1=O]

According to General Procedure 2, 60.0 mg (125 μmol) of 7-chloro-N-(2,6-dichlorophenyl)-1-(3,5-difluoropyridin-2-yl)-4-oxo-1,4-dihydro-1,8-naphthyridine-3-carboxamide (Example 11B) were reacted with 15.1 mg (149 μmol) of (4S)-4-hydroxypyrrolidin-2-one in the presence of 25.8 mg (187 μmol) of potassium carbonate, 5.60 mg (24.9 μmol) of palladium acetate and 14.4 mg (24.9 μmol) of Xantphos in 0.93 ml of dioxane at 80° C. The mixture was then cooled to RT, 100 mg of N-acetylcysteine were then added and the mixture for stirred for 15 min. The mixture was then diluted with 15 ml of saturated aqueous sodium bicarbonate solution and 20 ml of ethyl acetate and the phases were separated. The aqueous phase was extracted three times with ethyl acetate. The combined organic phases were dried over magnesium sulfate and filtered, and the solvent was removed under reduced pressure. The crude product was dissolved in 3 ml of acetonitrile and 1 ml of water and purified by preparative HPLC (column: Chromatorex C18, 10 μm, 125*40 mm, solvent: acetonitrile, water, 0.1% formic acid), giving 16.7 mg (25% of theory, purity 100%) of the title compound.

LC-MS (Methode 2): Rt=1.77 min; MS (ESIpos): m/z=546 [M+H]+.

$^1$H-NMR (400 MHz, DMSO-d6): δ [ppm]=11.59 (s, 1H), 9.13 (s, 1H), 8.77 (d, 1H), 8.63-8.71 (m, 1H), 8.53-8.61 (m, 1H), 8.34-8.45 (m, 1H), 7.60 (d, 2H), 7.34-7.44 (m, 1H), 5.22-5.44 (m, 1H), 4.30 (br. s, 1H), 3.64-3.82 (m, 1H), 3.45-3.60 (m, 1H), 2.87-3.06 (m, 1H), 2.39 (dd, 1H).

Example 17

1-(3,5-Difluoropyridin-2-yl)-7-[(4S)-4-hydroxy-2-oxopyrrolidin-1-yl]-4-oxo-N-[1-(trifluoromethoxy)butan-2-yl]-1,4-dihydro-1,8-naphthyridine-3-carboxamide (diastereomer mixture)

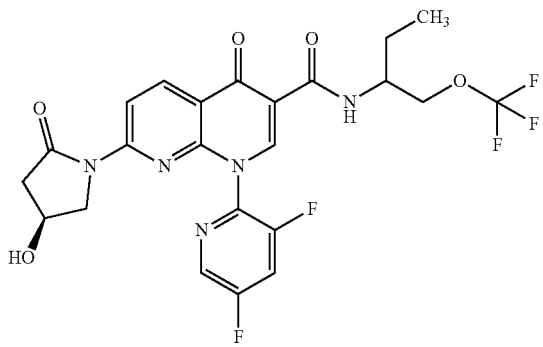 [SMILES: CCC(COC(F)(F)F)NC(=O)c1cn(-c2ncc(F)cc2F)c2nc(N3C[C@@H](O)CC3=O)ccc2c1=O]

According to General Procedure 2, 148 mg (311 μmol) of 7-chloro-1-(3,5-difluoropyridin-2-yl)-4-oxo-N-[1-(trifluoromethoxy)butan-2-yl]-1,4-dihydro-1,8-naphthyridine-3-carboxamide (Example 12A) were reacted with 31.4 mg (311 μmol) of (4S)-4-hydroxypyrrolidin-2-one in the presence of 64.5 mg (467 μmol) of potassium carbonate, 12.6 mg (56.0 μmol) of palladium acetate and 64.8 mg (112 μmol) of Xantphos in 2.6 ml of dioxane at 80° C. The reaction mixture was then diluted with ethyl acetate and washed with saturated aqueous sodium bicarbonate solution. The organic phase was dried over magnesium sulfate and filtered, and the solvent was removed under reduced pressure. The crude product was dissolved in a little acetonitrile, water and formic acid, filtered through a Millipore filter and purified by preparative HPLC (column: Chromatorex C18, 10 μm, 125*40 mm, solvent: acetonitrile, water, 0.1% formic acid). This gave 42.0 mg (25% of theory, purity 100%) of the title compound.

LC-MS (Methode 1): Rt=1.00 min; MS (ESIpos): m/z=542 [M+H]+.

$^1$H-NMR (400 MHz, DMSO-d6): δ [ppm]=9.81 (d, 1H), 9.00 (s, 1H), 8.71 (d, 1H), 8.63-8.68 (m, 1H), 8.52 (t, 1H), 8.34-8.43 (m, 1H), 5.22-5.40 (m, 1H), 4.14-4.33 (m, 4H), 3.64-3.79 (m, 1H), 3.44-3.58 (m, 1H), 2.87-3.03 (m, 1H), 2.38 (dd, 1H), 1.55-1.75 (m, 2H), 0.95 (td, 3H).

42.0 mg of the title compound (diastereomer mixture) were separated into the diastereomers by chiral HPLC (preparative HPLC: column: Daicel Chiralcel OZ-H 5 μm 250×20 mm; mobile phase: 40% isohexane, 60% ethanol; temperature: 24° C.; flow rate: 20 ml/min; UV detection: 220 nm).

This gave (in the sequence of elution from the column) 14.2 mg of diastereomer 1 (Example 18) (99% de), Rt=6.63 min and 15.1 mg of diastereomer 2 (Example 19) (99% de) Rt=9.45 min.

[Analytical HPLC: column: Daicel Chiralpak OX-3 3 μm 50×4.6 mm; mobile phase: 50% isohexane, 50% ethanol; flow rate: 1.0 ml/min; UV detection: 220 nm]

Diastereomer 1 was additionally purified by preparative HPLC (column: Chromatorex C18, 10 μm, 125*40 mm, solvent: acetonitrile, water, 0.1% formic acid), giving 11.5 mg (6.8% of theory, purity 100%) of the title compound from Example 18.

Diastereomer 2 was additionally purified by preparative HPLC (column: Chromatorex C18, 10 μm, 125*40 mm, solvent: acetonitrile, water, 0.1% formic acid), giving 11.3 mg (6.7% of theory, purity 100%) of the title compound from Example 19.

Example 18

1-(3,5-Difluoropyridin-2-yl)-7-[(4S)-4-hydroxy-2-oxopyrrolidin-1-yl]-4-oxo-N-[1-(trifluoromethoxy)butan-2-yl]-1,4-dihydro-1,8-naphthyridine-3-carboxamide (diastereomer 1)

LC-MS (Methode 2): Rt=1.77 min; MS (ESIpos): m/z=542 [M+H]+.

$^1$H-NMR (400 MHz, DMSO-d6): δ [ppm]=9.81 (d, 1H), 9.00 (s, 1H), 8.71 (d, 1H), 8.63-8.68 (m, 1H), 8.52 (t, 1H), 8.38 (ddd, 1H), 5.21-5.41 (m, 1H), 4.14-4.33 (m, 4H), 3.64-3.79 (m, 1H), 3.44-3.58 (m, 1H), 2.86-3.03 (m, 1H), 2.34-2.43 (m, 1H), 1.54-1.75 (m, 2H), 0.95 (t, 3H).

Example 19

1-(3,5-Difluoropyridin-2-yl)-7-[(4S)-4-hydroxy-2-oxopyrrolidin-1-yl]-4-oxo-N-[1-(trifluoromethoxy)butan-2-yl]-1,4-dihydro-1,8-naphthyridine-3-carboxamide (diastereomer 2)

LC-MS (Methode 2): Rt=1.76 min; MS (ESIpos): m/z=542 [M+H]+.

$^1$H-NMR (500 MHz, DMSO-d6): δ [ppm]=9.81 (d, 1H), 9.00 (s, 1H), 8.71 (d, 1H), 8.63-8.68 (m, 1H), 8.49-8.56 (m, 1H), 8.38 (td, 1H), 5.22-5.40 (m, 1H), 4.14-4.33 (m, 4H), 3.64-3.79 (m, 1H), 3.44-3.57 (m, 1H), 2.87-3.02 (m, 1H), 2.32-2.43 (m, 1H), 1.54-1.74 (m, 2H), 0.95 (td, 3H).

Example 20

1-(3-Chloro-5-fluoropyridin-2-yl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

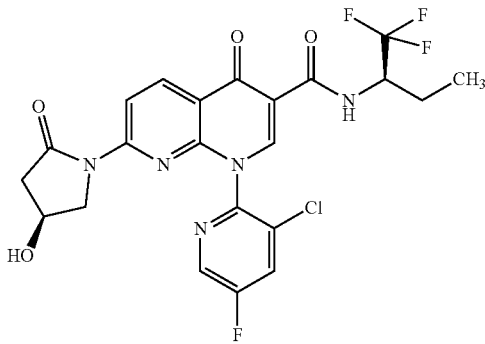 [SMILES: CC[C@@H](NC(=O)c1cn(-c2ncc(F)cc2Cl)c2nc(N3C[C@@H](O)CC3=O)ccc2c1=O)C(F)(F)F]

According to General Procedure 2, 60.0 mg (130 μmol) of 7-chloro-1-(3-chloro-5-fluoropyridin-2-yl)-4-oxo-N-[(2R)-1,1,1-trifluorobutan-2-yl]-1,4-dihydro-1,8-naphthyridine-3-carboxamide (Example 16C) were reacted with 15.7 mg (155 μmol) of (4S)-4-hydroxypyrrolidin-2-one in the presence of 26.9 mg (194 μmol) of potassium carbonate, 5.82 mg (26.0 μmol) of palladium acetate and 15.0 mg (26.0 μmol) of Xantphos in 1 ml of dioxane at 80° C. A little acetonitrile, water and formic acid were then added and the reaction solution was filtered through a Millipore filter and purified by preparative HPLC (column: Chromatorex C18, 10 μm, 125*40 mm, solvent: acetonitrile, water, 0.1% formic acid), giving 45.4 mg (66% of theory, purity 100%) of the title compound.

LC-MS (Methode 1): Rt=0.95 min; MS (ESIpos): m/z=528 [M]+.

$^1$H-NMR (500 MHz, DMSO-d6): δ [ppm]=10.14 (d, 1H), 9.08 (d, 1H), 8.76 (dd, 1H), 8.71 (dd, 1H), 8.49-8.58 (m, 2H), 5.24-5.38 (m, 1H), 4.72-4.83 (m, 1H), 4.23-4.31 (m, 1H), 3.59-3.70 (m, 1H), 3.42 (dd, 1H), 2.87-3.00 (m, 1H), 2.37 (dd, 1H), 1.85-1.94 (m, 1H), 1.62-1.73 (m, 1H), 0.98 (t, 3H).

Example 21

1-(3-Chloro-5-fluoropyridin-2-yl)-N-[(1R)-1-cyclopropyl-2,2,2-trifluoroethyl]-7-[(4S)-4-hydroxy-2-oxopyrrolidin-1-yl]-4-oxo-1,4-dihydro-1,8-naphthyridine-3-carboxamide

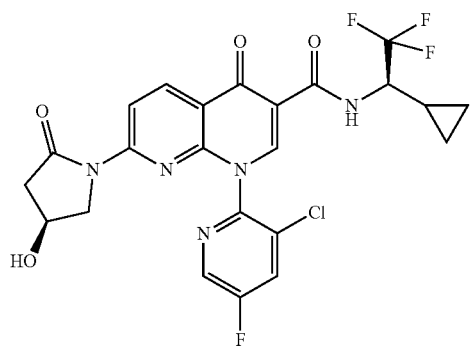 [SMILES: O=C(N[C@H](C1CC1)C(F)(F)F)c1cn(-c2ncc(F)cc2Cl)c2nc(N3C[C@@H](O)CC3=O)ccc2c1=O]

According to General Procedure 2, 60.0 mg (126 μmol) of 7-chloro-1-(3-chloro-5-fluoropyridin-2-yl)-N-[(1R)-1-cyclopropyl-2,2,2-trifluoroethyl]-4-oxo-1,4-dihydro-1,8-naphthyridine-3-carboxamide (Example 17A) were reacted with 15.3 mg (152 μmol) of (4S)-4-hydroxypyrrolidin-2-one in the presence of 26.2 mg (189 μmol) of potassium carbonate, 5.67 mg (25.0 μmol) of palladium acetate and 14.6 mg (25.0 μmol) of Xantphos in 1 ml of dioxane at 80° C. A little acetonitrile, water and formic acid were then added and the reaction solution was filtered through a Millipore filter and purified by preparative HPLC (column: Chromatorex C18, 10 μm, 125*40 mm, solvent: acetonitrile, water, 0.1% formic acid). Recrystallization from acetonitrile gave 30.1 mg (44% of theory, purity 100%) of the title compound.

LC-MS (Methode 1): Rt=0.97 min; MS (ESIpos): m/z=540 [M+H]+.

$^1$H-NMR (400 MHz, DMSO-d6): δ [ppm]=10.28 (dd, 1H), 9.07 (d, 1H), 8.69-8.79 (m, 2H), 8.49-8.59 (m, 2H), 5.23-5.38 (m, 1H), 4.36-4.49 (m, 1H), 4.22-4.31 (m, 1H), 3.64 (ddd, 1H), 3.43 (dd, 1H), 2.86-3.01 (m, 1H), 2.37 (dd, 1H), 1.18-1.29 (m, 1H), 0.50-0.72 (m, 3H), 0.30-0.40 (m, 1H).

Example 22

1-(3-Chloropyridin-2-yl)-N-[(1R)-1-cyclopropyl-2,2,2-trifluoroethyl]-7-[(4S)-4-hydroxy-2-oxopyrrolidin-1-yl]-4-oxo-1,4-dihydro-1,8-naphthyridine-3-carboxamide

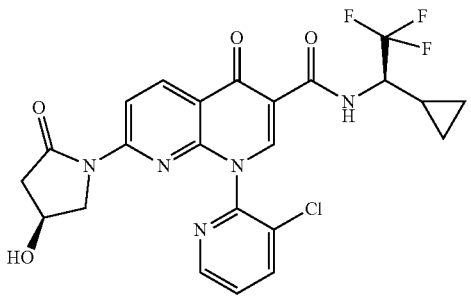 [SMILES: O=C(N[C@H](C1CC1)C(F)(F)F)c1cn(-c2ncccc2Cl)c2nc(N3C[C@@H](O)CC3=O)ccc2c1=O]

According to General Procedure 2, 60.0 mg (131 μmol) of 7-chloro-1-(3-chloropyridin-2-yl)-N-[(1R)-1-cyclopropyl-2,2,2-trifluoroethyl]-4-oxo-1,4-dihydro-1,8-naphthyridine-3-carboxamide (Example 19A) were reacted with 15.9 mg (157 μmol) of (4S)-4-hydroxypyrrolidin-2-one in the presence of 27.2 mg (197 μmol) of potassium carbonate, 5.89 mg (26.0 μmol) of palladium acetate and 15.2 mg (26.0 μmol) of Xantphos in 1 ml of dioxane at 80° C. A little acetonitrile, water and formic acid were then added and the reaction solution was filtered through a Millipore filter and purified by preparative HPLC (column: Chromatorex C18, 10 μm, 125*40 mm, solvent: acetonitrile, water, 0.1% formic acid). Recrystallization from acetonitrile gave 34.2 mg (50% of theory, purity 100%) of the title compound.

LC-MS (Methode 1): Rt=0.93 min; MS (ESIpos): m/z=522 [M+H]+.

$^1$H-NMR (400 MHz, DMSO-d6): δ [ppm]=10.30 (dd, 1H), 9.04 (d, 1H), 8.72 (d, 1H), 8.67 (ddd, 1H), 8.49-8.57 (m, 1H), 8.30-8.37 (m, 1H), 7.77 (ddd, 1H), 5.24-5.39 (m, 1H), 4.35-4.49 (m, 1H), 4.20-4.30 (m, 1H), 3.52-3.68 (m, 1H), 3.33-3.47 (m, 1H), 2.85-3.01 (m, 1H), 2.36 (dd, 1H), 1.18-1.29 (m, 1H), 0.50-0.72 (m, 3H), 0.30-0.40 (m, 1H).

Example 23

1-(3-Chloropyridin-2-yl)-7-[(4S)-4-hydroxy-2-oxopyrrolidin-1-yl]-4-oxo-N-[2,2,2-trifluoro-1-(3-fluorophenyl)ethyl]-1,4-dihydro-1,8-naphthyridine-3-carboxamide (diastereomer mixture)

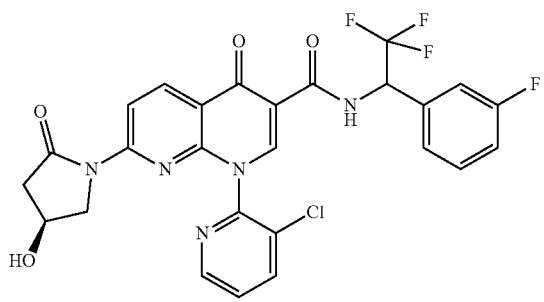 [SMILES: O=C(NC(c1cccc(F)c1)C(F)(F)F)c1cn(-c2ncccc2Cl)c2nc(N3C[C@@H](O)CC3=O)ccc2c1=O]

According to General Procedure 1, 75.0 mg (187 μmol) of 1-(3-chloropyridin-2-yl)-7-[(4S)-4-hydroxy-2-oxopyrrolidin-1-yl]-4-oxo-1,4-dihydro-1,8-naphthyridine-3-carboxylic acid (Example 27A) were reacted with 54.2 mg (281 μmol) of 2,2,2-trifluoro-1-(3-fluorophenyl)ethanamine in the presence of 85.4 mg (225 μmol) of HATU and 98 μl (561 μmol) of DIPEA in 1.2 ml of DMF. A little acetonitrile, water and formic acid were then added and the reaction solution was filtered through a Millipore filter and purified twice by preparative HPLC (column: Chromatorex C18, 10 μm, 125*40 mm, solvent: acetonitrile, water, 0.1% formic acid).

The product was re-purified by means of normal phase chromatography (ethyl acetate), giving 38.6 mg (36% of theory; purity 100%) of the title compound.

LC-MS (Methode 2): Rt=1.90 min; MS (ESIpos): m/z=576 [M+H]+.

$^1$H-NMR (400 MHz, DMSO-d6): δ [ppm]=11.14 (d, 1H), 9.07 (dd, 1H), 8.78 (d, 1H), 8.62-8.71 (m, 1H), 8.50-8.59 (m, 1H), 8.29-8.37 (m, 1H), 7.73-7.81 (m, 1H), 7.52-7.62 (m, 1H), 7.42-7.50 (m, 2H), 7.27-7.36 (m, 1H), 6.15-6.26 (m, 1H), 5.24-5.38 (m, 1H), 4.20-4.29 (m, 1H), 3.51-3.69 (m, 1H), 3.33-3.47 (m, 1H), 2.85-3.01 (m, 1H), 2.36 (dd, 1H).

Example 24

1-(3,5-Difluoropyridin-4-yl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide

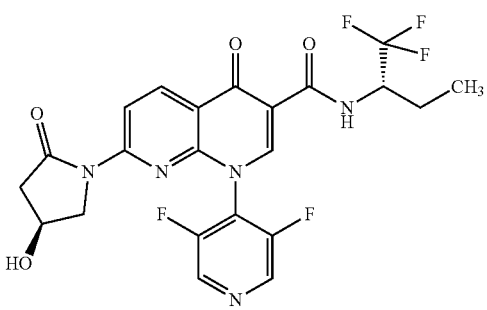 [SMILES: CC[C@H](NC(=O)c1cn(-c2c(F)cncc2F)c2nc(N3C[C@@H](O)CC3=O)ccc2c1=O)C(F)(F)F]

According to General Procedure 2, 40.0 mg (89.5 μmol) of 7-chloro-1-(3,5-difluoropyridin-4-yl)-4-oxo-N-[(2S)-1,1,1-trifluorobutan-2-yl]-1,4-dihydro-1,8-naphthyridine-3-carboxamide (Example 22C) were reacted with 10.9 mg (107 μmol) of (4S)-4-hydroxypyrrolidin-2-one in the presence of 18.6 mg (134 μmol) of potassium carbonate, 4.02 mg (18.0 μmol) of palladium acetate and 10.4 mg (18.0 μmol) of Xantphos in 3 ml of dioxane at 80° C. The mixture was then cooled to RT, water and acetonitrile were added, the mixture was filtered and the crude solution was purified by preparative HPLC (column: Reprosil, 10 μm, 125*30 mm, solvents: water, acetonitrile, 0.1% trifluoroacetic acid gradient), giving 25.9 mg (54% of theory, purity 96%) of the title compound.

LC-MS (Methode 2): Rt=1.71 min; MS (ESIpos): m/z=512 [M+H]+.

$^1$H-NMR (400 MHz, DMSO-d6): δ [ppm]=10.07 (d, 1H), 9.15 (s, 1H), 8.91 (m, 2H), 8.73 (d, 1H), 8.55 (d, 1H), 4.71-4.83 (m, 1H), 4.26-4.31 (m, 1H), 3.68 (dd, 1H), 3.43-3.51 (m, 1H), 2.94 (dd, 1H), 2.32-2.43 (m, 1H), 1.84-1.95 (m, 1H), 1.61-1.73 (m, 1H), 0.98 (t, 3H).

Example 25

N-[1-Cyclopropyl-2,2,2-trifluoroethyl]-1-(3,5-difluoropyridin-2-yl)-7-[(3S)-3-hydroxy-2-oxopyrrolidin-1-yl]-4-oxo-1,4-dihydro-1,8-naphthyridine-3-carboxamide (diastereomer mixture)

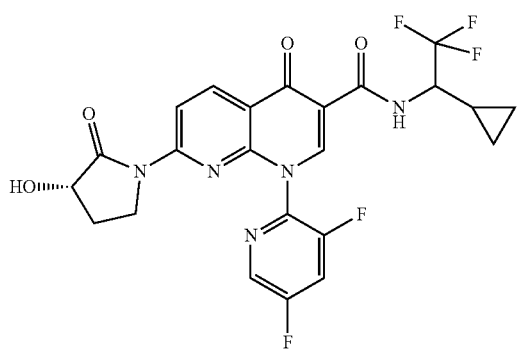 [SMILES: O=C(NC(C1CC1)C(F)(F)F)c1cn(-c2ncc(F)cc2F)c2nc(N3CC[C@H](O)C3=O)ccc2c1=O]

According to General Procedure 2, 50.0 mg (109 μmol) of 7-chloro-N-[1-cyclopropyl-2,2,2-trifluoroethyl]-1-(3,5-difluoropyridin-2-yl)-4-oxo-1,4-dihydro-1,8-naphthyridine-3-carboxamide (Example 7A) were reacted with 13.2 mg (131 μmol) of (3S)-3-hydroxypyrrolidin-2-one (CAS: 34368-52-0) in the presence of 22.6 mg (163 μmol) of potassium carbonate, 4.89 mg (22.0 μmol) of palladium acetate and 12.6 mg (22.0 μmol) of Xantphos in 1 ml of dioxane at 80° C. The mixture was then cooled to RT, water and acetonitrile were then added, the mixture was filtered and the crude solution was purified by preparative HPLC (column: Chromatorex C18, 10 μm, 125*40 mm, solvents: acetonitrile, water, 0.1% formic acid). The product was re-purified by normal phase chromatography (cyclohexane/ethyl acetate gradient), giving 20.4 mg (36% of theory; purity 100%) of the title compound.

LC-MS (Methode 2): Rt=1.77 min; MS (ESIpos): m/z=524 [M+H]+.

$^1$H-NMR (400 MHz, DMSO-d6): δ [ppm]=10.25 (d, 1H), 9.05 (s, 1H), 8.74 (d, 1H), 8.65 (d, 1H), 8.55 (t, 1H), 8.32-8.42 (m, 1H), 5.91 (dd, 1H), 4.31-4.49 (m, 2H), 3.54-3.69 (m, 1H), 3.33-3.45 (m, 1H), 2.26-2.38 (m, 1H), 1.70-1.87 (m, 1H), 1.18-1.29 (m, 1H), 0.50-0.71 (m, 3H), 0.28-0.40 (m, 1H).

Example 26

N-[1-Cyclopropyl-2,2,2-trifluoroethyl]-1-(3,5-difluoropyridin-2-yl)-7-[(3R)-3-hydroxy-2-oxopyrrolidin-1-yl]-4-oxo-1,4-dihydro-1,8-naphthyridine-3-carboxamide (diastereomer mixture)

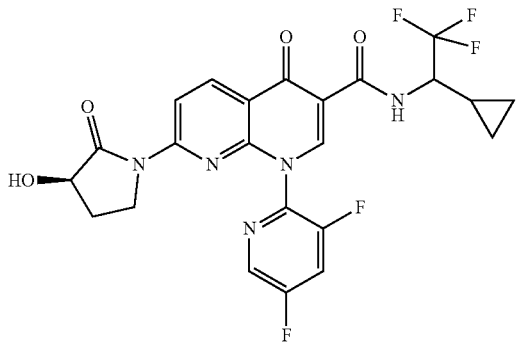 [SMILES: O=C(NC(C1CC1)C(F)(F)F)c1cn(-c2ncc(F)cc2F)c2nc(N3CC[C@@H](O)C3=O)ccc2c1=O]

According to General Procedure 2, 50.0 mg (109 μmol) of 7-chloro-N-[1-cyclopropyl-2,2,2-trifluoroethyl]-1-(3,5-difluoropyridin-2-yl)-4-oxo-1,4-dihydro-1,8-naphthyridine-3-carboxamide (Example 7A) were reacted with 13.2 mg (131 μmol) of (3R)-3-hydroxypyrrolidin-2-one (CAS: 77510-50-0) in the presence of 22.6 mg (163 μmol) of potassium carbonate, 4.89 mg (22.0 μmol) of palladium acetate and 12.6 mg (22.0 μmol) of Xantphos in 1 ml of dioxane at 80° C. The mixture was then cooled to RT, water and acetonitrile were then added, the mixture was filtered and the crude solution was purified by preparative HPLC (column: Chromatorex C18, 10 μm, 125*40 mm, solvents: acetonitrile, water, 0.1% formic acid). The product was re-purified by normal phase chromatography (cyclohexane/ethyl acetate gradient), giving 18.9 mg (32% of theory; purity 96%) of the title compound.

LC-MS (Methode 2): Rt=1.77 min; MS (ESIpos): m/z=524 [M+H]+.

$^1$H-NMR (400 MHz, DMSO-d6): δ [ppm]=10.25 (d, 1H), 9.05 (s, 1H), 8.74 (d, 1H), 8.65 (d, 1H), 8.55 (t, 1H), 8.31-8.42 (m, 1H), 5.92 (dd, 1H), 4.32-4.48 (m, 2H), 3.54-3.69 (m, 1H), 3.33-3.44 (m, 1H), 2.26-2.37 (m, 1H), 1.69-1.86 (m, 1H), 1.20-1.26 (m, 1H), 0.50-0.72 (m, 3H), 0.25-0.42 (m, 1H).

Example 27

N-[(1R)-1-Cyclopropyl-2,2,2-trifluoroethyl]-1-(3,5-difluoropyridin-2-yl)-7-[4-methyl-2-oxopyrrolidin-1-yl]-4-oxo-1,4-dihydro-1,8-naphthyridine-3-carboxamide (diastereomer mixture)

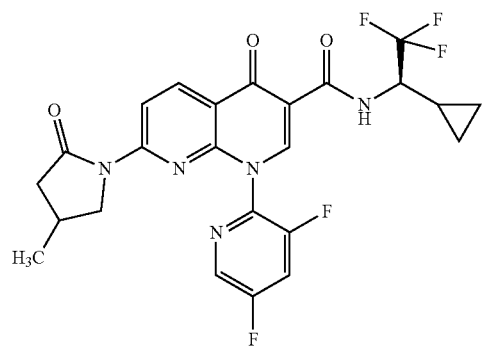 [SMILES: CC1CC(=O)N(c2ccc3c(=O)c(C(=O)N[C@H](C4CC4)C(F)(F)F)cn(-c4ncc(F)cc4F)c3n2)C1]

According to General Procedure 2, 150 mg (327 μmol) of 7-chloro-N-[(1R)-1-cyclopropyl-2,2,2-trifluoroethyl]-1-(3,5-difluoropyridin-2-yl)-4-oxo-1,4-dihydro-1,8-naphthyridine-3-carboxamide (Example 8A) were reacted with 35.8 mg (343 μmol, purity 95%) of 4-methylpyrrolidin-2-one in the presence of 67.8 mg (490 μmol) of potassium carbonate, 13.2 mg (59.0 μmol) of palladium acetate and 68.1 mg (118 μmol) of Xantphos in 2.9 ml of dioxane at 80° C. The mixture was then cooled to RT, water, formic acid and acetonitrile were added, the mixture was filtered and the crude solution was purified by preparative HPLC (column: Chromatorex C18, 10 μm, 125*40 mm, solvents: acetonitrile, water, 0.1% formic acid), giving 43.2 mg (25% of theory, purity 100%) of the title compound.

LC-MS (Methode 1): Rt=1.15 min; MS (ESIpos): m/z=522 [M+H]+.

$^1$H-NMR (400 MHz, DMSO-d6): δ [ppm]=10.26 (d, 1H), 9.04 (s, 1H), 8.70 (d, 1H), 8.65 (d, 1H), 8.52 (d, 1H), 8.34-8.45 (m, 1H), 4.35-4.49 (m, 1H), 3.67-3.83 (m, 1H), 3.09-3.24 (m, 1H), 2.68-2.81 (m, 1H), 2.22-2.47 (m, 2H), 1.18-1.29 (m, 1H), 1.03 (dd, 3H), 0.51-0.72 (m, 3H), 0.29-0.40 (m, 1H).

43.2 mg of the title compound (diastereomer mixture) were separated into the diastereomers by chiral HPLC (preparative HPLC: column: Daicel Chiralpak ID 5 μm 20×250 mm; mobile phase: 60% isohexane, 40% ethanol; temperature: 30° C.; flow rate: 15 ml/min; UV detection: 220 nm).

This gave (in the sequence of elution from the column) 17.0 mg (9.8% of theory, purity 100%) of diastereomer 1 (Example 28) (99% de) Rt=12.44 min and 16.0 mg (9.3% of theory, purity 100%) of diastereomer 2 (Example 29) (99% de) Rt=14.26 min.

[Analytical HPLC: column: Daicel Chiralpak ID 5 μm 250×4.6 mm; mobile phase: 50% isohexane, 50% ethanol; temperature: 30° C.; flow rate: 1.0 ml/min; UV detection: 220 nm]

Example 28

N-[(1R)-1-Cyclopropyl-2,2,2-trifluoroethyl]-1-(3,5-difluoropyridin-2-yl)-7-[4-methyl-2-oxopyrrolidin-1-yl]-4-oxo-1,4-dihydro-1,8-naphthyridine-3-carboxamide (diastereomer 1)

LC-MS (Methode 1): Rt=1.15 min; MS (ESIpos): m/z=522 [M+H]+.

$^1$H-NMR (400 MHz, DMSO-d6): δ [ppm]=10.26 (d, 1H), 9.04 (s, 1H), 8.70 (d, 1H), 8.65 (d, 1H), 8.52 (d, 1H), 8.33-8.44 (m, 1H), 4.42 (sxt, 1H), 3.67-3.83 (m, 1H), 3.09-3.24 (m, 1H), 2.68-2.81 (m, 1H), 2.22-2.48 (m, 2H), 1.18-1.29 (m, 1H), 1.04 (dd, 3H), 0.51-0.72 (m, 3H), 0.29-0.40 (m, 1H).

Example 29

N-[(1R)-1-Cyclopropyl-2,2,2-trifluoroethyl]-1-(3,5-difluoropyridin-2-yl)-7-[4-methyl-2-oxopyrrolidin-1-yl]-4-oxo-1,4-dihydro-1,8-naphthyridine-3-carboxamide (diastereomer 2)

LC-MS (Methode 1): Rt=1.15 min; MS (ESIpos): m/z=522 [M+H]+.

$^1$H-NMR (400 MHz, DMSO-d6): δ [ppm]=10.26 (d, 1H), 9.04 (s, 1H), 8.70 (d, 1H), 8.65 (d, 1H), 8.52 (d, 1H), 8.33-8.45 (m, 1H), 4.35-4.49 (m, 1H), 3.67-3.83 (m, 1H), 3.09-3.25 (m, 1H), 2.68-2.81 (m, 1H), 2.22-2.47 (m, 2H), 1.18-1.30 (m, 1H), 1.03 (dd, 3H), 0.50-0.72 (m, 3H), 0.28-0.40 (m, 1H).

Example 30

1-(3,5-Difluoropyridin-2-yl)-7-[4-methyl-2-oxopyrrolidin-1-yl]-4-oxo-N-[(2S)-1,1,1-trifluorobutan-2-yl]-1,4-dihydro-1,8-naphthyridine-3-carboxamide (diastereomer mixture)

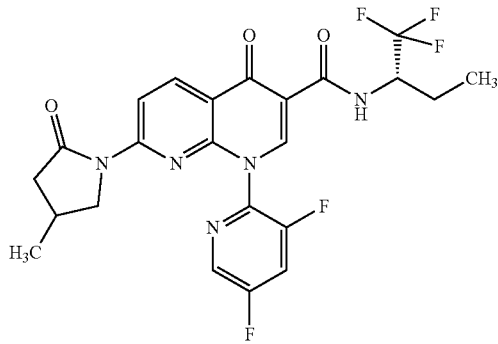 [SMILES: CC[C@H](NC(=O)c1cn(-c2ncc(F)cc2F)c2nc(N3CC(C)CC3=O)ccc2c1=O)C(F)(F)F]

According to General Procedure 2, 150.0 mg (336 µmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 36.8 mg (353 µmol, purity 95%) of 4-methylpyrrolidin-2-one in the presence of 69.6 mg (504 µmol) of potassium carbonate, 13.6 mg (60.0 µmol) of palladium acetate and 69.9 mg (121 µmol) of Xantphos in 3 ml of dioxane at 80° C. The mixture was then cooled to RT, water, formic acid and acetonitrile were added, the mixture was filtered and the crude solution was purified twice by preparative HPLC (column: Chromatorex C18, 10 µm, 125*40 mm, solvents: acetonitrile, water, 0.1% formic acid), giving 39.2 mg (23% of theory, purity 100%) of the title compound.

LC-MS (Methode 1): Rt=1.20 min; MS (ESIpos): m/z=510 [M+H]+.

$^1$H-NMR (500 MHz, DMSO-d6): δ [ppm]=10.11 (d, 1H), 9.05 (s, 1H), 8.70 (d, 1H), 8.66 (d, 1H), 8.52 (d, 1H), 8.34-8.44 (m, 1H), 4.71-4.83 (m, 1H), 3.67-3.82 (m, 1H), 3.09-3.24 (m, 1H), 2.74 (td, 1H), 2.23-2.47 (m, 2H), 1.84-1.96 (m, 1H), 1.60-1.73 (m, 1H), 0.93-1.09 (m, 6H).

Example 31

1-(3,5-Difluoropyridin-2-yl)-7-[7-hydroxy-6,6-dimethyl-5-oxo-4-azaspiro[2.4]hept-4-yl]-4-oxo-N-[(2S)-1,1,1-trifluorobutan-2-yl]-1,4-dihydro-1,8-naphthyridine-3-carboxamide (diastereomer mixture)

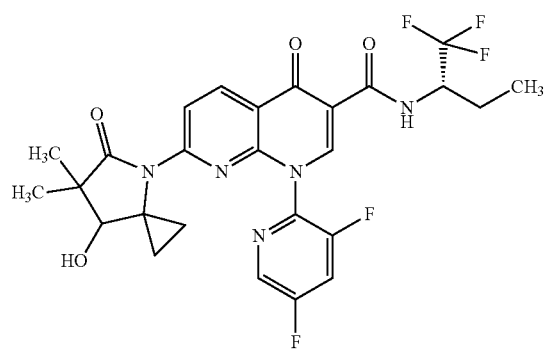 [SMILES: CC[C@H](NC(=O)c1cn(-c2ncc(F)cc2F)c2nc(N3C(=O)C(C)(C)C(O)C34CC4)ccc2c1=O)C(F)(F)F]

According to General Procedure 2, 36.0 mg (80.5 µmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 15.0 mg (96.7 µmol) of 7-hydroxy-6,6-dimethyl-4-azaspiro[2.4]heptan-5-one (Example 1D) in the presence of 16.7 mg (121 µmol) of potassium carbonate, 3.62 mg (16.1 µmol) of palladium acetate and 9.32 mg (16.1 µmol) of Xantphos in 0.6 ml of dioxane at 80° C. The mixture was then cooled to RT and then acidified with 1M aqueous hydrochloric acid, 100 mg of N-acetylcysteine were added and the mixture was stirred for 15 min. The mixture was then diluted with 15 ml of saturated aqueous sodium bicarbonate solution and 20 ml of ethyl acetate and the phases were separated. The aqueous phase was extracted three times with ethyl acetate. The combined organic phases were dried over magnesium sulfate and filtered, and the solvent was removed under reduced pressure. The crude product was dissolved in acetonitrile, water and formic acid and purified by preparative HPLC (column: Chromatorex C18, 10 µm, 125*40 mm, solvent: acetonitrile, water, 0.1% formic acid), giving 12.5 mg (27% of theory, purity 100%) of the title compound.

LC-MS (Methode 1): Rt=1.06 min; MS (ESIpos): m/z=566 [M+H]+.

1H-NMR (400 MHz, DMSO-d6): δ [ppm]=10.07 (d, 1H), 9.07 (s, 1H), 8.65-8.75 (m, 2H), 8.43-8.53 (m, 1H), 8.14 (t, 1H), 5.36 (dd, 1H), 4.69-4.85 (m, 1H), 3.42-3.59 (m, 1H), 1.83-1.96 (m, 1H), 1.59-1.74 (m, 1H), 1.13-1.21 (m, 3H), 1.08 (s, 3H), 0.88-1.05 (m, 5H), 0.36-0.75 (m, 2H).

Example 32

N-[(1R)-1-Cyclopropyl-2,2,2-trifluoroethyl]-difluoropyridin-2-yl)-7-[7-hydroxy-6,6-dimethyl-5-oxo-4-azaspiro[2.4]hept-4-yl]-4-oxo-1,4-dihydro-1,8-naphthyridine-3-carboxamide (diastereomer mixture)

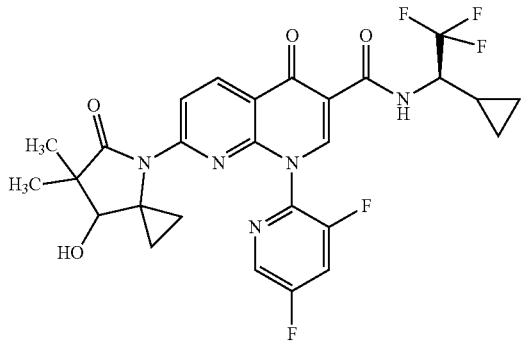 [SMILES: CC1(C)C(=O)N(c2ccc3c(=O)c(C(=O)N[C@H](C4CC4)C(F)(F)F)cn(-c4ncc(F)cc4F)c3n2)C2(CC2)C1O]

According to General Procedure 2, 24.6 mg (53.7 μmol) of 7-chloro-N-[(1R)-1-cyclopropyl-2,2,2-trifluoroethyl]-1-(3,5-difluoropyridin-2-yl)-4-oxo-1,4-dihydro-1,8-naphthyridine-3-carboxamide (Example 8A) were reacted with 10.0 mg (64.4 μmol) of 7-hydroxy-6,6-dimethyl-4-azaspiro[2.4]heptan-5-one (Example 1D) in the presence of 11.1 mg (80.5 μmol) of potassium carbonate, 2.14 mg (10.7 μmol) of palladium acetate and 6.21 mg (10.7 μmol) of Xantphos in 0.4 ml of dioxane at 80° C. The mixture was then cooled to RT and then acidified with 1M aqueous hydrochloric acid, 100 mg of N-acetylcysteine were added and the mixture was stirred for 15 min. The mixture was then diluted with 15 ml of saturated aqueous sodium bicarbonate solution and 20 ml of ethyl acetate and the phases were separated. The aqueous phase was extracted three times with ethyl acetate. The combined organic phases were dried over magnesium sulfate and filtered, and the solvent was removed under reduced pressure. The crude product was dissolved in acetonitrile and purified by preparative HPLC (column: Chromatorex C18, 10 μm, 125*40 mm, solvent: acetonitrile, water, 0.1% formic acid), giving 5.20 mg (16% of theory, purity 96%) of the title compound.

LC-MS (Methode 2): Rt=2.03 min; MS (ESIpos): m/z=578 [M+H]+.

$^1$H-NMR (400 MHz, DMSO-d6): δ [ppm]=10.21 (dd, 1H), 9.06 (s, 1H), 8.65-8.75 (m, 2H), 8.42-8.52 (m, 1H), 8.14 (t, 1H), 5.36 (dd, 1H), 4.41 (sxt, 1H), 3.42-3.58 (m, 1H), 1.19-1.29 (m, 1H), 1.17 (d, 3H), 1.08 (s, 3H), 0.95-1.06 (m, 2H), 0.31-0.73 (m, 6H).

Example 33

N-[(1S)-1-Cyclopropyl-2,2,2-trifluoroethyl]-1-(3,5-difluoropyridin-2-yl)-7-[7-hydroxy-6,6-dimethyl-5-oxo-4-azaspiro[2.4]hept-4-yl]-4-oxo-1,4-dihydro-1,8-naphthyridine-3-carboxamide (diastereomer mixture)

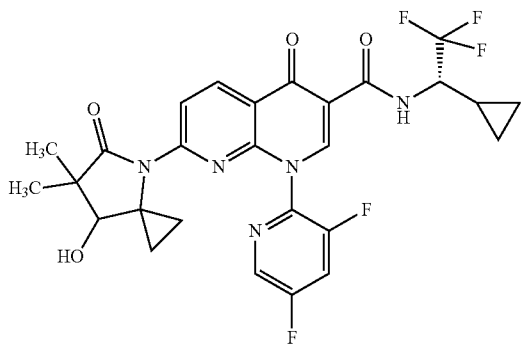 [SMILES: CC1(C)C(=O)N(c2ccc3c(=O)c(C(=O)N[C@@H](C4CC4)C(F)(F)F)cn(-c4ncc(F)cc4F)c3n2)C2(CC2)C1O]

According to General Procedure 2, 30.0 mg (65.4 μmol) of 7-chloro-N-[(1S)-1-cyclopropyl-2,2,2-trifluoroethyl]-1-(3,5-difluoropyridin-2-yl)-4-oxo-1,4-dihydro-1,8-naphthyridine-3-carboxamide (Example 9A) were reacted with 12.2 mg (78.5 μmol) of 7-hydroxy-6,6-dimethyl-4-azaspiro[2.4]heptan-5-one (Example 1D) in the presence of 13.6 mg (98.1 μmol) of potassium carbonate, 2.94 mg (13.1 μmol) of palladium acetate and 7.57 mg (13.1 μmol) of Xantphos in 0.5 ml of dioxane at 80° C. The mixture was then cooled to RT and then acidified with 1M aqueous hydrochloric acid, 100 mg of N-acetylcysteine were added and the mixture was stirred for 15 min. The mixture was then diluted with 15 ml of saturated aqueous sodium bicarbonate solution and 20 ml of ethyl acetate and the phases were separated. The aqueous phase was extracted three times with ethyl acetate. The combined organic phases were dried over magnesium sulfate and filtered, and the solvent was removed under reduced pressure. The crude product was dissolved in acetonitrile, water and formic acid, filtered through a Millipore filter and purified by preparative HPLC (column: Chromatorex C18, 10 μm, 125*40 mm, solvent: acetonitrile, water, 0.1% formic acid), giving 20.4 mg (52% of theory, purity 97%) of the title compound.

LC-MS (Methode 2): Rt=2.03 min; MS (ESIpos): m/z=578 [M+H]+.

$^1$H-NMR (400 MHz, DMSO-d6): δ [ppm]=10.21 (br. dd, 1H), 9.06 (s, 1H), 8.65-8.75 (m, 2H), 8.43-8.53 (m, 1H), 8.14 (t, 1H), 5.36 (dd, 1H), 4.34-4.48 (m, 1H), 3.42-3.59 (m, 1H), 1.20-1.28 (m, 1H), 1.13-1.20 (m, 3H), 1.08 (s, 3H), 0.89-1.06 (m, 2H), 0.29-0.75 (m, 6H).

Example 34

1-(3,5-Difluoropyridin-2-yl)-4-oxo-7-(2-oxopiperidin-1-yl)-N-[(2R)-1,1,1-trifluorobutan-2-yl]-1,4-dihydro-1,8-naphthyridine-3-carboxamide

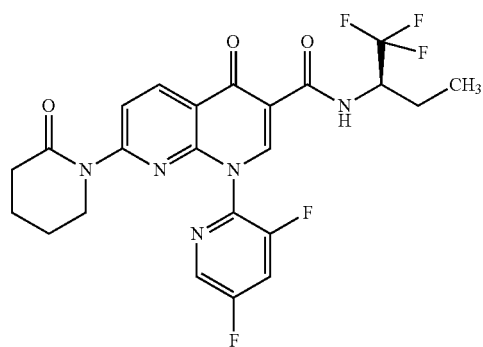 [SMILES: CC[C@@H](NC(=O)c1cn(-c2ncc(F)cc2F)c2nc(N3CCCCC3=O)ccc2c1=O)C(F)(F)F]

According to General Procedure 2, 25.0 mg (56.0 μmol) of 7-chloro-1-(3,5-difluoropyridin-2-yl)-4-oxo-N-[(2R)-1,1,1-trifluorobutan-2-yl]-1,4-dihydro-1,8-naphthyridine-3-carboxamide (Example 4C) were reacted with 6.66 mg (67.0 μmol) of piperidin-2-one in the presence of 11.6 mg (84.0 μmol) of potassium carbonate, 2.51 mg (11.0 μmol) of palladium acetate and 6.48 mg (11.0 μmol) of Xantphos in 0.5 ml of dioxane at 80° C. The mixture was then diluted with acetonitrile, water and formic acid, filtered through a Millipore filter and purified by preparative HPLC (column: Chromatorex C18, 10 μm, 125*40 mm, solvent: acetonitrile, water, 0.1% formic acid), giving 15.9 mg (56% of theory, purity 100%) of the title compound.

LC-MS (Methode 2): Rt=2.06 min; MS (ESIpos): m/z=510 [M+H]+.

$^1$H-NMR (400 MHz, DMSO-d6): δ [ppm]=10.10 (d, 1H), 9.06 (s, 1H), 8.59-8.69 (m, 2H), 8.38 (ddd, 1H), 8.16 (d, 1H), 4.70-4.85 (m, 1H), 3.47-3.63 (m, 2H), 1.84-1.97 (m, 1H), 1.60-1.82 (m, 5H), 0.92-1.04 (m, 3H).

Example 35

N-[1-Cyclopropyl-2,2,2-trifluoroethyl]-1-(3,5-difluoropyridin-2-yl)-7-[(3R,4S)-3,4-dihydroxypyrrolidin-1-yl]-4-oxo-1,4-dihydro-1,8-naphthyridine-3-carboxamide (diastereomer mixture)

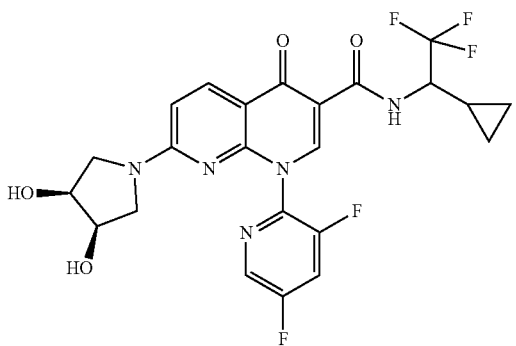 [SMILES: O=C(NC(C1CC1)C(F)(F)F)c1cn(-c2ncc(F)cc2F)c2nc(N3C[C@@H](O)[C@@H](O)C3)ccc2c1=O]

According to General Procedure 3, 50.0 mg (109 μmol) of 7-chloro-N-[1-cyclopropyl-2,2,2-trifluoroethyl]-1-(3,5-difluoropyridin-2-yl)-4-oxo-1,4-dihydro-1,8-naphthyridine-3-carboxamide (Example 7A) were reacted with 18.3 mg (131 μmol) of (3R,4S)-pyrrolidine-3,4-diol hydrochloride in the presence of 66.0 μl (381 μmol) of DIPEA in 0.5 ml of DMF. The mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 43 mg (75% of theory, purity 100%) of the title compound.

LC-MS (Methode 1): Rt=0.89 min; MS (ESIpos): m/z=526 [M+H]+.

$^1$H-NMR (400 MHz, DMSO-d6): δ [ppm]=10.55 (dd, 1H), 8.81 (s, 1H), 8.58-8.65 (m, 1H), 8.24-8.39 (m, 2H), 6.76 (d, 1H), 4.99-5.11 (m, 1H), 4.87-4.98 (m, 1H), 4.40 (sxt, 1H), 3.97-4.19 (m, 2H), 3.54-3.68 (m, 1H), 3.16-3.29 (m, 2H), 2.93-3.13 (m, 1H), 1.15-1.26 (m, 1H), 0.47-0.71 (m, 3H), 0.28-0.39 (m, 1H).

Example 36

N-[1-Cyclopropyl-2,2,2-trifluoroethyl]-1-(3,5-difluoropyridin-2-yl)-7-[1-hydroxy-3-azabicyclo[3.1.0]hex-3-yl]-4-oxo-1,4-dihydro-1,8-naphthyridine-3-carboxamide (diastereomer mixture)

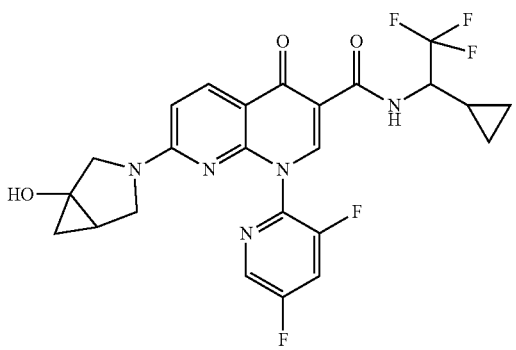 [SMILES: O=C(NC(C1CC1)C(F)(F)F)c1cn(-c2ncc(F)cc2F)c2nc(N3CC4CC4(O)C3)ccc2c1=O]

According to General Procedure 3, 60.0 mg (131 μmol) of 7-chloro-N-[1-cyclopropyl-2,2,2-trifluoroethyl]-1-(3,5-difluoropyridin-2-yl)-4-oxo-1,4-dihydro-1,8-naphthyridine-3-carboxamide (Example 7A) were reacted with 21.3 mg (157 μmol, purity 91%) of 3-azabicyclo[3.1.0]hexan-1-ol hydrochloride (racemate) in the presence of 79.7 μl (458 μmol) of DIPEA in 0.6 ml of DMF. The mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 48 mg (70% of theory, purity 100%) of the title compound.

LC-MS (Methode 2): Rt=1.90 min; MS (ESIpos): m/z=522 [M+H]+.

$^1$H-NMR (400 MHz, DMSO-d6): δ [ppm]=10.52 (dd, 1H), 8.82 (s, 1H), 8.61 (br. s, 1H), 8.24-8.43 (m, 2H), 6.68-6.85 (m, 1H), 5.91-6.12 (m, 1H), 4.39 (sxt, 1H), 3.34-3.95 (m, 3H), 3.05-3.27 (m, 1H), 1.49-1.71 (m, 1H), 1.15-1.26 (m, 1H), 0.97-1.10 (m, 1H), 0.27-0.70 (m, 5H).

Example 37

N-[(1R)-1-Cyclopropyl-2,2,2-trifluoroethyl]-1-(3,5-difluoropyridin-2-yl)-7-[1-hydroxy-3-azabicyclo[3.1.0]hex-3-yl]-4-oxo-1,4-dihydro-1,8-naphthyridine-3-carboxamide (diastereomer mixture)

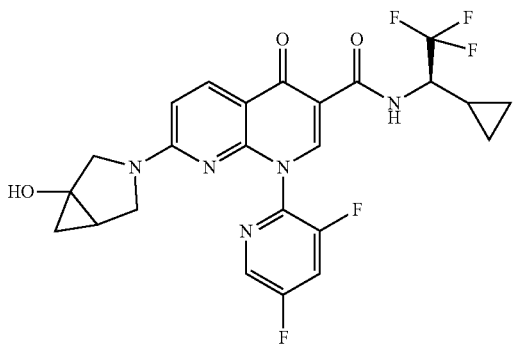 [SMILES: O=C(N[C@H](C1CC1)C(F)(F)F)c1cn(-c2ncc(F)cc2F)c2nc(N3CC4CC4(O)C3)ccc2c1=O]

According to General Procedure 3, 89.0 mg (194 μmol) of 7-chloro-N-[(1R)-1-cyclopropyl-2,2,2-trifluoroethyl]-1-(3,5-difluoropyridin-2-yl)-4-oxo-1,4-dihydro-1,8-naphthyridine-3-carboxamide (Example 8A) were reacted with 34.7 mg (233 μmol, purity 91%) of 3-azabicyclo[3.1.0]hexan-1-ol hydrochloride (racemate) in the presence of 118 μl (679 μmol) of DIPEA in 0.81 ml of DMF. The mixture was then diluted with acetonitrile, water and formic acid and the crude solution was purified by preparative HPLC (column: Chromatorex C18, 10 μm, 125*40 mm, solvent: acetonitrile, water, 0.1% formic acid), giving 60 mg (59% of theory, purity 100%) of the title compound.

LC-MS (Methode 1): Rt=1.06 min; MS (ESIpos): m/z=522 [M+H]+.

$^1$H-NMR (400 MHz, DMSO-d6): δ [ppm]=10.52 (dd, 1H), 8.82 (s, 1H), 8.61 (br. s, 1H), 8.23-8.44 (m, 2H), 6.68-6.85 (m, 1H), 5.89-6.13 (m, 1H), 4.39 (sxt, 1H), 3.35-3.96 (m, 3H), 3.04-3.26 (m, 1H), 1.49-1.71 (m, 1H), 1.15-1.26 (m, 1H), 0.95-1.10 (m, 1H), 0.26-0.71 (m, 5H).

60.0 mg of the title compound (diastereomer mixture) were separated into the diastereomers by chiral HPLC (preparative HPLC: column: Daicel Chiralpak AS-H 5 μm 250×20 mm; mobile phase: 80% isohexane, 20% isopropanol +0.2% DEA; temperature: 23° C.; flow rate: 20 ml/min; UV detection: 270 nm).

This gave (in the sequence of elution from the column) 15.5 mg of diastereomer 1 (99% de) Rt=7.52 min and 19.2 mg (96% de) of diastereomer 2 Rt=11.03 min.

[Analytical HPLC: column: Daicel Chiralpak AS-3 3 μm 50×4.6 mm; mobile phase: 80% isohexane, 20% isopropanol +0.2% DEA; flow rate: 1.0 ml/min; UV detection: 220 nm]

Diastereomer 1 was additionally purified by preparative HPLC (column: Chromatorex C18, 10 μm, 125*40 mm, solvent: acetonitrile, water, 0.1% formic acid), giving 10.0 mg (10% of theory, purity 100%) of the title compound from Example 38.

Diastereomer 2 was additionally purified by preparative HPLC (column: Chromatorex C18, 10 μm, 125*40 mm, solvent: acetonitrile, water, 0.1% formic acid), giving 9.5 mg (9% of theory, purity 100%) of the title compound from Example 39.

Example 38

N-[(1R)-1-Cyclopropyl-2,2,2-trifluoroethyl]-1-(3,5-difluoropyridin-2-yl)-7-[1-hydroxy-3-azabicyclo[3.1.0]hex-3-yl]-4-oxo-1,4-dihydro-1,8-naphthyridine-3-carboxamide (diastereomer 1)

LC-MS (Methode 2): Rt=1.90 min; MS (ESIpos): m/z=522 [M+H]+.

$^1$H-NMR (400 MHz, DMSO-d6): δ [ppm]=10.52 (dd, 1H), 8.82 (s, 1H), 8.61 (br. s, 1H), 8.24-8.43 (m, 2H), 6.68-6.85 (m, 1H), 5.90-6.12 (m, 1H), 4.33-4.46 (m, 1H), 3.37-3.97 (m, 3H), 3.06-3.26 (m, 1H), 1.50-1.70 (m, 1H), 1.16-1.26 (m, 1H), 0.97-1.11 (m, 1H), 0.28-0.70 (m, 5H).

Example 39

N-[(1R)-1-Cyclopropyl-2,2,2-trifluoroethyl]-1-(3,5-difluoropyridin-2-yl)-7-[1-hydroxy-3-azabicyclo[3.1.0]hex-3-yl]-4-oxo-1,4-dihydro-1,8-naphthyridine-3-carboxamide (diastereomer 2)

LC-MS (Methode 2): Rt=1.90 min; MS (ESIpos): m/z=522 [M+H]+.

$^1$H-NMR (400 MHz, DMSO-d6): δ [ppm]=10.52 (dd, 1H), 8.81 (s, 1H), 8.61 (br. s, 1H), 8.24-8.44 (m, 2H), 6.68-6.84 (m, 1H), 5.90-6.13 (m, 1H), 4.39 (sxt, 1H), 3.39-3.96 (m, 3H), 3.06-3.27 (m, 1H), 1.50-1.70 (m, 1H), 1.16-1.26 (m, 1H), 0.97-1.10 (m, 1H), 0.28-0.70 (m, 5H).

Example 40

N-[1-Cyclopropyl-2,2,2-trifluoroethyl]-1-(3,5-difluoropyridin-2-yl)-7-[(3R,4R)-3,4-dihydroxypyrrolidin-1-yl]-4-oxo-1,4-dihydro-1,8-naphthyridine-3-carboxamide (diastereomer mixture)

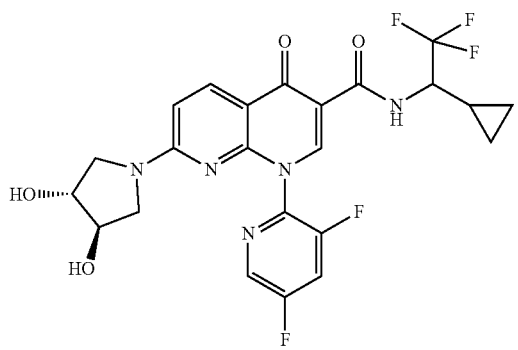 [SMILES: O=C(NC(C1CC1)C(F)(F)F)c1cn(-c2ncc(F)cc2F)c2nc(N3C[C@@H](O)[C@H](O)C3)ccc2c1=O]

According to General Procedure 3, 50.0 mg (109 μmol) of 7-chloro-N-[1-cyclopropyl-2,2,2trifluoroethyl]-1-(3,5-difluoropyridin-2-yl)-4-oxo-1,4-dihydro-1,8-naphthyridine-3-carboxamide (Example 7A) were reacted with 18.3 mg (131 μmol) of (3R,4R)-pyrrolidine-3,4-diol hydrochloride in the presence of 66.0 μl (381 μmol) of DIPEA in 0.5 ml of DMF. The mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 38.3 mg (67% of theory, purity 100%) of the title compound.

LC-MS (Methode 2): Rt=1.58 min; MS (ESIpos): m/z=526 [M+H]+.

$^1$H-NMR (400 MHz, DMSO-d6): δ [ppm]=10.56 (dd, 1H), 8.81 (s, 1H), 8.61 (d, 1H), 8.24-8.38 (m, 2H), 6.78 (d, 1H), 5.03-5.31 (m, 2H), 4.40 (sxt, 1H), 3.88-4.09 (m, 2H), 3.62 (ddd, 1H), 3.33-3.41 (m, 1H), 3.01-3.27 (m, 2H), 1.16-1.27 (m, 1H), 0.47-0.70 (m, 3H), 0.28-0.39 (m, 1H).

Example 41

1-(3,5-Difluoropyridin-2-yl)-7-[(3R,4S)-3,4-dihydroxypyrrolidin-1-yl]-4-oxo-N-[(2R)-1,1,1-trifluorobutan-2-yl]-1,4-dihydro-1,8-naphthyridine-3-carboxamide

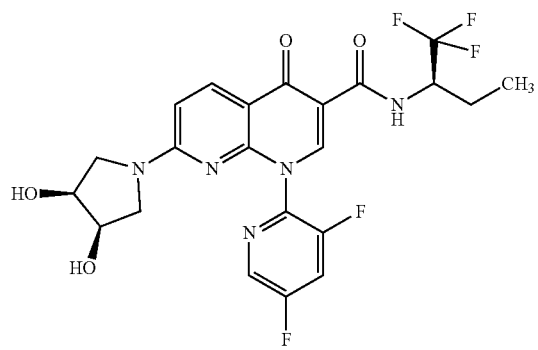 [SMILES: CC[C@@H](NC(=O)c1cn(-c2ncc(F)cc2F)c2nc(N3C[C@@H](O)[C@@H](O)C3)ccc2c1=O)C(F)(F)F]

According to General Procedure 3, 50.0 mg (112 μmol) of 7-chloro-1-(3,5-difluoropyridin-2-yl)-4-oxo-N-[(2R)-1,1,1-trifluorobutan-2-yl]-1,4-dihydro-1,8-naphthyridine-3-carboxamide (Example 4C) were reacted with 18.7 mg (134 μmol) of (3R,4S)-pyrrolidine-3,4-diol hydrochloride in the presence of 68.0 μl (392 μmol) of DIPEA in 0.5 ml of DMF. The mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 51.9 mg (90% of theory, purity 100%) of the title compound.

LC-MS (Methode 2): Rt=1.59 min; MS (ESIpos): m/z=514 [M+H]+.

$^1$H-NMR (400 MHz, DMSO-d6): δ [ppm]=10.42 (d, 1H), 8.82 (s, 1H), 8.62 (br. s, 1H), 8.30-8.39 (m, 1H), 8.27 (d, 1H), 6.76 (d, 1H), 5.04 (dd, 1H), 4.93 (dd, 1H), 4.68-4.81 (m, 1H), 4.09-4.19 (m, 1H), 3.96-4.09 (m, 1H), 3.54-3.68 (m, 1H), 3.16-3.27 (m, 1H), 2.93-3.13 (m, 1H), 1.81-1.94 (m, 1H), 1.57-1.71 (m, 1H), 0.92-1.03 (m, 3H).

Example 42

1-(3,5-Difluoropyridin-2-yl)-7-[(3R,4R)-3,4-dihydroxypyrrolidin-1-yl]-4-oxo-N-[(2R)-1,1,1-trifluorobutan-2-yl]-1,4-dihydro-1,8-naphthyridine-3-carboxamide

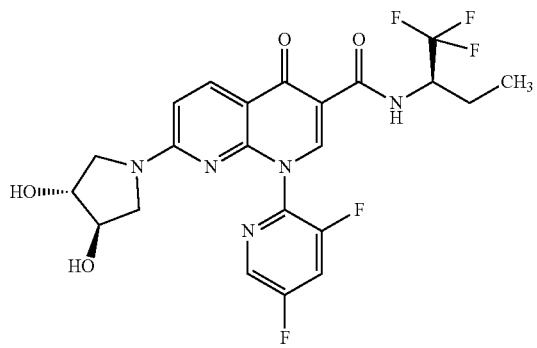 [SMILES: CC[C@@H](NC(=O)c1cn(-c2ncc(F)cc2F)c2nc(N3C[C@@H](O)[C@H](O)C3)ccc2c1=O)C(F)(F)F]

According to General Procedure 3, 50.0 mg (112 µmol) of 7-chloro-1-(3,5-difluoropyridin-2-yl)-4-oxo-N-[(2R)-1,1,1-trifluorobutan-2-yl]-1,4-dihydro-1,8-naphthyridine-3-carboxamide (Example 4C) were reacted with 18.7 mg (134 µmol) of (3R,4R)-pyrrolidine-3,4-diol hydrochloride in the presence of 68.0 µl (392 µmol) of DIPEA in 0.5 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 52.3 mg (91% of theory, purity 100%) of the title compound.

LC-MS (Methode 2): Rt=1.54 min; MS (ESIpos): m/z=514 [M+H]+.

$^1$H-NMR (400 MHz, DMSO-d6): δ [ppm]=10.43 (d, 1H), 8.82 (d, 1H), 8.62 (d, 1H), 8.30-8.37 (m, 1H), 8.28 (d, 1H), 6.78 (d, 1H), 5.01-5.32 (m, 2H), 4.66-4.83 (m, 1H), 3.86-4.11 (m, 2H), 3.55-3.70 (m, 1H), 3.33-3.40 (m, 1H), 3.19-3.29 (m, 1H), 3.01-3.18 (m, 1H), 1.81-1.96 (m, 1H), 1.56-1.73 (m, 1H), 0.97 (dd, 3H).

Example 43

1-(3,5-Difluoropyridin-2-yl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

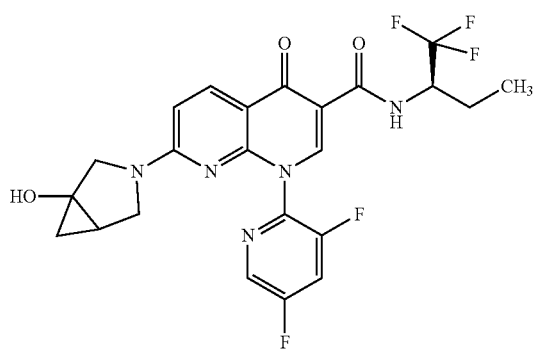 [SMILES: CC[C@@H](NC(=O)c1cn(-c2ncc(F)cc2F)c2nc(N3CC4CC4(O)C3)ccc2c1=O)C(F)(F)F]

According to General Procedure 3, 50.0 mg (112 µmol) of 7-chloro-1-(3,5-difluoropyridin-2-yl)-4-oxo-N-[(2R)-1,1,1-trifluorobutan-2-yl]-1,4-dihydro-1,8-naphthyridine-3-carboxamide (Example 4C) were reacted with 18.2 mg (134 µmol, purity 91%) of 3-azabicyclo[3.1.0]hexan-1-ol hydrochloride (racemate) in the presence of 66.0 µl (392 µmol) of DIPEA in 0.5 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 42.9 mg (75% of theory, purity 100%) of the title compound.

LC-MS (Methode 2): Rt=1.86 min; MS (ESIpos): m/z=510 [M+H]+.

$^1$H-NMR (400 MHz, DMSO-d6): δ [ppm]=10.38 (d, 1H), 8.82 (s, 1H), 8.62 (br. s, 1H), 8.23-8.44 (m, 2H), 6.67-6.84 (m, 1H), 5.90-6.13 (m, 1H), 4.67-4.82 (m, 1H), 3.35-3.96 (m, 3H), 3.04-3.27 (m, 1H), 1.81-1.94 (m, 1H), 1.50-1.71 (m, 2H), 0.90-1.10 (m, 4H), 0.35-0.50 (m, 1H).

31.0 mg of the title compound (diastereomer mixture) were separated into the diastereomers by chiral HPLC (preparative HPLC: column: Daicel Chiralcel OX-H 5 µm 250×20 mm; mobile phase: 75% isohexane, 25% isopropanol +0.2% DEA; temperature: 45° C.; flow rate: 15 ml/min; UV detection: 220 nm).

This gave (in the sequence of elution from the column) 14.0 mg of diastereomer 1 (99% de) Rt=11.78 min and 14.0 mg (99% de) of diastereomer 2 Rt=15.10 min.

[Analytical HPLC: column: Daicel Chiralcel OX-H 5 µm 250×4.6 mm; mobile phase: 75% isohexane, 25% isopropanol +0.2% DEA; temperature: 45° C.; flow rate: 1.0 ml/min; UV detection: 235 nm]

Diastereomer 1 was additionally purified by preparative HPLC (column: Chromatorex C18, 10 µm, 125*40 mm, solvent: acetonitrile, water, 0.1% formic acid), giving 9.4 mg (16% of theory, purity 100%) of the title compound from Example 44.

Diastereomer 2 was additionally purified by preparative HPLC (column: Chromatorex C18, 10 µm, 125*40 mm, solvent: acetonitrile, water, 0.1% formic acid), giving 9.2 mg (16% of theory, purity 100%) of the title compound from Example 45.

Example 44

1-(3,5-Difluoropyridin-2-yl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer 1)

LC-MS (Methode 2): Rt=1.88 min; MS (ESIpos): m/z=510 [M+H]+.

$^1$H-NMR (400 MHz, DMSO-d6): δ [ppm]=10.38 (d, 1H), 8.83 (s, 1H), 8.62 (br. s, 1H), 8.22-8.44 (m, 2H), 6.68-6.84 (m, 1H), 5.89-6.12 (m, 1H), 4.67-4.81 (m, 1H), 3.34-3.95 (m, 3H), 3.05-3.26 (m, 1H), 1.81-1.95 (m, 1H), 1.51-1.72 (m, 2H), 0.90-1.10 (m, 4H), 0.35-0.51 (m, 1H).

Example 45

1-(3,5-Difluoropyridin-2-yl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer 2)

LC-MS (Methode 2): Rt=1.88 min; MS (ESIpos): m/z=510 [M+H]+.

$^1$H-NMR (400 MHz, DMSO-d6): δ [ppm]=10.38 (d, 1H), 8.82 (s, 1H), 8.62 (br. s, 1H), 8.23-8.44 (m, 2H), 6.68-6.85 (m, 1H), 5.90-6.13 (m, 1H), 4.66-4.82 (m, 1H), 3.39-3.95

(m, 3H), 3.07-3.20 (m, 1H), 1.81-1.94 (m, 1H), 1.50-1.72 (m, 2H), 0.89-1.10 (m, 4H), 0.35-0.50 (m, 1H).

Example 46

1-(3,5-Difluoropyridin-2-yl)-7-[3-hydroxy-3-methylpyrrolidin-1-yl]-4-oxo-N-[(2R)-1,1,1-trifluorobutan-2-yl]-1,4-dihydro-1,8-naphthyridine-3-carboxamide (diastereomer mixture)

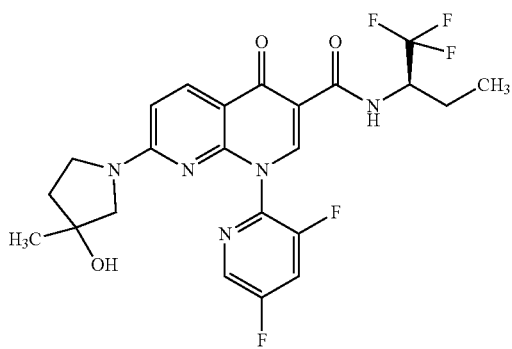 [SMILES: CC[C@@H](NC(=O)c1cn(-c2ncc(F)cc2F)c2nc(N3CCC(C)(O)C3)ccc2c1=O)C(F)(F)F]

According to General Procedure 3, 50.0 mg (112 µmol) of 7-chloro-1-(3,5-difluoropyridin-2-yl)-4-oxo--[(2R)-1,1,1-trifluorobutan-2-yl]-1,4-dihydro-1,8-naphthyridine-3-carboxamide (Example 4C) were reacted with 18.5 mg (134 µmol) of 3-methylpyrrolidin-3-ol hydrochloride (racemate) in the presence of 68.0 µl (392 µmol) of DIPEA in 0.5 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 49.4 mg (86% of theory, purity 100%) of the title compound.

LC-MS (Methode 2): Rt=1.89 min; MS (ESIpos): m/z=512 [M+H]+.

$^1$H-NMR (400 MHz, DMSO-d6): δ [ppm]=10.43 (d, 1H), 8.81 (s, 1H), 8.61 (br. s, 1H), 8.22-8.39 (m, 2H), 6.67-6.82 (m, 1H), 4.67-4.95 (m, 2H), 3.48-3.63 (m, 1H), 3.34-3.42 (m, 1H), 2.87-3.28 (m, 2H), 1.56-1.99 (m, 4H), 1.21-1.37 (m, 3H), 0.91-1.02 (m, 3H).

Example 47

1-(3-Chloropyridin-2-yl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

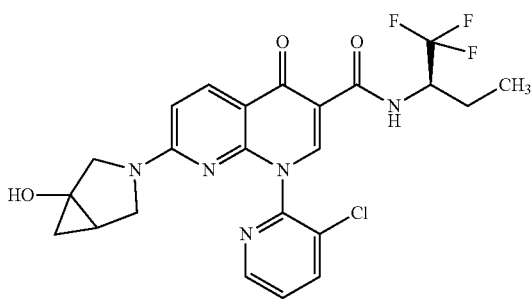 [SMILES: CC[C@@H](NC(=O)c1cn(-c2ncccc2Cl)c2nc(N3CC4CC4(O)C3)ccc2c1=O)C(F)(F)F]

According to General Procedure 3, 100 mg (225 µmol) of 7-chloro-1-(3-chloropyridin-2-yl)-4-oxo-N-[(2R)-1,1,1-trifluorobutan-2-yl]-1,4-dihydro-1,8-naphthyridine-3-carboxamide (Example 18C) were reacted with 36.5 mg (270 µmol, purity 91%) of 3-azabicyclo[3.1.0]hexan-1-ol hydrochloride (racemate) in the presence of 137 µl (786 µmol) of DIPEA in 1 ml of DMF. The mixture was then diluted with acetonitrile, water and formic acid and the crude solution was purified by preparative HPLC (column: Chromatorex C18, 10 µm, 125*40 mm, solvent: acetonitrile, water, 0.1% formic acid), giving 90.8 mg (80% of theory, purity 100%) of the title compound.

LC-MS (Methode 1): Rt=0.98 min; MS (ESIpos): m/z=508 [M+H]+.

$^1$H-NMR (400 MHz, DMSO-d6): δ [ppm]=10.43 (d, 1H), 8.78 (d, 1H), 8.59-8.67 (m, 1H), 8.28 (br. d, 2H), 7.67-7.77 (m, 1H), 6.67-6.82 (m, 1H), 5.87-6.10 (m, 1H), 4.67-4.80 (m, 1H), 3.58-3.94 (m, 1H), 3.36-3.57 (m, 2H), 2.94-3.19 (m, 1H), 1.81-1.94 (m, 1H), 1.47-1.71 (m, 2H), 0.97 (t, 4H), 0.39 (t, 1H).

Example 48

1-(3-Chloro-5-fluoropyridin-2-yl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

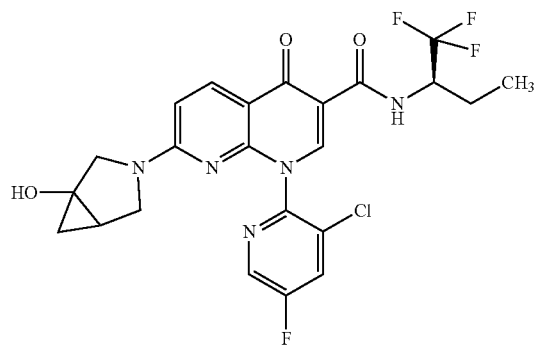 [SMILES: CC[C@@H](NC(=O)c1cn(-c2ncc(F)cc2Cl)c2nc(N3CC4CC4(O)C3)ccc2c1=O)C(F)(F)F]

According to General Procedure 3, 70.0 mg (151 µmol) of 7-chloro-1-(3-chloro-5-fluoropyridin-2-yl)-4-oxo-N-[(2R)-1,1,1-trifluorobutan-2-yl]-1,4-dihydro-1,8-naphthyridine-3-carboxamide (Example 16C) were reacted with 24.6 mg (181 µmol, purity 91%) of 3-azabicyclo[3.1.0]hexan-1-ol hydrochloride (racemate) in the presence of 92.0 µl (529 µmol) of DIPEA in 0.7 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 60.5 mg (76% of theory, purity 100%) of the title compound.

LC-MS (Methode 1): Rt=1.01 min; MS (ESIpos): m/z=526 [M+H]+.

$^1$H-NMR (500 MHz, DMSO-d6): δ [ppm]=10.42 (d, 1H), 8.82 (d, 1H), 8.68-8.76 (m, 1H), 8.45-8.57 (m, 1H), 8.27 (d, 1H), 6.68-6.81 (m, 1H), 5.89-6.11 (m, 1H), 4.68-4.80 (m, 1H), 3.59-3.93 (m, 1H), 3.35-3.58 (m, 2H), 3.02-3.21 (m, 1H), 1.83-1.93 (m, 1H), 1.49-1.70 (m, 2H), 0.94-1.07 (m, 4H), 0.40 (br. t, 1H).

Example 49

1-(3-Chloro-5-fluoropyridin-2-yl)-7-[3-hydroxy-3-methyl-pyrrolidin-1-yl]-4-oxo-N-[(2R)-1,1,1-trifluorobutan-2-yl]-1,4-dihydro-1,8-naphthyridine-3-carboxamide (diastereomer mixture)

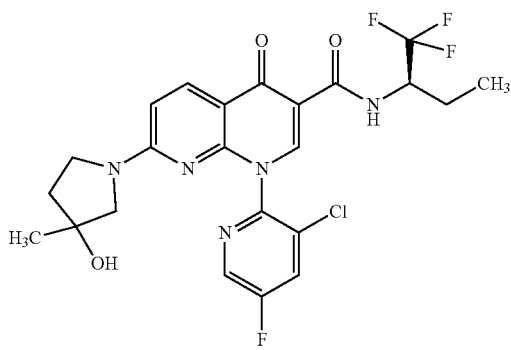 [SMILES: CC[C@@H](NC(=O)c1cn(-c2ncc(F)cc2Cl)c2nc(N3CCC(C)(O)C3)ccc2c1=O)C(F)(F)F]

According to General Procedure 3, 70.0 mg (151 μmol) of 7-chloro-1-(3-chloro-5-fluoropyridin-2-yl)-4-oxo-N-[(2R)-1,1,1-trifluorobutan-2-yl]-1,4-dihydro-1,8-naphthyridine-3-carboxamide (Example 16C) were reacted with 25.0 mg (181 μmol) of 3-methylpyrrolidin-3-ol hydrochloride (racemate) in the presence of 92.0 μl (529 μmol) of DIPEA in 0.7 ml of DMF. The mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 71.6 mg (90% of theory, purity 100%) of the title compound.

LC-MS (Methode 1): Rt=1.02 min; MS (ESIpos): m/z=528 [M+H]+.

$^1$H-NMR (500 MHz, DMSO-d6): δ [ppm]=10.46 (d, 1H), 8.80 (br. s, 1H), 8.68-8.76 (m, 1H), 8.45-8.55 (m, 1H), 8.27 (t, 1H), 6.66-6.79 (m, 1H), 4.67-4.91 (m, 2H), 3.48-3.59 (m, 1H), 2.84-3.40 (m, 3H), 1.58-1.96 (m, 4H), 1.19-1.36 (m, 3H), 0.97 (t, 3H).

Example 50

1-(3-Chloro-5-fluoropyridin-2-yl)-N-[(1R)-1-cyclopropyl-2,2,2-trifluoroethyl]-7-[(3R,4S)-3,4-dihydroxypyrrolidin-1-yl]-4-oxo-1,4-dihydro-1,8-naphthyridine-3-carboxamide

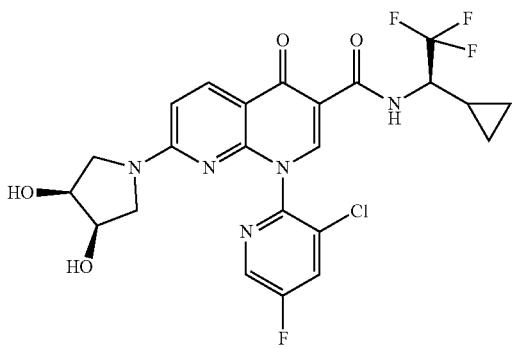 [SMILES: O=C(N[C@H](C1CC1)C(F)(F)F)c1cn(-c2ncc(F)cc2Cl)c2nc(N3C[C@@H](O)[C@@H](O)C3)ccc2c1=O]

According to General Procedure 3, 40.0 mg (84.2 μmol) of 7-chloro-1-(3-chloro-5-fluoropyridin-2-yl)-N-[(1R)-1-cyclopropyl-2,2,2-trifluoroethyl]-4-oxo-1,4-dihydro-1,8-naphthyridine-3-carboxamide (Example 17A) were reacted with 14.1 mg (101 μmol) of (3R,4S)-pyrrolidine-3,4-diol hydrochloride in the presence of 51.0 μl (295 μmol) of DIPEA in 0.4 ml of DMF. The mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 40.2 mg (88% of theory, purity 100%) of the title compound.

LC-MS (Methode 2): Rt=1.70 min; MS (ESIpos): m/z=542 [M+H]+.

$^1$H-NMR (400 MHz, DMSO-d6): δ [ppm]=10.58 (dd, 1H), 8.76-8.84 (m, 1H), 8.71 (dd, 1H), 8.50 (d, 1H), 8.27 (d, 1H), 6.74 (d, 1H), 4.84-5.10 (m, 2H), 4.31-4.47 (m, 1H), 3.92-4.19 (m, 2H), 3.50-3.67 (m, 1H), 3.08-3.28 (m, 2H), 2.87-3.06 (m, 1H), 1.13-1.27 (m, 1H), 0.46-0.71 (m, 3H), 0.27-0.39 (m, 1H).

Example 51

1-(3-Chloro-5-fluoropyridin-2-yl)-N-[(1R)-1-cyclopropyl-2,2,2-trifluoroethyl]-7-[(3R,4R)-3,4-dihydroxypyrrolidin-1-yl]-4-oxo-1,4-dihydro-1,8-naphthyridine-3-carboxamide

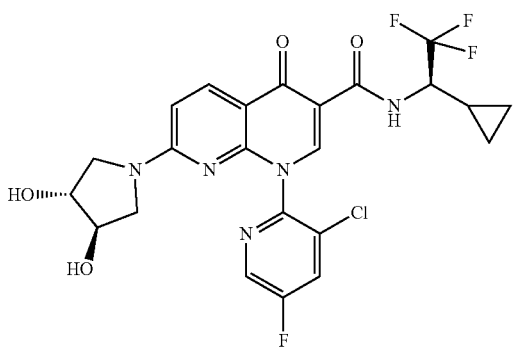 [SMILES: O=C(N[C@H](C1CC1)C(F)(F)F)c1cn(-c2ncc(F)cc2Cl)c2nc(N3C[C@@H](O)[C@H](O)C3)ccc2c1=O]

According to General Procedure 3, 40.0 mg (84.2 μmol) of 7-chloro-1-(3-chloro-5-fluoropyridin-2-yl)-N-[(1R)-1-cyclopropyl-2,2,2-trifluoroethyl]-4-oxo-1,4-dihydro-1,8-naphthyridine-3-carboxamide (Example 17A) were reacted with 14.1 mg (101 μmol) of (3R,4R)-pyrrolidine-3,4-diol hydrochloride in the presence of 51.0 μl (295 μmol) of DIPEA in 0.4 ml of DMF. The mixture was then diluted with acetonitrile, water and formic acid and the crude solution was purified by preparative HPLC (column: Chromatorex C18, 10 μm, 125*40 mm, solvent: acetonitrile, water, 0.1% formic acid), giving 39.4 mg (86% of theory, purity 100%) of the title compound.

LC-MS (Methode 2): Rt=1.65 min; MS (ESIpos): m/z=542 [M+H]+.

$^1$H-NMR (400 MHz, DMSO-d6): δ [ppm]=10.59 (dd, 1H), 8.80 (d, 1H), 8.71 (t, 1H), 8.50 (dt, 1H), 8.28 (d, 1H), 6.76 (d, 1H), 5.04-5.29 (m, 2H), 4.33-4.46 (m, 1H), 4.04 (br. s, 1H), 3.91 (br. s, 1H), 3.61 (td, 1H), 3.12-3.39 (m, 2H), 3.03 (dd, 1H), 1.14-1.27 (m, 1H), 0.46-0.71 (m, 3H), 0.29-0.39 (m, 1H).

Example 52

1-(3-Chloro-5-fluoropyridin-2-yl)-N-[(1R)-1-cyclopropyl-2,2,2-trifluoroethyl]-7-[1-hydroxy-3-azabicyclo[3.1.0]hex-3-yl]-4-oxo-1,4-dihydro-1,8-naphthyridine-3-carboxamide (diastereomer mixture)

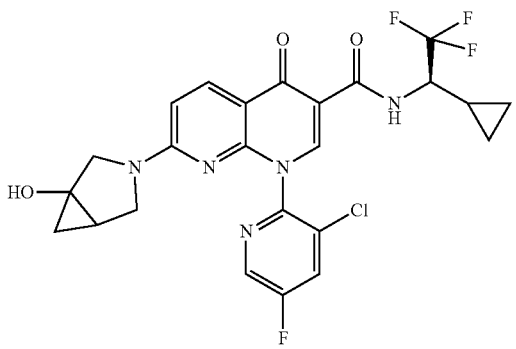 [SMILES: O=C(N[C@H](C1CC1)C(F)(F)F)c1cn(-c2ncc(F)cc2Cl)c2nc(N3CC4CC4(O)C3)ccc2c1=O]

According to General Procedure 3, 70.0 mg (147 µmol) of 7-chloro-1-(3-chloro-5-fluoropyridin-2-yl)-N-[(1R)-1-cyclopropyl-2,2,2-trifluoroethyl]-4-oxo-1,4-dihydro-1,8-naphthyridine-3-carboxamide (Example 17A) were reacted with 24.0 mg (177 µmol, purity 91%) of 3-azabicyclo[3.1.0]hexan-1-ol hydrochloride (racemate) in the presence of 90.0 µl (516 µmol) of DIPEA in 0.7 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 62.4 mg (78% of theory, purity 99%) of the title compound.

LC-MS (Methode 2): Rt=1.96 min; MS (ESIpos): m/z=538 [M+H]+.

$^1$H-NMR (400 MHz, DMSO-d6): δ [ppm]=10.55 (dd, 1H), 8.81 (d, 1H), 8.72 (br. s, 1H), 8.44-8.58 (m, 1H), 8.28 (d, 1H), 6.68-6.82 (m, 1H), 5.89-6.11 (m, 1H), 4.32-4.45 (m, 1H), 3.59-3.94 (m, 1H), 3.38-3.56 (m, 1.5H), 2.99-3.28 (m, 1.5H), 1.49-1.70 (m, 1H), 1.15-1.26 (m, 1H), 0.96-1.08 (m, 1H), 0.48-0.70 (m, 3H), 0.29-0.44 (m, 2H).

Example 53

1-(3-Chloro-5-fluoropyridin-2-yl)-N-[(1R)-1-cyclopropyl-2,2,2-trifluoroethyl]-7-[3-hydroxy-3-methylpyrrolidin-1-yl]-4-oxo-1,4-dihydro-1,8-naphthyridine-3-carboxamide (diastereomer mixture)

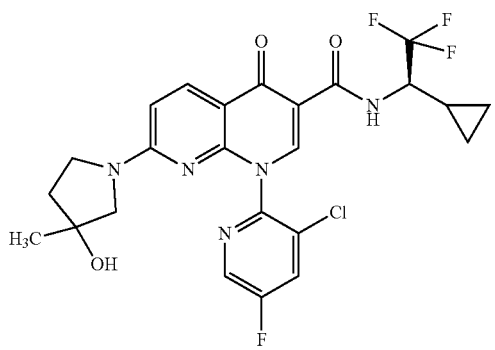 [SMILES: CC1(O)CCN(c2ccc3c(=O)c(C(=O)N[C@H](C4CC4)C(F)(F)F)cn(-c4ncc(F)cc4Cl)c3n2)C1]

According to General Procedure 3, 70.0 mg (147 µmol) of 7-chloro-1-(3-chloro-5-fluoropyridin-2-yl)-N-[(1R)-1-cyclopropyl-2,2,2-trifluoroethyl]-4-oxo-1,4-dihydro-1,8-naphthyridine-3-carboxamide (Example 17A) were reacted with 24.3 mg (177 µmol) of 3-methylpyrrolidin-3-ol hydrochloride (racemate) in the presence of 90.0 µl (516 µmol) of DIPEA in 0.7 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 71.7 mg (90% of theory, purity 100%) of the title compound.

LC-MS (Methode 2): Rt=1.98 min; MS (ESIpos): m/z=540 [M+H]+.

$^1$H-NMR (400 MHz, DMSO-d6): δ [ppm]=10.60 (dd, 1H), 8.79 (br. s, 1H), 8.66-8.75 (m, 1H), 8.49 (t, 1H), 8.27 (t, 1H), 6.65-6.80 (m, 1H), 4.73-4.91 (m, 1H), 4.33-4.45 (m, 1H), 3.48-3.60 (m, 1H), 3.28-3.44 (m, 1H), 2.84-3.27 (m, 2H), 1.71-1.96 (m, 2H), 1.15-1.36 (m, 4H), 0.46-0.71 (m, 3H), 0.29-0.39 (m, 1H).

Example 54

1-(3-Chloropyridin-2-yl)-N-[(1R)-1-cyclopropyl-2,2,2-trifluoroethyl]-7-[1-hydroxy-3-azabicyclo[3.1.0]hex-3-yl]-4-oxo-1,4-dihydro-1,8-naphthyridine-3-carboxamide (diastereomer mixture)

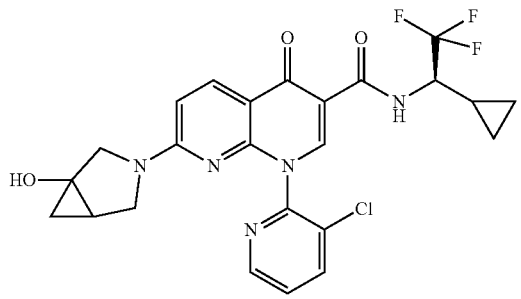 [SMILES: O=C(N[C@H](C1CC1)C(F)(F)F)c1cn(-c2ncccc2Cl)c2nc(N3CC4CC4(O)C3)ccc2c1=O]

According to General Procedure 3, 70.0 mg (153 µmol) of 7-chloro-1-(3-chloropyridin-2-yl)-N-[(1R)-1-cyclopropyl-2,2,2-trifluoroethyl]-4-oxo-1,4-dihydro-1,8-naphthyridine-3-carboxamide (Example 19A) were reacted with 24.9 mg (184 µmol, purity 91%) of 3-azabicyclo[3.1.0]hexan-1-ol hydrochloride (racemate) in the presence of 93.0 µl (536 µmol) of DIPEA in 0.7 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 61.5 mg (77% of theory, purity 100%) of the title compound.

LC-MS (Methode 1): Rt=0.99 min; MS (ESIpos): m/z=520 [M+H]+.

$^1$H-NMR (400 MHz, DMSO-d6): δ [ppm]=10.56 (dd, 1H), 8.77 (d, 1H), 8.63 (d, 1H), 8.28 (d, 2H), 7.66-7.77 (m, 1H), 6.66-6.82 (m, 1H), 5.86-6.11 (m, 1H), 4.32-4.46 (m, 1H), 3.57-3.94 (m, 1H), 3.38-3.55 (m, 1H), 2.90-3.29 (m, 2H), 1.46-1.69 (m, 1H), 1.13-1.26 (m, 1H), 0.95-1.10 (m, 1H), 0.47-0.71 (m, 3H), 0.28-0.45 (m, 2H).

Example 55

1-(3,5-Difluoropyridin-2-yl)-7-[(3R,4S)-3,4-dihydroxypyrrolidin-1-yl]-N-(1,1,1,3,3,3-hexafluoropropan-2-yl)-4-oxo-1,4-dihydro-1,8-naphthyridine-3-carboxamide

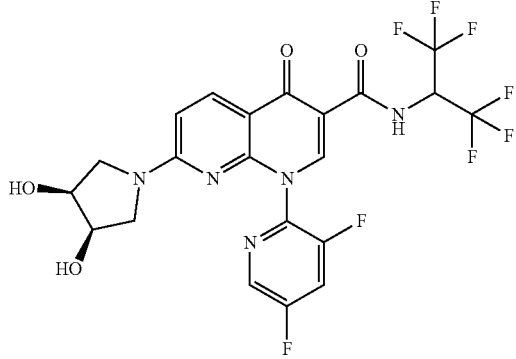 [SMILES: O=C(NC(C(F)(F)F)C(F)(F)F)c1cn(-c2ncc(F)cc2F)c2nc(N3C[C@@H](O)[C@@H](O)C3)ccc2c1=O]

According to General Procedure 3, 40.0 mg (82.2 µmol) of 7-chloro-1-(3,5-difluoropyridin-2-yl)-N-(1,1,1,3,3,3-hexafluoropropan-2-yl)-4-oxo-1,4-dihydro-1,8-naphthyridine-3-carboxamide (Example 10A) were reacted with 13.8 mg (98.6 µmol) of (3R,4S)-pyrrolidine-3,4-diol hydrochloride in the presence of 50.0 µl (288 µmol) of DIPEA in 0.4 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 35.6 mg (78% of theory, purity 100%) of the title compound.

LC-MS (Methode 2): Rt=1.76 min; MS (ESIpos): m/z=554 [M+H]+.

$^1$H-NMR (400 MHz, DMSO-d6): δ [ppm]=11.40 (d, 1H), 8.91 (s, 1H), 8.59-8.66 (m, 1H), 8.25-8.41 (m, 2H), 6.78 (d, 1H), 6.25-6.40 (m, 1H), 4.87-5.12 (m, 2H), 3.96-4.20 (m, 2H), 3.55-3.69 (m, 1H), 3.16-3.28 (m, 1H), 2.92-3.13 (m, 1H).

Example 56

1-(3,5-Difluoropyridin-2-yl)-7-[(3R,4R)-3,4-dihydroxypyrrolidin-1-yl]-N-(1,1,1,3,3,3-hexafluoropropan-2-yl)-4-oxo-1,4-dihydro-1,8-naphthyridine-3-carboxamide

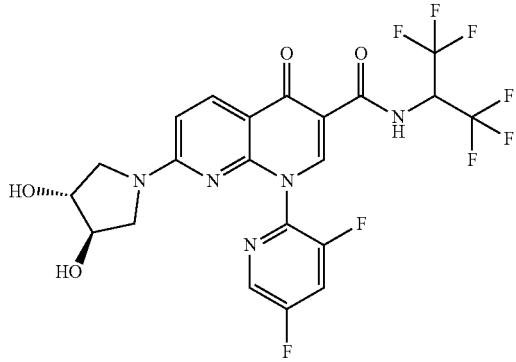 [SMILES: O=C(NC(C(F)(F)F)C(F)(F)F)c1cn(-c2ncc(F)cc2F)c2nc(N3C[C@@H](O)[C@H](O)C3)ccc2c1=O]

According to General Procedure 3, 40.0 mg (82.2 µmol) of 7-chloro-1-(3,5-difluoropyridin-2-yl)-N-(1,1, 1,3,3,3-hexafluoropropan-2-yl)-4-oxo-1,4-dihydro-1,8-naphthyridine-3-carboxamide (Example 10A) were reacted with 13.8 mg (98.6 µmol) of (3R,4R)-pyrrolidine-3,4-diol hydrochloride in the presence of 50.0 µl (288 µmol) of DIPEA in 0.4 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 39.3 mg (86% of theory, purity 100%) of the title compound.

LC-MS (Methode 2): Rt=1.71 min; MS (ESIpos): m/z=554 [M+H]+.

$^1$H-NMR (400 MHz, DMSO-d6): δ [ppm]=11.41 (d, 1H), 8.91 (d, 1H), 8.63 (d, 1H), 8.25-8.40 (m, 2H), 6.81 (d, 1H), 6.26-6.39 (m, 1H), 5.04-5.32 (m, 2H), 3.88-4.09 (m, 2H), 3.56-3.69 (m, 1H), 3.33-3.42 (m, 1H), 3.02-3.29 (m, 2H).

Example 57

1-(3,5-Difluoropyridin-2-yl)-N-(1,1,1,3,3,3-hexafluoropropan-2-yl)-7-[1-hydroxy-3-azabicyclo[3.1.0]hex-3-yl]-4-oxo-1,4-dihydro-1,8-naphthyridine-3-carboxamide (racemate)

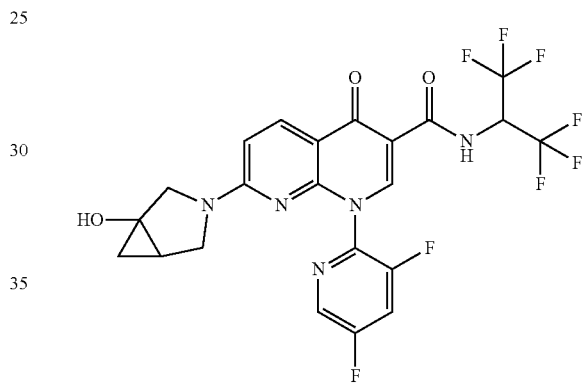

According to General Procedure 3, 70.0 mg (144 µmol) of 7-chloro-1-(3,5-difluoropyridin-2-yl)-N-(1,1,1,3,3,3-hexafluoropropan-2-yl)-4-oxo-1,4-dihydro-1,8-naphthyridine-3-carboxamide (Example 10A) were reacted with 23.4 mg (173 µmol, purity 91%) of 3-azabicyclo[3.1.0]hexan-1-ol hydrochloride (racemate) in the presence of 88.0 µl (503 µmol) of DIPEA in 0.7 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 56.1 mg (71% of theory, purity 100%) of the title compound.

LC-MS (Methode 2): Rt=2.03 min; MS (ESIpos): m/z=550 [M+H]+.

$^1$H-NMR (400 MHz, DMSO-d6): δ [ppm]=11.36 (d, 1H), 8.92 (s, 1H), 8.63 (br. s, 1H), 8.25-8.46 (m, 2H), 6.71-6.87 (m, 1H), 6.26-6.40 (m, 1H), 5.91-6.13 (m, 1H), 3.39-3.98 (m, 3H), 3.06-3.27 (m, 1H), 1.50-1.71 (m, 1H), 0.97-1.11 (m, 1H), 0.36-0.51 (m, 1H).

43.0 mg of the title compound (diastereomer mixture) were separated into the diastereomers by chiral HPLC (preparative HPLC: column: Daicel Chiralpak IA 5 µm 250×30 mm; mobile phase: 80% isohexane, 20% ethanol; temperature: 23° C.; flow rate: 20 ml/min; UV detection: 220 nm).

This gave (in the sequence of elution from the column) 17.2 mg of diastereomer 1 (99% de) Rt=7.50 min and 18.2 mg (99% de) of diastereomer 2 Rt=10.30 min.

[Analytical HPLC: column: Daicel Chiralpak IA-3 3 µm 50×4.6 mm; mobile phase: 80% isohexane, 20% ethanol; flow rate: 1.0 ml/min; UV detection: 220 nm]

Diastereomer 1 was additionally purified by preparative HPLC (column: Chromatorex C18, 10 µm, 125*40 mm, solvent: acetonitrile, water, 0.1% formic acid), giving 11.0 mg (14% of theory, purity 100%) of the title compound from Example 58.

Diastereomer 2 was additionally purified by preparative HPLC (column: Chromatorex C18, 10 µm, 125*40 mm, solvent: acetonitrile, water, 0.1% formic acid), giving 15.0 mg (19% of theory, purity 100%) of the title compound from Example 59.

Example 58

1-(3,5-Difluoropyridin-2-yl)-N-(1,1,1,3,3,3-hexafluoropropan-2-yl)-7-[1-hydroxy-3-azabicyclo[3.1.0]hex-3-yl]-4-oxo-1,4-dihydro-1,8-naphthyridine-3-carboxamide (diastereomer 1)

LC-MS (Methode 1): Rt=1.07 min; MS (ESIpos): m/z=550 [M+H]+.

$^1$H-NMR (400 MHz, DMSO-d6): δ [ppm]=11.36 (d, 1H), 8.92 (s, 1H), 8.58-8.68 (m, 1H), 8.25-8.44 (m, 2H), 6.72-6.86 (m, 1H), 6.27-6.39 (m, 1H), 5.92-6.12 (m, 1H), 3.38-3.95 (m, 3H), 3.07-3.25 (m, 1H), 1.51-1.70 (m, 1H), 0.97-1.11 (m, 1H), 0.37-0.50 (m, 1H).

Example 59

1-(3,5-Difluoropyridin-2-yl)-N-(1,1,1,3,3,3-hexafluoropropan-2-yl)-7-[1-hydroxy-3-azabicyclo[3.1.0]hex-3-yl]-4-oxo-1,4-dihydro-1,8-naphthyridine-3-carboxamide (diastereomer 2)

LC-MS (Methode 2): Rt=2.02 min; MS (ESIpos): m/z=550 [M+H]+.

$^1$H-NMR (400 MHz, DMSO-d6): δ [ppm]=11.36 (d, 1H), 8.92 (s, 1H), 8.63 (br. s, 1H), 8.25-8.45 (m, 2H), 6.71-6.87 (m, 1H), 6.26-6.40 (m, 1H), 5.91-6.14 (m, 1H), 3.40-3.97 (m, 3H), 3.07-3.26 (m, 1H), 1.50-1.71 (m, 1H), 0.96-1.11 (m, 1H), 0.36-0.51 (m, 1H).

Example 60

1-(3,5-Difluoropyridin-2-yl)-7-[(3S,4S)-3,4-dihydroxypyrrolidin-1-yl]-N-(1,1,1,3,3,3-hexafluoropropan-2-yl)-4-oxo-1,4-dihydro-1,8-naphthyridine-3-carboxamide

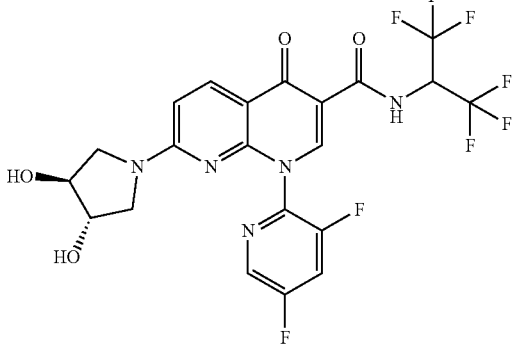

According to General Procedure 3, 40.0 mg (82.2 µmol) of 7-chloro-1-(3,5-difluoropyridin-2-yl)-N-(1,1 1,3,3,3-hexafluoropropan-2-yl)-4-oxo-1,4-dihydro-1,8-naphthyridine-3-carboxamide (Example 10A) were reacted with 10.2 mg (98.6 µmol) of (3S,4S)-pyrrolidine-3,4-diol hydrochloride in the presence of 50.0 µl (288 µmol) of DIPEA in 0.4 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 38.3 mg (84% of theory, purity 100%) of the title compound.

LC-MS (Methode 2): Rt=1.71 min; MS (ESIpos): m/z=554 [M+H]+.

$^1$H-NMR (400 MHz, DMSO-d6): δ [ppm]=11.41 (d, 1H), 8.91 (d, 1H), 8.63 (d, 1H), 8.25-8.40 (m, 2H), 6.81 (d, 1H), 6.25-6.39 (m, 1H), 5.04-5.33 (m, 2H), 3.88-4.10 (m, 2H), 3.63 (ddd, 1H), 3.34-3.40 (m, 1H), 3.19-3.29 (m, 1H), 3.01-3.18 (m, 1H).

Example 61

N-[(1S)-1-Cyclopropyl-2,2,2-trifluoroethyl]-1-(3,5-difluoropyridin-2-yl)-7-[(3S,4S)-3,4-dihydroxypyrrolidin-1-yl]-4-oxo-1,4-dihydro-1,8-naphthyridine-3-carboxamide

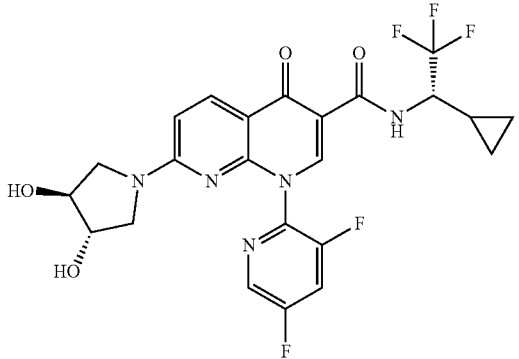 [SMILES: O=C(N[C@@H](C1CC1)C(F)(F)F)c1cn(-c2ncc(F)cc2F)c2nc(N3C[C@H](O)[C@@H](O)C3)ccc2c1=O]

According to General Procedure 3, 20.0 mg (43.6 µmol) of 7-chloro-N-[(1S)-1-cyclopropyl-2,2,2-trifluoroethyl]-1-(3,5-difluoropyridin-2-yl)-4-oxo-1,4-dihydro-1,8-naphthyridine-3-carboxamide (Example 9A) were reacted with 7.30 mg (52.0 µmol) of (3R,4S)-pyrrolidine-3,4-diol hydrochloride in the presence of 27.0 µl (153 µmol) of DIPEA in 0.2 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 11.7 mg (51% of theory, purity 100%) of the title compound.

LC-MS (Methode 2): Rt=1.59 min; MS (ESIpos): m/z=526 [M+H]+.

$^1$H-NMR (500 MHz, DMSO-d6): δ [ppm]=10.56 (dd, 1H), 8.81 (d, 1H), 8.61 (d, 1H), 8.30-8.37 (m, 1H), 8.28 (d, 1H), 6.78 (d, 1H), 5.02-5.32 (m, 2H), 4.35-4.46 (m, 1H), 4.05 (br. s, 1H), 3.93 (br. s, 1H), 3.62 (ddd, 1H), 3.33-3.39 (m, 1H), 3.19-3.28 (m, 1H), 3.01-3.18 (m, 1H), 1.16-1.26 (m, 1H), 0.47-0.71 (m, 3H), 0.29-0.39 (m, 1H).

Example 62

N-[(1S)-1-Cyclopropyl-2,2,2-trifluoroethyl]-1-(3,5-difluoropyridin-2-yl)-7-[(3R,4S)-3,4-dihydroxypyrrolidin-1-yl]-4-oxo-1,4-dihydro-1,8-naphthyridine-3-carboxamide

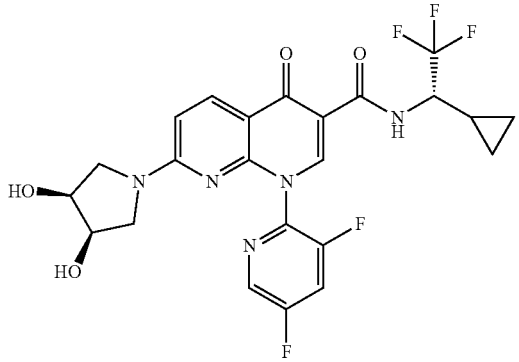 [SMILES: O=C(N[C@@H](C1CC1)C(F)(F)F)c1cn(-c2ncc(F)cc2F)c2nc(N3C[C@@H](O)[C@@H](O)C3)ccc2c1=O]

According to General Procedure 3, 20.0 mg (43.6 µmol) of 7-chloro-N-[(1S)-1-cyclopropyl-2,2,2-trifluoroethyl]-1-(3,5-difluoropyridin-2-yl)-4-oxo-1,4-dihydro-1,8-naphthyridine-3-carboxamide (Example 9A) were reacted with 7.30 mg (52.0 µmol) of (3R,4S)-pyrrolidine-3,4-diol hydrochloride in the presence of 27.0 µl (153 µmol) of DIPEA in 0.2 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 15.9 mg (69% of theory, purity 100%) of the title compound.

LC-MS (Methode 2): Rt=1.64 min; MS (ESIpos): m/z=526 [M+H]+.

$^1$H-NMR (500 MHz, DMSO-d6): δ [ppm]=10.55 (dd, 1H), 8.81 (s, 1H), 8.56-8.66 (m, 1H), 8.30-8.38 (m, 1H), 8.28 (d, 1H), 6.76 (d, 1H), 4.86-5.11 (m, 2H), 4.40 (sxt, 1H), 4.09-4.20 (m, 1H), 3.96-4.08 (m, 1H), 3.54-3.68 (m, 1H), 3.16-3.27 (m, 1H), 2.94-3.12 (m, 1H), 1.16-1.27 (m, 1H), 0.47-0.70 (m, 3H), 0.28-0.39 (m, 1H).

Example 63

N-[(1S)-1-Cyclopropyl-2,2,2-trifluoroethyl]-1-(3,5-difluoropyridin-2-yl)-7-[(3R,4R)-3,4-dihydroxypyrrolidin-1-yl]-4-oxo-1,4-dihydro-1,8-naphthyridine-3-carboxamide

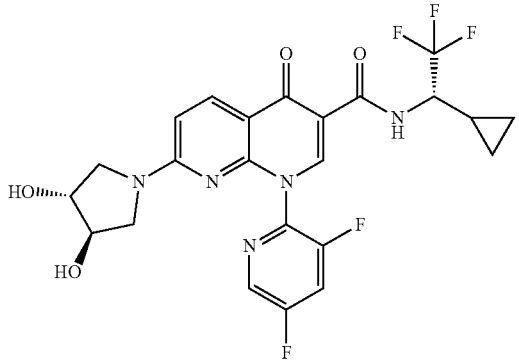 [SMILES: O=C(N[C@@H](C1CC1)C(F)(F)F)c1cn(-c2ncc(F)cc2F)c2nc(N3C[C@@H](O)[C@H](O)C3)ccc2c1=O]

According to General Procedure 3, 20.0 mg (43.6 µmol) of 7-chloro-N-[(1S)-1-cyclopropyl-2,2,2-trifluoroethyl]-1-(3,5-difluoropyridin-2-yl)-4-oxo-1,4-dihydro-1,8-naphthyridine-3-carboxamide (Example 9A) were reacted with 7.30 mg (52.0 µmol) of (3R,4R)-pyrrolidine-3,4-diol hydrochloride in the presence of 27.0 µl (153 µmol) of DIPEA in 0.2 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 18.1 mg (79% of theory, purity 100%) of the title compound.

LC-MS (Methode 1): Rt=0.86 min; MS (ESIpos): m/z=526 [M+H]+.

$^1$H-NMR (400 MHz, DMSO-d6): δ [ppm]=10.56 (dd, 1H), 8.81 (d, 1H), 8.61 (d, 1H), 8.30-8.37 (m, 1H), 8.28 (d, 1H), 6.78 (d, 1H), 5.04-5.30 (m, 2H), 4.40 (sxt, 1H), 4.05 (br. s, 1H), 3.88-3.98 (m, 1H), 3.56-3.68 (m, 1H), 3.32-3.40 (m, 1H), 3.19-3.29 (m, 1H), 3.02-3.18 (m, 1H), 1.16-1.26 (m, 1H), 0.48-0.70 (m, 3H), 0.29-0.40 (m, 1H).

Example 64

1-(3,5-Difluoropyridin-2-yl)-4-oxo-7-(2-oxoimidazolidin-1-yl)-N-[(2S)-1,1,1-trifluorobutan-2-yl]-1,4-dihydro-1,8-naphthyridine-3-carboxamide

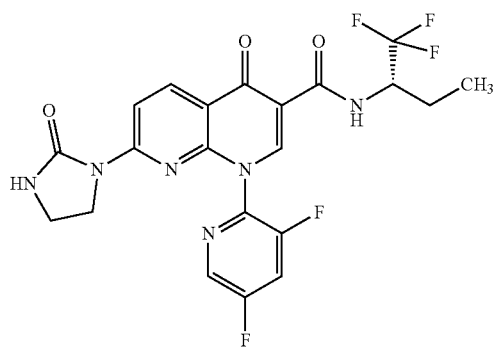 [SMILES: CC[C@H](NC(=O)c1cn(-c2ncc(F)cc2F)c2nc(N3CCNC3=O)ccc2c1=O)C(F)(F)F]

According to General Procedure 2, 60.0 mg (134 µmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 57.8 mg (671 µmol) of imidazolidin-2-one in the presence of 65.6 mg (201 µmol) of cesium carbonate, 1.51 mg (6.72 µmol) of palladium acetate and 7.77 mg (13.4 µmol) of Xantphos in 5 ml of dioxane at 80° C. The mixture was then cooled to RT and washed with 2 ml of chloroform and 0.5 ml of saturated aqueous sodium bicarbonate solution. The organic phase was dried over magnesium sulfate and filtered, and the solvent was removed under reduced pressure. The crude product was dissolved in a little water, acetonitrile and formic acid and purified by preparative HPLC (column: Chromatorex C18, 10 µm, 125*40 mm, solvent: acetonitrile, water, 0.1% formic acid), giving 19.8 mg (30% of theory, purity 100%) of the title compound.

LC-MS (Methode 1): Rt=0.95 min; MS (ESIpos): m/z=497 [M+H]+.

$^1$H-NMR (400 MHz, DMSO-d6): δ [ppm]=10.21 (d, 1H), 8.99 (s, 1H), 8.64 (d, 1H), 8.56 (d, 1H), 8.44 (d, 1H), 8.33 (ddd, 1H), 7.67 (s, 1H), 4.69-4.84 (m, 1H), 3.52-3.72 (m, 2H), 3.33-3.43 (m, 2H), 1.82-1.96 (m, 1H), 1.59-1.74 (m, 1H), 0.92-1.03 (m, 3H).

Example 65

N-[(1R)-1-Cyclopropyl-2,2,2-trifluoroethyl]-1-(3,5-difluoropyridin-2-yl)-4-oxo-7-(2-oxoimidazolidin-1-yl)-1,4-dihydro-1,8-naphthyridine-3-carboxamide

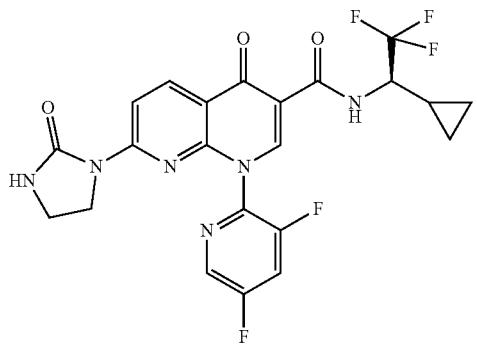 [SMILES: O=C(N[C@H](C1CC1)C(F)(F)F)c1cn(-c2ncc(F)cc2F)c2nc(N3CCNC3=O)ccc2c1=O]

According to General Procedure 2, 60.0 mg (131 μmol) of 7-chloro-N-[(1R)-1-cyclopropyl-2,2,2-trifluoroethyl]-1-(3,5-difluoropyridin-2-yl)-4-oxo-1,4-dihydro-1,8-naphthyridine-3-carboxamide (Example 8A) were reacted with 56.3 mg (654 μmol) of imidazolidin-2-one in the presence of 63.9 mg (196 μmol) of cesium carbonate, 1.47 mg (6.54 μmol) of palladium acetate and 7.57 mg (13.1 μmol) of Xantphos in 5 ml of dioxane at 100° C. The mixture was then cooled to RT and concentrated. The crude product was dissolved in a little water, acetonitrile and formic acid and purified by preparative HPLC (column: Chromatorex C18, 10 μm, 125*40 mm, solvent: acetonitrile, water, 0.1% formic acid), giving 30.3 mg (46% of theory, purity 100%) of the title compound.

LC-MS (Methode 2): Rt=1.82 min; MS (ESIpos): m/z=509 [M+H]+.

$^1$H-NMR (400 MHz, DMSO-d6): δ [ppm]=10.34 (d, 1H), 8.98 (s, 1H), 8.63 (d, 1H), 8.56 (d, 1H), 8.44 (d, 1H), 8.28-8.37 (m, 1H), 7.67 (s, 1H), 4.35-4.49 (m, 1H), 3.53-3.71 (m, 2H), 3.33-3.42 (m, 2H), 1.17-1.28 (m, 1H), 0.49-0.72 (m, 3H), 0.29-0.41 (m, 1H).

Example 66

N-(2,6-Dichlorophenyl)-1-(3,5-difluoropyridin-2-yl)-7-[(3R,4S)-3,4-dihydroxypyrrolidin-1-yl]-4-oxo-1,4-dihydro-1,8-naphthyridine-3-carboxamide

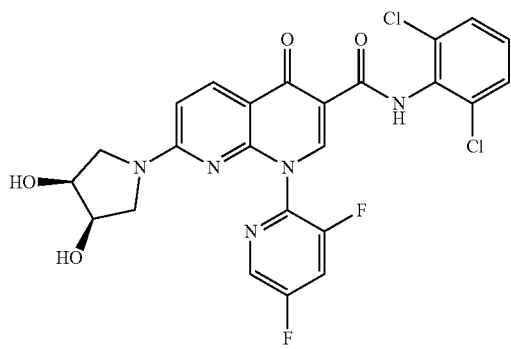 [SMILES: O=C(Nc1c(Cl)cccc1Cl)c1cn(-c2ncc(F)cc2F)c2nc(N3C[C@@H](O)[C@@H](O)C3)ccc2c1=O]

According to General Procedure 2, 60.0 mg (125 μmol) of 7-chloro-N-(2,6-dichlorophenyl)-1-(3,5-difluoropyridin-2-yl)-4-oxo-1,4-dihydro-1,8-naphthyridine-3-carboxamide (Example 11B) were reacted with 20.9 mg (149 μmol) of (3R,4S)-pyrrolidine-3,4-diol hydrochloride in the presence of 25.8 mg (187 μmol) of potassium carbonate, 5.59 mg (24.9 μmol) of palladium acetate and 14.4 mg (24.9 μmol) of Xantphos in 0.9 ml of dioxane at 80° C. The mixture was then cooled to RT and then acidified with 1M aqueous hydrochloric acid, 100 mg of N-acetylcysteine were added and the mixture was stirred for 15 min. The mixture was then diluted with 15 ml of saturated aqueous sodium bicarbonate solution and 20 ml of ethyl acetate and the phases were separated. The aqueous phase was extracted three times with ethyl acetate. The combined organic phases were dried over magnesium sulfate and filtered, and the solvent was removed under reduced pressure. The crude product was dissolved in 3 ml of acetonitrile and 1 ml of DMSO and purified by preparative HPLC (column: Chromatorex C18, 10 μm, 125*40 mm, solvent: acetonitrile, water, 0.1% formic acid), giving 7.10 mg (10% of theory, purity 100%) of the title compound.

LC-MS (Methode 1): Rt=0.88 min; MS (ESIpos): m/z=548 [M+H]+.

$^1$H-NMR (400 MHz, DMSO-d6): δ [ppm]=11.92 (s, 1H), 8.89 (s, 1H), 8.62 (br. s, 1H), 8.33 (d, 2H), 7.59 (d, 2H), 7.34-7.41 (m, 1H), 6.78 (d, 1H), 4.89-5.13 (m, 2H), 3.98-4.20 (m, 2H), 3.48-3.69 (m, 2H), 2.96-3.21 (m, 2H).

Example 67

N-(2,6-Dichlorophenyl)-1-(3,5-difluoropyridin-2-yl)-7-[(3R,4R)-3,4-dihydroxypyrrolidin-1-yl]-4-oxo-1,4-dihydro-1,8-naphthyridine-3-carboxamide

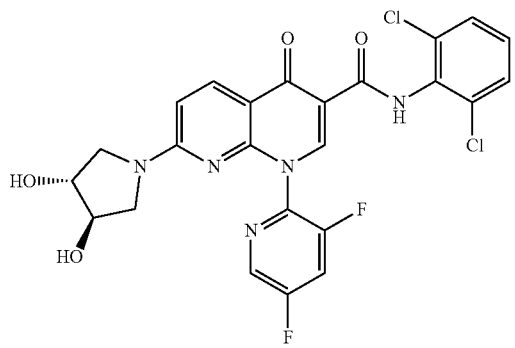 [SMILES: O=C(Nc1c(Cl)cccc1Cl)c1cn(-c2ncc(F)cc2F)c2nc(N3C[C@@H](O)[C@H](O)C3)ccc2c1=O]

According to General Procedure 2, 60.0 mg (125 μmol) of 7-chloro-N-(2,6-dichlorophenyl)-1-(3,5-difluoropyridin-2-yl)-4-oxo-1,4-dihydro-1,8-naphthyridine-3-carboxamide (Example 11B) were reacted with 20.9 mg (149 μmol) of (3R,4R)-pyrrolidine-3,4-diol hydrochloride in the presence of 25.8 mg (187 μmol) of potassium carbonate, 5.59 mg (24.9 μmol) of palladium acetate and 14.4 mg (24.9 μmol) of Xantphos in 0.9 ml of dioxane at 80° C. The mixture was then cooled to RT and then acidified with 1M aqueous hydrochloric acid, 100 mg of N-acetylcysteine were added and the mixture was stirred for 15 min. The mixture was then diluted with 15 ml of saturated aqueous sodium bicarbonate solution and 20 ml of ethyl acetate and the phases were separated. The aqueous phase was extracted three times with ethyl acetate. The combined organic phases were dried over magnesium sulfate and filtered, and the solvent was removed under reduced pressure. The crude product was dissolved in 3 ml of acetonitrile and 1 ml of DMSO and purified by preparative HPLC (column: Chromatorex C18, 10 μm, 125*40 mm, solvent: acetonitrile, water, 0.1% formic acid), giving 6.70 mg (10% of theory, purity 100%) of the title compound.

LC-MS (Methode 2): Rt=1.58 min; MS (ESIpos): m/z=548 [M+H]+.

$^1$H-NMR (400 MHz, DMSO-d6): δ [ppm]=11.94 (s, 1H), 8.89 (d, 1H), 8.62 (d, 1H), 8.34 (d, 2H), 7.59 (d, 2H), 7.34-7.41 (m, 1H), 6.80 (d, 1H), 5.05-5.32 (m, 2H), 3.90-4.10 (m, 2H), 3.58-3.70 (m, 1H), 3.36-3.41 (m, 1H), 3.04-3.27 (m, 2H).

Example 68

N-(2,6-Dichlorophenyl)-1-(3,5-difluoropyridin-2-yl)-7-[(3S,4S)-3,4-dihydroxypyrrolidin-1-yl]-4-oxo-1,4-dihydro-1,8-naphthyridine-3-carboxamide

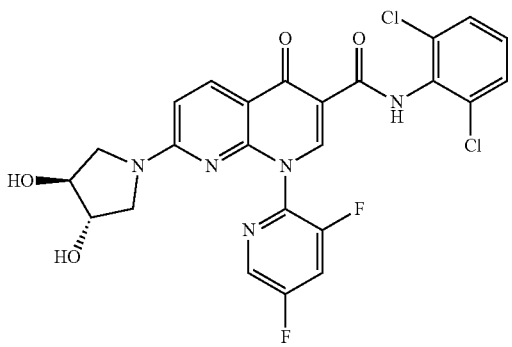 [SMILES: O=C(Nc1c(Cl)cccc1Cl)c1cn(-c2ncc(F)cc2F)c2nc(N3C[C@H](O)[C@@H](O)C3)ccc2c1=O]

According to General Procedure 3, 35.9 mg (74.5 µmol) of 7-chloro-N-(2,6-dichlorophenyl)-1-(3,5-difluoropyridin-2-yl)-4-oxo-1,4-dihydro-1,8-naphthyridine-3-carboxamide (Example 11B) were reacted with 12.5 mg (89.4 µmol) of (3R,4S)-pyrrolidine-3,4-diol hydrochloride in the presence of 45.0 µl (261 µmol) of DIPEA in 0.37 ml of DMF. The mixture was then diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 19.6 mg (48% of theory, purity 100%) of the title compound.

LC-MS (Methode 1): Rt=0.89 min; MS (ESIpos): m/z=548 [M+H]+.

$^1$H-NMR (400 MHz, DMSO-d6): δ [ppm]=11.94 (s, 1H), 8.89 (d, 1H), 8.62 (d, 1H), 8.34 (d, 2H), 7.59 (d, 2H), 7.38 (dd, 1H), 6.80 (d, 1H), 5.04-5.33 (m, 2H), 3.90-4.13 (m, 2H), 3.57-3.71 (m, 1H), 3.36-3.43 (m, 1H), 3.04-3.28 (m, 2H).

Example 69

N-(2,6-Dichlorophenyl)-1-(3,5-difluoropyridin-2-yl)-7-[3-hydroxy-3-methylpyrrolidin-1-yl]-4-oxo-1,4-dihydro-1,8-naphthyridine-3-carboxamide (racemate)

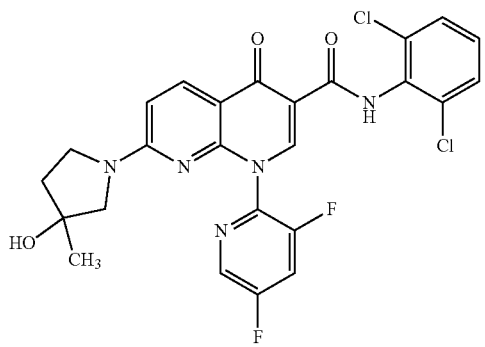 [SMILES: CC1(O)CCN(c2ccc3c(=O)c(C(=O)Nc4c(Cl)cccc4Cl)cn(-c4ncc(F)cc4F)c3n2)C1]

According to General Procedure 2, 100 mg (208 µmol) of 7-chloro-N-(2,6-dichlorophenyl)-1-(3,5-difluoropyridin-2-yl)-4-oxo-1,4-dihydro-1,8-naphthyridine-3-carboxamide (Example 11B) were reacted with 34.3 mg (249 µmol) of 3-methylpyrrolidin-3-ol hydrochloride (racemate) in the presence of 43.0 mg (311 µmol) of potassium carbonate, 9.32 mg (41.5 µmol) of palladium acetate and 24.0 mg (41.5 µmol) of Xantphos in 1.6 ml of dioxane at 80° C. The mixture was then cooled to RT and then acidified with 1M aqueous hydrochloric acid, 100 mg of N-acetylcysteine were added and the mixture for stirred for 15 min.

The mixture was then diluted with 15 ml of saturated aqueous sodium bicarbonate solution and 20 ml of ethyl acetate and the phases were separated. The aqueous phase was extracted three times with ethyl acetate. The combined organic phases were dried over magnesium sulfate and filtered, and the solvent was removed under reduced pressure. The crude product was dissolved in 3 ml of acetonitrile and 1 ml of DMSO and purified twice by preparative HPLC (column: Chromatorex C18, 10 µm, 125*40 mm, solvent: acetonitrile, water, 0.1% formic acid). The product fractions were then combined and concentrated and the crude product was re-purified by normal phase chromatography (ethyl acetate/cyclohexane gradient), giving 16.9 mg (15% of theory; purity 100%) of the title compound.

LC-MS (Methode 1): Rt=1.04 min; MS (ESIpos): m/z=546 [M+H]+.

$^1$H-NMR (400 MHz, DMSO-d6): δ [ppm]=11.94 (s, 1H), 8.88 (s, 1H), 8.61 (br. d, 1H), 8.33 (t, 2H), 7.59 (d, 2H), 7.33-7.43 (m, 1H), 6.70-6.85 (m, 1H), 4.74-4.96 (m, 1H), 3.51-3.64 (m, 1H), 3.36-3.45 (m, 1H), 2.93-3.25 (m, 1H), 1.68-2.00 (m, 2H), 1.12-1.38 (m, 4H).

Example 70

7-[(2,2-Difluoroethyl)amino]-1-(3,5-difluoropyridin-2-yl)-4-oxo-N-[(2R)-1,1,1-trifluorobutan-2-yl]-1,4-dihydro-1,8-naphthyridine-3-carboxamide

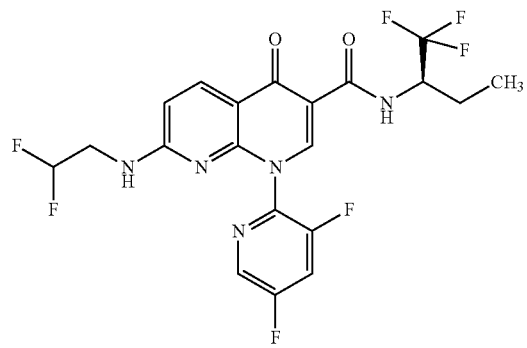 [SMILES: CC[C@@H](NC(=O)c1cn(-c2ncc(F)cc2F)c2nc(NCC(F)F)ccc2c1=O)C(F)(F)F]

According to General Procedure 3, 25.0 mg (56.0 µmol) 7-chloro-1-(3,5-difluoropyridin-2-yl)-4-oxo-N-[(2R)-1,1,1-trifluorobutan-2-yl]-1,4-dihydro-1,8-naphthyridine-3-carboxamide (Example 4C) were reacted with 5.44 mg (67.0 µmol) of 2,2-difluoroethanamine in the presence of 34.0 µl (196 µmol) of DIPEA in 0.4 ml of DMF overnight. More 2,2-difluoroethanamine and DIPEA were then added and the mixture was stirred at 50° C. for 3 h. The crude product was dissolved with acetonitrile, water and formic acid, filtered through a Millipore filter and purified by preparative HPLC (column: Chromatorex C18, 10 µm, 125*40 mm, solvent: acetonitrile, water, 0.1% formic acid), giving 21.9 mg (80% of theory, purity 100%) of the title compound.

LC-MS (Methode 2): Rt=1.96 min; MS (ESIpos): m/z=492 [M+H]+.

¹H-NMR (400 MHz, DMSO-d6): δ [ppm]=10.38 (d, 1H), 8.85 (s, 1H), 8.63 (d, 1H), 8.30-8.44 (m, 2H), 8.26 (d, 1H), 6.82 (d, 1H), 5.62-6.00 (m, 1H), 4.67-4.83 (m, 1H), 3.36-3.55 (m, 2H), 1.81-1.95 (m, 1H), 1.56-1.72 (m, 1H), 0.91-1.03 (m, 3H).

Example 71

1-(3,5-Difluoropyridin-2-yl)-7-(morpholin-4-yl)-4-oxo-N-[(2R)-1,1,1-trifluorobutan-2-yl]-1,4-dihydro-1,8-naphthyridine-3-carbonxamide

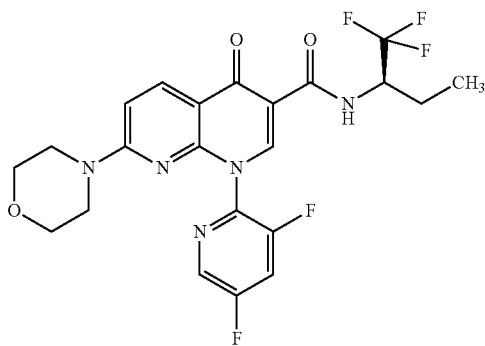 [SMILES: CC[C@@H](NC(=O)c1cn(-c2ncc(F)cc2F)c2nc(N3CCOCC3)ccc2c1=O)C(F)(F)F]

According to General Procedure 3, 25.0 mg (56.0 μmol) of 7-chloro-1-(3,5-difluoropyridin-2-yl)-4-oxo-N-[(2R)-1,1,1-trifluorobutan-2-yl]-1,4-dihydro-1,8-naphthyridine-3-carboxamide (Example 4C) were reacted with 6.0 μl (67.0 μmol) of morpholine in the presence of 34.0 μl (196 μmol) of DIPEA in 0.4 ml of DMF. The mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 22.9 mg (80% of theory, purity 97%) of the title compound.

LC-MS (Methode 2): Rt=1.98 min; MS (ESIpos): m/z=498 [M+H]+.

¹H-NMR (400 MHz, DMSO-d6): δ [ppm]=10.35 (d, 1H), 8.84 (s, 1H), 8.62 (d, 1H), 8.25-8.38 (m, 2H), 7.13 (d, 1H), 4.66-4.83 (m, 1H), 3.54-3.66 (m, 4H), 3.40-3.53 (m, 4H), 1.81-1.96 (m, 1H), 1.56-1.72 (m, 1H), 0.89-1.03 (m, 3H).

Example 72

7-(3,3-Difluoropiperidin-1-yl)-1-(3,5-difluoropyridin-2-yl)-4-oxo-N-[(2R)-1,1,1-trifluorobutan-2-yl]-1,4-dihydro-1,8-naphthyridine-3-carboxamide

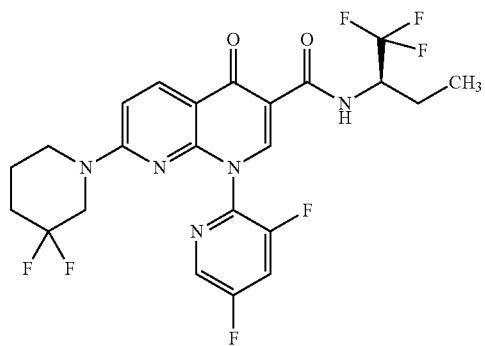 [SMILES: CC[C@@H](NC(=O)c1cn(-c2ncc(F)cc2F)c2nc(N3CCCC(F)(F)C3)ccc2c1=O)C(F)(F)F]

According to General Procedure 3, 25.0 mg (56.0 μmol) of 7-chloro-1-(3,5-difluoropyridin-2-yl)-4-oxo-N-[(2R)-1,1,1-trifluorobutan-2-yl]-1,4-dihydro-1,8-naphthyridine-3-carboxamide (Example 4C) were reacted with 10.6 mg (67.1 μmol) of 3,3-difluoropiperidine hydrochloride in the presence of 34.0 μl (196 μmol) of DIPEA in 0.4 ml of DMF. The mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 27.0 mg (91% of theory, purity 100%) of the title compound.

LC-MS (Methode 2): Rt=2.16 min; MS (ESIpos): m/z=532 [M+H]+.

¹H-NMR (400 MHz, DMSO-d6): δ [ppm]=10.33 (d, 1H), 8.86 (s, 1H), 8.64 (d, 1H), 8.28-8.44 (m, 2H), 7.26 (d, 1H), 4.67-4.83 (m, 1H), 3.78-3.99 (m, 2H), 3.50-3.63 (m, 2H), 1.99-2.14 (m, 2H), 1.82-1.95 (m, 1H), 1.57-1.72 (m, 3H), 0.91-1.04 (m, 3H).

Example 73

1-(3,5-Difluoropyridin-2-yl)-7-[(4S)-4-hydroxy-2-oxopyrrolidin-1-yl]-4-oxo-N-[(2R)-1,1,1-trifluoro-3,3-dimethylbutan-2-yl]-1,4-dihydro-1,8-naphthyridine-3-carboxamide

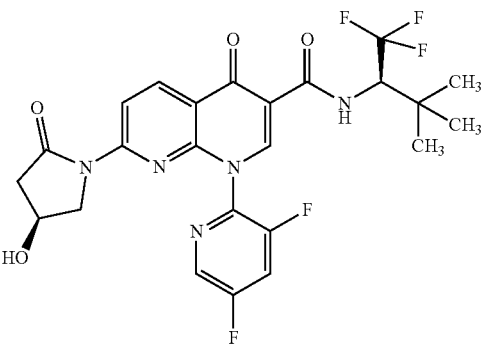 [SMILES: CC(C)(C)[C@@H](NC(=O)c1cn(-c2ncc(F)cc2F)c2nc(N3C[C@@H](O)CC3=O)ccc2c1=O)C(F)(F)F]

According to General Procedure 1, 70.0 mg (174 μmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 32.4 mg (209 μmol) of (2R)-1,1,1-trifluoro-3,3-dimethylbutan-2-amine in the presence of 79.4 mg (209 μmol) of HATU and 91.0 μl (522 μmol) of DIPEA in 0.7 ml of DMF. The reaction mixture was then diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 76.7 mg (82% of theory, purity 100%) of the title compound.

LC-MS (Methode 2): Rt=1.96 min; MS (ESIpos): m/z=540 [M+H]+.

¹H-NMR (500 MHz, DMSO-d6): δ [ppm]=10.48 (br. d, 1H), 9.07 (s, 1H), 8.74 (d, 1H), 8.66 (br. s, 1H), 8.54 (br. dd, 1H), 8.39 (ddd, 1H), 5.23-5.40 (m, 1H), 4.66 (quint, 1H), 4.30 (br. s, 1H), 3.65-3.78 (m, 1H), 3.45-3.57 (m, 1H), 2.89-3.02 (m, 1H), 2.34-2.43 (m, 1H), 1.10 (br. s, 9H).

Example 74

1-(3,5-Difluoropyridin-2-yl)-7-[(4S)-4-hydroxy-2-oxopyrrolidin-1-yl]-4-oxo-N-[(2R)-1,1,1-trifluoro-4-methylpentan-2-yl]-1,4-dihydro-1,8-naphthyridine-3-carboxamide

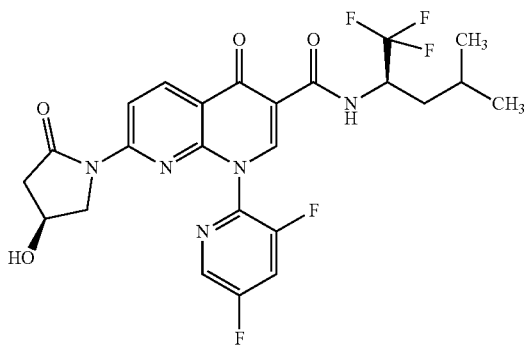 [SMILES: CC(C)C[C@@H](NC(=O)c1cn(-c2ncc(F)cc2F)c2nc(N3C[C@@H](O)CC3=O)ccc2c1=O)C(F)(F)F]

According to General Procedure 1, 70.0 mg (174 μmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 32.4 mg (209 μmol) of (2R)-1,1,1-trifluoro-4-methylpentan-2-amine in the presence of 79.4 mg (209 μmol) of HATU and 91.0 μl (522 μmol) of DIPEA in 0.7 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 78.0 mg (83% of theory, purity 100%) of the title compound.

LC-MS (Methode 2): Rt=2.01 min; MS (ESIpos): m/z=540 [M+H]+.

$^1$H-NMR (500 MHz, DMSO-d6): δ [ppm]=10.10 (br. d, 1H), 9.06 (s, 1H), 8.65-8.72 (m, 2H), 8.51-8.57 (m, 1H), 8.39 (ddd, 1H), 5.24-5.40 (m, 1H), 4.81-4.90 (m, 1H), 4.29 (br. s, 1H), 3.64-3.78 (m, 1H), 3.46-3.56 (m, 1H), 2.89-3.02 (m, 1H), 2.34-2.43 (m, 1H), 1.65-1.74 (m, 2H), 1.54-1.64 (m, 1H), 0.95 (br. dd, 3H), 0.90 (br. t, 3H).

Example 75

1-(3,5-Difluoropyridin-2-yl)-7-[(4S)-4-hydroxy-2-oxopyrrolidin-1-yl]-4-oxo-N-[(2S)-1,1,1-trifluoro-4-methylpentan-2-yl]-1,4-dihydro-1,8-naphthyridine-3-carboxamide

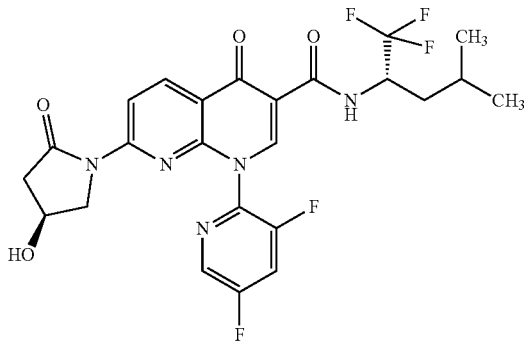 [SMILES: CC(C)C[C@H](NC(=O)c1cn(-c2ncc(F)cc2F)c2nc(N3C[C@@H](O)CC3=O)ccc2c1=O)C(F)(F)F]

According to General Procedure 1, 70.0 mg (174 μmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 32.4 mg (209 μmol) of (2S)-1,1,1-trifluoro-4-methylpentan-2-amine in the presence of 79.4 mg (209 μmol) of HATU and 91.0 μl (522 μmol) of DIPEA in 0.7 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 77.1 mg (82% of theory, purity 100%) of the title compound.

LC-MS (Methode 2): Rt=2.02 min; MS (ESIpos): m/z=540 [M+H]+.

$^1$H-NMR (500 MHz, DMSO-d6): δ [ppm]=10.10 (br. dd, 1H), 9.06 (s, 1H), 8.71 (d, 1H), 8.66 (br. dd, 1H), 8.54 (br. dd, 1H), 8.36-8.41 (m, 1H), 5.23-5.40 (m, 1H), 4.81-4.90 (m, 1H), 4.29 (br. s, 1H), 3.65-3.78 (m, 1H), 3.45-3.56 (m, 1H), 2.89-3.02 (m, 1H), 2.34-2.43 (m, 1H), 1.65-1.74 (m, 2H), 1.54-1.62 (m, 1H), 0.95 (br. dd, 3H), 0.89 (br. t, 3H).

Example 76

1-(3,5-Difluoropyridin-2-yl)-7-[(4S)-4-hydroxy-2-oxopyrrolidin-1-yl]-4-oxo-N-[3,3,4,4,4-pentafluorobutan-2-yl]-1,4-dihydro-1,8-naphthyridine-3-carboxamide (diastereomer mixture)

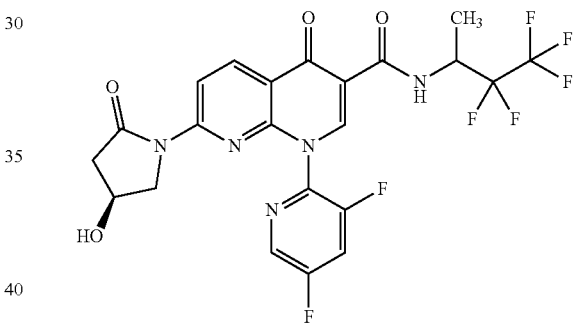

According to General Procedure 1, 125.0 mg (311 μmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 74.4 mg (373 μmol) of (2S)-3,3,4,4,4-pentafluorobutan-2-amine hydrochloride (Example 28B, racemate) in the presence of 142 mg (373 μmol) of HATU and 0.22 ml (1.24 mmol) of DIPEA in 1.25 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 119 mg (70% of theory, purity 100%) of the title compound.

LC-MS (Methode 1): Rt=0.99 min; MS (ESIpos): m/z=548 [M+H]+.

$^1$H-NMR (400 MHz, DMSO-d6): δ [ppm]=10.24 (d, 1H), 9.06 (s, 1H), 8.71 (d, 1H), 8.64-8.68 (m, 1H), 8.50-8.58 (m, 1H), 8.35-8.42 (m, 1H), 5.23-5.40 (m, 1H), 4.98-5.12 (m, 1H), 4.29 (br. s, 1H), 3.64-3.78 (m, 1H), 3.44-3.56 (m, 1H), 2.88-3.02 (m, 1H), 2.33-2.43 (m, 1H), 1.42 (br. d, 3H).

107 mg of the title compound (diastereomer mixture) were separated into the diastereomers by chiral HPLC (preparative HPLC: column: Daicel Chiralpak OX-H 5 μm 250×20 mm; mobile phase: 50% isohexane, 50% isopropanol; temperature: 50° C.; flow rate: 15 ml/min; UV detection: 220 nm).

This gave (in the sequence of elution from the column) 37 mg (22% of theory, purity 100%) of Example 77 (diastereomer 1, 99% de) Rt=5.29 min and 42 mg (25% of theory, purity 100%) of Example 78 (diastereomer 2, 99% de) Rt=6.21 min.

[Analytical HPLC: column: Daicel Chiralpak OX-H 5 μm 250×4.6 mm; mobile phase: 50% isohexane, 50% isopropanol; temperature: 50° C.; flow rate: 1.0 ml/min; UV detection: 220 nm]

Example 77

1-(3,5-Difluoropyridin-2-yl)-7-[(4S)-4-hydroxy-2-oxopyrrolidin-1-yl]-4-oxo-N-[3,3,4,4,4-pentafluorobutan-2-yl]-1,4-dihydro-1,8-naphthyridine-3-carboxamide (diastereomer 1)

LC-MS (Methode 2): $R_t$=1.78 min; MS (ESIpos): m/z=548 [M+H]+.

$^1$H NMR (400 MHz, DMSO-d6): δ [ppm]=10.24 (br d, 1H), 9.04-9.07 (m, 1H), 8.71 (d, 1H), 8.64-8.68 (m, 1H), 8.54 (br t, 1H), 8.35-8.42 (m, 1H), 5.22-5.39 (m, 1H), 4.98-5.12 (m, 1H), 4.26-4.32 (m, 1H), 3.65-3.78 (m, 1H), 3.44-3.56 (m, 1H), 2.89-3.02 (m, 1H), 2.33-2.42 (m, 1H), 1.42 (br d, 3H).

Example 78

1-(3,5-Difluoropyridin-2-yl)-7-[(4S)-4-hydroxy-2-oxopyrrolidin-1-yl]-4-oxo-N-[3,3,4,4,4-pentafluorobutan-2-yl]-1,4-dihydro-1,8-naphthyridine-3-carboxamide (diastereomer 2)

LC-MS (Methode 2): $R_t$=1.77 min; MS (ESIpos): m/z=548 [M+H]+.

$^1$H NMR (400 MHz, DMSO-d6): δ [ppm]=10.24 (d, 1H), 9.06 (s, 1H), 8.71 (d, 1H), 8.64-8.68 (m, 1H), 8.54 (br t, 1H), 8.36-8.42 (m, 1H), 5.24-5.41 (m, 1H), 4.99-5.13 (m, 1H), 4.26-4.32 (m, 1H), 3.64-3.79 (m, 1H), 3.44-3.57 (m, 1H), 2.87-3.02 (m, 1H), 2.34-2.43 (m, 1H), 1.41 (br d, 3H).

Example 79

1-(3,5-Difluoropyridin-2-yl)-7-[(4S)-4-hydroxy-2-oxopyrrolidin-1-yl]-4-oxo-N-[1-(trifluoromethyl)cyclopentyl]-1,4-dihydro-1,8-naphthyridine-3-carboxamide

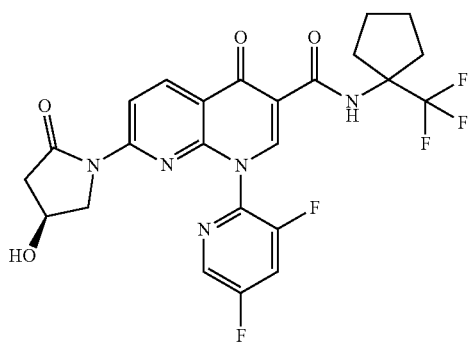 [SMILES: O=C(NC1(C(F)(F)F)CCCC1)c1cn(-c2ncc(F)cc2F)c2nc(N3C[C@@H](O)CC3=O)ccc2c1=O]

According to General Procedure 1, 70.0 mg (174 μmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 39.6 mg (209 μmol) of 1-(trifluoromethyl)cyclopentanamine hydrochloride in the presence of 79.4 mg (209 μmol) of HATU and 121 μl (696 μmol) of DIPEA in 0.7 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 77.8 mg (83% of theory, purity 100%) of the title compound.

LC-MS (Methode 2): Rt=1.92 min; MS (ESIpos): m/z=538 [M+H]+.

$^1$H-NMR (500 MHz, DMSO-d6): δ [ppm]=10.20 (s, 1H), 9.01 (s, 1H), 8.70 (d, 1H), 8.64-8.68 (m, 1H), 8.50-8.56 (m, 1H), 8.35-8.41 (m, 1H), 5.23-5.40 (m, 1H), 4.29 (br. s, 1H), 3.64-3.78 (m, 1H), 3.45-3.56 (m, 1H), 2.88-3.02 (m, 1H), 2.33-2.45 (m, 3H), 2.02-2.11 (m, 2H), 1.70-1.85 (m, 4H).

Example 80

1-(3,5-Difluoropyridin-2-yl)-7-[(4S)-4-hydroxy-2-oxopyrrolidin-1-yl]-4-oxo-N-(4,4,4-trifluoro-2-methylbutan-2-yl)-1,4-dihydro-1,8-naphthyridine-3-carboxamide

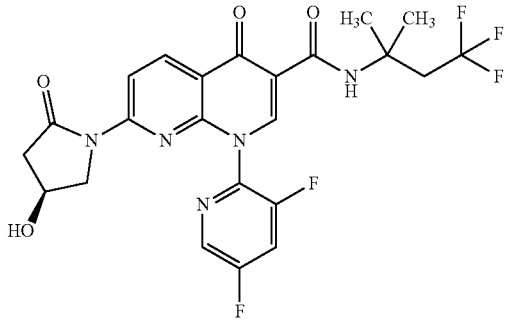 [SMILES: CC(C)(CC(F)(F)F)NC(=O)c1cn(-c2ncc(F)cc2F)c2nc(N3C[C@@H](O)CC3=O)ccc2c1=O]

According to General Procedure 1, 50.0 mg (124 μmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 26.5 mg (149 μmol) of 4,4,4-trifluoro-2-methylbutan-2-amine hydrochloride in the presence of 56.7 mg (149 μmol) of HATU and 65.0 μl (373 μmol) of DIPEA in 0.48 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 33.8 mg (52% of theory, purity 100%) of the title compound.

LC-MS (Methode 2): Rt=1.76 min; MS (ESIpos): m/z=526 [M+H]+.

$^1$H-NMR (400 MHz, DMSO-d6): δ [ppm]=9.90 (s, 1H), 8.98 (s, 1H), 8.69 (d, 1H), 8.64-8.67 (m, 1H), 8.49-8.56 (m, 1H), 8.35-8.41 (m, 1H), 5.37 (br. d, 0.5H), 5.25 (br. d, 0.5H), 4.26-4.32 (m, 1H), 3.65-3.78 (m, 1H), 3.44-3.57 (m, 1H), 2.88-3.02 (m, 3H), 2.34-2.43 (m, 1H), 1.50 (s, 6H).

Example 81

1-(3,5-Difluoropyridin-2-yl)-7-[(3R,4R)-3,4-dihydroxypyrrolidin-1-yl]-4-oxo-N-[(2R)-1,1,1-trifluoro-4-methylpentan-2-yl]-1,4-dihydro-1,8-naphthyridine-3-carboxamide

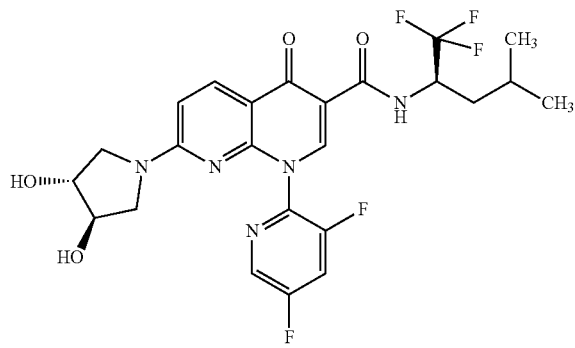 [SMILES: CC(C)C[C@@H](NC(=O)c1cn(-c2ncc(F)cc2F)c2nc(N3C[C@@H](O)[C@H](O)C3)ccc2c1=O)C(F)(F)F]

According to General Procedure 1, 30.0 mg (74.2 µmol) of 1-(3,5-difluoropyridin-2-yl)-7-[(3R,4R)-3,4-dihydroxypyrrolidin-1-yl-4-oxo-1,4-dihydro-1,8-naphthyridine-3-carboxylic acid (Example 23B) were reacted with 13.8 mg (89.0 µmol) of (2R)-1,1,1-trifluoro-4-methylpentan-2-amine in the presence of 33.9 mg (89.0 µmol) of HATU and 39.0 µl (223 µmol) of DIPEA in 0.3 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 27.6 mg (69% of theory, purity 100%) of the title compound.

LC-MS (Methode 2): Rt=1.80 min; MS (ESIpos): m/z=542 [M+H]+.

¹H-NMR (400 MHz, DMSO-d6): δ [ppm]=10.41 (dd, 1H), 8.82 (br. s, 1H), 8.61 (d, 1H), 8.29-8.36 (m, 1H), 8.27 (d, 1H), 6.78 (d, 1H), 5.27 (d, 0.5H), 5.19 (t, 1H), 5.07 (d, 0.5H), 4.77-4.89 (m, 1H), 4.05 (br. s, 1H), 3.93 (br. s, 1H), 3.57-3.67 (m, 1H), 3.33-3.39 (m, 1H), 3.19-3.29 (m, 1H), 3.03-3.17 (m, 1H), 1.62-1.72 (m, 2H), 1.52-1.62 (m, 1H), 0.86-0.97 (m, 6H).

Example 82

1-(3,5-Difluoropyridin-2-yl)-7-[(3R,4R)-3,4-dihydroxypyrrolidin-1-yl]-4-oxo-N-[(2S)-1,1,1-trifluoro-4-methylpentan-2-yl]-1,4-dihydro-1,8-naphthyridine-3-carboxamide

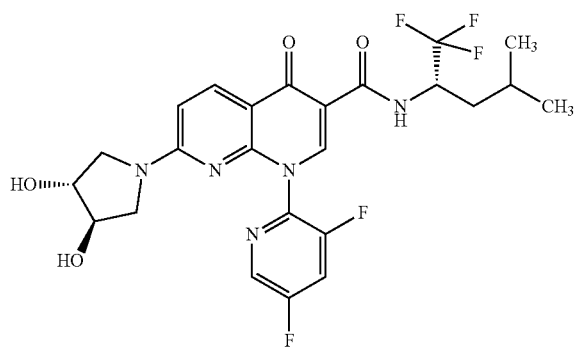 [SMILES: CC(C)C[C@H](NC(=O)c1cn(-c2ncc(F)cc2F)c2nc(N3C[C@@H](O)[C@H](O)C3)ccc2c1=O)C(F)(F)F]

According to General Procedure 1, 30.0 mg (74.2 µmol) of 1-(3,5-difluoropyridin-2-yl)-7-[(3R,4R)-3,4-dihydroxypyrrolidin-1-yl-4-oxo-1,4-dihydro-1,8-naphthyridine-3-carboxylic acid (Example 23B) were reacted with 13.8 mg (89.0 µmol) of (2S)-1,1,1-trifluoro-4-methylpentan-2-amine in the presence of 33.9 mg (89.0 µmol) of HATU and 39.0 µl (223 µmol) of DIPEA in 0.3 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 26.4 mg (66% of theory, purity 100%) of the title compound.

LC-MS (Methode 2): Rt=1.80 min; MS (ESIpos): m/z=542 [M+H]+.

¹H-NMR (400 MHz, DMSO-d6): δ [ppm]=10.42 (dd, 1H), 8.82 (d, 1H), 8.61 (br. t, 1H), 8.29-8.36 (m, 1H), 8.27 (d, 1H), 6.78 (d, 1H), 4.99-5.36 (m, 2H), 4.78-4.89 (m, 1H), 4.02-4.09 (m, 1H), 3.89-3.97 (m, 1H), 3.48-3.70 (m, 1H), 3.19-3.39 (m, 1H, unter dem Wasser Signal), 3.02-3.17 (m, 1H), 1.62-1.72 (m, 2H), 1.52-1.61 (m, 1H), 1.03 (br. d, 1H), 0.86-0.98 (m, 6H).

Example 83

N-[1-(2-Chlorophenyl)-2,2,2-trifluoroethyl]-1-(3,5-difluoropyridin-2-yl)-7-[(3R,4R)-3,4-dihydroxypyrrolidin-1-yl]-4-oxo-1,4-dihydro-1,8-naphthyridine-3-carboxamide (diastereomer mixture)

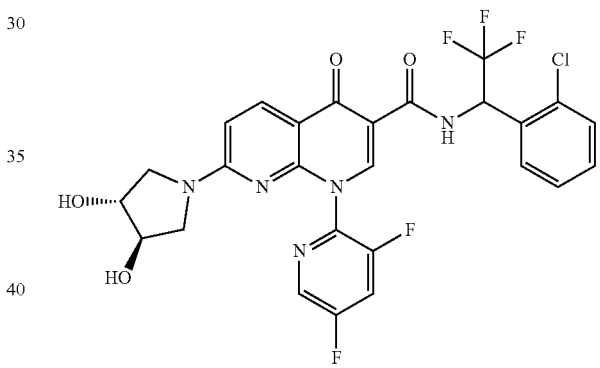

According to General Procedure 1, 30.0 mg (74.2 µmol) of 1-(3,5-difluoropyridin-2-yl)-7-[(3R,4R)-3,4-dihydroxypyrrolidin-1-yl-4-oxo-1,4-dihydro-1,8-naphthyridine-3-carboxylic acid (Example 23B) were reacted with 18.7 mg (89.0 µmol) of (1S)-1-(2-chlorophenyl)-2,2,2-trifluoroethanamine in the presence of 33.9 mg (89.0 µmol) of HATU and 39.0 µl (223 µmol) of DIPEA in 0.3 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 32.5 mg (74% of theory, purity 100%) of the title compound.

LC-MS (Methode 2): Rt=1.88 min; MS (ESIpos): m/z=596 [M+H]+.

¹H-NMR (400 MHz, DMSO-d6): δ [ppm]=11.52-11.58 (m, 1H), 8.79-8.86 (m, 1H), 8.57-8.65 (m, 1H), 8.26-8.38 (m, 2H), 7.45-7.67 (m, 4H), 6.80 (d, 1H), 6.40-6.50 (m, 1H), 5.24-5.30 (m, 0.5H), 5.15-5.23 (m, 1H), 5.03-5.10 (m, 0.5H), 4.05 (br. s, 1H), 3.93 (br. s, 1H), 3.56-3.68 (m, 1H), 3.34-3.40 (m, 1H), 3.19-3.28 (m, 1H), 3.01-3.18 (m, 1H).

28.7 mg of the title compound (diastereomer mixture) were separated into the diastereomers by chiral HPLC (preparative HPLC: column: Daicel Chiralcel OX-H 5 μm 250×20 mm; mobile phase: 30% n-heptane, 70% ethanol; temperature: 25° C.; flow rate: 15 ml/min; UV detection: 210 nm).

This gave in the sequence of elution from the column 13.8 mg (31% of theory, purity 100%) of Example 84 (99% de) Rt=1.19 min and 14.4 mg (33% of theory, purity 100%) of Example 85 (99% de) Rt=3.14 min.

[Analytical HPLC: column: Daicel Chiralpak OX-3 3 μm 50×4.6 mm; mobile phase: 50% n-heptane, 50% ethanol; temperature: 23° C.; flow rate: 1.0 ml/min; UV detection: 220 nm]

Example 84

N-[1-(2-Chlorophenyl)-2,2,2-trifluoroethyl]-1-(3,5-difluoropyridin-2-yl)-7-[(3R,4R)-3,4-dihydroxypyrrolidin-1-yl]-4-oxo-1,4-dihydro-1,8-naphthyridine-3-carboxamide (diastereomer 1)

LC-MS (Methode 2): $R_t$=1.86 min; MS (ESIpos): m/z=596 [M+H]+.

$^1$H NMR (400 MHz, DMSO-d6): δ [ppm]=11.53-11.58 (m, 1H), 8.83 (s, 1H), 8.61 (dd, 1H), 8.30-8.37 (m, 2H), 7.47-7.65 (m, 4H), 6.80 (d, 1H), 6.40-6.49 (m, 1H), 5.04-5.30 (m, 2H), 4.03-4.08 (m, 1H), 3.90-3.95 (m, 1H), 3.57-3.67 (m, 1H), 3.33-3.39 (m, 1H), 3.18-3.29 (m, 1H), 3.03-3.17 (m, 1H).

Example 85

N-[1-(2-Chlorophenyl)-2,2,2-trifluoroethyl]-1-(3,5-difluoropyridin-2-yl)-7-[(3R,4R)-3,4-dihydroxypyrrolidin-1-yl]-4-oxo-1,4-dihydro-1,8-naphthyridine-3-carboxamide (diastereomer 2)

LC-MS (Methode 2): $R_t$=1.86 min; MS (ESIpos): m/z=596 [M+H]+.

$^1$H NMR (400 MHz, DMSO-d6): δ [ppm]=11.56 (d, 1H), 8.83 (d, 1H), 8.61 (dd, 1H), 8.30-8.36 (m, 2H), 7.48-7.65 (m, 4H), 6.80 (d, 1H), 6.41-6.49 (m, 1H), 5.28 (d, 0.5H), 5.19 (d, 1H), 5.06 (d, 0.5H), 4.03-4.07 (m, 1H), 3.90-3.96 (m, 1H), 3.57-3.67 (m, 1H), 3.33-3.40 (m, 1H), 3.20-3.30 (m, 1H), 3.02-3.16 (m, 1H).

Example 86

1-(3,5-Difluoropyridin-2-yl)-7-[(3R,4R)-3,4-dihydroxypyrrolidin-1-yl]-4-oxo-N-[(2R)-1,1,1-trifluoro-3,3-dimethylbutan-2-yl]-1,4-dihydro-1,8-naphthyridine-3-carboxamide

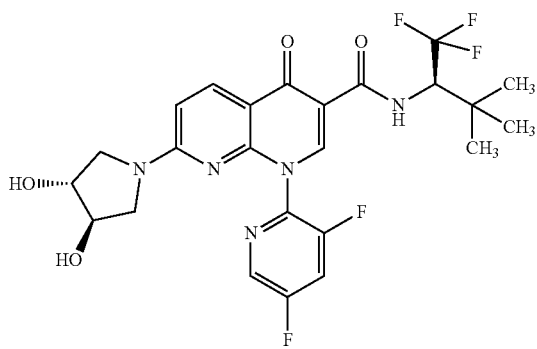 [SMILES: CC(C)(C)[C@@H](NC(=O)c1cn(-c2ncc(F)cc2F)c2nc(N3C[C@@H](O)[C@H](O)C3)ccc2c1=O)C(F)(F)F]

According to General Procedure 1, 30.0 mg (74.2 μmol) of 1-(3,5-difluoropyridin-2-yl)-7-[(3R,4R)-3,4-dihydroxypyrrolidin-1-yl]-4-oxo-1,4-dihydro-1,8-naphthyridine-3-carboxylic acid (Example 23B) were reacted with 13.8 mg (89.0 μmol) of (2R)-1,1,1-trifluoro-3,3-dimethylpentan-2-amine in the presence of 33.9 mg (89.0 μmol) of HATU and 39.0 μl (223 μmol) of DIPEA in 0.3 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 26.5 mg (66% of theory, purity 100%) of the title compound.

LC-MS (Methode 2): Rt=1.74 min; MS (ESIpos): m/z=542 [M+H]+.

$^1$H-NMR (400 MHz, DMSO-d6): δ [ppm]=10.77 (dd, 1H), 8.83 (d, 1H), 8.61 (d, 1H), 8.29-8.36 (m, 2H), 6.78 (d, 1H), 5.24-5.31 (m, 0.5H), 5.20 (br. s, 1H), 5.04-5.13 (m, 0.5H), 4.58-4.68 (m, 1H), 4.05 (br. s, 1H), 3.93 (br. s, 1H), 3.56-3.68 (m, 1H), 3.35-3.41 (m, 1H), 3.19-3.28 (m, 1H), 3.03-3.17 (m, 1H), 1.09 (br. s, 9H).

Example 87

1-(3,5-Difluoropyridin-2-yl)-7-[(3R,4R)-3,4-dihydroxypyrrolidin-1-yl]-4-oxo-N-[1-(trifluoromethyl)cyclopentyl]-1,4-dihydro-1,8-naphthyridine-3-carboxamide

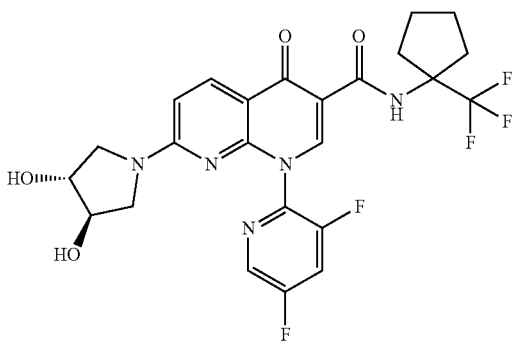 [SMILES: O=C(NC1(C(F)(F)F)CCCC1)c1cn(-c2ncc(F)cc2F)c2nc(N3C[C@@H](O)[C@H](O)C3)ccc2c1=O]

According to General Procedure 1, 30.0 mg (74.2 μmol) of 1-(3,5-difluoropyridin-2-yl)-7-[(3R,4R)-3,4-dihydroxypyrrolidin-1-yl]-4-oxo-1,4-dihydro-1,8-naphthyridine-3-carboxylic acid (Example 23B) were reacted with 16.9 mg (89.0 μmol) of 1-(trifluoromethyl)cyclopentanamine hydrochloride in the presence of 33.9 mg (89.0 μmol) of HATU and 39.0 μl (223 μmol) of DIPEA in 0.3 ml of DMF. The reaction mixture was diluted with acetonitrile, water and formic acid and filtered through a Millipore filter and the crude solution was purified twice by preparative HPLC (column: Chromatorex C18, 10 μm, 125*40 mm, solvent: acetonitrile, water, 0.1% formic acid), giving 18.3 mg (46% of theory, purity 100%) of the title compound.

LC-MS (Methode 2): Rt=1.72 min; MS (ESIpos): m/z=540 [M+H]+.

1H NMR (400 MHz, DMSO-d6): δ [ppm]=10.50 (s, 1H), 8.77 (d, 1H), 8.61 (d, 1H), 8.33 (td, 1H), 8.27 (d, 1H), 6.77 (d, 1H), 5.27 (d, 0.5H), 5.16-5.21 (m, 1H), 5.06 (d, 0.5H), 4.05 (br. s, 1H), 3.90-3.95 (m, 1H), 3.57-3.66 (m, 1H), 3.33-3.38 (m, 1H), 3.18-3.29 (m, 1H), 3.03-3.17 (m, 1H), 2.35-2.44 (m, 2H), 2.00-2.09 (m, 2H), 1.69-1.85 (m, 4H).

Example 88

1-(3,5-Difluoropyridin-2-yl)-7-[(3R,4R)-3,4-dihydroxypyrrolidin-1-yl]-4-oxo-N-[3,3,4,4,4-pentafluorobutan-2-yl]-1,4-dihydro-1,8-naphthyridine-3-carboxamide (diastereomer mixture)

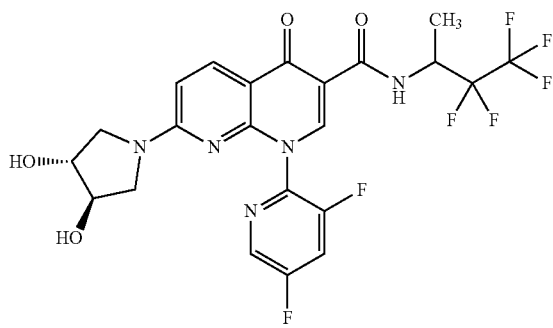 [SMILES: CC(NC(=O)c1cn(-c2ncc(F)cc2F)c2nc(N3C[C@@H](O)[C@H](O)C3)ccc2c1=O)C(F)(F)C(F)(F)F]

According to General Procedure 1, 30.0 mg (74.2 µmol) of 1-(3,5-difluoropyridin-2-yl)-7-[(3R,4R)-3,4-dihydroxypyrrolidin-1-yl]-4-oxo-1,4-dihydro-1,8-naphthyridine-3-carboxylic acid (Example 23B) were reacted with 17.8 mg (89.0 µmol) of (2S)-3,3,4,4,4-pentafluorobutan-2-amine hydrochloride (Example 28B, racemate) in the presence of 33.9 mg (89.0 µmol) of HATU and 52.0 µl (297 µmol) of DIPEA in 0.3 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 34.3 mg (84% of theory, purity 100%) of the title compound.

LC-MS (Methode 2): Rt=1.63 min; MS (ESIpos): m/z=550 [M+H]+.

$^1$H-NMR (400 MHz, DMSO-d6): δ [ppm]=10.55 (br. d, 1H), 8.82 (br. t, 1H), 8.59-8.64 (m, 1H), 8.29-8.37 (m, 1H), 8.27 (d, 1H), 6.77 (d, 1H), 5.23-5.30 (m, 0.5H), 5.15-5.23 (m, 1H), 5.06-5.10 (m, 0.5H), 4.96-5.06 (m, 1H), 4.05 (br. s, 1H), 3.93 (br. s, 1H), 3.56-3.68 (m, 1H), 3.33-3.40 (m, 1H), 3.19-3.29 (m, 1H), 3.02-3.18 (m, 1H), 1.39 (br. d, 3H).

17.0 mg of the title compound (diastereomer mixture) were separated into the diastereomers by chiral HPLC (preparative HPLC: column: Daicel Chiralcel OX-H 5 µm 250×20 mm; mobile phase: 70% n-heptane, 30% ethanol +0.2% DEA; temperature: 25° C.; flow rate: 15 ml/min; UV detection: 210 nm).

This gave (in the sequence of elution from the column) 6.20 mg (15% of theory, purity 100%) of diastereomer 1 (Example 89) (99% de) Rt=6.13 min and 7.30 mg (18% of theory, purity 100%) of diastereomer 2 (Example 90) (99% de) Rt=7.91 min.

[Analytical HPLC: column: Daicel Chiralpak OX-3 3 µm 50×4.6 mm; mobile phase: 80% n-heptane, 20% ethanol +0.2% DEA; flow rate: 1.0 ml/min; UV detection: 220 nm]

Example 89

1-(3,5-Difluoropyridin-2-yl)-7-[(3R,4R)-3,4-dihydroxypyrrolidin-1-yl]-4-oxo-N-[3,3,4,4,4-pentafluorobutan-2-yl]-1,4-dihydro-1,8-naphthyridine-3-carboxamide (diastereomer 1)

LC-MS (Methode 1): Rt=0.90 min; MS (ESIpos): m/z=550 [M+H]+.

$^1$H-NMR (400 MHz, DMSO-d6): δ [ppm]=10.56 (d, 1H), 8.82 (d, 1H), 8.61 (d, 1H), 8.29-8.36 (m, 1H), 8.27 (d, 1H), 6.77 (d, 1H), 5.25-5.31 (m, 0.5H), 5.19 (d, 1H), 4.96-5.10 (m, 1.5H), 4.05 (br. s, 1H), 3.93 (br. s, 1H), 3.56-3.67 (m, 1H), 3.34-3.43 (m, 1H), 3.19-3.30 (m, 1H), 3.02-3.17 (m, 1H), 1.40 (br. d, 3H).

Example 90

1-(3,5-Difluoropyridin-2-yl)-7-[(3R,4R)-3,4-dihydroxypyrrolidin-1-yl]-4-oxo-N-[3,3,4,4,4-pentafluorobutan-2-yl]-1,4-dihydro-1,8-naphthyridine-3-carboxamide (diastereomer 2)

LC-MS (Methode 1): Rt=0.90 min; MS (ESIpos): m/z=550 [M+H]+.

$^1$H-NMR (400 MHz, DMSO-d6): δ [ppm]=10.56 (br. d, 1H), 8.82 (s, 1H), 8.61 (t, 1H), 8.30-8.36 (m, 1H), 8.27 (d, 1H), 6.78 (d, 1H), 5.23-5.31 (m, 0.5H), 5.16-5.23 (m, 1H), 4.95-5.11 (m, 1.5H), 4.05 (br. s, 1H), 3.89-3.96 (m, 1H), 3.56-3.68 (m, 1H), 3.34-3.43 (m, 1H), 3.18-3.29 (m, 1H), 3.03-3.17 (m, 1H), 1.39 (br. d, 3H).

Example 91

1-(3,5-Difluoropyridin-2-yl)-7-[(3R,4R)-3,4-dihydroxypyrrolidin-1-yl]-4-oxo-N-(4,4,4-trifluoro-2-methylbutan-2-yl)-1,4-dihydro-1,8-naphthyridine-3-carboxamide

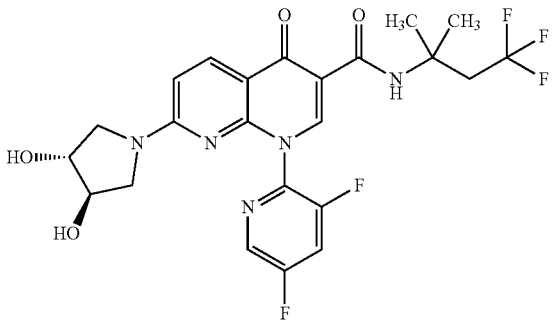 [SMILES: CC(C)(CC(F)(F)F)NC(=O)c1cn(-c2ncc(F)cc2F)c2nc(N3C[C@@H](O)[C@H](O)C3)ccc2c1=O]

According to General Procedure 1, 50.0 mg (124 µmol) of 1-(3,5-difluoropyridin-2-yl)-7-[(3R,4R)-3,4-dihydroxypyrrolidin-1-yl-4-oxo-1,4-dihydro-1,8-naphthyridine-3-carboxylic acid (Example 23B) were reacted with 26.4 mg (148 µmol) of 4,4,4-trifluoro-2-methylbutan-2-amine hydrochloride in the presence of 56.4 mg (148 µmol) of HATU and 65.0 µl (371 µmol) of DIPEA in 0.5 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 36.9 mg (57% of theory, purity 100%) of the title compound.

LC-MS (Methode 2): Rt=1.58 min; MS (ESIpos): m/z=528 [M+H]+.

$^1$H-NMR (400 MHz, DMSO-d6): δ [ppm]=10.16 (br. s, 1H), 8.73 (d, 1H), 8.61 (d, 1H), 8.29-8.35 (m, 1H), 8.26 (d, 1H), 6.75 (d, 1H), 5.01-5.33 (m, 2H), 4.00-4.09 (m, 1H), 3.87-3.96 (m, 1H), 3.56-3.66 (m, 1H), 3.35-3.45 (m, 1H), 3.02-3.23 (m, 2H), 2.89-3.01 (m, 2H), 1.48 (br. s, 6H).

Example 92

1-(3,5-Difluoropyridin-2-yl)-7-[(4S)-4-hydroxy-2-oxopyrrolidin-1-yl]-4-oxo-N-[1,1,1,2,2-pentafluoropentan-3-yl]-1,4-dihydro-1,8-naphthyridine-3-carboxamide (diastereomer mixture)

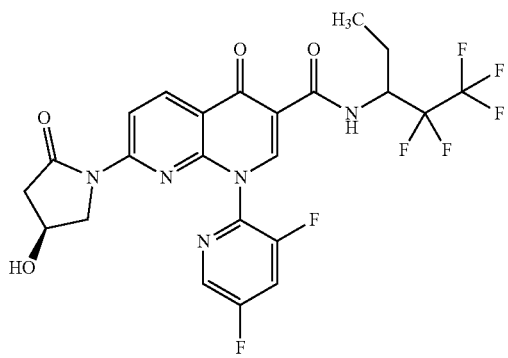 [SMILES: CCC(NC(=O)c1cn(-c2ncc(F)cc2F)c2nc(N3C[C@@H](O)CC3=O)ccc2c1=O)C(F)(F)C(F)(F)F]

According to General Procedure 1, 100 mg (249 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 63.7 mg (298 µmol) of (3S)-1,1,1,2,2-pentafluoropentan-3-amine hydrochloride (Example 14B, racemate) in the presence of 113 mg (298 µmol) of HATU and 173 µl (994 µmol) of DIPEA in 1 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 97.4 mg (70% of theory, purity 100%) of the title compound.

LC-MS (Methode 2): Rt=1.88 min; MS (ESIpos): m/z=562 [M+H]+.

$^1$H-NMR (400 MHz, DMSO-d6): δ [ppm]=10.16 (d, 1H), 9.06 (s, 1H), 8.72 (d, 1H), 8.63-8.69 (m, 1H), 8.51-8.58 (m, 1H), 8.39 (ddd, 1H), 5.31-5.41 (m, 0.5H), 5.26 (br. s, 0.5H), 4.83-4.97 (m, 1H), 4.29 (br. s, 1H), 3.65-3.79 (m, 1H), 3.44-3.57 (m, 1H), 2.88-3.03 (m, 1H), 2.32-2.44 (m, 1H), 1.88-1.99 (m, 1H), 1.62-1.74 (m, 1H), 0.94-1.01 (m, 3H).

83.0 mg of the title compound (diastereomer mixture) were separated into the diastereomers by chiral HPLC (preparative HPLC: column: Daicel Chiralpak IE 5 µm 250×20 mm; mobile phase: 70% n-heptane, 30% isopropanol; temperature: 35° C.; flow rate: 15 ml/min; UV detection: 220 nm).

This gave (in the sequence of elution from the column) 34.0 mg (24% of theory, purity 100%) of diastereomer 1 (Example 93) (98.9% de) Rt=9.56 min and 37.0 mg (27% of theory, purity 100%) of diastereomer 2 (Example 94) (95.8% de) Rt=13.40 min.

[Analytical HPLC: column: Daicel Chiralpak IE 5 µm 250×4.6 mm; mobile phase: 60% isohexane, 40% isopropanol; temperature: 35° C.; flow rate: 1.0 ml/min; UV detection: 220 nm]

Example 93

1-(3,5-Difluoropyridin-2-yl)-7-[(4S)-4-hydroxy-2-oxopyrrolidin-1-yl]-4-oxo-N-[1,1,1,2,2-pentafluoropentan-3-yl]-1,4-dihydro-1,8-naphthyridine-3-carboxamide (diastereomer 1)

LC-MS (Methode 2): Rt=1.90 min; MS (ESIpos): m/z=562 [M+H]+.

$^1$H-NMR (400 MHz, DMSO-d6): δ [ppm]=10.16 (d, 1H), 9.06 (s, 1H), 8.72 (d, 1H), 8.63-8.68 (m, 1H), 8.54 (br. t, 1H), 8.39 (ddd, 1H), 5.38 (br. d, 0.5H), 5.26 (br. d, 0.5H), 4.83-4.97 (m, 1H), 4.29 (br. s, 1H), 3.63-3.78 (m, 1H), 3.43-3.57 (m, 1H), 2.87-3.03 (m, 1H), 2.34-2.44 (m, 1H), 1.88-1.99 (m, 1H), 1.62-1.74 (m, 1H), 0.92-1.01 (m, 3H).

Example 94

1-(3,5-Difluoropyridin-2-yl)-7-[(4S)-4-hydroxy-2-oxopyrrolidin-1-yl]-4-oxo-N-[1,1,1,2,2-pentafluoropentan-3-yl]-1,4-dihydro-1,8-naphthyridine-3-carboxamide (diastereomer 2)

LC-MS (Methode 2): Rt=1.90 min; MS (ESIpos): m/z=562 [M+H]+.

$^1$H-NMR (400 MHz, DMSO-d6): δ [ppm]=10.16 (br. d, 1H), 9.06 (br. d, 1H), 8.72 (d, 1H), 8.66 (br. s, 1H), 8.54 (br. t, 1H), 8.39 (br. t, 1H), 5.38 (br. d, 0.5H), 5.26 (br. d, 0.5H), 4.83-4.97 (m, 1H), 4.26-4.32 (m, 1H), 3.64-3.79 (m, 1H), 3.45-3.57 (m, 1H), 2.88-3.03 (m, 1H), 2.34-2.43 (m, 1H), 1.88-1.99 (m, 1H), 1.62-1.74 (m, 1H), 0.93-1.02 (m, 3H).

Example 95

1-(3,5-Difluoropyridin-2-yl)-7-[(3R,4R)-3,4-dihydroxypyrrolidin-1-yl]-4-oxo-N-[1,1,1,2,2-pentafluoropentan-3-yl]-1,4-dihydro-1,8-naphthyridine-3-carboxamide (diastereomer mixture)

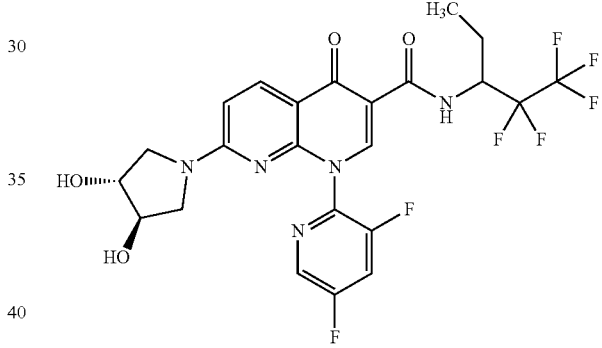

According to General Procedure 3, 50.0 mg (101 µmol) 7-chloro-1-(3,5-difluoropyridin-2-yl)-4-oxo-N-[(3S)-1,1,1,2,2-pentafluoropentan-3-yl-1,4-dihydro-1,8-naphthyridine-3-carboxamide (Example 15A, racemate) were reacted with 12.5 mg (121 µmol) of (3R,4R)-pyrrolidine-3,4-diol hydrochloride in the presence of 61.0 µl (352 µmol) of DIPEA in 0.5 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 51.3 mg (90% of theory, purity 100%) of the title compound.

LC-MS (Methode 1): Rt=0.97 min; MS (ESIpos): m/z=564 [M+H]+.

$^1$H-NMR (400 MHz, DMSO-d6): δ [ppm]=10.47 (br. d, 1H), 8.81 (br. s, 1H), 8.61 (br. s, 1H), 8.22-8.41 (m, 2H), 6.78 (br. d, 1H), 5.02-5.33 (m, 2H), 4.79-4.98 (m, 1H), 4.00-4.12 (m, 1H), 3.86-3.98 (m, 1H), 3.55-3.69 (m, 1H), 3.00-3.26 (m, 2H), 1.83-2.01 (m, 1H), 1.57-1.75 (m, 1H), 0.87-1.06 (m, 3H).

37.0 mg of the title compound (diastereomer mixture) were separated into the diastereomers by chiral HPLC (preparative HPLC: column: Daicel Chiralcel OX-H 5 µm 250×20 mm; mobile phase: 80% n-heptane, 20% ethanol; temperature: 35° C.; flow rate: 15 ml/min; UV detection: 220 nm).

This gave in the sequence of elution from the column 16.0 mg (28% of theory, purity 100%) of Example 96 (99.9% de) Rt=5.45 min and 16.0 mg (28% of theory, purity 100%) of Example 97 (99.9% de) Rt=6.39 min.

[Analytical HPLC: column: Daicel Chiralcel OX-H 5 μm 250×4.6 mm; mobile phase: 80% isohexane, 20% ethanol; temperature: 30° C.; flow rate: 1.0 ml/min; UV detection: 220 nm]

Example 96

1-(3,5-Difluoropyridin-2-yl)-7-[(3R,4R)-3,4-dihydroxypyrrolidin-1-yl]-4-oxo-N-[1,1,1,2,2-pentafluoropentan-3-yl]-1,4-dihydro-1,8-naphthyridine-3-carboxamide (diastereomer 1)

LC-MS (Methode 2): $R_t$=1.72 min; MS (ESIpos): m/z=564 [M+H]+.

$^1$H NMR (400 MHz, DMSO-d6): δ [ppm]=10.47 (d, 1H), 8.82 (d, 1H), 8.61 (d, 1H), 8.30-8.36 (m, 1H), 8.28 (d, 1H), 6.78 (d, 1H), 5.28 (br d, 0.5H), 5.15-5.23 (m, 1H), 5.07 (br d, 0.5H), 4.80-4.94 (m, 1H), 4.00-4.08 (m, 1H), 3.87-3.97 (m, 1H), 3.55-3.67 (m, 1H), 3.33-3.40 (m, 1H), 3.19-3.29 (m, 1H), 3.03-3.17 (m, 1H), 1.86-1.98 (m, 1H), 1.59-1.72 (m, 1H), 0.93-1.00 (m, 3H).

Example 97

1-(3,5-Difluoropyridin-2-yl)-7-[(3R,4R)-3,4-dihydroxypyrrolidin-1-yl]-4-oxo-N-[1,1,1,2,2-pentafluoropentan-3-yl]-1,4-dihydro-1,8-naphthyridine-3-carboxamide (diastereomer 2)

LC-MS (MCW-FT-MS-M1-Methode 2): $R_t$=1.72 min; MS (ESIpos): m/z=564 [M+H]+.

$^1$H NMR (400 MHz, DMSO-d6): δ [ppm]=10.47 (d, 1H), 8.82 (s, 1H), 8.61 (t, 1H), 8.30-8.37 (m, 1H), 8.28 (d, 1H), 6.78 (d, 1H), 5.28 (br d, 0.5H), 5.19 (br t, 1H), 5.07 (br d, 0.5H), 4.80-4.94 (m, 1H), 4.05 (br s, 1H), 3.93 (br s, 1H), 3.56-3.68 (m, 1H), 3.33-3.39 (m, 1H), 3.19-3.29 (m, 1H), 3.02-3.18 (m, 1H), 1.86-1.98 (m, 1H), 1.59-1.72 (m, 1H), 0.91-1.01 (m, 3H).

Example 98

1-(3,5-Difluoropyridin-2-yl)-7-[(4S)-4-hydroxy-2-oxopyrrolidin-1-yl]-4-oxo-N-[(2S)-1,1,1-trifluoro-3,3-dimethylbutan-2-yl]-1,4-dihydro-1,8-naphthyridine-3-carboxamide

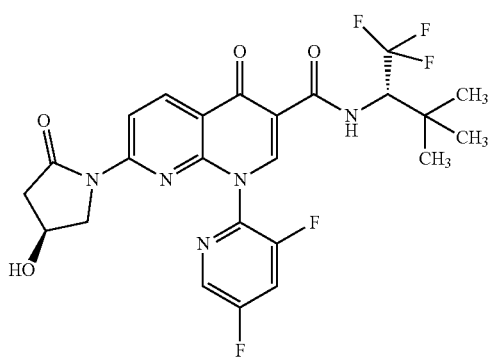 [SMILES: CC(C)(C)[C@H](NC(=O)c1cn(-c2ncc(F)cc2F)c2nc(N3C[C@@H](O)CC3=O)ccc2c1=O)C(F)(F)F]

According to General Procedure 1, 60.0 mg (149 μmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 27.8 mg (179 μmol) of (2S)-1,1,1-trifluoro-3,3-dimethylbutan-2-amine in the presence of 68.0 mg (179 μmol) of HATU and 104 μl (597 μmol) of DIPEA in 0.6 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 47.5 mg (59% of theory, purity 100%) of the title compound.

LC-MS (Methode 2): Rt=1.96 min; MS (ESIpos): m/z=540 [M+H]+.

$^1$H-NMR (400 MHz, DMSO-d6): δ [ppm]=10.48 (br. dd, 1H), 9.07 (s, 1H), 8.74 (d, 1H), 8.64-8.69 (m, 1H), 8.54 (t, 1H), 8.36-8.42 (m, 1H), 5.38 (br. d, 0.5H), 5.26 (br. d, 0.5H), 4.66 (quint, 1H), 4.26-4.32 (m, 1H), 3.65-3.78 (m, 1H), 3.46-3.57 (m, 1H), 2.89-3.02 (m, 1H), 2.33-2.44 (m, 1H), 1.10 (s, 9H).

Example 99

1-(3,5-Difluoropyridin-2-yl)-7-[(3R,4R)-3,4-dihydroxypyrrolidin-1-yl]-4-oxo-N-[(2S)-1,1,1-trifluoro-3,3-dimethylbutan-2-yl]-1,4-dihydro-1,8-naphthyridine-3-carboxamide

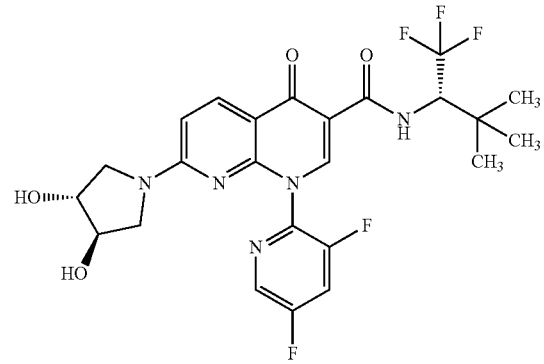 [SMILES: CC(C)(C)[C@H](NC(=O)c1cn(-c2ncc(F)cc2F)c2nc(N3C[C@@H](O)[C@H](O)C3)ccc2c1=O)C(F)(F)F]

According to General Procedure 3, 80.0 mg (168 μmol) of 7-chloro-1-(3,5-difluoropyridin-2-yl)-4-oxo-N-[(2S)-1,1,1-trifluoro-3,3-dimethylbutan-2-yl]-1,4-dihydro-1,8-naphthyridine-3-carboxamide (Example 13A) were reacted with 28.2 mg (202 μmol) of (3R,4R)-pyrrolidine-3,4-diol hydrochloride in the presence of 103 μl (590 μmol) of DIPEA in 0.8 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 85.3 mg (93% of theory, purity 100%) of the title compound.

LC-MS (Methode 2): Rt=1.76 min; MS (ESIpos): m/z=542 [M+H]+.

$^1$H-NMR (400 MHz, DMSO-d6): δ [ppm]=10.77 (dd, 1H), 8.83 (d, 1H), 8.61 (t, 1H), 8.28-8.36 (m, 2H), 6.78 (d, 1H), 5.28 (br. d, 0.5H), 5.20 (d, 1H), 5.07 (br. d, 0.5H), 4.63 (quintt, 1H), 4.05 (br. s, 1H), 3.93 (br. s, 1H), 3.56-3.68 (m, 1H), 3.33-3.40 (m, 1H), 3.19-3.30 (m, 1H), 3.03-3.18 (m, 1H), 1.09 (br. s, 9H).

Example 100

1-(3,5-Difluoropyridin-2-yl)-4-oxo-7-(2-oxoimidazolidin-1-yl)-N-[(2S)-1,1,1-trifluoro-3,3-dimethylbutan-2-yl]-1,4-dihydro-1,8-naphthyridine-3-carboxamide

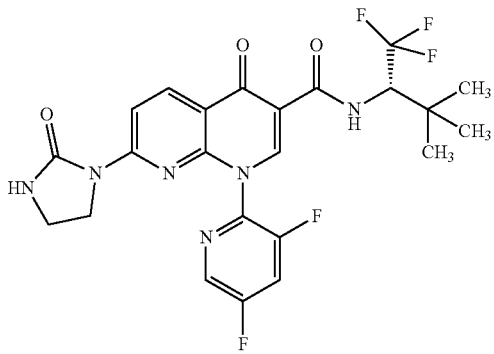 [SMILES: CC(C)(C)[C@H](NC(=O)c1cn(-c2ncc(F)cc2F)c2nc(N3CCNC3=O)ccc2c1=O)C(F)(F)F]

According to General Procedure 2, 80.0 mg (168 µmol) of 7-chloro-1-(3,5-difluoropyridin-2-yl)-4-oxo-N-[(2S)-1,1,1-trifluoro-3,3-dimethylbutan-2-yl]-1,4-dihydro-1,8-naphthyridine-3-carboxamide (Example 13A) were reacted with 145 mg (1.69 mmol) of imidazolidin-2-one in the presence of 34.9 mg (253 µmol) of potassium carbonate, 7.57 mg (34.0 µmol) of palladium acetate and 19.5 mg (34.0 µmol) of Xantphos in 1.6 ml of dioxane at 80° C. The mixture was diluted with acetonitrile, water and formic acid, filtered through a Millipore filter and purified by preparative HPLC (column: Chromatorex C18, 10 µm, 125*40 mm, solvent: acetonitrile, water, 0.1% formic acid), giving 40.5 mg (46% of theory, purity 100%) of the title compound.

LC-MS (Methode 2): Rt=1.97 min; MS (ESIpos): m/z=525 [M+H]+.

$^1$H-NMR (400 MHz, DMSO-d6): δ [ppm]=10.49-10.67 (m, 1H), 9.00 (br. s, 1H), 8.52-8.71 (m, 2H), 8.40-8.51 (m, 1H), 8.25-8.40 (m, 1H), 7.67 (br. s, 1H), 4.57-4.74 (m, 1H), 3.54-3.71 (m, 2H), 1.10 (br. s, 9H).

Example 101

N-(Bicyclo[1.1.1]pent-1-yl)-1-(3,5-difluoropyridin-2-yl)-7-[(4S)-4-hydroxy-2-oxopyrrolidin-1-yl]-4-oxo-1,4-dihydro-1,8-naphthyridine-3-carboxamide

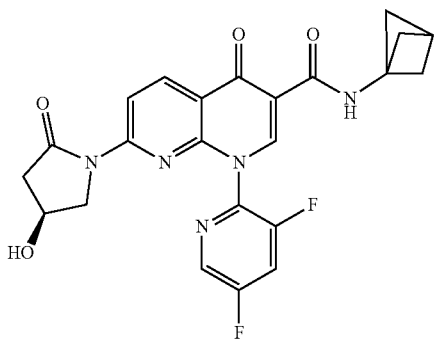

According to General Procedure 1, 60.0 mg (149 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 21.4 mg (179 µmol) of bicyclo[1.1.1]pentan-1-amine hydrochloride in the presence of 68.0 mg (179 µmol) of HATU and 78.0 µl (447 µmol) of DIPEA in 0.6 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 39.7 mg (57% of theory, purity 100%) of the title compound.

LC-MS (Methode 2): Rt=1.62 min; MS (ESIpos): m/z=468 [M+H]+.

$^1$H-NMR (400 MHz, DMSO-d6): δ [ppm]=10.02 (s, 1H), 8.95 (s, 1H), 8.65-8.69 (m, 2H), 8.49-8.55 (m, 1H), 8.36-8.42 (m, 1H), 5.35-5.39 (m, 0.5H), 5.24-5.27 (m, 0.5H), 4.26-4.31 (m, 1H), 3.64-3.77 (m, 1H), 3.44-3.55 (m, 1H), 2.88-3.01 (m, 1H), 2.32-2.42 (m, 1H), 2.11 (s, 6H).

Example 102

1-(3,5-Difluoropyridin-2-yl)-N-(3-fluorobicyclo[1.1.1]pent-1-yl)-7-[(4S)-4-hydroxy-2-oxopyrrolidin-1-yl]-4-oxo-1,4-dihydro-1,8-naphthyridine-3-carboxamide

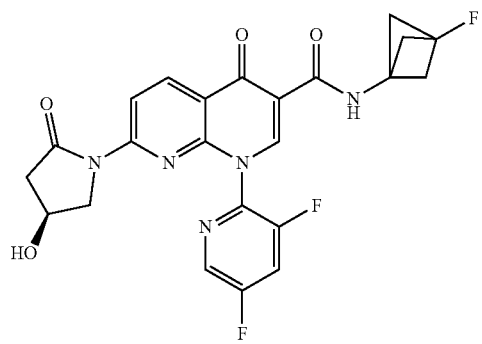

According to General Procedure 1, 60.0 mg (149 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 27.4 mg (179 µmol, purity 90%) of 3-fluorobicyclo[1.1.1]pentan-1-amine hydrochloride in the presence of 68.0 mg (179 µmol) of HATU and 78.0 µl (447 µmol) of DIPEA in 0.6 ml of DMF. The reaction mixture was diluted with acetonitrile, water and formic acid and filtered through a Millipore filter and the crude solution was purified twice by preparative HPLC (column: Chromatorex C18, 10 µm, 125*40 mm, solvent: acetonitrile, water, 0.1% formic acid), giving 9.00 mg (12% of theory, purity 100%) of the title compound.

LC-MS (Methode 2): Rt=1.57 min; MS (ESIpos): m/z=486 [M+H]+.

$^1$H-NMR (400 MHz, DMSO-d6): δ [ppm]=10.13 (s, 1H), 8.97 (s, 1H), 8.64-8.69 (m, 2H), 8.49-8.57 (m, 1H), 8.36-8.42 (m, 1H), 5.34-5.40 (m, 0.5H), 5.23-5.28 (m, 0.5H), 4.18-4.33 (m, 1H), 3.43-3.79 (m, 3H), 2.88-3.01 (m, 1H), 2.46 (d, 6H).

Example 103

N-(1,3-Difluoro-2-methylpropan-2-yl)-1-(3,5-difluoropyridin-2-yl)-7-[(3R,4R)-3,4-dihydroxypyrrolidin-1-yl]-4-oxo-1,4-dihydro-1,8-naphthyridine-3-carboxamide

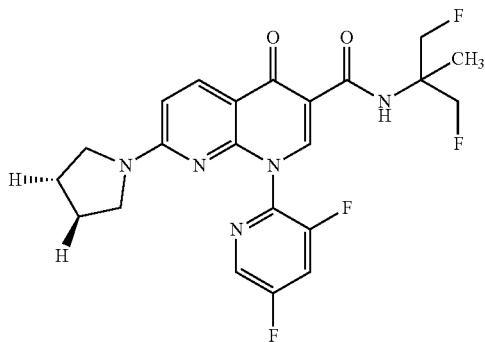

According to General Procedure 1, 30.0 mg (74.2 µmol) of 1-(3,5-difluoropyridin-2-yl)-7-[(3R,4R)-3,4-dihydroxypyrrolidin-1-yl-4-oxo-1,4-dihydro-1,8-naphthyridine-3-carboxylic acid (Example 23B) were reacted with 13.0 mg (89.0 µmol) of 1,3-difluoro-2-methylpropan-2-amine hydrochloride in the presence of 33.9 mg (89.0 µmol) of HATU and 39.0 µl (223 µmol) of DIPEA in 0.3 ml of DMF. The reaction mixture was diluted with acetonitrile, water and formic acid and filtered through a Millipore filter and the crude solution was purified by preparative HPLC (column: Chromatorex C18, 10 µm, 125*40 mm, solvent: acetonitrile, water, 0.1% formic acid), giving 28.6 mg (78% of theory, purity 100%) of the title compound.

LC-MS (Methode 2): Rt=1.37 min; MS (ESIpos): m/z=496 [M+H]+.

$^1$H-NMR (400 MHz, DMSO-d6): δ [ppm]=10.35 (s, 1H), 8.75 (d, 1H), 8.61 (d, 1H), 8.30-8.36 (m, 1H), 8.27 (d, 1H), 6.76 (d, 1H), 5.26 (br. d, 0.5H), 5.15-5.22 (m, 1H), 5.06 (br. d, 0.5H), 4.69-4.78 (m, 2H), 4.57-4.66 (m, 2H), 4.05 (br. s, 1H), 3.92 (br. s, 1H), 3.55-3.67 (m, 1H), 3.33-3.38 (m, 1H), 3.18-3.29 (m, 1H), 3.02-3.17 (m, 1H), 1.40-1.45 (m, 3H).

Example 104

N-[(1S)-1-Cyclopropyl-2,2,2-trifluoroethyl]-1-(3,5-difluoropyridin-2-yl)-7-[4-hydroxy-3-methyl-2-oxopyrrolidin-1-yl]-4-oxo-1,4-dihydro-1,8-naphthyridine-3-carboxamide (racemic diastereomer mixture)

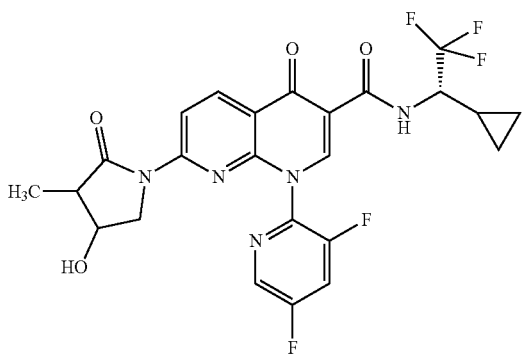 [SMILES: CC1C(=O)N(c2ccc3c(=O)c(C(=O)N[C@@H](C4CC4)C(F)(F)F)cn(-c4ncc(F)cc4F)c3n2)CC1O]

According to General Procedure 2, 50.0 mg (109 µmol) of 7-chloro-N-[(1S)-1-cyclopropyl-2,2,2-trifluoroethyl]-1-(3,5-difluoropyridin-2-yl)-4-oxo-1,4-dihydro-1,8-naphthyridine-3-carboxamide (Example 9A) were reacted with 15.1 mg (131 µmol) of 4-hydroxy-3-methylpyrrolidin-2-one (Example 2D) in the presence of 22.6 mg (163 µmol) of potassium carbonate, 4.89 mg (22.0 µmol) of palladium acetate and 12.6 mg (22.0 µmol) of Xantphos in 1 ml of dioxane at 80° C. A little acetonitrile, water and formic acid were then added and the reaction solution was filtered through a Millipore filter and purified by preparative HPLC (column: Chromatorex C18, 10 µm, 125*40 mm, solvent: acetonitrile, water, 0.1% formic acid). The product was recrystallized from acetonitrile giving 19.5 mg (33% of theory; 100% purity) of the title compound.

LC-MS (Methode 1): Rt=1.01 min; MS (ESIpos): m/z=538 [M+H]+.

$^1$H-NMR (400 MHz, DMSO-d6): δ [ppm]=10.23-10.30 (m, 1H), 9.03-9.06 (m, 1H), 8.71 (d, 1H), 8.65-8.69 (m, 1H), 8.50-8.59 (m, 1H), 8.36-8.43 (m, 1H), 5.43-5.54 (m, 0.25H), 5.10-5.33 (m, 0.75H), 4.37-4.47 (m, 1H), 4.19 (br. q, 0.75H), 3.75-3.98 (m, 0.5H), 3.48-3.69 (m, 1.5H), 3.22-3.28 (m, 0.25H), 2.77-2.92 (m, 0.75H), 1.05-1.28 (m, 4H), 0.52-0.70 (m, 3H), 0.30-0.39 (m, 1H).

13.0 mg of the title compound (diastereomer mixture) were separated into the diastereomers by chiral HPLC (preparative HPLC: column: Daicel Chiralcel OZ-H 5 µm 250×20 mm; mobile phase: 80% n-heptane, 20% ethanol; temperature: 23° C.; flow rate: 20 ml/min; UV detection: 258 nm).

This gave (in the sequence of elution from the column) 1.70 mg (2.9% of theory, purity 100%) of diastereomer 1 (racemate; Example 105) (55% de, rac) Rt=11.29 min, 1.30 mg (2.2% of theory, purity 100%) of diastereomer 2 (enantiomer A; Example 106) (95.6% de) Rt=14.43 min and 3.10 mg (5.2% of theory, purity 100%) of diastereomer 2 (enantiomer B; Example 107) (99.9% de) Rt=29.03 min.

[Analytical HPLC: column: Daicel Chiralpak OZ-3 3 µm 50×4.6 mm; mobile phase: 80% n-heptane, 20% ethanol; flow rate: 1.0 ml/min; UV detection: 220 nm]

Example 105

N-[(1S)-1-Cyclopropyl-2,2,2-trifluoroethyl]-1-(3,5-difluoropyridin-2-yl)-7-[4-hydroxy-3-methyl-2-oxopyrrolidin-1-yl]-4-oxo-1,4-dihydro-1,8-naphthyridine-3-carboxamide (diastereomer 1, racemate)

LC-MS (Methode 2): Rt=1.92 min; MS (ESIpos): m/z=538 [M+H]+.

1H NMR (400 MHz, DMSO-d6): δ [ppm]=10.13-10.32 (m, 1H), 9.02-9.08 (m, 1H), 8.71 (d, 1H), 8.67 (d, 1H), 8.48-8.59 (m, 1H), 8.36-8.44 (m, 1H), 5.45-5.53 (m, 1H), 4.37-4.46 (m, 1H), 3.44-4.04 (m, 2H), 1.06-1.31 (m, 6H), 0.51-0.71 (m, 3H), 0.31-0.39 (m, 1H).

Example 106

N-[(1S)-1-Cyclopropyl-2,2,2-trifluoroethyl]-1-(3,5-difluoropyridin-2-yl)-7-[4-hydroxy-3-methyl-2-oxopyrrolidin-1-yl]-4-oxo-1,4-dihydro-1,8-naphthyridine-3-carboxamide (diastereomer 2, enantiomer A)

LC-MS (Methode 2): Rt=1.91 min; MS (ESIpos): m/z=538 [M+H]+.

$^1$H NMR (400 MHz, DMSO-d6): δ [ppm]=10.26 (d, 1H), 9.04 (s, 1H), 8.71 (d, 1H), 8.65-8.69 (m, 1H), 8.51-8.59 (m, 1H), 8.36-8.42 (m, 1H), 5.29 (br. d, 0.5H), 5.15 (br. d, 0.5H), 4.37-4.48 (m, 1H), 4.19 (br. q, 1H), 3.46-3.68 (m, 2H), 2.77-2.92 (m, 1H), 1.05-1.30 (m, 4H), 0.51-0.71 (m, 3H), 0.30-0.39 (m, 1H).

Example 107

N-[(1S)-1-Cyclopropyl-2,2,2-trifluoroethyl]-1-(3,5-difluoropyridin-2-yl)-7-[4-hydroxy-3-methyl-2-oxopyrrolidin-1-yl]-4-oxo-1,4-dihydro-1,8-naphthyridine-3-carboxamide (diastereomer 2, enantiomer B)

LC-MS (Methode 2): Rt=1.91 min; MS (ESIpos): m/z=538 [M+H]+.

$^1$H-NMR (400 MHz, DMSO-d6): δ [ppm]=10.18-10.32 (m, 1H), 9.04 (s, 1H), 8.69-8.73 (m, 1H), 8.67 (br s, 1H), 8.49-8.60 (m, 1H), 8.35-8.43 (m, 1H), 5.11-5.54 (m, 1H), 4.38-4.46 (m, 1H), 4.13-4.23 (m, 1H), 3.45-3.70 (m, 1H), 2.75-2.94 (m, 1H), 1.04-1.32 (m, 5H), 0.47-0.75 (m, 3H), 0.27-0.43 (m, 1H).

Example 108

1-(3,5-Difluoropyridin-2-yl)-7-[4-hydroxy-3-methyl-2-oxopyrrolidin-1-yl]-4-oxo-N-[(2S)-1,1,1-trifluorobutan-2-yl]-1,4-dihydro-1,8-naphthyridine-3-carboxamide (racemic diastereomer mixture)

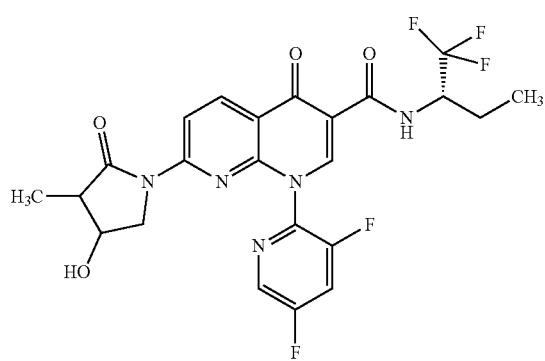 [SMILES: CC[C@H](NC(=O)c1cn(-c2ncc(F)cc2F)c2nc(N3CC(O)C(C)C3=O)ccc2c1=O)C(F)(F)F]

According to General Procedure 2, 50.0 mg (112 μmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 15.5 mg (134 μmol) of 4-hydroxy-3-methylpyrrolidin-2-one (Example 2D) in the presence of 23.2 mg (168 μmol) of potassium carbonate, 5.03 mg (22.0 μmol) of palladium acetate and 13.0 mg (22.0 μmol) of Xantphos in 1 ml of dioxane at 80° C. A little acetonitrile, water and formic acid were then added and the reaction solution was filtered through a Millipore filter and purified by preparative HPLC (column: Chromatorex C18, 10 μm, 125*40 mm, solvent: acetonitrile, water, 0.1% formic acid). The product was recrystallized from acetonitrile giving 23.7 mg (40% of theory; 100% purity) of the title compound.

LC-MS (Methode 1): Rt=0.99 min; MS (ESIpos): m/z=526 [M+H]+.

$^1$H-NMR 400 MHz, DMSO-d6): δ [ppm]=10.09-10.15 (m, 1H), 9.02-9.09 (m, 1H), 8.63-8.74 (m, 2H), 8.50-8.59 (m, 1H), 8.35-8.45 (m, 1H), 5.44-5.53 (m, 0.25H), 5.10-5.32 (m, 0.75H), 4.71-4.83 (m, 1H), 4.19 (br. q, 0.75H), 3.74-3.98 (m, 0.5H), 3.48-3.68 (m, 1.5H), 3.20-3.28 (m, 0.25H), 2.76-2.92 (m, 0.75H), 1.84-1.95 (m, 1H), 1.61-1.73 (m, 1H), 1.05-1.18 (m, 3H), 0.94-1.02 (m, 3H).

17.0 mg of the title compound (diastereomer mixture) were separated into the diastereomers by chiral HPLC (preparative HPLC: column: Daicel IA 250×20 mm; mobile phase: 80% n-heptane, 20% ethanol; temperature: 23° C.; flow rate: 20 ml/min; UV detection: 220 nm).

This gave (in the sequence of elution from the column) 3.30 mg (5.6% of theory, purity 100%) of diastereomer 1 (racemate; Example 109) (99.9 de, rac) R$_f$=10.37/10.83 min, 4.10 mg (6.9% of theory, purity 100%) of diastereomer 2 (enantiomer A; Example 110) (86.46% de) R$_f$=11.78 min and 4.50 mg (7.6% of theory, purity 100%) of diastereomer 2 (enantiomer B; Example 111) (99.9% de) R$_f$=13.61 min.

[Analytical HPLC: column: Daicel Chiralpak IA-3 3 μm 50×4.6 mm; mobile phase: 80% isohexane, 20% ethanol; flow rate: 1.0 ml/min; UV detection: 220 nm]

Example 109

1-(3,5-Difluoropyridin-2-yl)-7-[4-hydroxy-3-methyl-2-oxopyrrolidin-1-yl]-4-oxo-N-[(2S)-1,1,1-trifluorobutan-2-yl]-1,4-dihydro-1,8-naphthyridine-3-carboxamide (diastereomer 1, racemate)

LC-MS (Methode 2): Rt=1.89 min; MS (ESIpos): m/z=526 [M+H]+.

$^1$H-NMR (400 MHz, DMSO-d6): δ [ppm]=10.11 (d, 1H), 9.06 (s, 1H), 8.71 (d, 1H), 8.67 (d, 1H), 8.52 (d, 1H), 8.37-8.44 (m, 1H), 5.44-5.54 (m, 1H), 4.72-4.82 (m, 1H), 3.86-3.98 (m, 1H), 3.74-3.85 (m, 1H), 3.22-3.29 (m, 1H), 1.84-1.95 (m, 1H), 1.60-1.72 (m, 1H), 1.11-1.19 (m, 3H), 0.94-1.02 (m, 3H).

Example 110

1-(3,5-Difluoropyridin-2-yl)-7-[4-hydroxy-3-methyl-2-oxopyrrolidin-1-yl]-4-oxo-N-[(2S)-1,1,1-trifluorobutan-2-yl]-1,4-dihydro-1,8-naphthyridine-3-carboxamide (diastereomer 2, enantiomer A)

LC-MS (Methode 2): Rt=1.88 min; MS (ESIpos): m/z=526 [M+H]+.

$^1$H-NMR (400 MHz, DMSO-d6): δ [ppm]=10.12 (d, 1H), 9.05 (s, 1H), 8.71 (d, 1H), 8.67 (br. s, 1H), 8.56 (br. t, 1H), 8.39 (ddd, 1H), 5.29 (br. d, 0.5H), 5.16 (br. d, 0.5H), 4.72-4.83 (m, 1H), 4.17-4.22 (m, 1H), 3.47-3.71 (m, 2H), 2.76-2.92 (m, 1H), 1.84-1.95 (m, 1H), 1.61-1.73 (m, 1H), 1.05-1.12 (m, 3H), 0.94-1.03 (m, 3H).

Example 111

1-(3,5-Difluoropyridin-2-yl)-7-[4-hydroxy-3-methyl-2-oxopyrrolidin-1-yl]-4-oxo-N-[(2S)-1,1,1-trifluorobutan-2-yl]-1,4-dihydro-1,8-naphthyridine-3-carboxamide (diastereomer 2, enantiomer B)

LC-MS (Methode 2): Rt=1.88 min; MS (ESIpos): m/z=526 [M+H]+.

$^1$H-NMR (400 MHz, DMSO-d6): δ [ppm]=10.12 (br. d, 1H), 9.05 (s, 1H), 8.71 (d, 1H), 8.65-8.69 (m, 1H), 8.52-8.58 (m, 1H), 8.36-8.42 (m, 1H), 5.29 (br. d, 0.5H), 5.15 (br. d, 0.5H), 4.72-4.84 (m, 1H), 4.19 (q, 1H), 3.48-3.68 (m, 2H), 2.76-2.93 (m, 1H), 1.85-1.95 (m, 1H), 1.62-1.73 (m, 1H), 1.05-1.11 (m, 3H), 0.94-1.02 (m, 3H).

Example 112

1-(3,5-Difluoropyridin-2-yl)-7-[4-hydroxy-3-methyl-2-oxopyrrolidin-1-yl]-4-oxo-N-[(2S)-1,1,1-trifluoropropan-2-yl]-1,4-dihydro-1,8-naphthyridine-3-carboxamide (racemic diastereomer mixture)

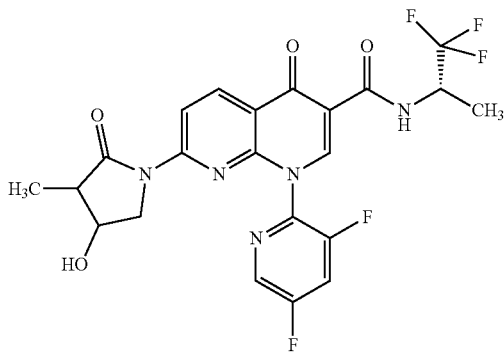 [SMILES: CC1C(=O)N(c2ccc3c(=O)c(C(=O)N[C@@H](C)C(F)(F)F)cn(-c4ncc(F)cc4F)c3n2)CC1O]

According to General Procedure 2, 50.0 mg (116 µmol) of 7-chloro-1-(3,5-difluoropyridin-2-yl)-4-oxo-N-[(2S)-1,1,1-trifluoropropan-2-yl]-1,4-dihydro-1,8-naphthyridine-3-carboxamide (Example 6A) were reacted with 16.0 mg (139 µmol) of 4-hydroxy-3-methylpyrrolidin-2-one (Example 2D) in the presence of 24.0 mg (173 µmol) of potassium carbonate, 5.19 mg (23.0 µmol) of palladium acetate and 13.4 mg (23.0 µmol) of Xantphos in 1 ml of dioxane at 80° C. A little acetonitrile, water and formic acid were then added and the reaction solution was filtered through a Millipore filter and purified by preparative HPLC (column: Chromatorex C18, 10 µm, 125*40 mm, solvent: acetonitrile, water, 0.1% formic acid). The product was recrystallized from acetonitrile giving 7.90 mg (13% of theory; 100% purity) of the title compound.

LC-MS (Methode 1): Rt=0.93 min; MS (ESIpos): m/z=512 [M+H]+.

$^1$H-NMR (400 MHz, DMSO-d6): δ [ppm]=10.14-10.20 (m, 1H), 9.03-9.06 (m, 1H), 8.64-8.72 (m, 2H), 8.50-8.58 (m, 1H), 8.36-8.43 (m, 1H), 5.45-5.53 (m, 0.25H), 5.13-5.31 (m, 0.75H), 4.87-4.98 (m, 1H), 4.19 (br. q, 0.75H), 3.88-3.97 (m, 0.25H), 3.74-3.85 (m, 0.25H), 3.47-3.68 (m, 1.50H), 3.21-3.28 (m, 0.25H), 2.76-2.92 (m, 0.75H), 1.40 (br. d, 3H), 1.05-1.18 (m, 3H).

Example 113

1-(3,5-Difluoropyridin-2-yl)-7-[7-hydroxy-6-methyl-4-oxo-5-azaspiro[2.4]hept-5-yl]-4-oxo-N-[(2S)-1,1,1-trifluorobutan-2-yl]-1,4-dihydro-1,8-naphthyridine-3-carboxamide (diastereomer mixture)

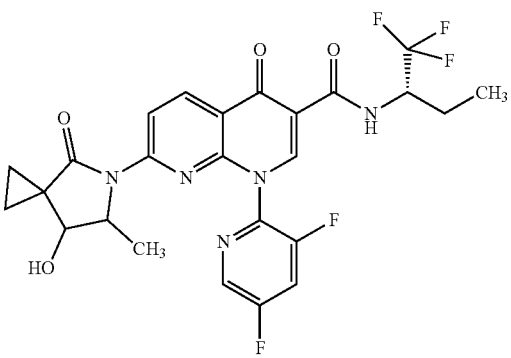 [SMILES: CC[C@H](NC(=O)c1cn(-c2ncc(F)cc2F)c2nc(N3C(=O)C4(CC4)C(O)C3C)ccc2c1=O)C(F)(F)F]

According to General Procedure 2, 100 mg (224 µmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 37.9 mg (269 µmol) of 7-hydroxy-6-methyl-5-azaspiro[2.4]heptan-4-one (Example 3E) in the presence of 46.4 mg (336 µmol) of potassium carbonate, 10.1 mg (45.0 µmol) of palladium acetate and 25.9 mg (45.0 µmol) of Xantphos in 2 ml of dioxane at 80° C. A little acetonitrile, water and formic acid were then added and the reaction solution was filtered through a Millipore filter and purified by preparative HPLC (column: Chromatorex C18, 10 µm, 125*40 mm, solvent: acetonitrile, water, 0.1% formic acid). The product was recrystallized from acetonitrile giving 57.1 mg (46% of theory; 100% purity) of the title compound.

LC-MS (Methode 1): Rt=1.08 min; MS (ESIpos): m/z=552 [M+H]+.

$^1$H-NMR (400 MHz, DMSO-d6): δ [ppm]=10.12 (d, 1H), 9.07 (d, 1H), 8.66-8.71 (m, 2H), 8.40-8.51 (m, 2H), 5.29-5.33 (m, 1H), 4.72-4.83 (m, 1H), 4.31-4.40 (m, 1H), 4.16-4.27 (m, 1H), 1.84-1.95 (m, 1H), 1.61-1.73 (m, 1H), 1.17-1.26 (m, 1H), 1.03-1.17 (m, 3H), 0.94-1.02 (m, 3H), 0.79-0.88 (m, 3H).

Example 114

N-[(1R)-1-Cyclopropyl-2,2,2-trifluoroethyl]-1-(3,5-difluoropyridin-2-yl)-7-[7-hydroxy-6-methyl-4-oxo-5-azaspiro[2.4]hept-5-yl]-4-oxo-1,4-dihydro-1,8-naphthyridine-3-carboxamide (diastereomer mixture)

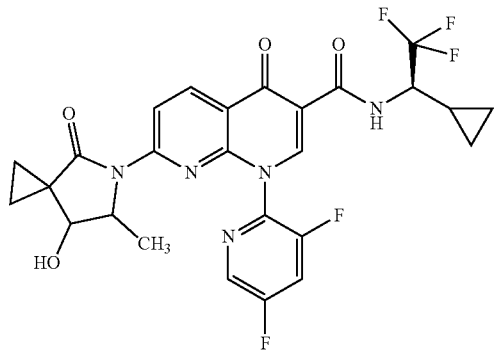 [SMILES: CC1C(O)C2(CC2)C(=O)N1c1ccc2c(=O)c(C(=O)N[C@H](C3CC3)C(F)(F)F)cn(-c3ncc(F)cc3F)c2n1]

According to General Procedure 2, 100 mg (218 µmol) of 7-chloro-N-[(1R)-1-cyclopropyl-2,2,2-trifluoroethyl]-1-(3,5-difluoropyridin-2-yl)-4-oxo-1,4-dihydro-1,8-naphthyridine-3-carboxamide (Example 8A) were reacted with 36.9 mg (262 µmol) of 7-hydroxy-6-methyl-5-azaspiro[2.4]heptan-4-one (Example 3E) in the presence of 45.2 mg (327 µmol) of potassium carbonate, 9.79 mg (44.0 µmol) of palladium acetate and 25.2 mg (44.0 µmol) of Xantphos in 2 ml of dioxane at 80° C. A little acetonitrile, water and formic acid were then added and the reaction solution was filtered through a Millipore filter and purified by preparative HPLC (column: Chromatorex C18, 10 µm, 125*40 mm, solvent: acetonitrile, water, 0.1% formic acid). The product was recrystallized from acetonitrile giving 71.9 mg (59% of theory; 100% purity) of the title compound.

LC-MS (Methode 2): Rt=2.08 min; MS (ESIpos): m/z=564 [M+H]+.

$^1$H-NMR (400 MHz, DMSO-d6): δ [ppm]=10.26 (d, 1H), 9.07 (d, 1H), 8.66-8.71 (m, 2H), 8.39-8.51 (m, 2H), 5.29-5.34 (m, 1H), 4.31-4.46 (m, 2H), 4.15-4.27 (m, 1H), 1.18-1.28 (m, 2H), 1.02-1.17 (m, 3H), 0.78-0.87 (m, 3H), 0.52-0.70 (m, 3H), 0.30-0.39 (m, 1H).

Example 115

N-[(1S)-1-Cyclopropyl-2,2,2-trifluoroethyl]-1-(3,5-difluoropyridin-2-yl)-7-[7-hydroxy-6-methyl-4-oxo-5-azaspiro[2.4]hept-5-yl]-4-oxo-1,4-dihydro-1,8-naphthyridine-3-carboxamide (diastereomer mixture)

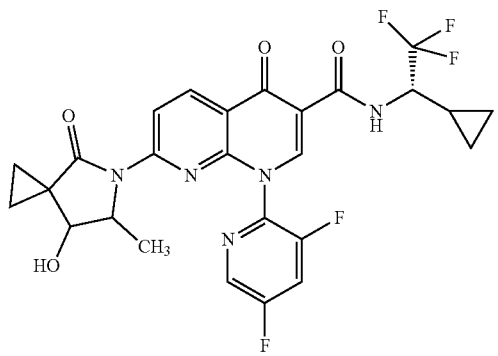 [SMILES: CC1C(O)C2(CC2)C(=O)N1c1ccc2c(=O)c(C(=O)N[C@@H](C3CC3)C(F)(F)F)cn(-c3ncc(F)cc3F)c2n1]

According to General Procedure 2, 100 mg (218 μmol) of 7-chloro-N-[(1S)-1-cyclopropyl-2,2,2-trifluoroethyl]-1-(3,5-difluoropyridin-2-yl)-4-oxo-1,4-dihydro-1,8-naphthyridine-3-carboxamide (Example 9A) were reacted with 36.9 mg (262 μmol) of 7-hydroxy-6-methyl-5-azaspiro[2.4]heptan-4-one (Example 3E) in the presence of 45.2 mg (327 μmol) of potassium carbonate, 9.79 mg (44.0 μmol) of palladium acetate and 25.2 mg (44.0 μmol) of Xantphos in 2 ml of dioxane at 80° C. A little acetonitrile, water and formic acid were then added and the reaction solution was filtered through a Millipore filter and purified by preparative HPLC (column: Chromatorex C18, 10 μm, 125*40 mm, solvent: acetonitrile, water, 0.1% formic acid). The product was recrystallized from acetonitrile giving 43.9 mg (36% of theory; 100% purity) of the title compound.

LC-MS (Methode 2): Rt=2.08 min; MS (ESIpos): m/z=564 [M+H]+.

$^1$H-NMR (400 MHz, DMSO-d6): δ [ppm]=10.26 (d, 1H), 9.07 (d, 1H), 8.65-8.72 (m, 2H), 8.39-8.52 (m, 2H), 5.31 (br s, 1H), 4.31-4.46 (m, 2H), 4.16-4.27 (m, 1H), 1.18-1.28 (m, 2H), 1.05-1.18 (m, 3H), 0.77-0.90 (m, 3H), 0.52-0.70 (m, 3H), 0.31-0.39 (m, 1H).

Example 116

1-(3,5-Difluoropyridin-2-yl)-7-[7-hydroxy-6-methyl-4-oxo-5-azaspiro[2.4]hept-5-yl]-4-oxo-N-[(2S)-1,1,1-trifluoropropan-2-yl]-1,4-dihydro-1,8-naphthyridine-3-carboxamide (diastereomer mixture)

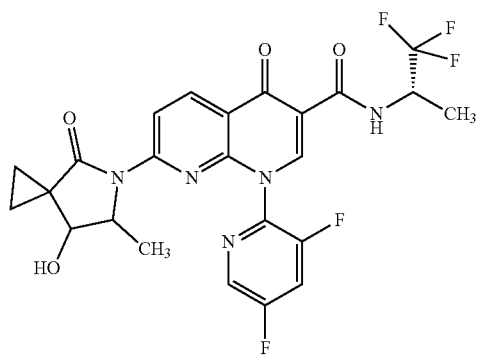 [SMILES: CC1C(O)C2(CC2)C(=O)N1c1ccc2c(=O)c(C(=O)N[C@@H](C)C(F)(F)F)cn(-c3ncc(F)cc3F)c2n1]

According to General Procedure 2, 100 mg (231 μmol) of 7-chloro-1-(3,5-difluoropyridin-2-yl)-4-oxo-N-[(2S)-1,1,1-trifluoropropan-2-yl]-1,4-dihydro-1,8-naphthyridine-3-carboxamide (Example 6A) were reacted with 39.1 mg (277 μmol) of 7-hydroxy-6-methyl-5-azaspiro[2.4]heptan-4-one (Example 3E) in the presence of 47.9 mg (347 μmol) of potassium carbonate, 10.4 mg (46.0 μmol) of palladium acetate and 26.7 mg (46.0 μmol) of Xantphos in 2 ml of dioxane at 80° C. A little acetonitrile, water and formic acid were then added and the reaction solution was filtered through a Millipore filter and purified by preparative HPLC (column: Chromatorex C18, 10 μm, 125*40 mm, solvent: acetonitrile, water, 0.1% formic acid). The product was recrystallized from acetonitrile giving 80.5 mg (65% of theory; 100% purity) of the title compound.

LC-MS (Methode 1): Rt=1.02 min; MS (ESIpos): m/z=538 [M+H]+.

$^1$H-NMR (400 MHz, DMSO-d6): δ [ppm]=10.17 (d, 1H), 9.07 (d, 1H), 8.63-8.72 (m, 2H), 8.39-8.51 (m, 2H), 5.29-5.33 (m, 1H), 4.87-4.98 (m, 1H), 4.31-4.40 (m, 1H), 4.15-4.27 (m, 1H), 1.40 (d, 3H), 1.18-1.26 (m, 1H), 1.03-1.18 (m, 3H), 0.76-0.88 (m, 3H).

Example 117

1-(3,5-Difluoropyridin-2-yl)-7-[3-hydroxypiperidin-1-yl]-4-oxo-N-[(2R)-1,1,1-trifluorobutan-2-yl]-1,4-dihydro-1,8-naphthyridine-3-carboxamide (diastereomer mixture)

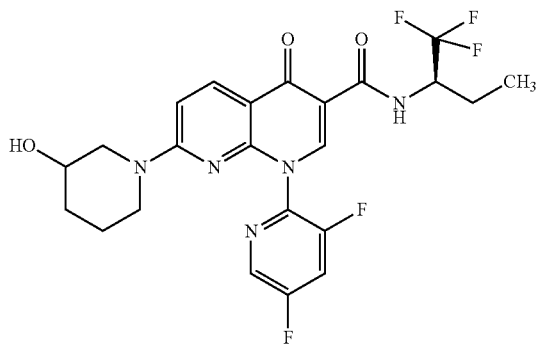 [SMILES: CC[C@@H](NC(=O)c1cn(-c2ncc(F)cc2F)c2nc(N3CCCC(O)C3)ccc2c1=O)C(F)(F)F]

According to General Procedure 3, 25.0 mg (56.0 μmol) of 7-chloro-1-(3,5-difluoropyridin-2-yl)-4-oxo-N-[(2R)-1,1,1-trifluorobutan-2-yl]-1,4-dihydro-1,8-naphthyridine-3-carboxamide (Example 4C) were reacted with 6.79 mg (67.1 μmol) of piperidin-3-ol (racemate) in the presence of 34.0 μl (196 μmol) of DIPEA in 0.28 ml of DMF. The reaction mixture was diluted with water, acetonitrile and formic acid, filtered through a Millipore filter and purified by preparative HPLC (column: Chromatorex C18, 10 μm, 125*40 mm, solvent: acetonitrile, water, 0.1% formic acid), giving 25.5 mg (89% of theory, purity 100%) of the title compound.

LC-MS (Methode 2): Rt=1.85 min; MS (ESIpos): m/z=512 [M+H]+.

$^1$H-NMR (500 MHz, DMSO-d6): δ [ppm]=10.39 (d, 1H), 8.81 (br s, 1H), 8.62 (br d, 1H), 8.28-8.36 (m, 1H), 8.25 (dd, 1H), 7.10 (d, 1H), 4.81-4.86 (m, 1H), 4.69-4.79 (m, 1H), 3.58-3.90 (m, 2H), 3.38-3.53 (m, 1H), 2.89-3.25 (m, 2H), 1.79-1.92 (m, 2H), 1.59-1.70 (m, 2H), 1.26-1.46 (m, 2H), 0.96 (br dd, 3H).

Example 118

1-(3,5-Difluoropyridin-4-yl)-7-[(3R,4R)-3,4-dihydroxypyrrolidin-1-yl]-4-oxo-N-[(2S)-1,1,1-trifluorobutan-2-yl]-1,4-dihydro-1,8-naphthyridine-3-carboxamide

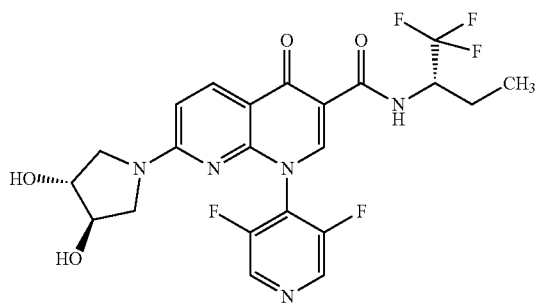 [SMILES: CC[C@H](NC(=O)c1cn(-c2c(F)cncc2F)c2nc(N3C[C@@H](O)[C@H](O)C3)ccc2c1=O)C(F)(F)F]

According to General Procedure 3, 40.0 mg (89.5 µmol) of 7-chloro-1-(3,5-difluoropyridin-4-yl)-4-oxo-N-[(2S)-1,1,1-trifluorobutan-2-yl]-1,4-dihydro-1,8-naphthyridine-3-carboxamide (Example 22C) were reacted with 15.0 mg (107 µmol) of (3R,4R)-pyrrolidine-3,4-diol hydrochloride in the presence of 55.0 µl (313 µmol) of DIPEA in 3 ml of DMF. The reaction mixture was diluted with water and acetonitrile, filtered and purified by preparative HPLC (water/acetonitrile gradient, 0.1% trifluoroacetic acid gradient), giving 37.8 mg (82% of theory, purity 100%) of the title compound.

LC-MS (Methode 2): Rt=1.53 min; MS (ESIpos): m/z=514 [M+H]+.

$^1$H-NMR (400 MHz, DMSO-d6): δ [ppm]=10.39 (d, 1H), 8.91 (s, 1H), 8.86 (d, 2H), 8.28 (d, 1H), 6.80 (d, 1H), 4.64-4.85 (m, 1H), 3.99-4.11 (m, 1H), 3.88-3.95 (m, 1H), 3.60-3.64 (m, 3H), 3.30-3.46 (m, 1H), 3.16-3.30 (m, 1H), 3.03-3.06 (m, 1H), 1.83-1.93 (m, 1H), 1.59-1.70 (m, 1H), 0.97 (t, 3H).

Example 119

1-(3,5-Difluoropyridin-2-yl)-7-[3-(2-hydroxyethyl)-2-oxoimidazolidin-1-yl]-4-oxo-N-[(2S)-1,1,1-trifluorobutan-2-yl]-1,4-dihydro-1,8-naphthyridine-3-carboxamide

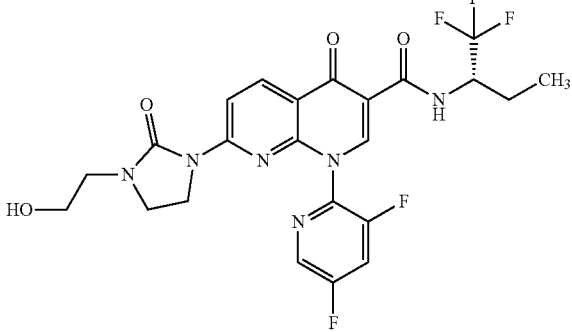

According to General Procedure 1, 40.0 mg (92.7 µmol) of 1-(3,5-difluoropyridin-2-yl)-7-[3-(2-hydroxyethyl)-2-oxoimidazolidin-1-yl]-4-oxo-1,4-dihydro-1,8-naphthyridine-3-carboxylic acid (Example 25A) were reacted with 18.2 mg (111 µmol) of (2S)-1,1,1-trifluorobutan-2-amine hydrochloride in the presence of 42.3 mg (111 µmol) of HATU and 65.0 µl (371 µmol) of DIPEA in 0.6 ml of DMF. The reaction mixture was diluted with water, acetonitrile and formic acid, filtered through a Millipore filter and purified by preparative HPLC (column: Chromatorex C18, 10 µm, 125*40 mm, solvent: acetonitrile, water, 0.1% formic acid), giving 36.8 mg (73% of theory, purity 100%) of the title compound.

LC-MS (Methode 2): Rt=1.73 min; MS (ESIpos): m/z=541 [M+H]+.

$^1$H-NMR (400 MHz, DMSO-d6): δ [ppm]=10.21 (d, 1H), 8.99 (s, 1H), 8.64 (br. d, 1H), 8.57 (d, 1H), 8.44 (d, 1H), 8.33 (ddd, 1H), 4.71-4.83 (m, 2H), 3.43-3.63 (m, 6H), 3.21-3.30 (m, 2H), 1.84-1.95 (m, 1H), 1.60-1.72 (m, 1H), 0.94-1.01 (m, 3H).

Example 120

1-(3,5-Difluoropyridin-2-yl)-7-[3-(2-hydroxyethyl)-2-oxotetrahydropyrimidin-1(2H)-yl]-4-oxo-N-[(2S)-1,1,1-trifluorobutan-2-yl]-1,4-dihydro-1,8-naphthyridine-3-carboxamide

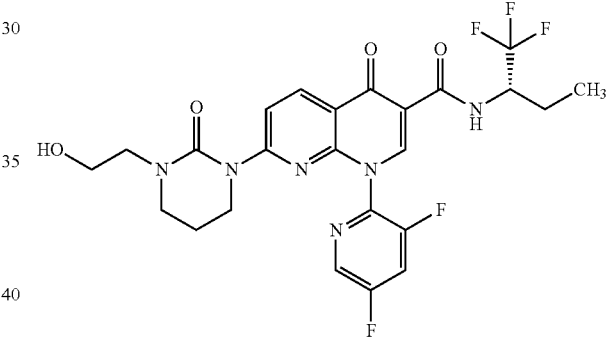

According to General Procedure 1, 40.0 mg (89.8 µmol, purity 86%) of 1-(3,5-difluoropyridin-2-yl)-7-[3-(2-hydroxyethyl)-2-oxotetrahydropyrimidin-1(2H)-yl]-4-oxo-1,4-dihydro-1,8-naphthyridine-3-carboxylic acid (Example 26B) were reacted with 17.6 mg (108 µmol) of (2S)-1,1,1-trifluorobutan-2-amine hydrochloride in the presence of 41.0 mg (108 µmol) of HATU and 63.0 µl (359 µmol) of DIPEA in 0.6 ml of DMF. The reaction mixture was diluted with water, acetonitrile and formic acid, filtered through a Millipore filter and purified by preparative HPLC (column: Chromatorex C18, 10 µm, 125*40 mm, solvent: acetonitrile, water, 0.1% formic acid), giving 37.1 mg (75% of theory, purity 100%) of the title compound.

LC-MS (Methode 1): Rt=0.98 min; MS (ESIpos): m/z=555 [M+H]+.

$^1$H-NMR (400 MHz, DMSO-d6): δ [ppm]=10.18 (d, 1H), 9.01 (s, 1H), 8.65 (d, 1H), 8.50 (d, 1H), 8.36 (ddd, 1H), 8.17 (d, 1H), 4.73-4.82 (m, 1H), 4.71 (t, 1H), 3.48-3.60 (m, 4H), 3.35-3.42 (m, 4H), 1.85-1.96 (m, 3H), 1.60-1.72 (m, 1H), 0.94-1.02 (m, 3H).

Example 121

N-[(1R)-1-Cyclopropyl-2,2,2-trifluoroethyl]-1-(3,5-difluoropyridin-2-yl)-7-[3-(2-hydroxyethyl)-2-oxoimidazolidin-1-yl]-4-oxo-1,4-dihydro-1,8-naphthyridine-3-carboxamide

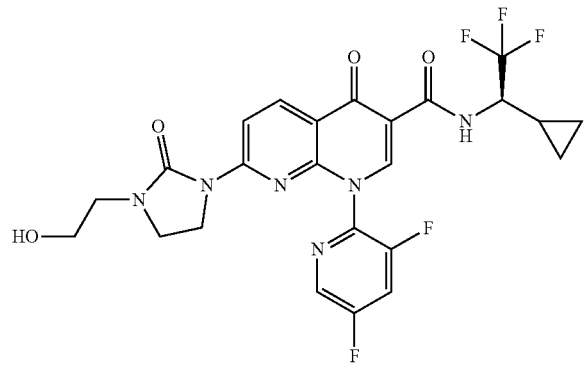 [SMILES: O=C(N[C@H](C1CC1)C(F)(F)F)c1cn(-c2ncc(F)cc2F)c2nc(N3CCN(CCO)C3=O)ccc2c1=O]

According to General Procedure 1, 40.0 mg (92.7 µmol) of 1-(3,5-difluoropyridin-2-yl)-7-[3-(2-hydroxyethyl)-2-oxoimidazolidin-1-yl]-4-oxo-1,4-dihydro-1,8-naphthyridine-3-carboxylic acid (Example 25A) were reacted with 19.5 mg (111 µmol) of (1R)-1-cyclopropyl-2,2,2-trifluoroethanamine hydrochloride in the presence of 42.3 mg (111 µmol) of HATU and 65.0 µl (371 µmol) of DIPEA in 0.6 ml of DMF. The reaction mixture was diluted with water, acetonitrile and formic acid, filtered through a Millipore filter and purified by preparative HPLC (column: Chromatorex C18, 10 µm, 125*40 mm, solvent: acetonitrile, water, 0.1% formic acid), giving 32.3 mg (63% of theory, purity 100%) of the title compound.

LC-MS (Methode 2): Rt=1.77 min; MS (ESIpos): m/z=553 [M+H]+.

$^1$H-NMR (400 MHz, DMSO-d6): δ [ppm]=10.34 (br d, 1H), 8.98 (s, 1H), 8.64 (d, 1H), 8.57 (d, 1H), 8.45 (d, 1H), 8.33 (ddd, 1H), 4.75 (t, 1H), 4.37-4.47 (m, 1H), 3.44-3.62 (m, 6H), 3.21-3.30 (m, 2H), 1.19-1.27 (m, 1H), 0.51-0.70 (m, 3H), 0.30-0.39 (m, 1H).

Example 122

N-[(1R)-1-Cyclopropyl-2,2,2-trifluoroethyl]-1-(3,5-difluoropyridin-2-yl)-7-[3-(2-hydroxyethyl)-2-oxotetrahydropyrimidin-1(2H)-yl]-4-oxo-1,4-dihydro-1,8-naphthyridine-3-carboxamide

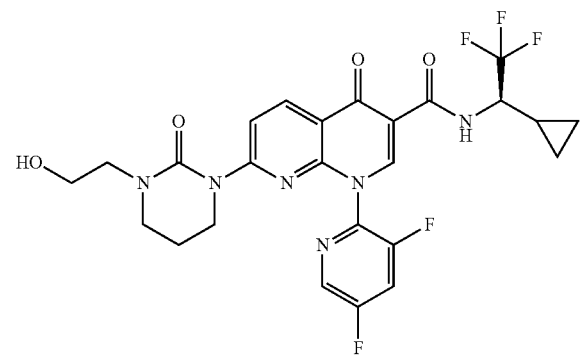 [SMILES: O=C(N[C@H](C1CC1)C(F)(F)F)c1cn(-c2ncc(F)cc2F)c2nc(N3CCCN(CCO)C3=O)ccc2c1=O]

According to General Procedure 1, 40.0 mg (89.8 µmol, purity 86%) of 1-(3,5-difluoropyridin-2-yl)-7-[3-(2-hydroxyethyl)-2-oxotetrahydropyrimidin-1(2H)-yl]-4-oxo-1,4-dihydro-1,8-naphthyridine-3-carboxylic acid (Example 26B) were reacted with 18.9 mg (108 µmol) of (1R)-1-cyclopropyl-2,2,2-trifluoroethanamine hydrochloride in the presence of 41.0 mg (108 µmol) of HATU and 63.0 µl (359 µmol) of DIPEA in 0.6 ml of DMF. The reaction mixture was diluted with water, acetonitrile and formic acid, filtered through a Millipore filter and purified by preparative HPLC (column: Chromatorex C18, 10 µm, 125*40 mm, solvent: acetonitrile, water, 0.1% formic acid), giving 37.3 mg (73% of theory, purity 100%) of the title compound.

LC-MS (Methode 1): Rt=1.00 min; MS (ESIpos): m/z=567 [M+H]+.

$^1$H-NMR (400 MHz, DMSO-d6): δ [ppm]=10.33 (d, 1H), 9.00 (s, 1H), 8.65 (d, 1H), 8.51 (d, 1H), 8.36 (ddd, 1H), 8.17 (d, 1H), 4.71 (t, 1H), 4.36-4.47 (m, 1H), 3.48-3.58 (m, 4H), 3.36-3.42 (m, 4H), 1.87-1.96 (m, 2H), 1.18-1.28 (m, 1H), 0.51-0.70 (m, 3H), 0.31-0.39 (m, 1H).

Example 123

N-[(1S)-1-Cyclopropyl-2,2,2-trifluoroethyl]-1-(3,5-difluoropyridin-2-yl)-7-[3-(2-hydroxyethyl)-2-oxotetrahydropyrimidin-1(2H)-yl]-4-oxo-1,4-dihydro-1,8-naphthyridine-3-carboxamide

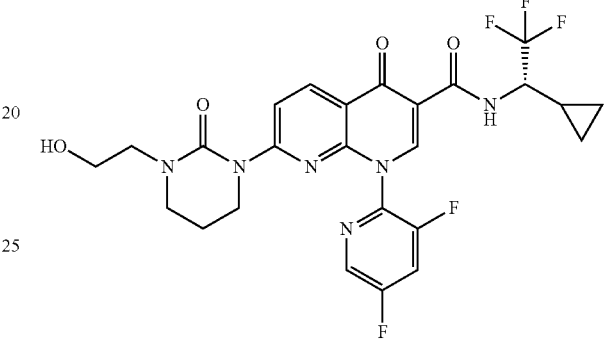

According to General Procedure 1, 30.0 mg (67.4 µmol, purity 86%) of 1-(3,5-difluoropyridin-2-yl)-7-[3-(2-hydroxyethyl)-2-oxotetrahydropyrimidin-1(2H)-yl]-4-oxo-1,4-dihydro-1,8-naphthyridine-3-carboxylic acid (Example 26B) were reacted with 14.2 mg (81.0 µmol) of (1S)-1-cyclopropyl-2,2,2-trifluoroethanamine hydrochloride in the presence of 30.7 mg (81.0 µmol) of HATU and 47.0 µl (269 µmol) of DIPEA in 0.5 ml of DMF. The reaction mixture was diluted with water, acetonitrile and formic acid, filtered through a Millipore filter and purified by preparative HPLC (column: Chromatorex C18, 10 µm, 125*40 mm, solvent: acetonitrile, water, 0.1% formic acid), giving 26.5 mg (69% of theory, purity 100%) of the title compound.

LC-MS (Methode 1): Rt=1.00 min; MS (ESIpos): m/z=567 [M+H]+.

$^1$H-NMR (400 MHz, DMSO-d6): δ [ppm]=10.33 (d, 1H), 9.00 (s, 1H), 8.65 (d, 1H), 8.51 (d, 1H), 8.36 (ddd, 1H), 8.17 (d, 1H), 4.71 (t, 1H), 4.35-4.50 (m, 1H), 3.47-3.60 (m, 4H), 3.35-3.42 (m, 4H), 1.86-1.96 (m, 2H), 1.18-1.28 (m, 1H), 0.52-0.70 (m, 3H), 0.30-0.39 (m, 1H).

Example 124

1-(3,5-Difluoropyridin-2-yl)-7-[3-(2-hydroxyethyl)-2-oxoimidazolidin-1-yl]-4-oxo-N-[(2S)-1,1,1-trifluoro-3,3-dimethylbutan-2-yl]-1,4-dihydro-1,8-naphthyridine-3-carboxamide

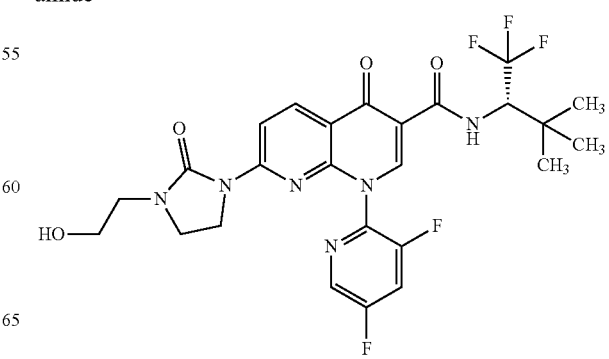

According to General Procedure 2, 60.0 mg (126 μmol) of 7-chloro-1-(3,5-difluoropyridin-2-yl)-4-oxo-N-[(2S)-1,1,1-trifluoro-3,3-dimethylbutan-2-yl]-1,4-dihydro-1,8-naphthyridine-3-carboxamide (Example 13A) were reacted with 37.1 mg (152 μmol) of 1-(2-{[tert-butyl(dimethyl)silyl]oxy}ethyl)imidazolidin-2-one (EP 1721905 A1, Ex. 43) in the presence of 43.7 mg (316 μmol) of potassium carbonate, 5.67 mg (25.0 μmol) of palladium acetate and 14.6 mg (25.0 μmol) of Xantphos in 1.6 ml of dioxane at 90° C. for 90 min. The crude product was partially purified by preparative HPLC. The crude product was then taken up in 5 ml of dioxane, 5 ml of 1N aqueous hydrochloric acid were added and the mixture was stirred at 40° C. for 1 h. All volatile components were removed under reduced pressure and the residue was dissolved in a little DMSO, water, acetonitrile and formic acid, filtered through a Millipore filter and purified by preparative HPLC (column: Chromatorex C18, 10 μm, 125*40 mm, solvent: acetonitrile, water, 0.1% formic acid), giving 17.4 mg (24% of theory, purity 100%) of the title compound.

LC-MS (Methode 2): Rt=1.93 min; MS (ESIpos): m/z=569 [M+H]+.

$^1$H-NMR (400 MHz, DMSO-d6): δ [ppm]=10.57 (br. dd, 1H), 9.00 (s, 1H), 8.64 (br. d, 1H), 8.60 (d, 1H), 8.45 (d, 1H), 8.29-8.37 (m, 1H), 4.75 (t, 1H), 4.65 (quint, 1H), 3.40-3.70 (m, 7H), 3.21-3.28 (m, 1H), 1.10 (br. s, 9H).

Example 125

1-(3,5-Difluoropyridin-2-yl)-7-[3-(2-hydroxyethyl)-2-oxotetrahydropyrimidin-1(2H)-yl]-4-oxo-N-[(2S)-1,1,1-trifluoro-3,3-dimethylbutan-2-yl]-1,4-dihydro-1,8-naphthyridine-3-carboxamide

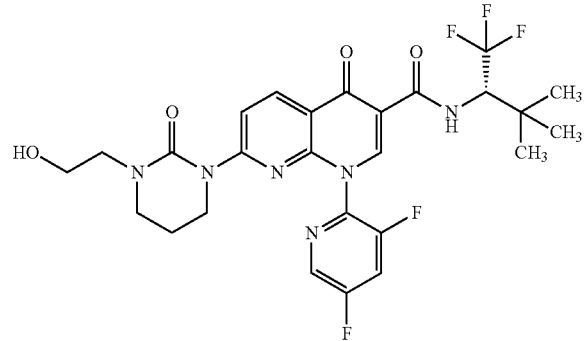 [SMILES: CC(C)(C)[C@H](NC(=O)c1cn(-c2ncc(F)cc2F)c2nc(N3CCCN(CCO)C3=O)ccc2c1=O)C(F)(F)F]

According to General Procedure 2, 60.0 mg (126 μmol) of 7-chloro-1-(3,5-difluoropyridin-2-yl)-4-oxo-N-[(2S)-1,1,1-trifluoro-3,3-dimethylbutan-2-yl]-1,4-dihydro-1,8-naphthyridine-3-carboxamide (Example 13A) were reacted with 39.2 mg (152 μmol) of 1-(2-{[tert-butyl(dimethyl)silyl]oxy}ethyl)tetrahydropyrimidin-2(1H)-one (Example 26A) in the presence of 43.7 mg (316 μmol) of potassium carbonate, 5.67 mg (25.0 μmol) of palladium acetate and 14.6 mg (25.0 μmol) of
Xantphos in 1.6 ml of dioxane at 90° C. for 90 min. The crude product was partially purified by preparative HPLC. The crude product was then taken up in 5 ml of dioxane, 5 ml of 1N aqueous hydrochloric acid were added and the mixture was stirred at 40° C. for 1 h. All volatile components were removed under reduced pressure and the residue was dissolved in a little DMSO, water, acetonitrile and formic acid, filtered through a Millipore filter and purified by preparative HPLC (column: Chromatorex C18, 10 μm, 125*40 mm, solvent: acetonitrile, water, 0.1% formic acid), giving 37.7 mg (51% of theory, purity 100%) of the title compound.

LC-MS (Methode 2): R$_t$=1.93 min; MS (ESIpos): m/z=583 [M+H]+.

$^1$H-NMR (400 MHz, DMSO-d6): δ [ppm]=10.54 (br. d, 1H), 9.02 (s, 1H), 8.62-8.67 (m, 1H), 8.53 (d, 1H), 8.32-8.40 (m, 1H), 8.18 (d, 1H), 4.71 (t, 1H), 4.60-4.69 (m, 1H), 3.48-3.60 (m, 4H), 3.36-3.42 (m, 4H), 1.86-1.97 (m, 2H), 1.10 (s, 9H).

Example 126

1-(3,5-Difluoropyridin-2-yl)-7-[3-(2-hydroxyethyl)-2-oxoimidazolidin-1-yl]-4-oxo-N-[(2R)-1,1,1-trifluoro-3,3-dimethylbutan-2-yl]-1,4-dihydro-1,8-naphthyridine-3-carboxamide

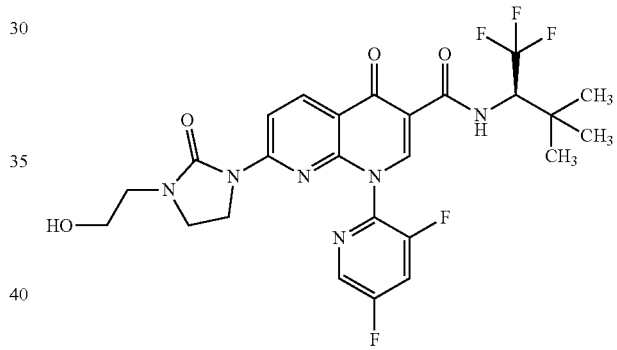

According to General Procedure 1, 40.0 mg (92.7 μmol) of 1-(3,5-difluoropyridin-2-yl)-7-[3-(2-hydroxyethyl)-2-oxoimidazolidin-1-yl]-4-oxo-1,4-dihydro-1,8-naphthyridine-3-carboxylic acid (Example 25A) were reacted with 17.3 mg (111 μmol) of (2R)-1,1,1-trifluoro-3,3-dimethylbutan-2-amine in the presence of 42.3 mg (111 μmol) of HATU and 48.0 μl (278 μmol) of DIPEA in 0.6 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 37.3 mg (71% of theory, purity 100%) of the title compound.

LC-MS (Methode 2): Rt=1.93 min; MS (ESIpos): m/z=569 [M+H]+.

$^1$HNMR (400 MHz, DMSO-d6): δ [ppm]=10.57 (br dd, 1H), 9.00 (s, 1H), 8.64 (br d, 1H), 8.60 (d, 1H), 8.45 (d, 1H), 8.29-8.36 (m, 1H), 4.75 (t, 1H), 4.65 (quintt, 1H), 3.44-3.63 (m, 6H), 3.22-3.30 (m, 2H), 1.10 (s, 9H).

Example 127

1-(3,5-Difluoropyridin-2-yl)-7-[3-(2-hydroxyethyl)-2-oxo-tetrahydropyrimidin-1(2H)-yl]-4-oxo-N-[(2R)-1,1,1-trifluoro-3,3-dimethylbutan-2-yl]-1,4-dihydro-1,8-naphthyridine-3-carboxamide

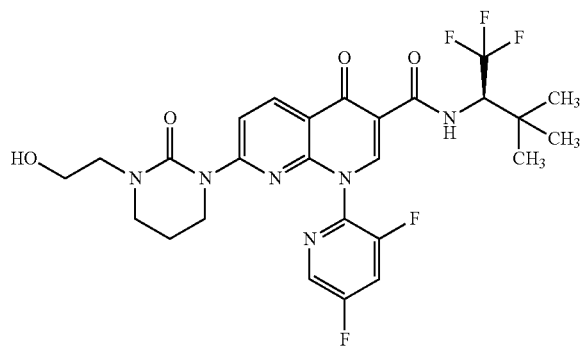 [SMILES: CC(C)(C)[C@@H](NC(=O)c1cn(-c2ncc(F)cc2F)c2nc(N3CCCN(CCO)C3=O)ccc2c1=O)C(F)(F)F]

According to General Procedure 1, 40.0 mg (89.8 μmol, purity 86%) of 1-(3,5-difluoropyridin-2-yl)-7-[3-(2-hydroxyethyl)-2-oxotetrahydropyrimidin-1(2H)-yl]-4-oxo-1,4-dihydro-1,8-naphthyridine-3-carboxylic acid (Example 26B) were reacted with 16.7 mg (108 μmol) of (2R)-1,1,1-trifluoro-3,3-dimethylbutan-2-amine in the presence of 41.0 mg (108 μmol) of HATU and 47.0 μl (269 μmol) of DIPEA in 0.6 ml of DMF. The reaction mixture was diluted with acetonitrile, water and formic acid and filtered through a Millipore filter and the crude solution was purified by preparative HPLC (column: Chromatorex C18, 10 μm, 125*40 mm, solvent: acetonitrile, water, 0.1% formic acid), giving 36.0 mg (66% of theory, purity 96%) of the title compound.

LC-MS (Methode 1): Rt=1.08 min; MS (ESIpos): m/z=583 [M+H]+.

$^1$H-NMR (400 MHz, DMSO-d6): δ [ppm]=10.55 (br. d, 1H), 9.02 (s, 1H), 8.65 (d, 1H), 8.53 (d, 1H), 8.36 (ddd, 1H), 8.18 (d, 1H), 4.71 (t, 1H), 4.61-4.69 (m, 1H), 3.48-3.60 (m, 4H), 3.35-3.43 (m, 4H), 1.86-1.97 (m, 2H), 1.10 (s, 9H).

Example 128

1-(3,5-Difluoropyridin-4-yl)-4-oxo-7-(2-oxoimidazolidin-1-yl)-N-[(2S)-1,1,1-trifluorobutan-2-yl]-1,4-dihydro-1,8-naphthyridine-3-carboxamide

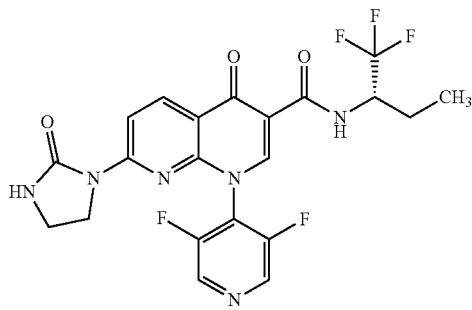 [SMILES: CC[C@H](NC(=O)c1cn(-c2c(F)cncc2F)c2nc(N3CCNC3=O)ccc2c1=O)C(F)(F)F]

Under argon, 18.6 mg (134 μmol) of potassium carbonate, 1.00 mg (4 μmol) of palladium acetate and 5.18 mg (8.95 μmol) of 9,9-dimethyl-4,5-bis(diphenylphosphino)xanthene were initially charged in 3 ml of degassed dioxane. The reaction was stirred at RT for 10 min, and 40.0 mg (89.5 μmol) of 7-chloro-1-(3,5-difluoropyridin-4-yl)-4-oxo-N-[(2S)-1,1,1-trifluorobutan-2-yl]-1,4-dihydro-1,8-naphthyridine-3-carboxamide (Example 22C) and 77.1 mg (895 μmol) of imidazolidin-2-one were then added. The mixture was stirred at 80° C. for 4 h, water and acetonitrile were then added and the mixture was filtered and purified directly by preparative RP-HPLC (column: Reprosil 125×30; 10μ, flow rate: 50 ml/min, MeCN/water; 0.1% TFA). The solvents were evaporated under reduced pressure and the residue was dried under high vacuum. This gave 21.3 mg (48% of theory, purity 100%) of the title compound.

LC-MS (Methode 2): R$_t$=1.75 min; MS (ESIpos): m/z=497 [M+H]+

$^1$H NMR (400 MHz, DMSO-d$_6$) δ [ppm]=10.16 (d, 1H) 9.08 (s, 1H) 8.88 (s, 2H) 8.57 (d, 1H) 8.45 (d, 1H) 7.68 (s, 1H) 4.71-4.82 (m, 1H) 3.52-3.63 (m, 2H) 3.33-3.42 (m, 2H) 1.84-1.95 (m, 1H) 1.61-1.73 (m, 1H) 0.98 (t, 3H).

Example 129

1-(3,5-Difluoropyridin-2-yl)-7-[(3S)-3-fluoropyrrolidin-1-yl]-4-oxo-N-[(2S)-1,1,1-trifluorobutan-2-yl]-1,4-dihydro-1,8-naphthyridine-3-carboxamide

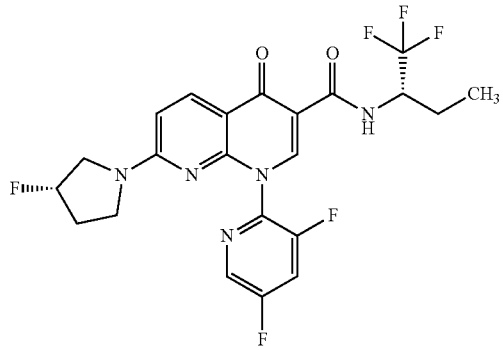 [SMILES: CC[C@H](NC(=O)c1cn(-c2ncc(F)cc2F)c2nc(N3CC[C@H](F)C3)ccc2c1=O)C(F)(F)F]

According to General Procedure 3, 25.0 mg (56.0 μmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 7.73 mg (62.0 μmol) of (3S)-3-fluoropyrrolidine hydrochloride in the presence of 34 μl (0.20 mmol) of DIPEA in 0.5 ml of DMF overnight. The pH was then adjusted to pH 1 with 1M aqueous hydrochloric acid, the mixture was diluted with 1 ml acetonitrile and the crude solution was purified by preparative HPLC [column: Chromatorex C18, 10 μm, 125*30 mm, mobile phase: acetonitrile/0.05% formic acid gradient; (0 to 2.5 min 10% acetonitrile to 23 min 90% acetonitrile and 90% acetonitrile for a further 2 min)]. This gave 21.2 mg (75% of theory, purity 99%) of the title compound.

LC-MS (Methode 2): R$_t$=2.09 min; MS (ESIpos): m/z=500 [M+H]+.

NMR (400 MHz, DMSO-d6): δ [ppm]=10.41 (br. s, 1H), 8.84 (s, 1H), 8.62 (s, 1H), 8.32 (br. s, 2H), 6.83 (br. s, 1H), 5.61-5.19 (m, 1H), 4.83-4.65 (m, 1H), 3.91-2.00 (m, 6H, partially under solvent signals), 1.91-1.85 (m, 1H), 1.73-1.54 (m, 1H), 0.96 (br. s, 3H).

Example 130

1-(3,5-Difluoropyridin-2-yl)-7-(dimethylamino)-4-oxo-N-[(2S)-1,1,1-trifluorobutan-2-yl]-1,4-dihydro-1,8-naphthyridine-3-carboxamide

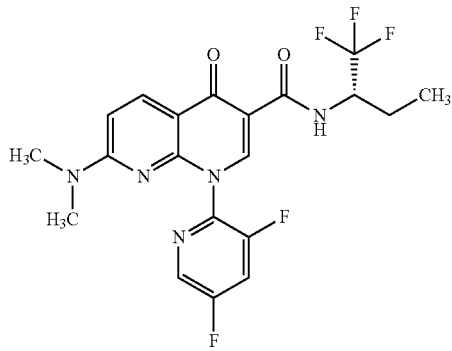 [SMILES: CC[C@H](NC(=O)c1cn(-c2ncc(F)cc2F)c2nc(N(C)C)ccc2c1=O)C(F)(F)F]

According to General Procedure 3, 25.0 mg (56.0 μmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 31 μl (62 μmol) of dimethylamine (2M in THF) in the presence of 34 μl (0.20 mmol) of DIPEA in 0.5 ml of DMF overnight. The mixture was then adjusted to pH 1 with 1 M aqueous hydrochloric acid, 2 ml of acetonitrile and 1 ml of water were added, the mixture was decanted and centrifuged and the precipitate was stirred with 3 ml of diethyl ether. The precipitate that remained was then dried under high vacuum and purified by normal phase chromatography (ethyl acetate/cyclohexane gradient), giving 10.3 mg (40% of theory, purity 99%) of the title compound.

LC-MS (Methode 2): Rt=2.08 min; MS (ESIpos): m/z=456 [M+H]+.

$^1$HNMR (400 MHz, DMSO-d6): δ [ppm]=10.42 (d, 1H), 8.82 (s, 1H), 8.63-8.61 (m, 1H), 8.36-8.27 (m, 2H), 6.96 (d, 1H), 4.81-4.68 (m, 1H), 2.96 (br. s, 6H), 1.94-1.82 (m, 1H), 1.71-1.57 (m, 1H), 1.00-0.93 (m, 3H).

Example 131

1-(3,5-Difluoropyridin-2-yl)-7-[3-hydroxy-3-(trifluoromethyl)azetidin-1-yl]-4-oxo-N-[(2S)-1,1,1-trifluorobutan-2-yl]-1,4-dihydro-1,8-naphthyridine-3-carboxamide

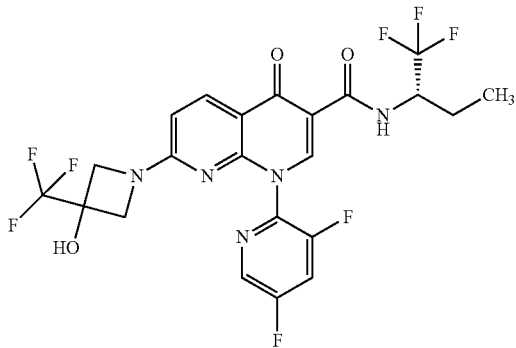 [SMILES: CC[C@H](NC(=O)c1cn(-c2ncc(F)cc2F)c2nc(N3CC(O)(C(F)(F)F)C3)ccc2c1=O)C(F)(F)F]

According to General Procedure 3, 25.0 mg (56 μmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 10.9 mg (62.0 μmol) of 3-(trifluoromethyl)azetidin-3-ol hydrochloride in the presence of 34 μl (0.20 mmol) of DIPEA in 0.5 ml of DMF overnight. The pH was then adjusted to pH 1 with 1M aqueous hydrochloric acid, the mixture was diluted with 1 ml acetonitrile and the crude solution was purified by preparative HPLC [column: Chromatorex C18,10 μm, 125*30 mm, mobile phase: acetonitrile/0.05% formic acid gradient; (0 to 2.5 min 10% acetonitrile to 23 min 90% acetonitrile and 90% acetonitrile for a further 2 min)]. This gave 26.4 mg (85% of theory, purity 99%) of the title compound.

LC-MS (Methode 1): Rt=1.10 min; MS (ESIpos): m/z=552 [M+H]+.

$^1$HNMR (400 MHz, DMSO-d6): δ [ppm]=10.32 (br. d, 1H), 8.87 (s, 1H), 8.61 (s, 1H), 8.44-8.23 (m, 2H), 7.47 (s, 1H), 6.76 (d, 1H), 4.83-4.68 (m, 1H), 4.43-3.71 (br. m, 4H), 1.95-1.79 (m, 1H), 1.72-1.56 (m, 1H), 0.96 (br. s, 3H).

Example 132

1-(3,5-Difluoropyridin-2-yl)-7-(3-fluoroazetidin-1-yl)-4-oxo-N-[(2S)-1,1,1-trifluorobutan-2-yl]-1,4-dihydro-1,8-naphthyridine-3-carboxamide

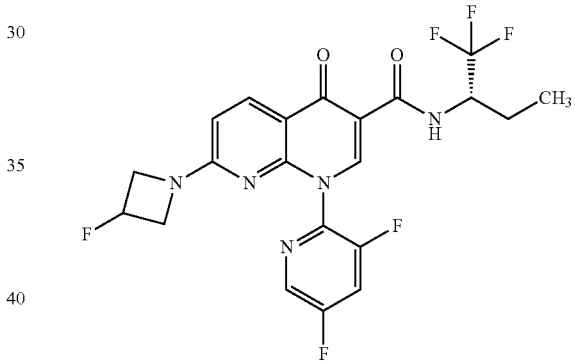

According to General Procedure 3, 25.0 mg (56.0 μmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 6.87 mg (62.0 μmol) of 3-fluoroazetidine hydrochloride in the presence of 34 μl (0.20 mmol) of DIPEA in 0.5 ml of DMF overnight. The pH was then adjusted to pH 1 with 1M aqueous hydrochloric acid, the mixture was diluted with 0.5 ml acetonitrile and the crude solution was purified by preparative HPLC [column: Chromatorex C18,10 μm, 125*30 mm, mobile phase: acetonitrile/0.05% formic acid gradient; (0 to 2.5 min 10% acetonitrile to 23 min 90% acetonitrile and 90% acetonitrile for a further 2 min)]. This gave 24.3 mg (89% of theory, purity 100%) of the title compound.

LC-MS (Methode 1): Rt=1.09 min; MS (ESIpos): m/z=486 [M+H]+.

$^1$HNMR (400 MHz, DMSO-d6): δ [ppm]=10.35 (d, 1H), 8.85 (s, 1H), 8.62-8.59 (m, 1H), 8.35-8.27 (m, 2H), 6.68 (d, 1H), 5.55-5.37 (m, 1H), 4.80-4.69 (m, 1H), 4.43-3.85 (br. m, 4H), 1.93-1.83 (m, 1H), 1.69-1.59 (m, 1H), 1.00-0.92 (m, 3H).

Example 133

1-(3,5-Difluoropyridin-2-yl)-7-(3-hydroxyazetidin-1-yl)-4-oxo-N-[(2S)-1,1,1-trifluorobutan-2-yl]-1,4-dihydro-1,8-naphthyridine-3-carboxamide

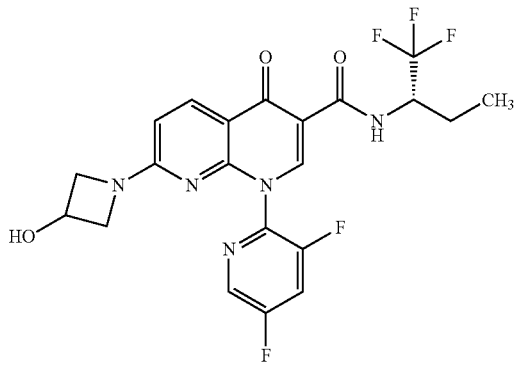 [SMILES: CC[C@H](NC(=O)c1cn(-c2ncc(F)cc2F)c2nc(N3CC(O)C3)ccc2c1=O)C(F)(F)F]

According to General Procedure 3, 25.0 mg (56.0 µmol) of 7-chloro-1-(3,5-difluoropyridin-2-yl)-4-oxo-N-[(2S)-1,1,1-trifluorobutan-2-yl]-1,4-dihydro-1,8-naphthyridine-3-carboxamide (Example 5A) were reacted with 6.74 mg (62.0 µmol) of azetidin-3-ol hydrochloride in the presence of 34 µl (0.20 mmol) of DIPEA in 0.5 ml of DMF overnight. The pH was then adjusted to pH 1 with 1M aqueous hydrochloric acid, the mixture was diluted with 0.5 ml acetonitrile and the crude solution was purified by preparative HPLC [column: Chromatorex C18, 10 µm, 125*30 mm, mobile phase: acetonitrile/0.05% formic acid gradient; (0 to 3 min 10% acetonitrile to 35 min 90% acetonitrile and 90% acetonitrile for a further 3 min)]. This gave 21.2 mg (78% of theory, purity 99%) of the title compound.

LC-MS (Methode 2): Rt=1.75 min; MS (ESIpos): m/z=484 [M+H]+.

$^1$HNMR (400 MHz, DMSO-d6): δ [ppm]=10.39 (d, 1H), 8.82 (s, 1H), 8.62-8.59 (m, 1H), 8.34-8.25 (m, 2H), 6.61 (d, 1H), 5.75 (d, 1H), 4.80-4.69 (m, 1H), 4.58-4.50 (m, 1H), 4.35-3.43 (br. m, 4H), 1.93-1.83 (m, 1H), 1.70-1.58 (m, 1H), 1.00-0.91 (m, 3H).

Example 134

1-(3-Fluoropyridin-2-yl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

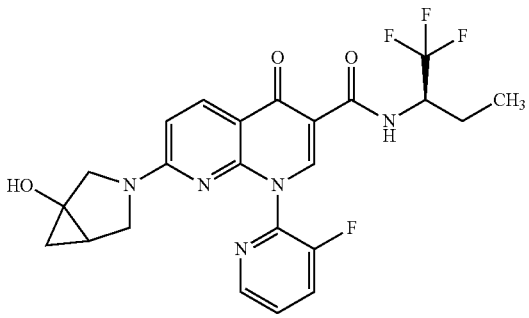 [SMILES: CC[C@@H](NC(=O)c1cn(-c2ncccc2F)c2nc(N3CC4CC4(O)C3)ccc2c1=O)C(F)(F)F]

According to General Procedure 3, 100 mg (23.3 µmol) of 7-chloro-1-(3-fluoropyridin-2-yl)-4-oxo-N-((R)-1,1,1-trifluorobutan-2-yl)-1,4-dihydro-1,8-naphthyridine-3-carboxamide (Example 21A) were reacted with 38.2 mg (257 µmol, purity 91%) of 3-azabicyclo[3.1.0]hexan-1-ol hydrochloride (racemate) in the presence of 142 µl (816 µmol) of DIPEA in 2.2 ml of DMF overnight. The mixture was then diluted with 0.5 ml acetonitrile and the crude solution was purified by preparative HPLC [column: Chromatorex C18, 10 µm, 125*30 mm, mobile phase: acetonitrile/0.05% formic acid gradient; (0 to 3 min 10% acetonitrile to 35 min 90% acetonitrile and 90% acetonitrile for a further 3 min)]. This gave 64.9 mg (56% of theory, purity 99%) of the title compound.

LC-MS (Methode 2): Rt=1.82 min; MS (ESIpos): m/z=492 [M+H]+.

$^1$HNMR (400 MHz, DMSO-d6): δ [ppm]=10.40 (d, 1H), 8.82 (s, 1H), 8.52 (br. s, 1H), 8.28 (d, 1H), 8.14-8.01 (m, 1H), 7.82-7.70 (m, 1H), 6.84-6.67 (m, 1H), 6.12-5.86 (m, 1H), 4.82-4.67 (m, 1H), 3.97-3.00 (br. m, 4H, partially under the water peak), 1.93-1.81 (m, 1H), 1.71-1.46 (m, 2H), 1.10-0.85 (m, 4H), 0.50-0.34 (m, 1H).

Example 135

N-[(1R)-1-Cyclopropyl-2,2,2-trifluoroethyl]-1-(3-fluoropyridin-2-yl)-7-[(1S)-1-hydroxy-3-azabicyclo[3.1.0]hex-3-yl]-4-oxo-1,4-dihydro-1,8-naphthyridine-3-carboxamide (diastereomer mixture)

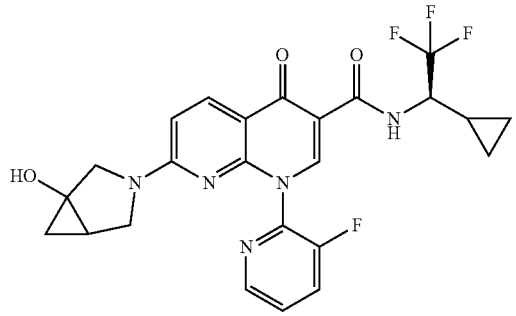 [SMILES: O=C(N[C@H](C1CC1)C(F)(F)F)c1cn(-c2ncccc2F)c2nc(N3CC4CC4(O)C3)ccc2c1=O]

According to General Procedure 3, 50.0 mg (113 µmol) of 7-chloro-N-[(R)-1-cyclopropyl-2,2,2-trifluoroethyl]-1-(3-fluoropyridin-2-yl)-4-oxo-1,4-dihydro-1,8-naphthyridine-3-carboxamide (Example 20C) were reacted with 18.6 mg (125 µmol, purity 91%) of 3-azabicyclo[3.1.0]hexan-1-ol hydrochloride (racemate) in the presence of 69.0 µl (397 µmol) of DIPEA in 1 ml of DMF overnight. The mixture was then diluted with 0.5 ml acetonitrile and the crude solution was purified by preparative HPLC [column: Chromatorex C18, 10 µm, 125*30 mm, mobile phase: acetonitrile/0.05% formic acid gradient; (0 to 3 min 10% acetonitrile to 35 min 90% acetonitrile and 90% acetonitrile for a further 3 min)]. This gave 37.2 mg (65% of theory, purity 100%) of the title compound.

LC-MS (Methode 1): Rt=0.98 min; MS (ESIpos): m/z=504 [M+H]+.

$^1$HNMR (400 MHz, DMSO-d6): δ [ppm]=10.54 (d, 1H), 8.81 (s, 1H), 8.51 (br. s, 1H), 8.29 (d, 1H), 8.15-8.02 (m, 1H), 7.82-7.71 (m, 1H), 6.84-6.68 (m, 1H), 6.12-5.87 (m, 1H), 4.46-4.33 (m, 1H), 3.95-3.01 (br. m, 4H, partially under the water peak), 1.69-1.48 (m, 1H), 1.26-1.15 (m, 1H), 1.10-0.95 (m, 1H), 0.70-0.28 (m, 5H).

35 mg of the title compound (diastereomer mixture) were separated into the diastereomers by chiral HPLC (preparative HPLC: column: Daicel Chiralcel AS-H 5 µm 250×20 mm; mobile phase: 35% isopropanol, 65% isohexane; temperature: 45° C.; flow rate: 15 ml/min; UV detection: 220 nm).

This gave (in the sequence of elution from the column) 13 mg of diastereomer 1 (99% de) Rt=5.04 min and 15 mg (96% de) of diastereomer 2 Rt=6.15 min.

[Analytical HPLC: column: Chiralcel AS-H 5 µm 250× 4.6 mm; mobile phase: 35% isopropanol, 65% isohexane; temperature: 40° C.; flow rate: 1.0 ml/min; UV detection: 220 nm]

Diastereomer 1 was additionally purified by means of preparative HPLC (column: Chromatorex C18, 10 µm, 125*30 mm, solvent: acetonitrile/0.05% formic acid gradient; (0 to 3 min. 10% acetonitrile to 35 min. 90% acetonitrile and a further 3 min. 90% acetonitrile)), and 10.6 mg (18% of theory, 99% purity) of the title compound from Example 136 were obtained.

Diastereomer 2 was additionally purified by means of preparative HPLC (column: Chromatorex C18, 10 µm, 125*30 mm, solvent: acetonitrile/0.05% formic acid gradient; (0 to 3 min. 10% acetonitrile to 35 min. 90% acetonitrile and a further 3 min. 90% acetonitrile)), and 11.8 mg (20% of theory, 99% purity) of the title compound from Example 137 were obtained.

Example 136

N-[(1R)-1-Cyclopropyl-2,2,2-trifluoroethyl]-1-(3-fluoropyridin-2-yl)-7-[(1S)-1-hydroxy-3-azabicyclo[3.1.0]hex-3-yl]-4-oxo-1,4-dihydro-1,8-naphthyridine-3-carboxamide (diastereomer 1)

LC-MS (Methode 2): Rt=1.85 min; MS (ESIpos): m/z=504 [M+H]+.

$^1$HNMR (400 MHz, DMSO-d6): δ [ppm]=10.53 (d, 1H), 8.81 (s, 1H), 8.51 (br. s, 1H), 8.29 (d, 1H), 8.14-8.01 (m, 1H), 7.82-7.71 (m, 1H), 6.82-6.68 (m, 1H), 6.11-5.89 (m, 1H), 4.46-4.33 (m, 1H), 3.95-3.02 (br. m, 4H, partially under the water peak), 1.69-1.48 (m, 1H), 1.26-1.14 (m, 1H), 1.10-0.95 (m, 1H), 0.71-0.26 (m, 5H).

Example 137

N-[(1R)-1-Cyclopropyl-2,2,2-trifluoroethyl]-1-(3-fluoropyridin-2-yl)-7-[(1S)-1-hydroxy-3-azabicyclo[3.1.0]hex-3-yl]-4-oxo-1,4-dihydro-1,8-naphthyridine-3-carboxamide (diastereomer 2)

LC-MS (Methode 2): Rt=1.84 min; MS (ESIpos): m/z=504 [M+H]+.

$^1$HNMR (400 MHz, DMSO-d6): δ [ppm]=10.54 (d, 1H), 8.81 (s, 1H), 8.51 (br. s, 1H), 8.29 (d, 1H), 8.14-8.03 (m, 1H), 7.82-7.72 (m, 1H), 6.83-6.69 (m, 1H), 6.11-5.90 (m, 1H), 4.46-4.34 (m, 1H), 3.95-3.02(br. m, 4H, partially under the water peak), 1.68-1.49 (m, 1H), 1.25-1.16 (m, 1H), 1.10-0.95 (m, 1H), 0.70-0.27 (m, 5H).

Example 138

N-[(1R)-1-Cyclopropyl-2,2,2-trifluoroethyl]-1-(3,5-difluoropyridin-2-yl)-7-[(4S)-4-hydroxy-2-oxopyrrolidin-1-yl]-4-oxo-1,4-dihydro-1,8-naphthyridine-3-carboxamide

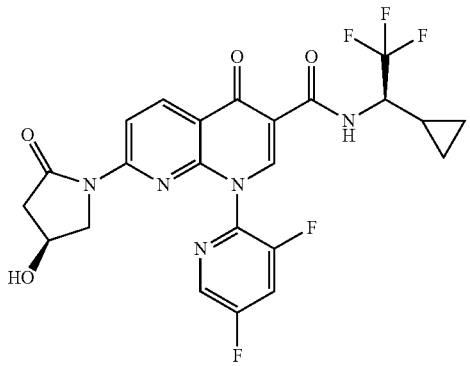 [SMILES: O=C(N[C@H](C1CC1)C(F)(F)F)c1cn(-c2ncc(F)cc2F)c2nc(N3C[C@@H](O)CC3=O)ccc2c1=O]

According to General Procedure 1, 50.0 mg (124 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 32.7 mg (186 µmol) of (1R)-1-cyclopropyl-2,2,2-trifluoroethanamine hydrochloride in the presence of 47.3 mg (124 µmol) of HATU and 52 µl (0.30 mmol) of DIPEA in 1.3 ml of DMF. The pH was then adjusted to pH 1 with 1M aqueous hydrochloric acid and the crude product was, after aqueous work-up, purified by normal phase chromatography (ethyl acetate/cyclohexane gradient). This gave 48.4 mg (74% of theory, purity 100%) of the title compound.

LC-MS (Methode 1): Rt=1.01 min; MS (ESIpos): m/z=524 [M+H]+.

$^1$HNMR (400 MHz, DMSO-d6): δ [ppm]=10.26 (d, 1H), 9.05 (s, 1H), 8.72 (d, 1H), 8.67 (br. s, 1H), 8.59-8.51 (m, 1H), 8.43-8.35 (m, 1H), 5.41-5.22 (m, 1H), 4.49-4.36 (m, 1H), 4.33-4.26 (m, 1H), 3.79-3.64 (m, 1H), 3.58-3.44 (m, 1H), 3.03-2.87 (m, 1H), 2.44-2.33 (m, 1H), 1.30-1.18 (m, 1H), 0.71-0.51 (m, 3H), 0.40-0.29 (m, 1H).

Example 139

N-[(1R)-1-Cyclopropyl-2,2,2-trifluoroethyl]-1-(3-fluoropyridin-2-yl)-7-[(4S)-4-hydroxy-2-oxopyrrolidin-1-yl]-4-oxo-1,4-dihydro-1,8-naphthyridine-3-carboxamide

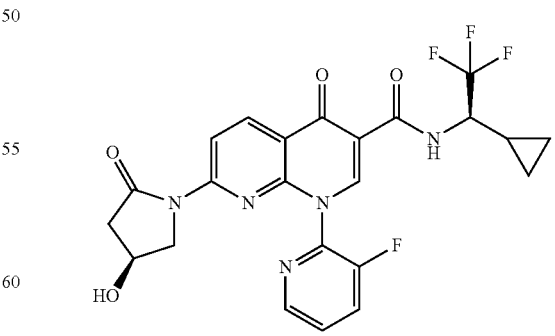

According to General Procedure 2, 50.0 mg (113 µmol) of 7-chloro-N-[(1R)-1-cyclopropyl-2,2,2-trifluoroethyl]-1-(3-fluoropyridin-2-yl)-4-oxo-1,4-dihydro-1,8-naphthyridine-3-carboxamide (Example 20C) and 12.6 mg (125 µmol) of (S)-4-hydroxypyrrolidine were reacted in the presence of 23.5 mg (170 µmol) of potassium carbonate, 2.55 mg (11.0 µmol) of palladium acetate and 13.3 mg (23.0 µmol) of Xantphos in 1.5 ml of dioxane at 110° C. The solvent was then removed under reduced pressure. The residue was dissolved in 3 ml of acetonitrile and 0.5 ml of water and purified by means of preparative HPLC (column: Chromatorex C18, 10 µm, 125*30 mm, solvent: acetonitrile/0.05% formic acid gradient; 0 to 3 min 10% acetonitrile, to 35 min 90% acetonitrile and for a further 13 min 90% acetonitrile). This gave 22.2 mg (38% of theory, purity 98%) of the title compound.

LC-MS (Methode 2): $R_t$=1.69 min; MS (ESIpos): m/z=506 [M+H]+.

$^1$HNMR (400 MHz, DMSO-d6): δ [ppm]=10.27 (d, 1H), 9.05 (s, 1H), 8.72 (d, 1H), 8.58-8.51 (m, 2H), 8.15-8.08 (m, 1H), 7.85-7.79 (m, 1H), 5.40-5.23 (m, 1H), 4.50-4.36 (m, 1H), 4.32-4.23 (m, 1H), 3.79-3.40 (m, 2H), 3.03-2.86 (m, 1H), 2.43-2.32 (m, 1H), 1.30-1.18 (m, 1H), 0.72-0.51 (m, 3H), 0.42-0.30 (m, 1H).

Example 140

1-(3-Fluoropyridin-2-yl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

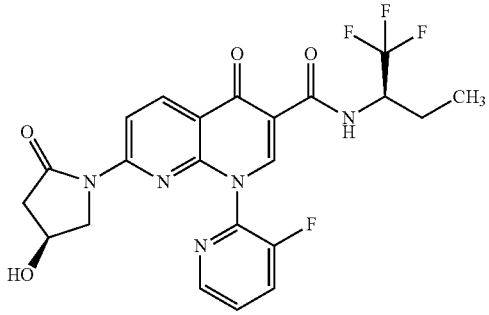 [SMILES: CC[C@@H](NC(=O)c1cn(-c2ncccc2F)c2nc(N3C[C@@H](O)CC3=O)ccc2c1=O)C(F)(F)F]

According to General Procedure 2, 35.0 mg (82.0 µmol) of 7-chloro-1-(3-fluoropyridin-2-yl)-4-oxo-N-[(2R)-1,1,1-trifluorobutan-2-yl]-1,4-dihydro-1,8-naphthyridine-3-carboxamide (Example 21A) and 8.25 mg (82.0 µmol) of (S)-4-hydroxypyrrolidine were reacted in the presence of 39.9 mg (122 µmol) of cesium carbonate, 3.30 mg (15.0 µmol) of palladium acetate and 17.0 mg (29.0 µmol) of Xantphos in 1.6 ml of dioxane. The solvent was then removed under reduced pressure. The residue was dissolved in 3 ml of acetonitrile and 0.5 ml of water and purified by means of preparative HPLC (column: Chromatorex C18, 10 µm, 125*30 mm, solvent: acetonitrile/0.05% formic acid gradient; 0 to 3 min 10% acetonitrile, to 34 min 60% acetonitrile, over 1 min to 90% acetonitrile and for a further 10 min 90% acetonitrile). This gave 8.40 mg (21% of theory, purity 99%) of the title compound.

LC-MS (Methode 1): $R_t$=0.97 min; MS (ESIpos): m/z=494 [M+H]+.

$^1$HNMR (400 MHz, DMSO-d6): δ [ppm]=10.14 (d, 1H), 9.06 (s, 1H), 8.72 (d, 1H), 8.58-8.51 (m, 2H), 8.16-8.09 (m, 1H), 7.85-7.79 (m, 1H), 5.42-5.23 (m, 1H), 4.84-4.68 (m, 1H), 4.31-4.23 (m, 1H), 3.79-3.40 (m, 2H), 3.03-2.86 (m, 1H), 2.43-2.30 (m, 1H), 1.96-1.81 (m, 1H), 1.74-1.59 (m, 1H), 0.98 (br. s, 3H).

Example 141

1-(3,5-Difluoropyridin-2-yl)-7-[(4R)-4-methyl-2-oxoimidazolidin-1-yl]-4-oxo-N-[1-(trifluoromethoxy)butan-2-yl]-1,4-dihydro-1,8-naphthyridine-3-carboxamide (diastereomer mixture)

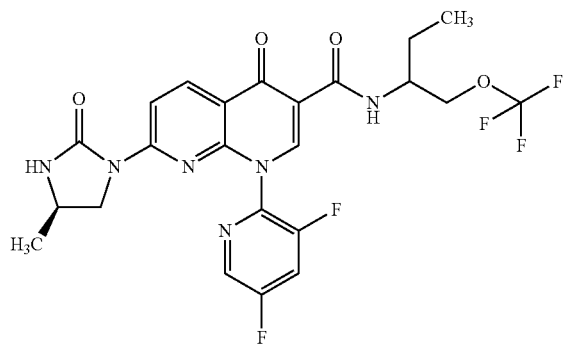 [SMILES: CCC(COC(F)(F)F)NC(=O)c1cn(-c2ncc(F)cc2F)c2nc(N3C[C@@H](C)NC3=O)ccc2c1=O]

The compound from Example 31D (40.0 mg, 99.7 µmol) was dissolved in 990 µl of DMF, HATU (45.5 mg, 120 µmol) and N,N-diisopropylethylamine (69 400 µmol) were added and the mixture was stirred at room temperature for 15 min. rac-1-(Trifluoromethoxy)butan-2-amine hydrochloride (23.2 mg, 120 µmol) was then added and the mixture was stirred at room temperature for 2.5 h. The reaction solution was diluted with water, acidified with 1 N hydrochloric acid and extracted twice with ethyl acetate. The combined organic phases were washed once with water, dried over sodium sulfate, filtered and concentrated on a rotary evaporator. The residue was purified by thick-layer chromatography (mobile phase: dichloromethane/methanol=10/1). This gave 36 mg of the target compound (66% of theory, purity 98%).

LC-MS (Methode 2): $R_t$=1.89 min; MS (ESIpos): m/z=541 [M+H]+

$^1$H-NMR (400 MHz, DMSO-d$_6$) δ [ppm]: −0.149 (1.25), −0.008 (16.00), 0.008 (8.99), 0.146 (1.14), 0.933 (5.79), 0.945 (9.60), 0.951 (9.57), 0.962 (5.23), 1.099 (5.82), 1.111 (5.82), 1.156 (6.07), 1.168 (5.43), 1.235 (0.67), 1.566 (0.97), 1.584 (1.61), 1.600 (2.14), 1.618 (2.20), 1.638 (1.59), 1.661 (1.92), 1.673 (2.17), 1.693 (2.09), 2.328 (1.42), 2.366 (1.03), 2.519 (7.68), 2.524 (6.90), 2.670 (1.36), 2.710 (0.92), 3.092 (1.47), 3.105 (1.56), 3.150 (1.67), 3.163 (1.53), 3.723 (3.06), 3.736 (3.31), 3.779 (2.89), 3.797 (1.98), 4.197 (7.71), 5.754 (2.34), 7.812 (8.93), 8.322 (1.61), 8.343 (1.70), 8.365 (1.59), 8.384 (1.03), 8.407 (6.73), 8.430 (8.82), 8.531 (1.70), 8.539 (12.41), 8.553 (1.34), 8.562 (9.04), 8.636 (6.46), 8.931 (8.60), 9.877 (3.81), 9.896 (3.45).

Analogously to Example 141, the example compounds shown in Table 1 were prepared by reacting 1-(3,5-difluoropyridin-2-yl)-7-[(4R)-4-methyl-2-oxoimidazolidin-1-yl]-4-oxo-1,4-dihydro-1,8-naphthyridine-3-carboxylic acid (Example 31D) with the appropriate amines (or salts thereof; 1.2 equivalents) under the reaction conditions described (2.5 h at room temperature).

TABLE 1

| Ex. | IUPAC name<br>Structure<br>Amine used<br>Yield | LC-MS method<br>Retention time<br>Mass detected<br>NMR data |
|---|---|---|
| 142 | N-[(1S)-1-cyclopropyl-2,2,2-trifluoroethyl]-1-(3,5-difluoropyridin-2-yl)-7-[(4R)-4-methyl-2-oxoimidazolidin-1-yl]-4-oxo-1,4-dihydro-1,8-naphthyridine-3-carboxamide<br>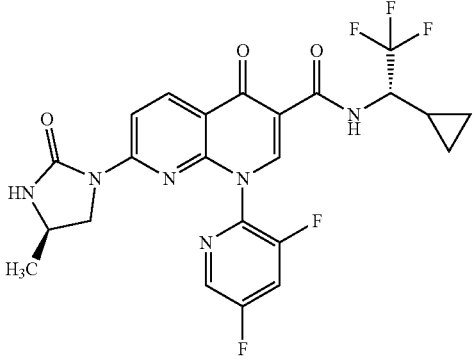 [SMILES: C[C@@H]1CN(c2ccc3c(=O)c(C(=O)N[C@@H](C4CC4)C(F)(F)F)cn(-c4ncc(F)cc4F)c3n2)C(=O)N1]<br>(1S)-1-cyclopropyl-2,2,2-trifluoroethanamine hydrochloride (73% of theory) | LC-MS (Methode 2):<br>$R_t$ = 1.89 min<br>m/z = 523 [M + H]$^+$<br>$^1$H-NMR (400 MHz, DMSO-d$_6$) δ [ppm]: −0.149 (1.18), −0.008 (9.38), 0.008 (8.84), 0.146 (1.08), 0.348 (2.59), 0.552 (3.29), 0.656 (2.72), 1.099 (6.22), 1.111 (6.45), 1.157 (6.96), 1.169 (6.62), 1.198 (1.61), 1.206 (2.08), 1.219 (3.50), 1.238 (3.73), 1.251 (1.88), 2.328 (1.85), 2.367 (1.34), 2.524 (5.82), 2.670 (1.78), 2.710 (1.41), 3.096 (1.61), 3.109 (1.71), 3.152 (1.88), 3.165 (1.82), 3.724 (3.43), 3.740 (3.76), 3.778 (3.16), 4.390 (1.71), 4.411 (3.13), 4.432 (3.06), 4.452 (1.65), 7.830 (10.79), 8.306 (0.94), 8.328 (1.82), 8.346 (2.02), 8.368 (1.88), 8.428 (8.13), 8.450 (11.29), 8.549 (16.00), 8.572 (11.19), 8.639 (8.13), 8.978 (6.89), 10.334 (3.93), 10.356 (3.83). |
| 143 | 1-(3,5-difluoropyridin-2-yl)-7-[(4R)-4-methyl-2-oxoimidazolidin-1-yl]-4-oxo-N-[(2S)-1,1,1-trifluorobutan-2-yl]-1,4-dihydro-1,8-naphthyridine-3-carboxamide<br>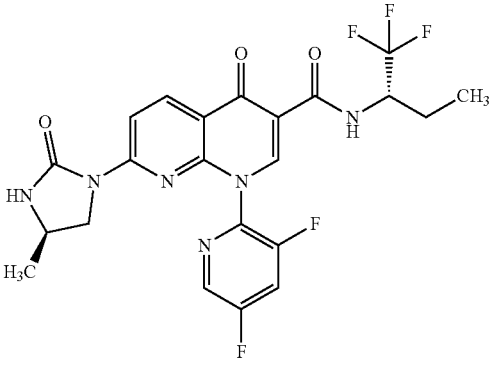 [SMILES: CC[C@H](NC(=O)c1cn(-c2ncc(F)cc2F)c2nc(N3C[C@@H](C)NC3=O)ccc2c1=O)C(F)(F)F]<br>(2S)-1,1,1-trifluorobutan-2-amine hydrochloride (75% of theory) | LC-MS (Methode 2):<br>$R_t$ = 1.86 min<br>m/z = 511 [M + H]$^+$<br>$^1$H-NMR (400 MHz, DMSO-d$_6$) δ [ppm]: −0.149 (0.89), −0.008 (8.18), 0.008 (7.53), 0.146 (0.92), 0.969 (9.50), 0.983 (9.98), 1.000 (4.34), 1.100 (6.07), 1.112 (6.45), 1.158 (6.91), 1.170 (6.53), 1.622 (1.16), 1.640 (1.67), 1.656 (1.97), 1.682 (1.97), 1.700 (1.43), 1.863 (1.51), 1.882 (1.86), 1.891 (2.08), 1.908 (1.62), 1.925 (1.13), 2.328 (1.40), 2.367 (1.05), 2.524 (4.83), 2.670 (1.51), 2.711 (1.16), 3.097 (1.59), 3.110 (1.70), 3.152 (1.83), 3.166 (1.81), 3.725 (3.35), 3.740 (3.75), 3.781 (3.21), 3.799 (2.37), 4.763 (2.02), 4.783 (1.92), 7.829 (10.55), 8.308 (0.89), 8.329 (1.75), 8.352 (1.94), 8.372 (1.83), 8.391 (0.92), 8.427 (7.80), 8.449 (11.14), 8.546 (16.00), 8.568 (11.22), 8.642 (6.26), 8.988 (6.72), 10.196 (5.83), 10.220 (5.67). |
| 144 | N-(1,1-difluoro-2-methylpropan-2-yl)-1-(3,5-difluoropyridin-2-yl)-7-[(4R)-4-methyl-2-oxoimidazolidin-1-yl]-4-oxo-1,4-dihydro-1,8-naphthyridine-3-carboxamide<br>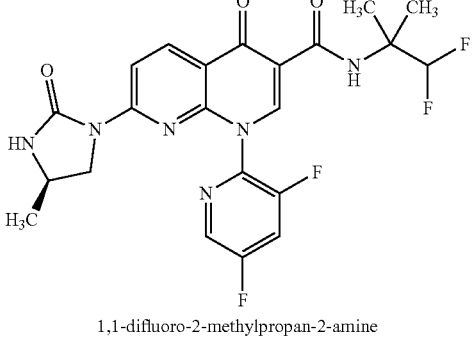<br>1,1-difluoro-2-methylpropan-2-amine hydrochloride (67% of theory) | LC-MS (Methode 2):<br>$R_t$ = 1.80 min<br>m/z = 493 [M + H]$^+$<br>$^1$H-NMR (400 MHz, DMSO-d$_6$) δ [ppm]: −0.008 (3.23), 0.008 (3.30), 1.108 (1.47), 1.154 (1.51), 1.166 (1.42), 1.450 (16.00), 2.328 (0.49), 2.524 (1.59), 2.670 (0.50), 3.102 (0.40), 3.146 (0.42), 3.733 (0.82), 3.774 (0.76), 6.292 (0.98), 6.434 (1.81), 6.577 (0.80), 7.815 (2.53), 8.323 (0.42), 8.346 (0.46), 8.411 (2.13), 8.433 (2.87), 8.532 (4.37), 8.555 (3.00), 8.635 (1.98), 8.918 (2.96), 10.119 (3.31). |

Example 145

1-(3,5-Difluoropyridin-2-yl)-4-oxo-7-(2-oxoimidazolidin-1-yl)-N-(4,4,4-trifluoro-2-methylbutan-2-yl)-1,4-dihydro-1,8-naphthyridine-3-carboxamide

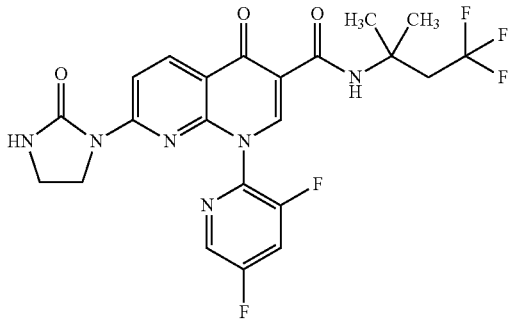 [SMILES: CC(C)(CC(F)(F)F)NC(=O)c1cn(-c2ncc(F)cc2F)c2nc(N3CCNC3=O)ccc2c1=O]

According to General Procedure 1, 50.0 mg (100 µmol, purity 78%) of 1-(3,5-difluoropyridin-2-yl)-4-oxo-7-(2-oxoimidazolidin-1-yl)-1,4-dihydro-1,8-naphthyridine-3-carboxylic acid (Example 30A) were reacted with 21.4 mg (121 µmol) of 4,4,4-trifluoro-2-methylbutan-2-amine hydrochloride in the presence of 45.8 mg (121 µmol) of HATU and 52 µl (300 µmol) of DIPEA in 0.39 ml of DMF. The reaction mixture was diluted with water, acetonitrile and formic acid, filtered through a Millipore filter and purified by preparative HPLC (acetonitrile/water/0.1% formic acid), giving 15.3 mg (30% of theory, purity 100%) of the title compound.

LC-MS (Methode 2): $R_t$=1.83 min; MS (ESIpos): m/z=511 [M+H]+.

$^1$H NMR (400 MHz, DMSO-d6): δ [ppm]=9.98 (s, 1H), 8.91 (s, 1H), 8.63 (d, 1H), 8.54 (d, 1H), 8.42 (d, 1H), 8.32 (ddd, 1H), 7.65 (br s, 1H), 3.54-3.70 (m, 2H), 3.32-3.41 (m, 2H), 2.90-3.02 (m, 2H), 1.50 (s, 6H).

Example 146

N-Cyclobutyl-1-(3,5-difluoropyridin-2-yl)-4-oxo-7-(2-oxoimidazolidin-1-yl)-1,4-dihydro-1,8-naphthyridine-3-carboxamide

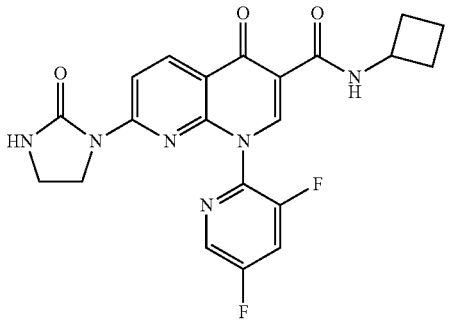 [SMILES: O=C(NC1CCC1)c1cn(-c2ncc(F)cc2F)c2nc(N3CCNC3=O)ccc2c1=O]

According to General Procedure 1, 25.0 mg (64.5 µmol, purity 78%) of 1-(3,5-difluoropyridin-2-yl)-4-oxo-7-(2-oxoimidazolidin-1-yl)-1,4-dihydro-1,8-naphthyridine-3-carboxylic acid (Example 30A) were reacted with 8.33 mg (77.5 µmol) of cyclobutanamine hydrochloride in the presence of 29.5 mg (77.5 µmol) of HATU and 34 µl (190 µmol) of DIPEA in 0.25 ml of DMF. The reaction mixture was diluted with acetonitrile, water and formic acid and filtered through a Millipore filter and the crude solution was purified by preparative HPLC (acetonitrile/water/0.1% formic acid), giving 5.50 mg (19% of theory, purity 100%) of the title compound.

LC-MS (Methode 2): $R_t$=1.53 min; MS (ESIpos): m/z=441 [M+H]+.

$^1$H NMR (400 MHz, DMSO-d6): δ [ppm]=9.94 (d, 1H), 8.89 (s, 1H), 8.63 (d, 1H), 8.54 (d, 1H), 8.41 (d, 1H), 8.32 (td, 1H), 7.60-7.66 (m, 1H), 4.39-4.48 (m, 1H), 3.53-3.69 (m, 2H), 3.32-3.40 (m, 2H), 2.26-2.33 (m, 2H), 1.93-2.03 (m, 2H), 1.66-1.78 (m, 2H).

Example 147

N-[1-(2-Chlorophenyl)-2,2,2-trifluoroethyl]-1-(3,5-difluoropyridin-2-yl)-4-oxo-7-(2-oxoimidazolidin-1-yl)-1,4-dihydro-1,8-naphthyridine-3-carboxamide (racemate)

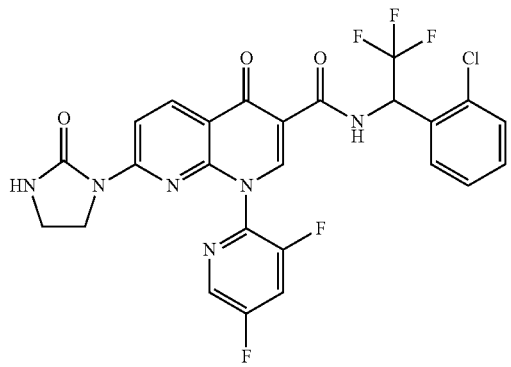 [SMILES: O=C(NC(c1ccccc1Cl)C(F)(F)F)c1cn(-c2ncc(F)cc2F)c2nc(N3CCNC3=O)ccc2c1=O]

According to General Procedure 1, 50.0 mg (99.4 µmol, purity 78%) of 1-(3,5-difluoropyridin-2-yl)-4-oxo-7-(2-oxoimidazolidin-1-yl)-1,4-dihydro-1,8-naphthyridine-3-carboxylic acid (Example 30A) were reacted with 62.5 mg (298 µmol) of 1-(2-chlorophenyl)-2,2,2-trifluoroethanamine in the presence of 45.4 mg (119 µmol) of HATU and 52 µl (300 µmol) of DIPEA in 0.38 ml of DMF. The reaction mixture was diluted with acetonitrile, water and formic acid and filtered through a Millipore filter and the crude solution was purified by preparative HPLC (acetonitrile/water/0.1% formic acid), giving 17.2 mg (30% of theory, purity 100%) of the title compound.

LC-MS (Methode 2): $R_t$=2.07 min; MS (ESIpos): m/z=579 [M+H]+.

$^1$H NMR (400 MHz, DMSO-d6): δ [ppm]=11.32 (d, 1H), 9.00 (s, 1H), 8.63 (d, 1H), 8.60 (d, 1H), 8.46 (d, 1H), 8.29-8.36 (m, 1H), 7.48-7.69 (m, 5H), 6.42-6.51 (m, 1H), 3.53-3.70 (m, 2H), 3.33-3.43 (m, 2H).

15.5 mg of the title compound (racemate) were separated into the enantiomers by chiral HPLC (preparative HPLC: column: YMC Chiralart Amylose 5 µm 250×30 mm; mobile phase: 50% n-heptane, 50% isopropanol; temperature: 35° C.; flow rate: 30 ml/min; UV detection: 220 nm).

This gave (in the sequence of elution from the column) 4.00 mg of enantiomer A (99% ee) Rt=8.67 min and 6.00 mg of enantiomer B (98% ee) Rt=13.68 min.

[Analytical HPLC: column: YMC Chiralart Amylose 5 µm 250×4.6 mm; mobile phase: 50% isohexane, 50% isopropanol; temperature: 35° C.; flow rate: 1.0 ml/min; UV detection: 220 nm]

Enantiomer A was additionally obtained by preparative HPLC (acetonitrile/water/0.1% formic acid), giving 3.50 mg (6% of theory, purity 100%) of the title compound from Example 148.

Enantiomer B was additionally obtained by preparative HPLC (acetonitrile/water/0.1% formic acid), giving 3.70 mg (6.5% of theory, purity 100%) of the title compound from Example 149.

Example 148

N-[1-(2-Chlorophenyl)-2,2,2-trifluoroethyl]-1-(3,5-difluoropyridin-2-yl)-4-oxo-7-(2-oxoimidazolidin-1-yl)-1,4-dihydro-1,8-naphthyridine-3-carboxamide (enantiomer A)

LC-MS (Methode 1): R_f=1.10 min; MS (ESIpos): m/z=579 [M+H]+

$^1$H-NMR (500 MHz, DMSO-d6): δ [ppm]=11.32 (br d, 1H), 9.00 (s, 1H), 8.61-8.66 (m, 1H), 8.60 (d, 1H), 8.46 (d, 1H), 8.30-8.36 (m, 1H), 7.68 (s, 1H), 7.59-7.67 (m, 2H), 7.48-7.59 (m, 2H), 6.43-6.50 (m, 1H), 3.54-3.69 (m, 2H), 3.32-3.40 (m, 2H).

Example 149

N-[1-(2-Chlorophenyl)-2,2,2-trifluoroethyl]-1-(3,5-difluoropyridin-2-yl)-4-oxo-7-(2-oxoimidazolidin-1-yl)-1,4-dihydro-1,8-naphthyridine-3-carboxamide (enantiomer B)

LC-MS (Methode 1): R_f=1.10 min; MS (ESIpos): m/z=579 [M+H]+

$^1$H-NMR (400 MHz, DMSO-d6): δ [ppm]=11.32 (br d, 1H), 9.00 (s, 1H), 8.62-8.67 (m, 1H), 8.60 (d, 1H), 8.46 (d, 1H), 8.29-8.38 (m, 1H), 8.34 (br d, 1H), 7.68 (s, 1H), 7.59-7.67 (m, 2H), 7.47-7.59 (m, 2H), 6.39-6.51 (m, 1H), 3.53-3.71 (m, 2H), 3.34-3.40 (m, 2H).

Example 150

1-(3,5-Difluoropyridin-2-yl)-4-oxo-7-(2-oxoimidazolidin-1-yl)-N-[1-(trifluoromethyl)cyclobutyl]-1,4-dihydro-1,8-naphthyridine-3-carboxamide

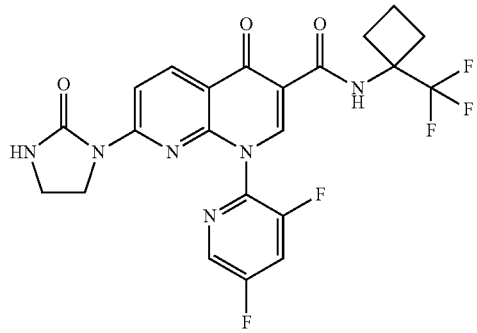 [SMILES: O=C(NC1(C(F)(F)F)CCC1)c1cn(-c2ncc(F)cc2F)c2nc(N3CCNC3=O)ccc2c1=O]

According to General Procedure 1, 50.0 mg (99.4 µmol, purity 78%) of 1-(3,5-difluoropyridin-2-yl)-4-oxo-7-(2-oxoimidazolidin-1-yl)-1,4-dihydro-1,8-naphthyridine-3-carboxylic acid (Example 30A) were reacted with 41.5 mg (298 µmol) of 1-(trifluoromethyl)cyclobutanamine in the presence of 45.4 mg (119 µmol) of HATU and 52 µl (300 µmol) of DIPEA in 0.38 ml of DMF. The reaction mixture was diluted with acetonitrile, water and formic acid and filtered through a Millipore filter and the crude solution was purified by preparative HPLC (acetonitrile/water/0.1% formic acid), giving 15.9 mg (31% of theory, purity 100%) of the title compound.

LC-MS (Methode 2): R_f=1.82 min; MS (ESIpos): m/z=509 [M+H]+.

$^1$H NMR (400 MHz, DMSO-d6): δ [ppm]=10.32 (s, 1H), 8.94 (s, 1H), 8.64 (d, 1H), 8.55 (d, 1H), 8.43 (d, 1H), 8.29-8.36 (m, 1H), 7.66 (s, 1H), 3.53-3.71 (m, 2H), 3.35-3.43 (m, 2H), 2.55-2.64 (m, 2H), 1.89-2.09 (m, 2H).

Example 151

1-(3,5-Difluoropyridin-2-yl)-7-[(4S)-4-hydroxy-2-oxopyrrolidin-1-yl]-4-oxo-N-[1-(trifluoromethyl)cyclobutyl]-1,4-dihydro-1,8-naphthyridine-3-carboxamide

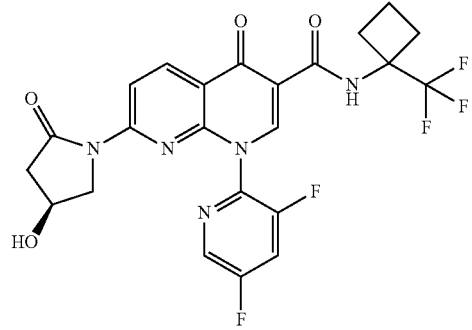 [SMILES: O=C(NC1(C(F)(F)F)CCC1)c1cn(-c2ncc(F)cc2F)c2nc(N3C[C@@H](O)CC3=O)ccc2c1=O]

According to General Procedure 1, 50.0 mg (124 µmol, purity 96%) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid (Example 24A) were reacted with 20.7 mg (149 µmol) of 1-(trifluoromethyl)cyclobutanamine in the presence of 56.7 mg (149 µmol) of HATU and 65 µl (370 µmol) of DIPEA in 0.48 ml of DMF. The reaction mixture was diluted with acetonitrile, water and formic acid and filtered through a Millipore filter and the crude solution was purified by preparative HPLC (acetonitrile/water/0.1% formic acid), giving 48.0 mg (74% of theory, purity 100%) of the title compound.

LC-MS (Methode 2): R_f=1.76 min; MS (ESIpos): m/z=524 [M+H]+.

$^1$H NMR (400 MHz, DMSO-d6): δ [ppm]=10.22 (s, 1H), 9.01 (s, 1H), 8.71 (d, 1H), 8.65-8.69 (m, 1H), 8.51-8.57 (m, 1H), 8.39 (td, 1H), 5.24-5.40 (m, 1H), 4.26-4.32 (m, 1H), 3.65-3.78 (m, 1H), 3.45-3.56 (m, 1H), 2.88-3.02 (m, 1H), 2.55-2.65 (m, 4H), 2.34-2.42 (m, 1H), 1.91-2.10 (m, 2H).

Example 152

1-(3,5-Difluoropyridin-2-yl)-7-[(3R,4R)-3,4-dihydroxypyrrolidin-1-yl]-N-(1,1,1,3,3,3-hexafluoro-2-methylpropan-2-yl)-4-oxo-1,4-dihydro-1,8-naphthyridine-3-carboxamide

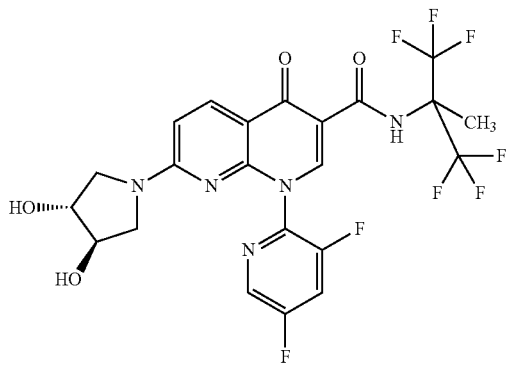 [SMILES: CC(NC(=O)c1cn(-c2ncc(F)cc2F)c2nc(N3C[C@@H](O)[C@H](O)C3)ccc2c1=O)(C(F)(F)F)C(F)(F)F]

According to General Procedure 3, 23.2 mg (46.3 µmol) of 7-chloro-1-(3,5-difluoropyridin-2-yl)-N-(1,1,1,3,3,3-hexafluoro-2-methylpropan-2-yl)-4-oxo-1,4-dihydro-1,8-naphthyridine-3-carboxamide (Example 29A) were reacted with 7.76 mg (55.6 µmol) of (3R,4R)-pyrrolidine-3,4-diol hydrochloride in the presence of 24 µl (140 µmol) of DIPEA in 0.19 ml of DMF. The mixture was diluted with acetonitrile, water and formic acid and filtered through a Millipore filter and the crude solution was purified by preparative HPLC (acetonitrile/water/0.1% formic acid), giving 13.4 mg (51% of theory, purity 100%) of the title compound.

LC-MS (Methode 2): $R_t$=1.79 min; MS (ESIpos): m/z=568 [M+H]+.

$^1$H NMR (400 MHz, DMSO-d6): δ [ppm]=11.61 (s, 1H), 8.83 (d, 1H), 8.62 (d, 1H), 8.32-8.37 (m, 1H), 8.30 (d, 1H), 6.79 (d, 1H), 5.05-5.30 (m, 2H), 4.02-4.08 (m, 1H), 3.90-3.95 (m, 1H), 3.57-3.68 (m, 1H), 3.33-3.39 (m, 1H), 3.18-3.28 (m, 1H), 3.03-3.16 (m, 1H), 2.06 (br s, 3H).

Example 153

N-[(2-Cyclopropyl-1,1,1-trifluoropropan-2-yl]-1-(3,5-difluoropyridin-2-yl)-7-[(3R,4R)-3,4-dihydroxypyrrolidin-1-yl]-4-oxo-1,4-dihydro-1,8-naphthyridine-3-carboxamide (diastereomer mixture)

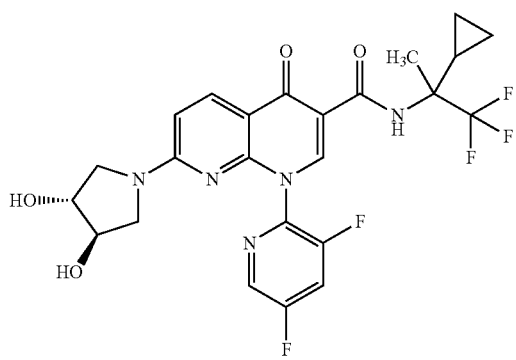 [SMILES: CC(NC(=O)c1cn(-c2ncc(F)cc2F)c2nc(N3C[C@@H](O)[C@H](O)C3)ccc2c1=O)(C1CC1)C(F)(F)F]

According to GP1, 50.0 mg (124 µmol) of 1-(3,5-difluoropyridin-2-yl)-7-[(3R,4R)-3,4-dihydroxypyrrolidin-1-yl]-4-oxo-1,4-dihydro-1,8-naphthyridine-3-carboxylic acid were reacted with 22.7 mg (148 µmol) of 2-cyclopropyl-1,1,1-trifluoropropan-2-amine in the presence of 56.4 mg (148 µmol) of HATU and 65 µl (370 µmol) of DIPEA in 500 µl of DMF. The crude product was purified twice by preparative HPLC (acetonitrile/water/0.1% formic acid). This gave 30.7 mg (46% of theory, purity 100%) of the title compound.

LC-MS (Methode 1): $R_t$=0.91 min; MS (ESIpos): m/z=540 [M+H]+

$^1$H-NMR (400 MHz, DMSO-d6): δ [ppm]=10.38 (d, 1H), 8.75 (d, 1H), 8.61 (d, 1H), 8.30-8.36 (m, 1H), 8.28 (d, 1H), 6.76 (d, 1H), 5.25-5.29 (m, 0.50H), 5.17-5.21 (m, 1H), 5.05-5.08 (m, 0.50H), 4.02-4.07 (m, 1H), 3.90-3.95 (m, 1H), 3.57-3.66 (m, 1H), 3.32-3.38 (m, 1H), 3.19-3.25 (m, 0.50H), 3.10-3.18 (m, 0.50H), 3.03-3.08 (m, 0.50H), 1.60 (s, 3H), 1.37-1.45 (m, 1H), 0.65-0.72 (m, 1H), 0.54-0.60 (m, 2H), 0.45-0.52 (m, 1H).

Example 154

1-(3,5-Difluoropyridin-2-yl)-7-[(4S)-4-hydroxy-2-oxopyrrolidin-1-yl]-4-oxo-N-[1,1,1-trifluoro-3-methylbutan-2-yl]-1,4-dihydro-1,8-naphthyridine-3-carboxamide (diastereomer mixture)

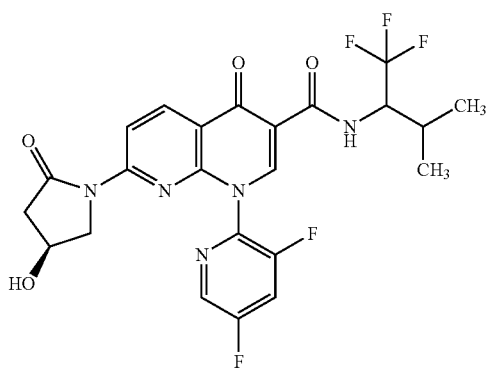 [SMILES: CC(C)C(NC(=O)c1cn(-c2ncc(F)cc2F)c2nc(N3C[C@@H](O)CC3=O)ccc2c1=O)C(F)(F)F]

According to GP1, 80.0 mg (199 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid were reacted with 33.7 mg (239 µmol) of 1,1,1-trifluoro-3-methylbutan-2-amine in the presence of 90.7 mg (239 µmol) of HATU and 100 µl (600 µmol) of DIPEA in 1.4 ml of DMF. The crude product was purified by preparative HPLC (acetonitrile/water/0.1% formic acid). This gave 72.9 mg (67% of theory, purity 96%) of the title compound.

LC-MS (Methode 2): $R_t$=1.85 min; MS (ESIpos): m/z=526 [M+H]+

$^1$H-NMR (400 MHz, DMSO-d6): δ [ppm]=10.33 (br d, 1H), 9.07 (s, 1H), 8.74 (d, 1H), 8.63-8.70 (m, 1H), 8.55 (br t, 1H), 8.35-8.43 (m, 1H), 5.38 (br d, 0.5H), 5.26 (br d, 0.5H), 4.75-4.85 (m, 1H), 4.29 (br s, 1H), 3.65-3.78 (m, 1H), 3.45-3.57 (m, 1H), 2.88-3.03 (m, 1H), 2.34-2.43 (m, 1H), 2.22-2.31 (m, 1H), 1.04 (br d, 3H), 0.94-1.00 (m, 3H).

Example 155

1-(3,5-Difluoropyridin-2-yl)-7-[(3R,4R)-3,4-dihydroxypyrrolidin-1-yl]-4-oxo-N-[1-(trifluoromethyl)cyclobutyl]-1,4-dihydro-1,8-naphthyridine-3-carboxamide

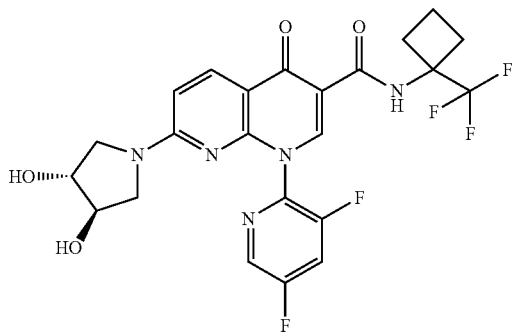 [SMILES: O=C(NC1(C(F)(F)F)CCC1)c1cn(-c2ncc(F)cc2F)c2nc(N3C[C@@H](O)[C@H](O)C3)ccc2c1=O]

According to GP1, 60.0 mg (148 µmol) of 1-(3,5-difluoropyridin-2-yl)-7-[(3R,4R)-3,4-dihydroxypyrrolidin-1-yl]-4-oxo-1,4-dihydro-1,8-naphthyridine-3-carboxylic acid were reacted with 31.3 mg (178 µmol) of 1-(trifluoromethyl)cyclobutanamine hydrochloride in the presence of 67.7 mg (178 µmol) of HATU and 90 µl (520 µmol) of DIPEA in 660 µl of DMF. The crude product was purified by preparative HPLC (acetonitrile/water/0.1% formic acid). This gave 59.8 mg (77% of theory, purity 100%) of the title compound.

LC-MS (Methode 2): $R_t$=1.58 min; MS (ESIpos): m/z=526 [M+H]+

¹H-NMR (400 MHz, DMSO-d6): δ [ppm]=10.54 (s, 1H), 8.77 (d, 1H), 8.62 (d, 1H), 8.33 (td, 1H), 8.27 (d, 1H), 6.77 (d, 1H), 5.27 (br d, 0.50H), 5.19 (br s, 1H), 5.07 (br d, 0.50H), 4.05 (br s, 1H), 3.93 (br s, 1H), 3.57-3.67 (m, 1H), 3.33-3.38 (m, 1H), 3.19-3.26 (m, 0.50H), 3.03-3.17 (m, 1H), 2.54-2.63 (m, 3H), 1.90-2.06 (m, 2H).

Example 156

1-(3,5-Difluoropyridin-2-yl)-4-oxo-7-(2-oxoimidazolidin-1-yl)-N-[-(2R)-1,1,1-trifluoro-4-methylpentan-2-yl]-1,4-dihydro-1,8-naphthyridine-3-carboxamide

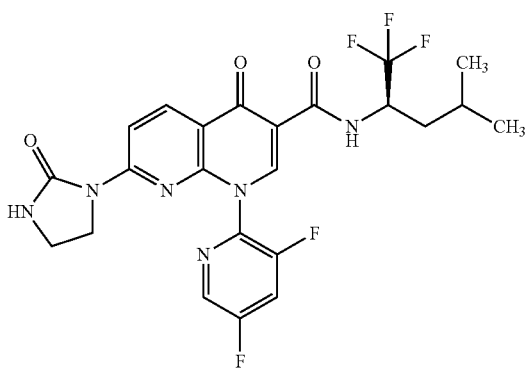 [SMILES: CC(C)C[C@@H](NC(=O)c1cn(-c2ncc(F)cc2F)c2nc(N3CCNC3=O)ccc2c1=O)C(F)(F)F]

According to GP1, 50.0 mg (129 µmol) of 1-(3,5-difluoropyridin-2-yl)-4-oxo-7-(2-oxoimidazolidin-1-yl)-1,4-dihydro-1,8-naphthyridine-3-carboxylic acid were reacted with 40.1 mg (258 µmol) of (2R)-1,1,1-trifluoro-4-methylpentan-2-amine in the presence of 98.2 mg (258 µmol) of HATU and 90 al (520 µmol) of DIPEA in 750 µl of DMF. The crude product was purified by preparative HPLC (acetonitrile/water/0.1% formic acid). This gave 18.9 mg (28% of theory, purity 99%) of the title compound.

LC-MS (Methode 2): $R_t$=2.05 min; MS (ESIpos): m/z=525 [M+H]+

¹H-NMR (400 MHz, DMSO-d6): δ [ppm]=10.16-10.23 (m, 1H), 8.99 (s, 1H), 8.63 (br d, 1H), 8.55 (d, 1H), 8.44 (d, 1H), 8.29-8.36 (m, 1H), 7.67 (s, 1H), 4.80-4.91 (m, 1H), 3.54-3.71 (m, 2H), 3.33-3.42 (m, 2H), 1.54-1.74 (m, 3H), 0.95 (br d, 3H), 0.89 (br t, 3H).

Example 157

1-(3,5-Difluoropyridin-2-yl)-4-oxo-7-(2-oxoimidazolidin-1-yl)-N-[(2S)-1,1,1-trifluoro-4-methylpentan-2-yl]-1,4-dihydro-1,8-naphthyridine-3-carboxamide

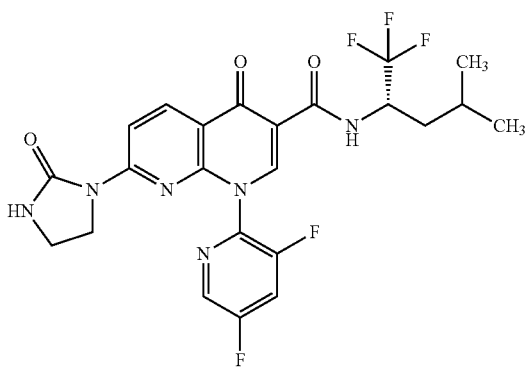 [SMILES: CC(C)C[C@H](NC(=O)c1cn(-c2ncc(F)cc2F)c2nc(N3CCNC3=O)ccc2c1=O)C(F)(F)F]

According to GP1, 50.0 mg (129 µmol) of 1-(3,5-difluoropyridin-2-yl)-4-oxo-7-(2-oxoimidazolidin-1-yl)-1,4-dihydro-1,8-naphthyridine-3-carboxylic acid were reacted with 40.0 mg (258 µmol) of (2S)-1,1,1-trifluoro-4-methylpentan-2-amine in the presence of 98.2 mg (258 µmol) of HATU and 90 µl (520 µmol) of DIPEA in 750 µl of DMF. The crude product was purified by preparative HPLC (acetonitrile/water/0.1% formic acid). This gave 19.2 mg (28% of theory, purity 100%) of the title compound.

LC-MS (Methode 2): $R_t$=2.05 min; MS (ESIpos): m/z=525 [M+H]+

¹H-NMR (400 MHz, DMSO-d6): δ [ppm]=10.20 (br dd, 1H), 8.99 (s, 1H), 8.63 (d, 1H), 8.55 (d, 1H), 8.44 (d, 1H), 8.30-8.36 (m, 1H), 7.67 (s, 1H), 4.79-4.91 (m, 1H), 3.54-3.70 (m, 2H), 3.33-3.41 (m, 2H), 1.63-1.74 (m, 2H), 1.54-1.63 (m, 1H), 0.93-0.98 (m, 3H), 0.89 (br t, 3H).

Example 158

1-(3,5-Difluoropyridin-2-yl)-N-(1,1,1,3,3,3-hexafluoropropan-2-yl)-4-oxo-7-(2-oxoimidazolidin-1-yl)-1,4-dihydro-1,8-naphthyridine-3-carboxamide

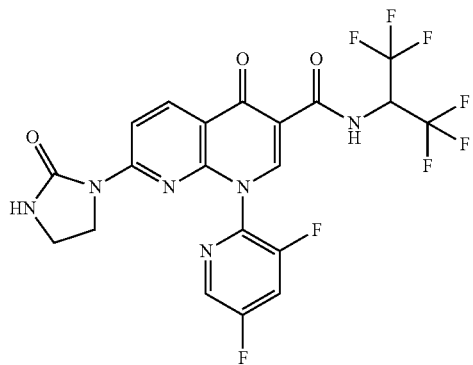 [SMILES: O=C(NC(C(F)(F)F)C(F)(F)F)c1cn(-c2ncc(F)cc2F)c2nc(N3CCNC3=O)ccc2c1=O]

According to GP2, 70.0 mg (144 µmol) of 7-chloro-1-(3,5-difluoropyridin-2-yl)-N-(1,1,1,3,3,3-hexafluoropropan-2-yl)-4-oxo-1,4-dihydro-1,8-naphthyridine-3-carboxamide were reacted with 124 mg (1.44 mmol) of imidazolidin-2-one in the presence of 29.8 mg (216 µmol) of potassium carbonate, 6.46 mg (28.8 µmol) of palladium acetate and 16.6 mg (28.8 µmol) of Xantphos in 1.4 ml of 1,4-dioxane. The crude product was purified by preparative HPLC (acetonitrile/water/0.1% formic acid). The substance was finally recrystallized from acetonitrile, filtered off with suction, rinsed with a little acetonitrile, dried and once more purified by preparative HPLC (acetonitrile/water/0.1% formic acid). This gave 32.7 mg (40% of theory, purity 95%) of the title compound.

LC-MS (Methode 2): $R_t$=1.93 min; MS (ESIpos): m/z=537 [M+H]+

¹H-NMR (400 MHz, DMSO-d6): δ [ppm]=11.14 (d, 1H), 9.08 (s, 1H), 8.65 (d, 1H), 8.58 (d, 1H), 8.46 (d, 1H), 8.31-8.37 (m, 1H), 7.69 (s, 1H), 6.32-6.42 (m, 1H), 3.54-3.70 (m, 2H), 3.33-3.41 (m, 2H).

Example 159

1-(3,5-Difluoropyridin-2-yl)-N-[1,1,1,4,4,4-hexafluorobutan-2-yl]-7-[(4S)-4-hydroxy-2-oxopyrrolidin-1-yl]-4-oxo-1,4-dihydro-1,8-naphthyridine-3-carboxamide (diastereomer mixture)

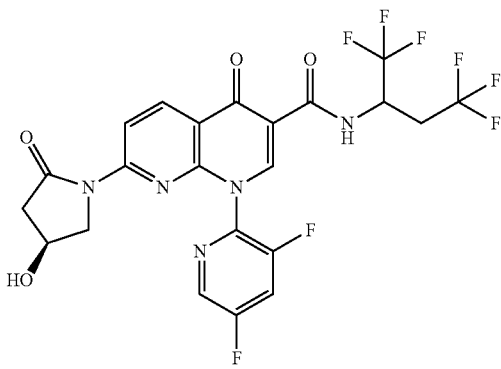 [SMILES: O=C(NC(CC(F)(F)F)C(F)(F)F)c1cn(-c2ncc(F)cc2F)c2nc(N3C[C@@H](O)CC3=O)ccc2c1=O]

According to GP1, 40.0 mg (99.4 μmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid were reacted with 30.3 mg (139 μmol) of 1,1,1,4,4,4-hexafluorobutan-2-amine hydrochloride in the presence of 45.4 mg (119 μmol) of HATU and 52 μl (300 μmol) of DIPEA in 370 μl of DMF. The crude product was purified by preparative HPLC (acetonitrile/water/0.1% formic acid). This gave 37.0 mg (63% of theory, purity 95%) of the title compound.

LC-MS (Methode 2): $R_t$=1.74 min; MS (ESIpos): m/z=566 [M+H]+

$^1$H-NMR (400 MHz, DMSO-d6): δ [ppm]=10.37 (d, 1H), 9.07 (s, 1H), 8.71 (d, 1H), 8.64-8.68 (m, 1H), 8.55 (br t, 1H), 8.36-8.42 (m, 1H), 5.38 (br d, 0.50H), 5.23-5.34 (m, 1.50H), 4.29 (br s, 1H), 3.62-3.78 (m, 1H), 3.44-3.57 (m, 1H), 3.10-3.22 (m, 1H), 2.88-3.03 (m, 2H), 2.34-2.43 (m, 1H).

Example 160

1-(3,5-Difluoropyridin-2-yl)-7-[(3R,4R)-3,4-dihydroxypyrrolidin-1-yl]-N-[1,1,1,4,4,4-hexafluorobutan-2-yl]-4-oxo-1,4-dihydro-1,8-naphthyridine-3-carboxamide (diastereomer mixture)

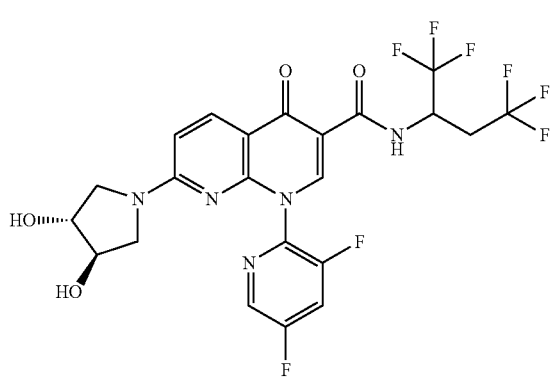 [SMILES: O=C(NC(CC(F)(F)F)C(F)(F)F)c1cn(-c2ncc(F)cc2F)c2nc(N3C[C@@H](O)[C@H](O)C3)ccc2c1=O]

According to GP1, 40.0 mg (98.9 μmol) of 1-(3,5-difluoropyridin-2-yl)-7-[(3R,4R)-3,4-dihydroxypyrrolidin-1-yl]-4-oxo-1,4-dihydro-1,8-naphthyridine-3-carboxylic acid were reacted with 30.1 mg (138 μmol) of 1,1,1,4,4,4-hexafluorobutan-2-amine hydrochloride in the presence of 45.1 mg (119 μmol) of HATU and 52 μl (300 μmol) of DIPEA in 370 μl of DMF. The crude product was purified by preparative HPLC (acetonitrile/water/0.1% formic acid). This gave 22.1 mg (37% of theory, purity 95%) of the title compound.

LC-MS (Methode 2): $R_t$=1.57 min; MS (ESIpos): m/z=568 [M+H]+

$^1$H-NMR (400 MHz, DMSO-d6): δ [ppm]=10.70 (d, 1H), 8.83 (t, 1H), 8.61 (d, 1H), 8.30-8.36 (m, 1H), 8.27 (d, 1H), 8.20 (s, 1H), 6.78 (d, 1H), 4.99-5.33 (m, 3H), 4.02-4.09 (m, 1H), 3.88-3.97 (m, 1H), 3.56-3.67 (m, 1H), 3.02-3.19 (m, 3H), 2.90-3.01 (m, 1H).

Example 161

1-(3,5-Difluoropyridin-2-yl)-4-oxo-7-(2-oxoimidazolidin-1-yl)-N-[3,3,4,4,4-pentafluorobutan-2-yl]-1,4-dihydro-1,8-naphthyridine-3-carboxamide (racemate)

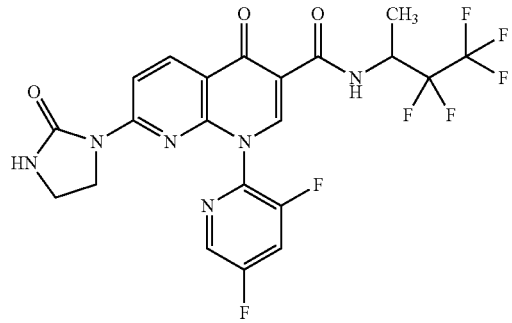 [SMILES: CC(NC(=O)c1cn(-c2ncc(F)cc2F)c2nc(N3CCNC3=O)ccc2c1=O)C(F)(F)C(F)(F)F]

According to GP1, 220 mg (568 μmol) of 1-(3,5-difluoropyridin-2-yl)-4-oxo-7-(2-oxoimidazolidin-1-yl)-1,4-dihydro-1,8-naphthyridine-3-carboxylic acid were reacted with 147 mg (738 μmol) of 3,3,4,4,4-pentafluorobutan-2-amine hydrochloride in the presence of 302 mg (795 μmol) of HATU and 430 μl (2.40 mmol) of DIPEA in 5.1 ml of DMF. The crude product was purified by preparative HPLC (acetonitrile/water/0.1% formic acid). This gave 165 mg (55% of theory, purity 100% by LC/MS) of the title compound.

LC-MS (Methode 1): $R_t$=0.98 min; MS (ESIpos): m/z=533 [M+H]+

$^1$H-NMR (400 MHz, DMSO-d6): δ [ppm]=10.34 (d, 1H), 8.99 (s, 1H), 8.63 (d, 1H), 8.55 (d, 1H), 8.44 (d, 1H), 8.36-8.30 (m, 1H), 7.67 (br s, 1H), 6.53 (br. dd, 1H), 5.10-4.99 (m, 1H), 4.65-4.49 (m, 1H), 3.69-3.55 (m, 2H), 3.40-3.33 (m, 2H), 1.41 (br d, 3H), 1.25-1.21 (m, 3H).

(no $EC_{50}$ is given for the title compound since purity according to $^1$H-NMR is less than 50%.)

165 mg of the title compound (racemate) were separated into the enantiomers by chiral HPLC (preparative HPLC: column: YMC Chiralart Cellulose SC 5 μm 250×20 mm; eluent: 50% n-heptane, 50% ethanol+0.2% DEA; temperature: 35° C.; flow rate: 15 ml/min; UV detection: 265 nm).

This gave (in the sequence of elution from the column) 48.0 mg of enantiomer 1 (99% ee) Rt=8.52 min and 50.0 mg of enantiomer 2 (97.4% ee) Rt=9.48 min.

[Analytical HPLC: column: Daicel Chiralpak IC 5 μm 250×4.6 mm; mobile phase: 50% isohexane, 50% ethanol +0.2% DEA; temperature: 35° C.; flow rate: 1.0 ml/min; UV detection: 265 nm].

Enantiomer 1 was additionally obtained by preparative HPLC (acetonitrile/water/0.1% formic acid), giving 41.0 mg (14% of theory, purity 100%) of the title compound from Example 162.

Enantiomer 2 was additionally obtained by preparative HPLC (acetonitrile/water/0.1% formic acid), giving 42.0 mg (14% of theory, purity 100%) of the title compound from Example 163.

Example 162

1-(3,5-Difluoropyridin-2-yl)-4-oxo-7-(2-oxoimidazolidin-1-yl)-N-[3,3,4,4,4-pentafluorobutan-2-yl]-1,4-dihydro-1,8-naphthyridine-3-carboxamide (enantiomer 1)

LC-MS (Methode 2): $R_t$=1.85 min; MS (ESIpos): m/z=533 [M+H]+

$^1$H NMR (400 MHz, DMSO-d$_6$): 6 ppm=10.34 (br d, 1H), 8.99 (br d, 1H), 8.63 (d, 1H), 8.55 (d, 1H), 8.44 (d, 1H), 8.33 (br t, 1H), 7.67 (s, 1H), 4.98-5.11 (m, 1H), 3.54-3.70 (m, 2H), 3.33-3.41 (m, 2H), 1.41 (br d, 3H).

Example 163

1-(3,5-Difluoropyridin-2-yl)-4-oxo-7-(2-oxoimidazolidin-1-yl)-N-[3,3,4,4,4-pentafluorobutan-2-yl]-1,4-dihydro-1,8-naphthyridine-3-carboxamide (enantiomer 2)

LC-MS (Methode 2): $R_t$=1.85 min; MS (ESIpos): m/z=533 [M+H]+

$^1$H NMR (400 MHz, DMSO-d$_6$): 6 ppm=10.34 (br d, 1H), 8.99 (br d, 1H), 8.63 (d, 1H), 8.55 (d, 1H), 8.43 (d, 1H), 8.33 (br t, 1H), 7.67 (s, 1H), 4.97-5.11 (m, 1H), 3.53-3.70 (m, 2H), 3.32-3.41 (m, 2H), 1.41 (br d, 3H).

Example 164

1-(3,5-Difluoropyridin-2-yl)-4-oxo-7-(2-oxoimidazolidin-1-yl)-N-[1,1,1,2,2-pentafluoropentan-3-yl]-1,4-dihydro-1,8-naphthyridine-3-carboxamide (racemate)

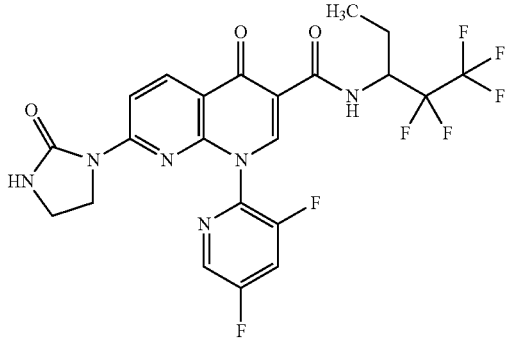 [SMILES: CCC(NC(=O)c1cn(-c2ncc(F)cc2F)c2nc(N3CCNC3=O)ccc2c1=O)C(F)(F)C(F)(F)F]

According to GP1, 213 mg (550 µmol) of 1-(3,5-difluoropyridin-2-yl)-4-oxo-7-(2-oxoimidazolidin-1-yl)-1,4-dihydro-1,8-naphthyridine-3-carboxylic acid were reacted with 153 mg (715 µmol) of 1,1,1,2,2-pentafluoropentan-3-amine hydrochloride in the presence of 293 mg (770 µmol) of HATU and 410 µl (2.4 mmol) of DIPEA in 4.9 ml of DMF. The crude product was purified by preparative HPLC (column: acetonitrile/water/0.1% formic acid). The substance was recrystallized from acetonitrile and DMF and the precipitate was filtered off with suction, washed with a little acetonitrile and dried. The substance was then purified by preparative HPLC (acetonitrile/water/0.1% formic acid). This gave 117 mg (39% of theory, purity 96%) of the title compound.

LC-MS (Methode 1): $R_t$=1.03 min; MS (ESIpos): m/z=547 [M+H]+

$^1$H-NMR (400 MHz, DMSO-d6): δ [ppm]=10.26 (d, 1H), 8.97-9.02 (m, 1H), 8.63 (d, 1H), 8.56 (d, 1H), 8.44 (d, 1H), 8.30-8.36 (m, 1H), 7.67 (s, 1H), 4.83-4.96 (m, 1H), 3.54-3.70 (m, 2H), 3.33-3.41 (m, 2H), 1.88-1.98 (m, 1H), 1.62-1.73 (m, 1H), 0.94-1.00 (m, 3H).

117 mg of 1-(3,5-difluoropyridin-2-yl)-4-oxo-7-(2-oxoimidazolidin-1-yl)-N-[1,1,1,2,2-pentafluoropentan-3-yl]-1,4-dihydro-1,8-naphthyridine-3-carboxamide (racemate) were separated into the enantiomers by chiral HPLC (preparative HPLC: column YMC Chiralart Cellulose SB, 5 µm, 250×20 mm; mobile phase: 50% n-heptane/50% isopropanol +0.2% DEA; flow rate 15 ml/min; temperature: 30° C., detection: 220 nm).

This gave (in the sequence of elution from the column) 55.0 mg of enantiomer A (>99% ee) Rt=5.65 min and 57.0 mg of enantiomer B (96.4% ee) $R_t$=6.44 min. [HPLC: column YMC Cellulose SB, 1 ml/min; 5 µm, 250×4.6 mm; mobile phase: 50% n-heptane/50% isopropanol +0.2% DEA; detection: 265 nm].

Enantiomer A was additionally obtained by preparative HPLC (column: acetonitrile/water/0.1% formic acid), giving 42.0 mg (purity 100%) of the title compound from Example 165.

Enantiomer B was additionally obtained by preparative HPLC (column: acetonitrile/water/0.1% formic acid), giving 40.0 mg (purity 100%) of the title compound from Example 166.

Example 165

1-(3,5-Difluoropyridin-2-yl)-4-oxo-7-(2-oxoimidazolidin-1-yl)-N-[1,1,1,2,2-pentafluoropentan-3-yl]-1,4-dihydro-1,8-naphthyridine-3-carboxamide (enantiomer A)

LC-MS (Methode 2): $R_t$=1.98 min; MS (ESIpos): m/z=547 [M+H]$^+$ $^1$H-NMR (400 MHz, DMSO-d6) δ [ppm]: −0.149 (0.60), −0.008 (5.43), 0.008 (5.16), 0.146 (0.60), 0.948 (4.38), 0.965 (10.46), 0.977 (11.06), 0.995 (5.03), 1.637 (1.34), 1.655 (1.87), 1.663 (1.71), 1.671 (2.27), 1.681 (2.11), 1.690 (1.91), 1.698 (2.23), 1.716 (1.58), 1.734 (0.45), 1.931 (2.00), 2.329 (0.71), 2.367 (0.69), 2.524 (2.58), 2.671 (0.80), 2.711 (0.80), 3.342 (5.10), 3.361 (5.16), 3.383 (3.27), 3.552 (1.00), 3.578 (2.96), 3.595 (2.98), 3.618 (1.89), 3.632 (2.18), 3.655 (3.16), 3.672 (2.47), 3.698 (0.71), 4.854 (1.31), 4.880 (1.74), 4.906 (1.76), 4.931 (1.29), 7.671 (11.17), 8.310 (2.27), 8.331 (4.25), 8.354 (2.23), 8.429 (11.53), 8.452 (16.00), 8.549 (15.98), 8.572 (11.33), 8.630 (10.19), 8.636 (9.75), 8.995 (7.23), 8.999 (7.61), 10.247 (6.25), 10.272 (6.05).

Example 166

1-(3,5-Difluoropyridin-2-yl)-4-oxo-7-(2-oxoimidazolidin-1-yl)-N-[1,1,1,2,2-pentafluoropentan-3-yl]-1,4-dihydro-1,8-naphthyridine-3-carboxamide (enantiomer B)

LC-MS (Methode 2): $R_t$=1.99 min; MS (ESIpos): m/z=547 [M+H]

$^1$H-NMR (400 MHz, DMSO-d6) δ [ppm]: −0.008 (2.79), 0.008 (2.51), 0.948 (4.46), 0.966 (10.56), 0.977 (11.21), 0.995 (5.10), 1.637 (1.35), 1.655 (1.92), 1.663 (1.73), 1.671 (2.32), 1.681 (2.12), 1.690 (1.92), 1.698 (2.24), 1.716 (1.61), 1.734 (0.47), 1.933 (2.02), 2.074 (1.14), 2.329 (0.49), 2.368 (0.47), 2.671 (0.61), 2.711 (0.51), 3.342 (5.10), 3.361 (5.24), 3.384 (3.36), 3.553 (0.96), 3.578 (3.06), 3.595 (3.04), 3.618 (1.92), 3.633 (2.24), 3.655 (3.22), 3.673 (2.51), 3.699 (0.71), 4.855 (1.33), 4.880 (1.79), 4.906 (1.77), 4.932 (1.32), 7.671 (11.39), 8.310 (2.30), 8.330 (4.28), 8.354 (2.24), 8.429

(11.43), 8.452 (16.00), 8.549 (15.71), 8.572 (11.19), 8.630 (10.19), 8.636 (9.78), 8.995 (7.19), 9.000 (7.58), 10.247 (6.36), 10.272 (6.16).

Example 167

N-[(1S)-1-Cyclopropyl-2,2,2-trifluoroethyl]-1-(3,5-difluoropyridin-2-yl)-7-[3-(2-hydroxyethyl)-2-oxoimidazolidin-1-yl]-4-oxo-1,4-dihydro-1,8-naphthyridine-3-carboxamide

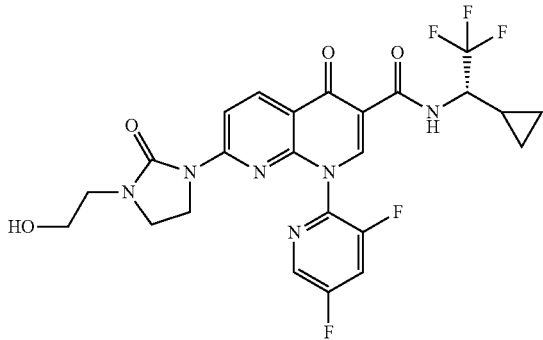 [SMILES: O=C(N[C@@H](C1CC1)C(F)(F)F)c1cn(-c2ncc(F)cc2F)c2nc(N3CCN(CCO)C3=O)ccc2c1=O]

According to GP1, 40.0 mg (92.7 µmol, purity 100%) of 1-(3,5-difluoropyridin-2-yl)-7-[3-(2-hydroxyethyl)-2-oxoimidazolidin-1-yl]-4-oxo-1,4-dihydro-1,8-naphthyridine-3-carboxylic acid (Example 25A) were reacted with 19.5 mg (111 µmol) of (1S)-1-cyclopropyl-2,2,2-trifluoroethanamine hydrochloride in the presence of 42.3 mg (111 µmol) of HATU and 65.0 µl (371 µmol) of DIPEA in 0.6 ml of DMF. The reaction mixture was diluted with water, acetonitrile and formic acid, filtered through a Millipore filter and purified by preparative HPLC (acetonitrile/water/0.1% formic acid), giving 35.3 mg (69% of theory, purity 100%) of the title compound.

LC-MS (Methode 2): $R_t$=1.77 min; MS (ESIpos): m/z=553 [M+H]+.

$^1$H-NMR (400 MHz, DMSO-d6): δ [ppm]=10.34 (br d, 1H), 8.98 (s, 1H), 8.64 (d, 1H), 8.57 (d, 1H), 8.45 (d, 1H), 8.33 (ddd, 1H), 4.75 (t, 1H), 4.42 (sxt, 1H), 3.44-3.62 (m, 6H), 3.22-3.30 (m, 2H), 1.19-1.27 (m, 1H), 0.51-0.70 (m, 3H), 0.30-0.39 (m, 1H).

Example 168

N-Cyclobutyl-1-(3,5-difluoropyridin-2-yl)-7-[(3R,4R)-3,4-dihydroxypyrrolidin-1-yl]-4-oxo-1,4-dihydro-1,8-naphthyridine-3-carboxamide

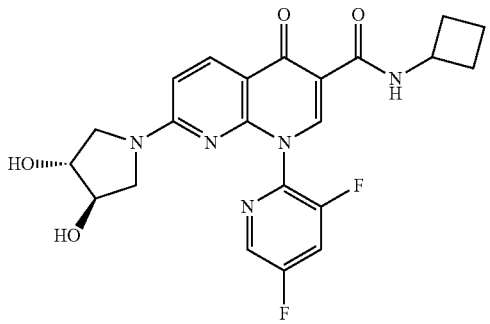 [SMILES: O=C(NC1CCC1)c1cn(-c2ncc(F)cc2F)c2nc(N3C[C@@H](O)[C@H](O)C3)ccc2c1=O]

According to GP1, 20.7 mg (51.2 µmol) of 1-(3,5-difluoropyridin-2-yl)-7-[(3R,4R)-3,4-dihydroxypyrrolidin-1-yl]-4-oxo-1,4-dihydro-1,8-naphthyridine-3-carboxylic acid were reacted with 6.61 mg (61.4 µmol) of cyclobutanamine hydrochloride in the presence of 23.4 mg (61.4 µmol) of HATU and 27 µl (150 µmol) of DIPEA in 200 µl of DMF. The crude product was purified twice by preparative HPLC (column: acetonitrile/water/0.1% formic acid). This gave 7.90 mg (34% of theory, purity 100%) of the title compound.

LC-MS (Methode 1): $R_t$=0.71 min; MS (ESIpos): m/z=458 [M+H]+

$^1$H-NMR (400 MHz, DMSO-d6) δ [ppm]: −0.149 (2.35), 0.146 (2.30), 0.948 (0.81), 0.956 (1.15), 0.973 (1.10), 1.235 (0.86), 1.658 (1.63), 1.677 (3.40), 1.683 (3.21), 1.703 (6.66), 1.721 (7.95), 1.728 (6.37), 1.744 (4.55), 1.943 (4.74), 1.965 (6.56), 1.987 (4.41), 2.073 (6.18), 2.086 (2.54), 2.281 (7.86), 2.291 (6.90), 2.300 (7.33), 2.319 (3.45), 2.327 (3.50), 2.367 (1.05), 2.670 (1.72), 2.710 (1.05), 3.033 (2.49), 3.065 (3.11), 3.111 (1.87), 3.144 (3.21), 3.208 (2.87), 3.582 (2.40), 3.610 (3.35), 3.637 (1.82), 3.924 (6.61), 4.049 (6.85), 4.379 (0.67), 4.398 (2.83), 4.419 (5.41), 4.439 (5.32), 4.459 (2.78), 4.479 (0.72), 5.063 (1.72), 5.187 (3.02), 5.266 (1.68), 6.739 (14.04), 6.761 (14.42), 8.252 (15.19), 8.274 (16.00), 8.302 (3.45), 8.324 (6.04), 8.341 (3.21), 8.346 (3.31), 8.607 (13.56), 8.613 (13.08), 8.710 (9.39), 8.716 (10.78), 10.110 (9.39), 10.129 (9.20).

Example 169

1-(3,5-Difluoropyridin-2-yl)-4-oxo-7-(2-oxoimidazolidin-1-yl)-N-[1,1,1-trifluoro-3-methylbutan-2-yl]-1,4-dihydro-1,8-naphthyridine-3-carboxamide (racemate)

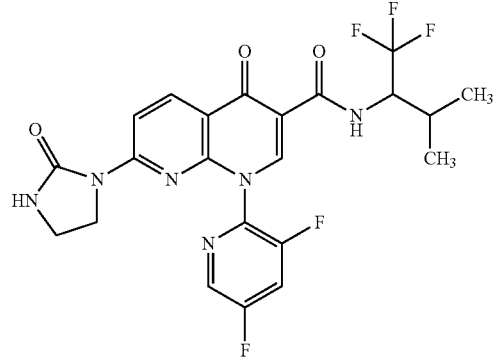 [SMILES: CC(C)C(NC(=O)c1cn(-c2ncc(F)cc2F)c2nc(N3CCNC3=O)ccc2c1=O)C(F)(F)F]

According to GP1, 80.0 mg (207 µmol) of 1-(3,5-difluoropyridin-2-yl)-4-oxo-7-(2-oxoimidazolidin-1-yl)-1,4-dihydro-1,8-naphthyridine-3-carboxylic acid were reacted with 58.3 mg (413 µmol) of 1,1,1-trifluoro-3-methylbutan-2-amine in the presence of 157 mg (413 µmol) of HATU and 140 µl (830 µmol) of DIPEA in 1.4 ml of DMF. The crude product was purified by preparative HPLC (column: acetonitrile/water/0.1% formic acid). This gave 33.7 mg (32% of theory, purity 100%) of the title compound.

LC-MS (Methode 2): $R_t$=1.90 min; MS (ESIpos): m/z=511 [M+H]

$^1$H-NMR (400 MHz, DMSO-d6) δ [ppm]: 0.889 (9.48), 0.899 (9.69), 0.906 (10.59), 0.915 (8.34), 0.959 (8.58), 0.972 (13.09), 0.986 (8.58), 1.032 (12.36), 1.048 (12.28), 2.074 (3.55), 2.093 (0.98), 2.109 (0.62), 2.237 (1.99), 2.254 (2.67), 2.263 (2.63), 2.281 (1.86), 2.328 (0.79), 2.367 (0.45), 2.671 (0.73), 3.342 (5.03), 3.362 (4.86), 3.385 (2.99), 3.582 (2.72), 3.598 (2.78), 3.622 (1.84), 3.635 (2.12), 3.656 (2.99), 3.674 (2.29), 4.254 (0.77), 4.266 (0.81), 4.278 (1.07), 4.288 (0.92), 4.301 (0.79), 4.768 (1.63), 4.777 (1.80), 4.791 (2.42), 4.800 (2.48), 4.813 (1.73), 4.823 (1.62), 6.568 (0.79), 6.584 (1.41), 6.609 (1.26), 7.673 (9.80), 8.307 (2.08), 8.313 (2.40), 8.334 (4.13), 8.351 (2.31), 8.357 (2.37), 8.432 (8.13), 8.455

(11.06), 8.574 (10.57), 8.597 (8.06), 8.637 (8.19), 8.642 (7.94), 9.002 (16.00), 10.408 (3.08), 10.426 (3.12).

Example 170

N-(3,3-Difluoro-1-methylcyclobutyl)-1-(3,5-difluoropyridin-2-yl)-7-[(3R,4R)-3,4-dihydroxypyrrolidin-1-yl]-4-oxo-1,4-dihydro-1,8-naphthyridine-3-carboxamide

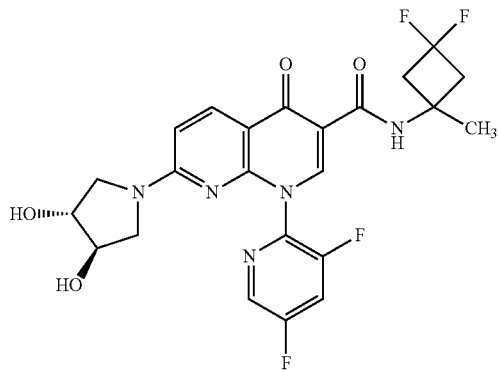 [SMILES: CC1(NC(=O)c2cn(-c3ncc(F)cc3F)c3nc(N4C[C@@H](O)[C@H](O)C4)ccc3c2=O)CC(F)(F)C1]

According to GP1, 60.0 mg (148 µmol) of 1-(3,5-difluoropyridin-2-yl)-7-[(3R,4R)-3,4-dihydroxypyrrolidin-1-yl]-4-oxo-1,4-dihydro-1,8-naphthyridine-3-carboxylic acid were reacted with 28.1 mg (178 µmol) of 3,3-difluoro-1-methylcyclobutanamine hydrochloride in the presence of 67.7 mg (178 µmol) of HATU and 90 µl (520 µmol) of DIPEA in 660 µl of DMF. The crude product was purified by preparative HPLC (column: acetonitrile/water/0.1% formic acid). This gave 45.5 mg (60% of theory, purity 100%) of the title compound.

LC-MS (Methode 2): $R_t$=1.43 min; MS (ESIpos): m/z=508 [M+H]

$^1$H-NMR (400 MHz, DMSO-d6) δ [ppm]: 1.555 (16.00), 2.073 (3.51), 2.328 (0.71), 2.665 (1.27), 2.697 (1.92), 2.721 (1.91), 2.753 (0.98), 2.977 (1.00), 3.013 (2.65), 3.047 (2.62), 3.147 (1.17), 3.330 (5.13), 3.613 (0.99), 3.925 (1.94), 4.051 (1.96), 5.207 (0.48), 6.746 (4.28), 6.769 (4.23), 8.216 (1.05), 8.250 (5.12), 8.272 (4.71), 8.309 (1.01), 8.331 (1.78), 8.348 (0.94), 8.612 (4.56), 8.618 (4.23), 8.735 (3.84), 8.741 (4.17), 10.275 (5.29).

Example 171

N-(3,3-Difluoro-1-methylcyclobutyl)-1-(3,5-difluoropyridin-2-yl)-4-oxo-7-(2-oxoimidazolidin-1-yl)-1,4-dihydro-1,8-naphthyridine-3-carboxamide

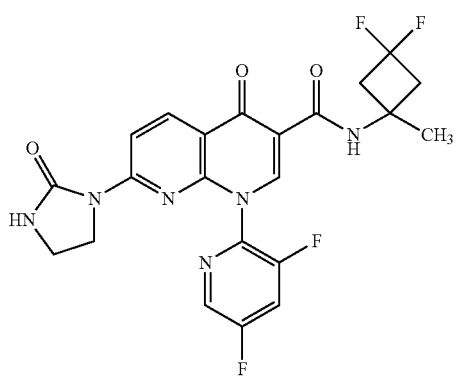 [SMILES: CC1(NC(=O)c2cn(-c3ncc(F)cc3F)c3nc(N4CCNC4=O)ccc3c2=O)CC(F)(F)C1]

According to GP1, 50.0 mg (129 µmol) of 1-(3,5-difluoropyridin-2-yl)-4-oxo-7-(2-oxoimidazolidin-1-yl)-1,4-dihydro-1,8-naphthyridine-3-carboxylic acid were reacted with 40.7 mg (258 µmol) of 3,3-difluoro-1-methylcyclobutanamine hydrochloride in the presence of 98.2 mg (258 µmol) of HATU and 90 µl (520 µmol) of DIPEA in 750 µl of DMF. The crude product was purified by preparative HPLC (column: acetonitrile/water/0.1% formic acid). This gave 17.6 mg (26% of theory, purity 95%) of the title compound.

LC-MS (Methode 2): $R_t$=1.69 min; MS (ESIpos): m/z=491 [M+H]

$^1$H-NMR (400 MHz, DMSO-d6) δ [ppm]: −0.008 (2.82), 0.008 (2.53), 1.382 (16.00), 1.567 (12.75), 2.073 (2.14), 2.328 (0.62), 2.446 (1.00), 2.465 (1.20), 2.670 (0.81), 2.679 (0.92), 2.712 (1.75), 2.737 (1.51), 2.770 (0.79), 2.821 (1.05), 2.856 (2.83), 2.893 (2.63), 2.929 (0.84), 2.989 (0.73), 3.023 (2.00), 3.059 (1.79), 3.093 (0.58), 3.356 (1.59), 3.378 (0.96), 3.573 (0.83), 3.589 (0.88), 3.625 (0.66), 3.648 (0.94), 3.664 (0.71), 6.237 (2.55), 7.649 (3.22), 8.301 (0.82), 8.307 (0.95), 8.328 (1.39), 8.345 (0.82), 8.351 (0.90), 8.410 (3.70), 8.432 (5.00), 8.527 (5.13), 8.549 (3.54), 8.631 (4.29), 8.638 (4.07), 8.911 (8.53), 10.081 (4.04).

Example 172

N-(3,3-Difluoro-1-methylcyclobutyl)-1-(3,5-difluoropyridin-2-yl)-7-[(4S)-4-hydroxy-2-oxopyrrolidin-1-yl]-4-oxo-1,4-dihydro-1,8-naphthyridine-3-carboxamide

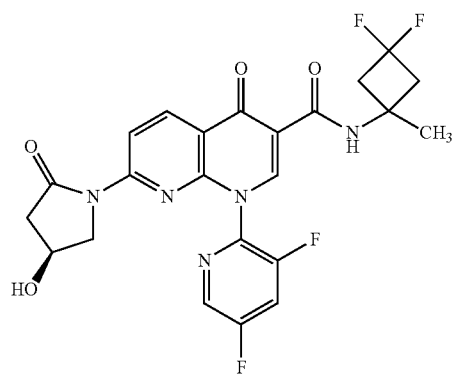 [SMILES: CC1(NC(=O)c2cn(-c3ncc(F)cc3F)c3nc(N4C[C@@H](O)CC4=O)ccc3c2=O)CC(F)(F)C1]

According to GP1, 50.0 mg (124 µmol) of 1-(3,5-difluoropyridin-2-yl)-7-[(4S)-4-hydroxy-2-oxopyrrolidin-1-yl]-4-oxo-1,4-dihydro-1,8-naphthyridine-3-carboxylic acid were reacted with 23.5 mg (149 µmol) of 3,3-difluoro-1-methylcyclobutanamine hydrochloride in the presence of 56.7 mg (149 µmol) of HATU and 87 µl (500 µmol) of DIPEA in 750 µl of DMF. The crude product was purified by preparative HPLC (column: acetonitrile/water/0.1% formic acid). This gave 37.7 mg (60% of theory, purity 100%) of the title compound.

LC-MS (Methode 2): $R_t$=1.63 min; MS (ESIpos): m/z=506 [M+H]

$^1$H-NMR (400 MHz, DMSO-d6) δ [ppm]: −0.008 (0.93), 0.008 (0.87), 1.572 (16.00), 2.074 (0.87), 2.344 (0.67), 2.368 (0.78), 2.387 (0.79), 2.411 (0.73), 2.524 (0.72), 2.685 (0.81), 2.721 (1.81), 2.744 (1.82), 2.755 (1.25), 2.778 (0.94), 2.888 (0.46), 2.902 (0.49), 2.931 (0.46), 2.950 (0.65), 2.967 (0.53), 2.991 (1.16), 3.025 (2.48), 3.060 (2.21), 3.095 (0.69), 3.460 (0.60), 3.490 (0.77), 3.519 (0.57), 3.549 (0.74), 3.657 (0.48), 3.668 (0.56), 3.687 (0.42), 3.699 (0.40), 3.728 (0.53), 3.738 (0.55), 3.757 (0.44), 4.292 (1.37), 5.253 (0.96), 5.260 (0.96), 5.373 (0.92), 5.382 (0.88), 8.361 (0.81), 8.367 (0.92), 8.388 (1.53), 8.406 (0.85), 8.412 (0.89), 8.504 (0.74), 8.525 (1.66), 8.547 (1.03), 8.664 (2.25), 8.681 (4.96), 8.704 (3.86), 8.977 (5.82), 9.999 (4.93).

Example 173

1-(3,5-Difluoropyridin-2-yl)-7-[(2R)-2-(hydroxymethyl)piperidin-1-yl]-4-oxo-N-(3,3,4,4,4-pentafluoro-2-methylbutan-2-yl)-1,4-dihydro-1,8-naphthyridine-3-carboxamide

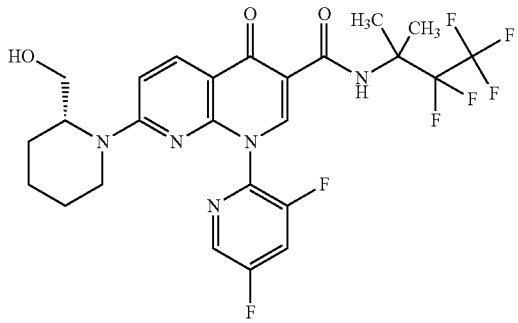 [SMILES: CC(C)(NC(=O)c1cn(-c2ncc(F)cc2F)c2nc(N3CCCC[C@@H]3CO)ccc2c1=O)C(F)(F)C(F)(F)F]

7-Chloro-1-(3,5-difluoropyridin-2-yl)-4-oxo-N-(3,3,4,4,4-pentafluoro-2-methylbutan-2-yl)-1,4-dihydro-1,8-naphthyridine-3-carboxamide (50.0 mg, 101 µmol) was dissolved in 1.1 ml of DMF, (2R)-piperidin-2-ylmethanol (12.8 mg, 111 µmol) and N,N-diisopropylethylamine (61 µl, 350 µmol) were added and the mixture was stirred at 55° C. for 18 h. More (2R)-piperidin-2-ylmethanol (11.6 mg, 101 µmol) and N,N-diisopropylethylamine (18 µl, 100 µmol) were added and the mixture was stirred at 55° C. overnight. The reaction mixture was cooled and purified by preparative HPLC (column: acetonitrile/water/0.1% formic acid). This gave 40.8 mg (70% of theory, purity 99%) of the title compound.

LC-MS (Methode 3): $R_t$=2.17 min; MS (ESIpos): m/z=576 [M+H]$^+$ $^1$H-NMR (400 MHz, DMSO-d6) δ [ppm]: −0.008 (1.61), 0.008 (1.62), 1.510 (1.42), 1.547 (1.15), 1.577 (0.84), 1.612 (0.70), 1.682 (16.00), 1.778 (1.06), 1.810 (0.94), 3.503 (0.99), 3.516 (0.93), 4.049 (0.81), 4.081 (0.77), 4.225 (0.92), 4.690 (1.00), 7.075 (3.25), 7.099 (3.39), 8.231 (2.79), 8.254 (2.91), 8.278 (0.55), 8.298 (0.60), 8.322 (0.60), 8.602 (4.13), 8.608 (4.02), 8.756 (6.43), 10.638 (5.18).

Example 174

1-(3,5-Difluoropyridin-2-yl)-7-[4-hydroxy-4-(hydroxymethyl)piperidin-1-yl]-4-oxo-N-(3,3,4,4,4-pentafluoro-2-methylbutan-2-yl)-1,4-dihydro-1,8-naphthyridine-3-carboxamide

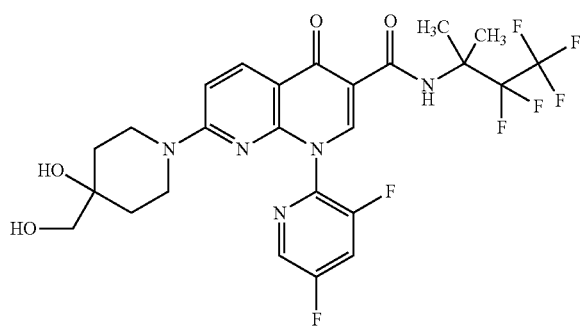 [SMILES: CC(C)(NC(=O)c1cn(-c2ncc(F)cc2F)c2nc(N3CCC(O)(CO)CC3)ccc2c1=O)C(F)(F)C(F)(F)F]

7-Chloro-1-(3,5-difluoropyridin-2-yl)-4-oxo-N-(3,3,4,4,4-pentafluoro-2-methylbutan-2-yl)-1,4-dihydro-1,8-naphthyridine-3-carboxamide (50.0 mg, 101 µmol) was dissolved in 1.1 ml of DMF, 4-(hydroxymethyl)piperidin-4-ol hydrochloride (19.5 mg, purity 95%, 111 µmol) and N,N-diisopropylethylamine (79 µl, 450 µmol) were added and the mixture was stirred at 55° C. for 18 h. The reaction mixture was cooled and purified by preparative HPLC (column: acetonitrile/water/0.1% formic acid). This gave 49 mg (82% of theory, purity 100%) of the title compound.

LC-MS (Methode 3): $R_t$=1.82 min; MS (ESIpos): m/z=592 [M+H]$^+$ $^1$H-NMR (400 MHz, DMSO-d6) δ [ppm]: 1.337 (1.29), 1.371 (1.16), 1.469 (0.99), 1.492 (1.08), 1.520 (0.53), 1.681 (16.00), 2.328 (0.48), 2.670 (0.47), 3.148 (4.54), 3.162 (4.61), 3.915 (1.39), 3.942 (1.25), 4.319 (5.79), 4.554 (1.11), 4.568 (2.37), 4.583 (1.07), 7.111 (3.27), 7.134 (3.41), 8.249 (4.45), 8.272 (4.15), 8.313 (0.90), 8.319 (1.07), 8.340 (1.60), 8.358 (0.95), 8.364 (1.03), 8.611 (4.88), 8.617 (4.69), 8.764 (10.14), 10.621 (5.45).

Example 175

1-(3,5-Difluoropyridin-2-yl)-7-[(2R)-2-(hydroxymethyl)pyrrolidin-1-yl]-4-oxo-N-(3,3,4,4,4-pentafluorobutan-2-yl)-1,4-dihydro-1,8-naphthyridine-3-carboxamide (enantiomerically pure)

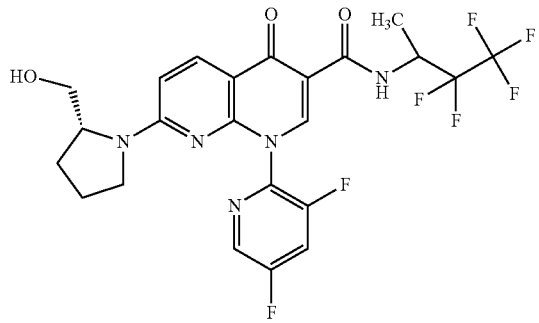 [SMILES: CC(NC(=O)c1cn(-c2ncc(F)cc2F)c2nc(N3CCC[C@@H]3CO)ccc2c1=O)C(F)(F)C(F)(F)F]

7-Chloro-1-(3,5-difluoropyridin-2-yl)-4-oxo-N-[3,3,4,4,4-pentafluorobutan-2-yl]-1,4-dihydro-1,8-naphthyridine-3-carboxamide (50.0 mg, 104 µmol) was dissolved in 1.1 ml of DMF, (2R)-pyrrolidin-2-ylmethanol (11 purity 99%, 110 µmol) and N,N-diisopropylethylamine (63 µl, 360 µmol) were added and the mixture was stirred at 55° C. for 18 h. The reaction mixture was cooled and purified by preparative HPLC (column: acetonitrile/water/0.1% formic acid). This gave 52 mg (92% of theory, purity 100%) of the title compound.

LC-MS (Methode 3): $R_t$=1.98 min; MS (ESIpos): m/z=548 [M+H]$^+$ $^1$H-NMR (400 MHz, DMSO-d6) δ [ppm]: 1.387 (15.87), 1.404 (16.00), 1.953 (3.83), 2.328 (1.78), 2.366 (0.61), 2.670 (1.96), 2.710 (0.61), 3.015 (1.22), 3.167 (1.04), 3.487 (1.17), 3.652 (1.04), 3.768 (0.87), 4.019 (0.70), 4.383 (1.00), 4.562 (1.22), 4.973 (1.09), 4.993 (1.78), 5.018 (2.04), 5.039 (2.04), 5.063 (1.74), 5.082 (0.91), 6.742 (1.96), 6.762 (2.04), 6.914 (0.91), 8.258 (4.52), 8.279 (5.17), 8.305 (2.65), 8.591 (13.61), 8.597 (13.48), 8.824 (9.26), 10.541 (4.70), 10.564 (4.61).

Example 176

1-(3,5-Difluoropyridin-2-yl)-7-[(2R)-2-(hydroxymethyl)piperidin-1-yl]-4-oxo-N-(3,3,4,4,4-pentafluorobutan-2-yl)-1,4-dihydro-1,8-naphthyridine-3-carboxamide (enantiomerically pure)

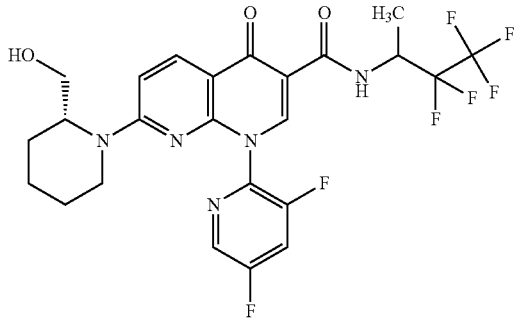 [SMILES: CC(NC(=O)c1cn(-c2ncc(F)cc2F)c2nc(N3CCCC[C@@H]3CO)ccc2c1=O)C(F)(F)C(F)(F)F]

7-Chloro-1-(3,5-difluoropyridin-2-yl)-4-oxo-N-[3,3,4,4,4-pentafluorobutan-2-yl]-1,4-dihydro-1,8-naphthyridine-3-carboxamide (50.0 mg, 104 µmol) was dissolved in 1.1 ml of DMF, (2R)-piperidin-2-ylmethanol (13.1 mg, 114 µmol) and N,N-diisopropylethylamine (63 µl, 360 µmol) were added and the mixture was stirred at 55° C. for 18 h. More (2R)-piperidin-2-ylmethanol (11.9 mg, 104 µmol) and N,N-diisopropylethylamine (18 µl, 100 µmol) were added and the mixture was stirred at 55° C. overnight. The reaction mixture was cooled and purified by preparative HPLC (column: acetonitrile/water/0.1% formic acid). This gave 39 mg (66% of theory, purity 99%) of the title compound.

LC-MS (Methode 3): R$_t$=2.07 min; MS (ESIpos): m/z=562 [M+H]$^+$ $^1$H-NMR (400 MHz, DMSO-d6) δ [ppm]: −0.149 (0.39), 0.146 (0.41), 1.314 (1.37), 1.342 (1.52), 1.387 (16.00), 1.404 (16.00), 1.504 (4.80), 1.549 (3.76), 1.579 (2.65), 1.614 (2.21), 1.647 (1.48), 1.780 (3.39), 1.809 (3.03), 2.328 (0.69), 2.670 (0.79), 2.831 (1.18), 3.503 (3.17), 3.519 (3.00), 4.048 (2.68), 4.079 (2.54), 4.228 (3.12), 4.694 (3.09), 4.971 (0.92), 4.992 (1.65), 5.015 (1.95), 5.036 (1.95), 5.060 (1.67), 5.080 (0.88), 7.086 (9.59), 7.109 (9.99), 8.223 (8.59), 8.246 (8.73), 8.273 (1.76), 8.303 (1.51), 8.330 (1.73), 8.348 (0.91), 8.608 (9.36), 8.807 (12.83), 10.531 (7.24), 10.555 (6.98).

Example 177

1-(3,5-Difluoropyridin-2-yl)-7-[4-hydroxy-4-(hydroxymethyl)piperidin-1-yl]-4-oxo-N-(3,3,4,4,4-pentafluorobutan-2-yl)-1,4-dihydro-1,8-naphthyridine-3-carboxamide (enantiomerically pure)

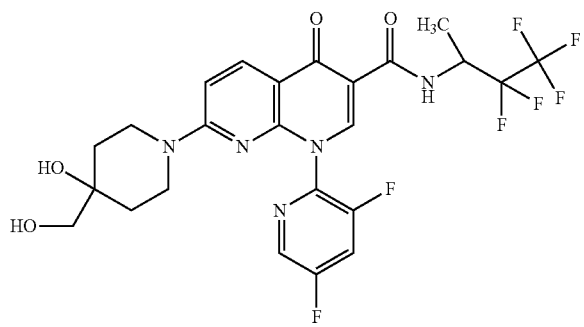 [SMILES: CC(NC(=O)c1cn(-c2ncc(F)cc2F)c2nc(N3CCC(O)(CO)CC3)ccc2c1=O)C(F)(F)C(F)(F)F]

7-Chloro-1-(3,5-difluoropyridin-2-yl)-4-oxo-N-[3,3,4,4,4-pentafluorobutan-2-yl]-1,4-dihydro-1,8-naphthyridine-3-carboxamide (50.0 mg, 104 µmol) was dissolved in 1.1 ml of DMF, 4-(hydroxymethyl)piperidin-4-ol hydrochloride (20.1 mg, purity 95%, 114 µmol) and N,N-diisopropylethylamine (63 µl, 360 µmol) were added and the mixture was stirred at 55° C. for 18 h. The reaction mixture was cooled and purified by preparative HPLC (column: acetonitrile/water/0.1% formic acid). The product was re-purified by preparative HPLC (column: acetonitrile/water/0.1% of formic acid). The product-containing fractions were combined, concentrated and lyophilized from water/acetonitrile. This gave 17.2 mg (28% of theory, purity 99%) of the title compound.

LC-MS (Methode 3): R$_t$=1.72 min; MS (ESIpos): m/z=578 [M+H]$^+$ $^1$H-NMR (400 MHz, DMSO-d6) δ [ppm]: −0.149 (0.79), −0.008 (9.63), 0.008 (6.77), 0.146 (0.79), 0.936 (0.62), 0.953 (0.62), 1.340 (3.98), 1.386 (14.49), 1.403 (13.31), 1.459 (2.99), 1.492 (3.19), 1.524 (1.38), 2.328 (1.25), 2.670 (1.28), 3.149 (13.21), 3.163 (13.17), 3.917 (4.24), 3.941 (3.68), 4.322 (16.00), 4.555 (3.32), 4.569 (6.67), 4.583 (3.02), 4.971 (0.89), 4.994 (1.51), 5.013 (1.71), 5.037 (1.68), 5.060 (1.41), 5.081 (0.72), 7.121 (9.03), 7.144 (9.17), 8.242 (12.42), 8.264 (11.33), 8.319 (2.27), 8.341 (3.81), 8.363 (2.07), 8.613 (9.03), 8.619 (8.51), 8.808 (6.51), 8.816 (6.97), 10.516 (5.03), 10.540 (4.86).

Example 178

1-(3,5-Difluoropyridin-2-yl)-N-(1,1,1,3,3,3-hexafluoropropan-2-yl)-7-[(2R)-2-(hydroxymethyl)piperidin-1-yl]-4-oxo-1,4-dihydro-1,8-naphthyridine-3-carboxamide

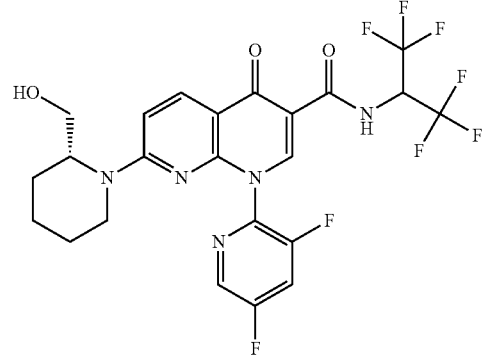 [SMILES: O=C(NC(C(F)(F)F)C(F)(F)F)c1cn(-c2ncc(F)cc2F)c2nc(N3CCCC[C@@H]3CO)ccc2c1=O]

7-Chloro-1-(3,5-difluoropyridin-2-yl)-N-(1,1,1,3,3,3-hexafluoropropan-2-yl)-4-oxo-1,4-dihydro-1,8-naphthyridine-3-carboxamide (50.0 mg, 103 µmol) was dissolved in 1 ml of DMF, (2R)-piperidin-2-ylmethanol (13.0 mg, 113 µmol) and N,N-diisopropylethylamine (63 µl, 360 µmol) were added and the mixture was stirred at 55° C. over the weekend. The reaction mixture was cooled and purified by preparative HPLC (column: acetonitrile/water/0.1% formic acid). The product-containing fractions were combined, concentrated and lyophilized from water/acetonitrile. This gave 33.4 mg (57% of theory, purity 99%) of the title compound.

LC-MS (Methode 3): R$_t$=2.13 min; MS (ESIpos): m/z=566 [M+H]$^+$ $^1$H-NMR (400 MHz, DMSO-d6) δ [ppm]: −0.149 (0.80), −0.008 (7.72), 0.008 (8.00), 0.146 (0.82), 1.315 (1.38), 1.505 (5.30), 1.551 (3.89), 1.581 (2.75), 1.617 (2.23), 1.782 (3.63), 1.810 (3.26), 2.328 (1.02), 2.671 (1.17), 2.871 (1.17), 3.508 (3.74), 3.522 (3.57), 4.057 (2.83), 4.089 (2.79), 4.239 (3.26), 4.702 (3.52), 6.276 (0.76), 6.294 (1.97), 6.319 (2.79), 6.337 (2.96), 6.355 (1.95), 7.115 (11.76), 7.139 (12.41), 8.247 (10.66), 8.270 (10.94), 8.295 (1.77), 8.316 (2.14), 8.342 (2.23), 8.361 (1.21), 8.619 (16.00), 8.626 (15.72), 8.900 (15.11), 11.382 (9.10), 11.407 (8.71).

Example 179

1-(3,5-Difluoropyridin-2-yl)-N-(1,1,1,3,3,3-hexafluoropropan-2-yl)-7-[4-hydroxy-4-hydroxymethyl)piperidin-1-yl]-4-oxo-1,4-dihydro-1,8-naphthyridine-3-carboxamide

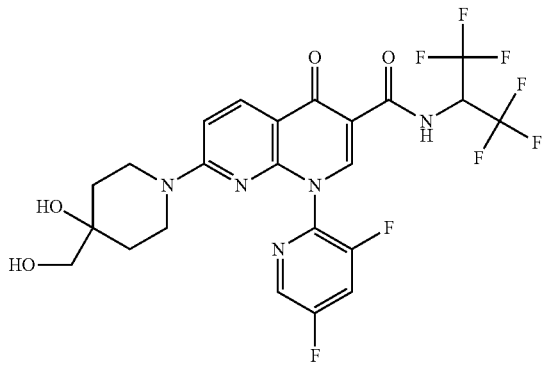 [SMILES: O=C(NC(C(F)(F)F)C(F)(F)F)c1cn(-c2ncc(F)cc2F)c2nc(N3CCC(O)(CO)CC3)ccc2c1=O]

7-Chloro-1-(3,5-difluoropyridin-2-yl)-N-(1,1,1,3,3,3-hexafluoropropan-2-yl)-4-oxo-1,4-dihydro-1,8-naphthyridine-3-carboxamide (50.0 mg, 103 µmol) was dissolved in 1 ml of DMF, 4-(hydroxymethyl)piperidin-4-ol hydrochloride (1:1) (19.9 mg, purity 95%, 113 µmol) and N,N-diisopropylethylamine (81 µl, 460 µmol) were added and the mixture was stirred at 55° C. over the weekend. The reaction mixture was cooled and purified by preparative HPLC (column: acetonitrile/water/0.1% formic acid). The product-containing fractions were combined, concentrated and lyophilized from water/acetonitrile. This gave 31.5 mg (52% of theory, purity 99%) of the title compound.

LC-MS (Methode 3): $R_t$=1.80 min; MS (ESIpos): m/z=582 [M+H]$^+$ $^1$H-NMR (400 MHz, DMSO-d6) δ [ppm]: -0.149 (0.70), 0.146 (0.72), 1.350 (2.52), 1.382 (2.54), 1.475 (2.14), 1.499 (2.32), 1.529 (1.10), 2.329 (0.85), 2.368 (0.66), 2.671 (0.98), 2.711 (0.72), 3.153 (8.93), 3.167 (9.21), 3.931 (3.22), 3.961 (2.80), 4.334 (10.99), 4.563 (2.14), 4.577 (4.38), 4.591 (2.14), 6.296 (1.09), 6.320 (1.64), 6.338 (1.71), 6.357 (1.16), 7.150 (6.04), 7.173 (6.32), 8.266 (7.77), 8.288 (7.29), 8.332 (1.71), 8.337 (2.01), 8.359 (3.41), 8.376 (1.84), 8.382 (2.01), 8.628 (8.38), 8.634 (8.49), 8.907 (16.00), 11.365 (5.14), 11.390 (4.93).

Example 180

1-(3,5-Difluoropyridin-2-yl)-N-(1,1,1,3,3,3-hexafluoropropan-2-yl)-7-[(2R)-2-(hydroxymethyl)pyrrolidin-1-yl]-4-oxo-1,4-dihydro-1,8-naphthyridine-3-carboxamide

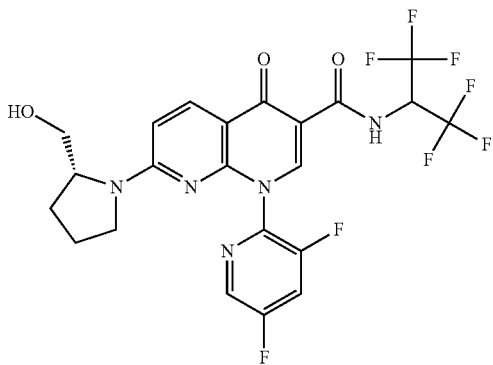 [SMILES: O=C(NC(C(F)(F)F)C(F)(F)F)c1cn(-c2ncc(F)cc2F)c2nc(N3CCC[C@@H]3CO)ccc2c1=O]

7-Chloro-1-(3,5-difluoropyridin-2-yl)-N-(1,1,1,3,3,3-hexafluoropropan-2-yl)-4-oxo-1,4-dihydro-1,8-naphthyridine-3-carboxamide (50.0 mg, 103 µmol) was dissolved in 1 ml of DMF, (2R)-pyrrolidin-2-ylmethanol (11 µl, purity 99%, 110 µmol) and N,N-diisopropylethylamine (63 µl, 360 µmol) were added and the mixture was stirred at 55° C. over the weekend. The reaction mixture was cooled and purified by preparative HPLC (column: acetonitrile/water/0.1% formic acid). The product-containing fractions were combined, concentrated and lyophilized from water/acetonitrile. This gave 34 mg (59% of theory, purity 99%) of the title compound.

$^1$H-NMR (400 MHz, DMSO-d6) δ [ppm]: -0.149 (1.69), -0.008 (15.45), 0.008 (16.00), 0.146 (1.69), 1.958 (3.28), 2.328 (1.31), 2.366 (0.55), 2.670 (1.47), 2.710 (0.60), 3.011 (1.09), 3.046 (0.98), 3.158 (0.98), 3.521 (1.04), 3.654 (0.87), 3.774 (0.82), 4.039 (0.55), 4.392 (1.04), 4.570 (1.20), 4.881 (0.60), 4.946 (0.44), 6.295 (1.58), 6.314 (2.29), 6.338 (2.40), 6.356 (1.58), 6.772 (1.86), 6.792 (2.02), 6.961 (0.87), 8.234 (0.93), 8.286 (3.93), 8.309 (3.93), 8.606 (10.87), 8.612 (10.48), 8.921 (3.60), 11.391 (3.71), 11.415 (3.71).

Example 181

1-(3,5-Difluoropyridin-2-yl)-7-(2-oxa-6-azaspiro[3.3]hept-6-yl)-4-oxo-N-[3,3,4,4,4-pentafluorobutan-2-yl]-1,4-dihydro-1,8-naphthyridine-3-carboxamide (enantiomerically pure)

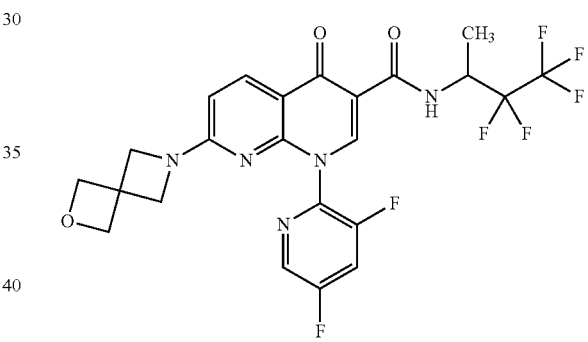

1-(3,5-Difluoropyridin-2-yl)-7-(2-oxa-6-azaspiro[3.3]hept-6-yl)-4-oxo-1,4-dihydro-1,8-naphthyridine-3-carboxylic acid (150 mg, 375 µmol) was initially charged in 2.8 ml of DMF, HATU (171 mg, 450 µmol) and N,N-diisopropylethylamine (290 µl, 1.7 mmol) were added and 3,3,4,4,4-pentafluorobutan-2-amine hydrochloride (89.7 mg, 450 µmol) was added. The mixture was stirred at room temperature for two nights. Water was added and the reaction solution was extracted three times with ethyl acetate and concentrated. Acetonitrile, water and TFA were added to the mixture. This resulted in the precipitation of a solid. The suspension was dissolved in ethyl acetate and washed twice with water and twice with sodium bicarbonate solution. The combined aqueous phases were re-extracted with ethyl acetate. The mixture was concentrated and the residue was purified by silica gel chromatography (mobile phase: dichloromethane/cyclohexane/methanol gradient: 100:50:1 to 100:20:1). This gave 158 mg of the target compound (76% of theory, purity 98%).

LC-MS (Methode 1): $R_t$=1.03 min; MS (ESIpos): m/z=546 [M+H]$^+$ $^1$H-NMR (400 MHz, DMSO-d6) δ [ppm]: -0.149 (0.75), -0.008 (5.81), 0.008 (6.07), 0.147 (0.70), 1.381 (4.23), 1.398 (6.18), 2.328 (1.23), 2.366 (0.60), 2.670 (1.26), 2.710 (0.60), 4.109 (0.68), 4.660 (16.00), 5.009 (0.57), 6.590

(4.12), 6.612 (4.16), 8.263 (4.53), 8.285 (4.60), 8.315 (1.25), 8.603 (3.34), 8.609 (3.30), 8.812 (2.31), 8.820 (2.58), 10.491 (1.92), 10.514 (1.89).

Example 182

1-(3,5-Difluoropyridin-2-yl)-7-(2-oxa-6-azaspiro[3.3]hept-6-yl)-4-oxo-N-(3,3,4,4,4-pentafluoro-2-methylbutan-2-yl)-1,4-dihydro-1,8-naphthyridine-3-carboxamide

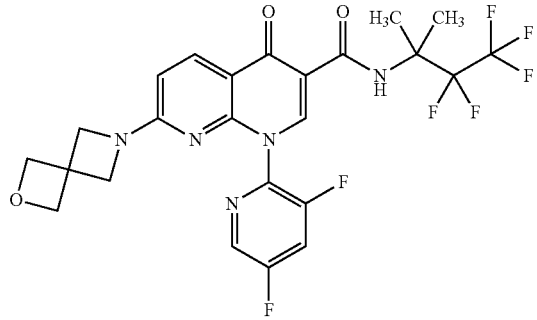 [SMILES: CC(C)(NC(=O)c1cn(-c2ncc(F)cc2F)c2nc(N3CC4(COC4)C3)ccc2c1=O)C(F)(F)C(F)(F)F]

1-(3,5-Difluoropyridin-2-yl)-7-(2-oxa-6-azaspiro[3.3]hept-6-yl)-4-oxo-1,4-dihydro-1,8-naphthyridine-3-carboxylic acid (150 mg, 374 µmol) was initially charged in 2.8 ml of DMF, HATU (171 mg, 449 µmol) and N,N-diisopropylethylamine (290 µl, 1.7 mmol) were added and 3,3,4,4,4-pentafluoro-2-methylbutan-2-amine hydrochloride (95.9 mg, 449 µmol) was added. The reaction was stirred at room temperature for two nights. Ethyl acetate was added and the reaction solution was extracted twice with water. The combined aqueous phases were reextracted twice with ethyl acetate. The combined organic phases were dried over sodium sulfate, filtered and concentrated by evaporation. The residue was purified by silica gel chromatography (mobile phase: dichloromethane/cyclohexane/methanol gradient: 100:50:1 to 100:20:1). This gave 187 mg of the target compound (87% of theory, purity 97%).

LC-MS (Methode 1): $R_t$=1.12 min; MS (ESIpos): m/z=560 [M+H]$^+$ $^1$H-NMR (400 MHz, DMSO-d6) δ [ppm]: −0.149 (0.47), −0.008 (3.55), 0.008 (3.46), 0.146 (0.42), 1.398 (5.78), 1.676 (15.55), 2.323 (0.64), 2.328 (0.91), 2.332 (0.66), 2.366 (0.55), 2.523 (2.42), 2.665 (0.74), 2.670 (1.02), 2.674 (0.72), 2.710 (0.59), 4.112 (0.62), 4.659 (16.00), 6.581 (4.53), 6.603 (4.59), 8.272 (4.78), 8.288 (1.00), 8.294 (5.46), 8.310 (1.34), 8.315 (1.42), 8.332 (0.89), 8.338 (0.96), 8.600 (4.29), 8.607 (4.12), 8.767 (8.03), 10.600 (5.01).

Example 183

7-[3,3-Bis(hydroxymethyl)azetidin-1-yl]-1-(3,5-difluoropyridin-2-yl)-4-oxo-N-[3,3,4,4,4-pentafluorobutan-2-yl]-1,4-dihydro-1,8-naphthyridine-3-carboxamide (enantiomerically pure)

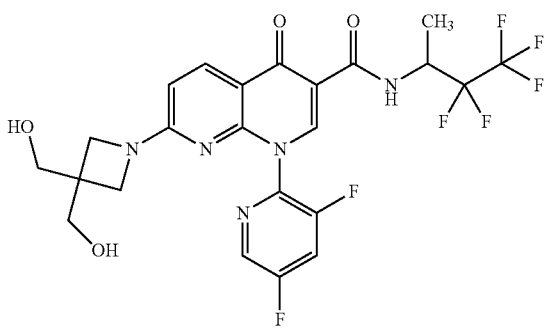 [SMILES: CC(NC(=O)c1cn(-c2ncc(F)cc2F)c2nc(N3CC(CO)(CO)C3)ccc2c1=O)C(F)(F)C(F)(F)F]

1-(3,5-Difluoropyridin-2-yl)-7-(2-oxa-6-azaspiro[3.3]hept-6-yl)-4-oxo-N-[3,3,4,4,4-pentafluorobutan-2-yl]-1,4-dihydro-1,8-naphthyridine-3-carboxamide (enantiomerically pure) (152 mg, purity 98%, 273 µmol) was initially charged in trifluoroacetic acid (1.7 ml, 22 mmol), 1.7 ml of water and 1.7 ml of acetonitrile were added and the mixture was stirred at room temperature for two days. The reaction solution was purified by preparative HPLC (RP18 column, mobile phase: acetonitrile/water gradient with addition of 0.1% TFA). The product fractions were concentrated on a rotary evaporator. The residue was taken up in dichloromethane and washed twice with saturated aqueous sodium bicarbonate solution. The combined aqueous phases were re-extracted with dichloromethane. The combined organic phases were dried over sodium sulfate, filtered and concentrated by evaporation. This gave 86 mg of the target compound (55% of theory, purity 99%).

LC-MS (Methode 2): $R_t$=1.66 min; MS (ESIpos): m/z=564 [M+H]$^+$ $^1$H-NMR (400 MHz, DMSO-d6) δ [ppm]: −0.149 (1.11), −0.008 (8.96), 0.008 (8.69), 0.146 (1.11), 1.146 (0.49), 1.234 (1.29), 1.383 (13.86), 1.400 (13.86), 2.328 (2.54), 2.366 (1.16), 2.670 (2.76), 2.710 (1.20), 3.473 (14.08), 3.803 (2.54), 4.831 (3.57), 5.013 (1.78), 5.033 (1.83), 5.056 (1.60), 6.585 (14.13), 6.607 (14.04), 8.238 (16.00), 8.260 (15.06), 8.286 (2.23), 8.309 (4.06), 8.330 (2.14), 8.594 (11.81), 8.601 (11.59), 8.795 (7.44), 8.803 (8.38), 10.527 (6.11), 10.551 (5.84).

Example 184

7-[3,3-Bis(hydroxymethyl)azetidin-1-yl]-1-(3,5-difluoropyridin-2-yl)-4-oxo-N-(3,3,4,4,4-pentafluoro-2-methylbutan-2-yl)-1,4-dihydro-1,8-naphthyridine-3-carboxamide

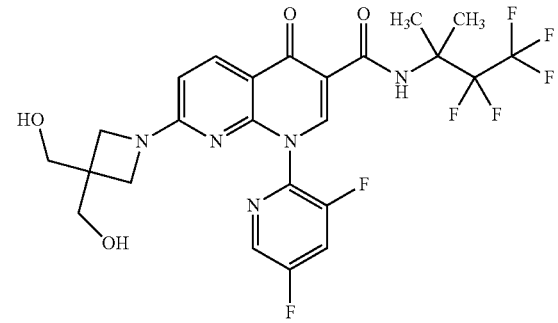 [SMILES: CC(C)(NC(=O)c1cn(-c2ncc(F)cc2F)c2nc(N3CC(CO)(CO)C3)ccc2c1=O)C(F)(F)C(F)(F)F]

1-(3,5-Difluoropyridin-2-yl)-7-(2-oxa-6-azaspiro[3.3]hept-6-yl)-4-oxo-N-(3,3,4,4,4-pentafluoro-2-methylbutan-2-yl)-1,4-dihydro-1,8-naphthyridine-3-carboxamide (181 mg, 324 µmol) was initially charged in 2 ml of trifluoroacetic acid, 2 ml of water and 2 ml of acetonitrile were added and the mixture was stirred at room temperature for two days. The reaction solution was purified by preparative HPLC (RP18 column, mobile phase: acetonitrile/water gradient with addition of 0.1% TFA). The product fractions were concentrated on a rotary evaporator. The residue was taken up in dichloromethane and washed twice with saturated aqueous sodium bicarbonate solution. The combined aqueous phases were re-extracted with dichloromethane. The combined organic phases were dried over sodium sulfate, filtered and concentrated by rotary evaporation. This gave 133 mg of the target compound (70% of theory, purity 99%).

LC-MS (Methode 2): $R_t$=1.79 min; MS (ESIpos): m/z=578 [M+H]$^+$ $^1$H-NMR (400 MHz, DMSO-d6) δ [ppm]: −0.149 (0.64), −0.008 (5.13), 0.008 (4.91), 0.146 (0.62), 1.678 (16.00), 2.328 (1.15), 2.366 (0.44), 2.670 (1.10), 2.710 (0.44), 3.471 (4.27), 3.801 (0.80), 4.839 (1.11), 5.754 (2.74), 6.574 (4.42), 6.597 (4.42), 8.246 (5.02), 8.267 (4.71), 8.281 (0.99), 8.287 (1.08), 8.308 (1.53), 8.325 (0.95), 8.331 (1.06), 8.592 (4.93), 8.598 (4.75), 8.750 (10.54), 10.635 (5.19).

Example 185

7-[4,4-Bis(hydroxymethyl)piperidin-1-yl]-1-(3,5-difluoropyridin-2-yl)-4-oxo-N-[3,3,4,4,4-pentafluorobutan-2-yl]-1,4-dihydro-1,8-naphthyridine-3-carboxamide (enantiomerically pure)

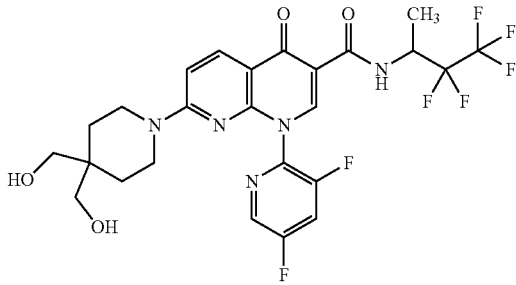 [SMILES: CC(NC(=O)c1cn(-c2ncc(F)cc2F)c2nc(N3CCC(CO)(CO)CC3)ccc2c1=O)C(F)(F)C(F)(F)F]

7-Chloro-1-(3,5-difluoropyridin-2-yl)-4-oxo-N-[3,3,4,4,4-pentafluorobutan-2-yl]-1,4-dihydro-1,8-naphthyridine-3-carboxamide (enantiomerically pure) (50.0 mg, 104 µmol) was dissolved in 1.1 ml of DMF, piperidin-4,4-diyldimethanol hydrochloride (21.8 mg, purity 95%, 114 µmol) and N,N-diisopropylethylamine (81 µl, 470 µmol) were added and the mixture was stirred at 55° C. for 18 h. The reaction mixture was cooled and purified by preparative HPLC (column: acetonitrile/water/0.1% formic acid). This gave 50.0 mg (81% of theory, purity 99%) of the title compound.

LC-MS (Methode 3): $R_t$=1.75 min; MS (ESIpos): m/z=592 [M+H]$^+$ $^1$H-NMR (400 MHz, DMSO-d6) δ [ppm]: −0.008 (1.25), 0.008 (1.21), 1.345 (6.70), 1.386 (7.98), 1.403 (7.69), 2.328 (0.52), 2.666 (0.43), 2.671 (0.61), 3.280 (15.22), 3.293 (16.00), 3.483 (4.39), 4.405 (4.66), 4.418 (10.58), 4.432 (4.62), 4.972 (0.45), 4.992 (0.83), 5.015 (0.96), 5.037 (0.96), 5.060 (0.85), 5.081 (0.45), 7.074 (5.67), 7.097 (5.78), 8.236 (7.58), 8.259 (7.08), 8.315 (1.21), 8.337 (2.22), 8.359 (1.23), 8.612 (5.44), 8.617 (5.26), 8.804 (3.86), 8.813 (4.35), 10.525 (2.98), 10.549 (2.89).

Example 186

7-[4,4-Bis(hydroxymethyl)piperidin-1-yl]-1-(3,5-difluoropyridin-2-yl)-N-(1,1,1,3,3,3-hexafluoropropan-2-yl)-4-oxo-1,4-dihydro-1,8-naphthyridine-3-carboxamide

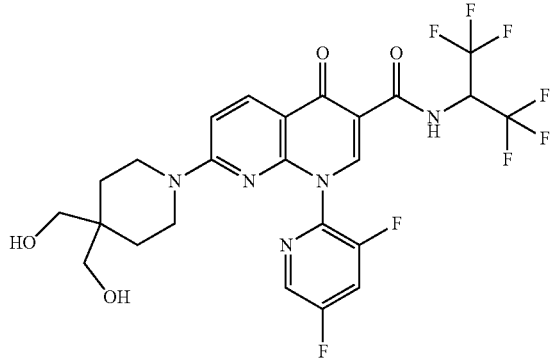 [SMILES: O=C(NC(C(F)(F)F)C(F)(F)F)c1cn(-c2ncc(F)cc2F)c2nc(N3CCC(CO)(CO)CC3)ccc2c1=O]

7-Chloro-1-(3,5-difluoropyridin-2-yl)-N-(1,1,1,3,3,3-hexafluoropropan-2-yl)-4-oxo-1,4-dihydro-1,8-naphthyridine-3-carboxamide (50.0 mg, 103 µmol) was dissolved in 1.0 ml of DMF, piperidin-4,4-diyldimethanol hydrochloride (21.6 mg, purity 95%, 113 µmol) and N,N-diisopropylethylamine (81 µl, 460 µmol) were added and the mixture was stirred at 55° C. for 80 h. The reaction mixture was cooled and purified by preparative HPLC (column: acetonitrile/water/0.1% formic acid). This gave 43.1 mg (70% of theory, purity 99%) of the title compound.

LC-MS (Methode 3): $R_t$=1.84 min; MS (ESIpos): m/z=596 [M+H]$^+$ $^1$H-NMR (400 MHz, DMSO-d6) δ [ppm]: −0.008 (0.57), 0.008 (0.57), 1.352 (0.65), 3.282 (1.64), 3.295 (1.74), 3.312 (16.00), 3.492 (0.44), 4.409 (0.50), 4.422 (1.13), 4.436 (0.49), 7.102 (0.61), 7.126 (0.62), 8.260 (0.81), 8.283 (0.76), 8.626 (0.89), 8.632 (0.84), 8.903 (1.73), 11.374 (0.48), 11.399 (0.45).

Example 187

7-[4,4-Bis(hydroxymethyl)piperidin-1-yl]-difluoropyridin-2-yl)-4-oxo-N-(3,3,4,4,4-pentafluoro-2-methylbutan-2-yl)-1,4-dihydro-1,8-naphthyridine-3-carboxamide

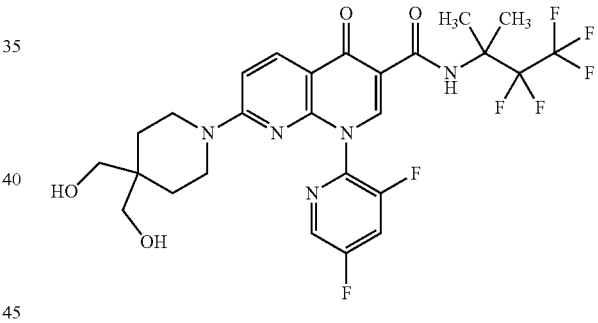

7-Chloro-1-(3,5-difluoropyridin-2-yl)-4-oxo-N-(3,3,4,4,4-pentafluoro-2-methylbutan-2-yl)-1,4-dihydro-1,8-naphthyridine-3-carboxamide (50.0 mg, 101 µmol) was dissolved in 1.1 ml of DMF, piperidin-4,4-diyldimethanol hydrochloride (21.2 mg, purity 95%, 111 µmol) and N,N-diisopropylethylamine (79 µl, 450 µmol) were added and the mixture was stirred at 55° C. for 18 h. The reaction mixture was cooled and purified by preparative HPLC (column: acetonitrile/water/0.1% formic acid). This gave 49.1 mg (80% of theory, purity 99%) of the title compound.

LC-MS (Methode 3): $R_t$=1.85 min; MS (ESIpos): m/z=606 [M+H]$^+$ $^1$H-NMR (400 MHz, DMSO-d6) δ [ppm]: 1.344 (0.75), 1.681 (2.97), 3.279 (1.60), 3.292 (1.71), 3.312 (16.00), 3.481 (0.49), 4.405 (0.45), 4.418 (0.99), 4.432 (0.45), 7.064 (0.61), 7.086 (0.63), 8.244 (0.82), 8.266 (0.77), 8.609 (0.90), 8.615 (0.87), 8.760 (1.82), 10.629 (1.02).

Example 188

1-(3,5-Difluoropyridin-2-yl)-7-[(2R)-2-(hydroxymethyl)pyrrolidin-1-yl]-4-oxo-N-(3,3,4,4,4-pentafluoro-2-methylbutan-2-yl)-1,4-dihydro-1,8-naphthyridine-3-carboxamide

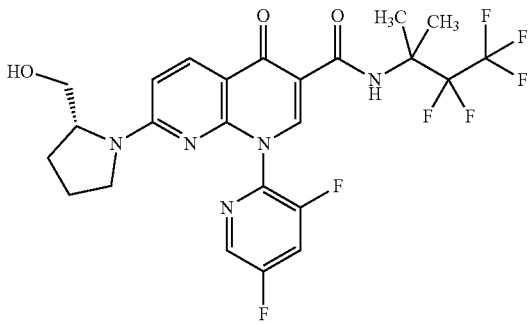 [SMILES: CC(C)(NC(=O)c1cn(-c2ncc(F)cc2F)c2nc(N3CCC[C@@H]3CO)ccc2c1=O)C(F)(F)C(F)(F)F]

7-Chloro-1-(3,5-difluoropyridin-2-yl)-4-oxo-N-(3,3,4,4,4-pentafluoro-2-methylbutan-2-yl)-1,4-dihydro-1,8-naphthyridine-3-carboxamide (50.0 mg, 101 µmol) was dissolved in 1.1 ml of DMF, (2R)-pyrrolidin-2-ylmethanol (11 µl, purity 99%, 110 µmol) and N,N-diisopropylethylamine (61 µl, 350 µmol) were added and the mixture was stirred at 55° C. for 18 h. The reaction mixture was cooled and purified by preparative HPLC (column: acetonitrile/water/0.1% formic acid). This gave 49.9 mg (88% of theory, purity 99%) of the title compound.

LC-MS (Methode 3): $R_t$=2.07 min; MS (ESIpos): m/z=562 [M+H]$^+$ $^1$H-NMR (400 MHz, DMSO-d6) δ [ppm]: 1.683 (16.00), 1.873 (0.93), 1.953 (1.11), 2.328 (0.49), 2.670 (0.50), 6.731 (0.53), 6.754 (0.59), 8.264 (1.43), 8.287 (1.55), 8.590 (4.26), 8.596 (4.12), 8.767 (2.37), 10.649 (2.98).

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

| Abbreviations and acronyms: | |
|---|---|
| $B_{Max}$ | number of specific binding sites of the radioligand |
| CAFTY | calcium free tyrode |
| CHO | chinese hamster ovary |
| CRE | cAMP-responsive element |
| DMEM | Dulbecco's modified eagle medium |
| DMSO | dimethyl sulfoxide |
| FCS | fetal calf serum |
| FRET | fluorescence resonance energy transfer |
| GIRK1/4 | G-protein-coupled inward rectifier potassium channel, member 1/4 |
| HEPES | hydroxyethylpiperazine-ethanesulfonic acid |
| HTRF | homogeneous time resolved fluorescence |
| $K_d$ | equilibrium dissociation constant |
| $K_i$ | equilibrium inhibitor constant |
| $k_{off}$ | rate of dissociation |
| $k_{on}$ | rate of association |
| nM | nanomolar |
| MEM | minimum essential medium |

| Abbreviations and acronyms: | |
|---|---|
| µl | microliters |
| µM | micromolar |
| ml | milliliters |
| mM | millimolar |
| mtClytin | mitochondrial clytin |
| min | minutes |
| NMS | N-Me-scopolamine |
| PAM | positive allosteric modulator |
| PEI | polyethylenimine |
| Pen/Strep | penicillin/streptomycin |
| s | seconds |

B-1. Functional M2-GIRK1/4 Activation Test

Both the activation of the M2 receptor by orthosteric agonists alone and the allosteric boosting of orthosterically induced activation by positive allosteric modulators (PAMs) can be determined by means of a cell-based functional GIRK1/4 activity test. The binding of orthosteric agonists (endogenous ligand: acetylcholine) to the M2 receptor leads to receptor activation or a change in conformation of the receptor in the manner of a shift in equilibrium in favor of the active receptor conformation. The binding of the orthosteric agonists to the M2 receptor and hence the activation thereof can be boosted by positive allosteric modulators which bind not to the orthosteric binding site of the agonists but to a separate allosteric binding site.

The agonist-induced change in conformation of the M2 receptor results in a Gαi protein activation. The activation of the Gα subunit leads in turn to dissociation and hence release of the Gβγ subunits from the Gα subunit and the activation of separate downstream signal transduction cascades. The heterodimeric Gβγ complex released binds to the GIRK1/4 potassium channel and induces a ligand-controlled channel activation or opening (Reuveny et al., Nature, July 1994, 370, 143-146). Under physiological conditions, the result is then a selective efflux of potassium from the cell along the electrochemical gradient. The export of positive charge leads to lowering of the transmembrane potential and hence to hyperpolarization of the cell. The extent of hyperpolarization can therefore be regarded as a measure of the activation of the M2 receptor.

The test cell used is a recombinant CHO-DUKX cell line which has been stably transfected with cDNA coding for the human M2 receptor and with cDNA coding for both GIRK1/4 subunits (CHO-DUKX-M2-GIRK). The transmembrane potential, or the relative changes in the transmembrane potential as a function of substance addition or M2 activation, is determined by means of a voltage-sensitive dye (FLIPR Membrane Potential Assay Kit Blue, Molecular Devices #R8034) and the measurement of cell fluorescence using a proprietary fluorescence imaging instrument.

B-1.1. Determination of the Allosteric Potency of the Test Substances ($EC_{50}$ Value)

The test substances are dissolved in dimethyl sulfoxide (DMSO) at a concentration of 10 mM and serially diluted with DMSO in steps of 1:3.16 for a 10-point dose/activity analysis. In accordance with the desired test concentrations, the substances are pre-diluted in loading buffer (composition: 0.6 ml of FLIPR Membrane Potential Assay Kit Blue (10 mg/ml), 0.6 ml of Brilliant Black (10 mg/ml), 2 mM $CaCl_2$ and 2 mM KCl ad 50 ml. sodium gluconate Tyrode (PAA, #T21-155)).

The reporter cells cultivated in MEM alpha medium (supplemented with 10% FCS, 2% Glutamax, 1 mg/ml genticin) were sown with 2000 cells (measurement after 48 h) or 4000 cells (measurement after 24 h) in 30 µl per 384-well in µCLEAR/black Greiner cell culture plates (#781092) and incubated at 37° C. for 24 h or 48 h. The sowing medium consisted of MEM alpha medium (supplemented with 5% FCS, 2% Glutamax, no genticin).

For the particular measurement, the medium was removed and the cells were laden with the voltage-sensitive dye for at least 6 min at room temperature (30 µl of loading buffer per 384-well). This was followed, in a first measurement, by the determination of the fluorescence for the resting transmembrane potential for a period of 5 sec. Thereafter, 10 µl in each case of the test substances diluted in loading buffer were added, followed by a second measurement to determine the transmembrane potential for a period of 50 sec. Finally, the cells were admixed with 10 µl of agonist solution (acetylcholine dissolved in loading buffer). Acetylcholine was used at the concentration corresponding to the $EC_{20}$, which had been determined in a preliminary test. The M2-mediated GIRK1/4 activation or hyperpolarization was then monitored in a third measurement over a period of 60 sec. The $EC_{50}$ value (degree of allosteric potency of test compound) and the efficiency (measure of the boosting of the acetylcholine effect at an $EC_{20}$ acetylcholine concentration) were determined with the aid of a 4-parameter logistic function (Hill function).

B-1.2. Determination of Positive Cooperativity (α Factor)

The test substances were dissolved in DMSO at a concentration of 10 mM and serially diluted with DMSO in steps of 1:3.16 for a 10-point dose/activity analysis. In accordance with the desired test concentrations, the substances were pre-diluted in loading buffer (see above).

The reporter cells cultivated in MEM alpha medium (supplemented with 10% FCS, 2% Glutamax, 1 mg/ml genticin) are sown with 2000 cells (measurement after 48 h) or 4000 cells (measurement after 24 h) in 30 µl per 384-well in µCLEAR/black Greiner cell culture plates (#781092) and incubated at 37° C. for 24 h or 48 h. The sowing medium consisted of MEM alpha medium (supplemented with 5% FCS, 2% Glutamax, no genticin).

For the particular measurement, the medium was removed and the cells were laden with the voltage-sensitive dye for at least 6 min at room temperature (30 µl of loading buffer per 384-well). This was followed, in a first measurement, by the determination of the resting transmembrane potential for a period of 5 sec in 1 sec increments. Thereafter, 10 µl in each case of the test substances diluted in loading buffer are added, followed by a second measurement to determine the transmembrane potential for a period of 50 sec in 1 sec increments.

Finally, the cells are admixed with 10 µl of agonist solution (acetylcholine dissolved in loading buffer). In contrast to the $EC_{50}$ determination of the test substances (see B-1.1), however, this is not done using one acetylcholine concentration; instead, every concentration of the test substance is combined with an acetylcholine 8-point dose-response curve. For the acetylcholine dilution series, the agonist is serially prediluted in loading buffer in accordance with the desired end concentrations, starting with a maximum end concentration of 3 µM in steps of 1:3.16. The M2-mediated GIRK1/4 activation or hyperpolarization is then monitored in a third measurement over a period of 60 sec in 1 sec increments. The shift in the acetylcholine dose-response curve in the presence of increasing concentrations of the test substance is analyzed and quantified by means of GraphPad PRISM (Allosteric $EC_{50}$ shift). The cc factor determined is a measure of the strength and direction of the allosteric effect. α-values>1 reflect a lowering of the $EC_{50}$ value or an increase in the potency of the agonist (acetylcholine) in the presence of allosterics and mean positive cooperativity between orthosterics (acetylcholine) and allosterics (test substance). Positive cooperativity is the hallmark of a positive allosteric modulator. Conversely, α values<1 are indicative of negative cooperativity between orthosterics and allosterics, and hence characterize negative allosteric modulators. α values=1 mean no cooperativity between orthosteric and allosteric, meaning that the binding affinities of orthosteric and allosteric to the receptor do not affect one another. The greater the magnitude of the cc value, the greater the extent of cooperativity between orthosteric and allosteric.

Table 2 below lists, for individual working examples, the $EC_{50}$ and efficiency values thus determined and the α values from this assay (in some cases as mean values from two or more independent individual determinations):

TABLE 2

| Ex. No. | Receptor activity $EC_{50}$ [µmol/l] | Efficiency [%] | Cooperativity (alpha factor) |
|---|---|---|---|
| 1 | 0.073 | 97.71 | 46 |
| 2 | 0.092 | 97.50 | 35 |
| 3 | 0.240 | 97.75 | |
| 4 | 0.014 | 98.25 | 63 |
| 5 | 0.031 | 98.25 | 63 |
| 6 | 0.014 | 95.00 | |
| 7 | 0.022 | 100.00 | |
| 8 | 0.083 | 100.00 | |
| 9 | 0.020 | 94.50 | |
| 10 | 0.025 | 95.50 | |
| 11 | 0.037 | 99.50 | |
| 12 | 0.055 | 100.00 | |
| 13 | 0.130 | 99.50 | |
| 14 | 0.087 | 98.50 | 50 |
| 15 | 0.043 | 96.17 | 63 |
| 16 | 0.048 | 99.00 | 40 |
| 17 | 0.111 | 88.00 | 24 |
| 18 | 0.067 | 87.00 | 34 |
| 19 | 0.086 | 91.50 | 38 |
| 20 | 0.330 | 87.00 | |
| 21 | 0.195 | 98.50 | |
| 22 | 0.575 | 85.00 | |
| 23 | 0.145 | 92.00 | |
| 24 | 0.560 | 87.00 | |
| 25 | 0.210 | 98.00 | |
| 26 | 0.200 | 94.50 | |
| 27 | 0.036 | 79.00 | 10 |
| 28 | 0.019 | 100.00 | 17 |
| 29 | 0.059 | 98.00 | |
| 30 | 0.064 | 99.00 | 14 |
| 31 | 0.645 | 88.50 | |
| 32 | 0.400 | 89.50 | |
| 33 | 0.505 | 83.00 | |
| 34 | 0.880 | 82.00 | |
| 35 | 0.170 | 99.50 | |
| 36 | 0.022 | 100.00 | |
| 37 | 0.021 | 99.00 | |
| 38 | 0.018 | 98.00 | |
| 39 | 0.051 | 99.00 | |
| 40 | 0.160 | 100.00 | |
| 41 | 0.330 | 100.00 | |
| 42 | 0.295 | 100.00 | |
| 43 | 0.065 | 100.00 | |
| 44 | 0.031 | 98.50 | |
| 45 | 0.057 | 96.00 | |
| 46 | 0.385 | 97.00 | |
| 47 | 0.640 | 89.00 | |
| 48 | 0.074 | 92.50 | |
| 49 | 0.560 | 97.00 | |
| 50 | 0.730 | 92.00 | |
| 51 | 0.527 | 84.33 | |

TABLE 2-continued

| Ex. No. | Receptor activity EC$_{50}$ [μmol/l] | Efficiency [%] | Cooperativity (alpha factor) |
|---|---|---|---|
| 52 | 0.048 | 90.50 | |
| 53 | 0.555 | 96.50 | |
| 54 | 0.350 | 94.67 | |
| 55 | 0.110 | 100.00 | 79 |
| 56 | 0.034 | 100.00 | 68 |
| 57 | 0.010 | 94.00 | |
| 58 | 0.011 | 96.00 | |
| 59 | 0.023 | 99.00 | |
| 60 | 0.275 | 100.00 | |
| 61 | 0.795 | 100.00 | |
| 62 | 0.220 | 100.00 | |
| 63 | 0.170 | 100.00 | |
| 64 | 0.154 | 91.33 | 32 |
| 65 | 0.087 | 100.00 | |
| 66 | 0.310 | 92.50 | |
| 67 | 0.053 | 97.00 | 36 |
| 68 | 0.195 | 96.00 | |
| 69 | 0.365 | 92.00 | |
| 70 | 0.220 | 91.00 | |
| 71 | 0.360 | 97.50 | |
| 72 | 0.045 | 90.00 | |
| 73 | 0.010 | 100.00 | 68 |
| 74 | 0.014 | 100.00 | |
| 75 | 0.019 | 100.00 | |
| 76 | 0.035 | 94.00 | |
| 77 | 0.260 | 100.00 | |
| 78 | 0.044 | 91.50 | |
| 79 | 0.054 | 100.00 | |
| 80 | 0.120 | 100.00 | |
| 81 | 0.015 | 100.00 | |
| 82 | 0.028 | 100.00 | |
| 83 | 0.017 | 100.00 | |
| 84 | 0.020 | 100.00 | 57 |
| 85 | 0.085 | 99.00 | |
| 86 | 0.019 | 100.00 | |
| 87 | 0.063 | 100.00 | |
| 88 | 0.059 | 99.50 | |
| 89 | 0.275 | 98.00 | |
| 90 | 0.024 | 100.00 | 41 |
| 91 | 0.280 | 99.00 | |
| 92 | 0.017 | 100.00 | |
| 93 | 0.014 | 98.00 | 41 |
| 94 | 0.032 | 100.00 | |
| 95 | 0.026 | 100.00 | |
| 96 | 0.068 | 100.00 | |
| 97 | 0.038 | 96.50 | 53 |
| 98 | 0.023 | 100.00 | 56 |
| 99 | 0.038 | 100.00 | |
| 100 | 0.026 | 100.00 | |
| 101 | 0.585 | 78.50 | |
| 102 | 1.065 | 89.00 | |
| 103 | 0.305 | 100.00 | |
| 104 | 0.250 | 98.50 | |
| 105 | 0.098 | 100.00 | |
| 106 | 0.165 | 91.50 | |
| 107 | 0.097 | 98.00 | |
| 108 | 0.185 | 84.00 | |
| 109 | 0.135 | 96.00 | |
| 110 | 0.190 | 94.50 | |
| 111 | 0.100 | 99.00 | |
| 112 | 0.525 | 98.00 | |
| 113 | 0.145 | 97.00 | |
| 114 | 0.111 | 96.50 | |
| 115 | 0.150 | 89.00 | |
| 116 | 0.335 | 96.00 | |
| 117 | 0.400 | 94.50 | |
| 118 | 0.500 | 100.00 | |
| 119 | 0.790 | 92.00 | |
| 120 | 0.400 | 100.00 | |
| 121 | 0.320 | 99.00 | |
| 122 | 0.220 | 92.00 | |
| 123 | 0.240 | 98.00 | |
| 124 | 0.130 | 97.00 | |
| 125 | 0.073 | 97.00 | |
| 126 | 0.087 | 98.00 | |
| 127 | 0.050 | 96.00 | |
| 128 | 0.520 | 89.00 | |
| 129 | 0.021 | 96.50 | |
| 130 | 0.053 | 93.00 | |
| 131 | 0.108 | 95.50 | |
| 132 | 0.325 | 98.00 | |
| 133 | 0.315 | 92.00 | |
| 134 | 0.105 | 100.00 | |
| 135 | 0.097 | 100.00 | |
| 136 | 0.064 | 97.50 | |
| 137 | 0.110 | 99.00 | |
| 138 | 0.070 | 98.50 | 61 |
| 139 | 0.230 | 100.00 | |
| 140 | 0.253 | 92.00 | 47 |
| 141 | 0.018 | 95.00 | |
| 142 | 0.047 | 94.50 | |
| 143 | 0.090 | 90.00 | |
| 144 | 0.150 | 92.00 | |
| 145 | 0.435 | 98.50 | |
| 146 | 0.910 | 96.00 | |
| 147 | 0.055 | 98.50 | |
| 148 | 0.066 | 100.00 | |
| 149 | 0.032 | 100.00 | |
| 150 | 0.375 | 88.00 | |
| 151 | 0.290 | 99.00 | |
| 152 | 0.103 | 99.50 | |
| 153 | 0.200 | 100.00 | |
| 154 | 0.089 | 100.00 | |
| 155 | 0.360 | 100.00 | |
| 156 | 0.036 | 100.00 | |
| 157 | 0.050 | 100.00 | |
| 158 | 0.115 | 90.50 | |
| 159 | 0.094 | 100.00 | |
| 160 | 0.155 | 90.50 | |
| 161 | 0.070 | 100.00 | |
| 162 | 0.024 | 96.00 | |
| 163 | 0.120 | 100.00 | |
| 164 | 0.014 | 100.00 | |
| 165 | 0.013 | 84.00 | 30 |
| 166 | 0.030 | 81.00 | |
| 167 | 0.420 | 92.00 | |
| 168 | 2.850 | 84.50 | |
| 169 | 0.120 | 97.50 | |
| 170 | 2.250 | 86.00 | |
| 171 | 3.100 | 90.50 | |
| 172 | 1.600 | 98.00 | |
| 173 | 0.088 | 100.00 | |
| 174 | 0.083 | 100.00 | |
| 175 | 0.060 | 98.50 | |
| 176 | 0.028 | 100.00 | |
| 177 | 0.038 | 100.00 | |
| 178 | 0.056 | 100.00 | |
| 179 | 0.095 | 100.00 | |
| 180 | 0.089 | 100.00 | |
| 181 | 0.220 | 100.00 | |
| 182 | 0.410 | 100.00 | |
| 183 | 0.053 | 100.00 | |
| 184 | 0.130 | 100.00 | |
| 185 | 0.121 | 100.00 | |
| 186 | 0.110 | 100.00 | |
| 187 | 0.265 | 97.50 | |
| 188 | 0.118 | 100.00 | |

B-2. Functional Ca2+ Release Test by M2-Gα16 Reporter Cells

Any potentially agonistic or else potentially allosteric effect of the test substances on the M2 receptor can be determined by a functional $Ca^{2+}$ release test. The activation of the M2 receptor by binding of orthosteric agonists (acetylcholine) or other substances having an agonistic effect leads to a change in conformation of the receptor, which, in the endogenous state, results in Gαi protein activation. However, coupling of the M2 receptor to the exogenously expressed promiscuous Gαq protein Gα16 results in Gα16 protein activation after activation of the M2 receptor, which causes—via a downstream signal transduction cascade—intracellular $Ca^{2+}$ release. The extent of intracellular $Ca^{2+}$ mobilization can therefore be regarded as a measure of the activation of the M2 receptor.

The test cell used is a recombinant CHO cell line which has been stably transfected with cDNA coding for the human M2 receptor and the Gα16 protein and with cDNA coding for the mitochondrially expressed photoprotein clytin (mt-Clytin) (CHO mtClytin Gα16 M2). The determination of the intracellular $Ca^{2+}$ release as a function of substance addition or M2 activation is effected by a $Ca^{2+}$-sensitive dye (Fluo-8) and the measurement of cell fluorescence using an FLIP-R$^{TETRA}$ instrument (Molecular Devices).

B-2.1. Agonism Assay

The test substances are dissolved in DMSO at a concentration of 10 mM and serially diluted with DMSO in steps of 1:3.16 for a 10-point dose/activity analysis. In accordance with the desired test concentrations, the substances are prediluted in Fluo-8 buffer (composition per 100 ml: 500 µl probenecid, 2 ml Brilliant Black (20 mg/ml), 440 µl Fluo-8, 2 mM $CaCl_2$ ad 100 ml CAFTY Tyrode (130 mM NaCl, 5 mM KCl, 20 mM HEPES, 1 mM $MgCl_2$, 5 mM $NaHCO_3$, pH 7.4)).

The reporter cells cultivated in MEM alpha medium (supplemented with 10% FCS, 2% Glutamax) were sown with 3000 cells in 30 µl of sowing medium per 384-well in µCLEAR/black Greiner cell culture plates (#781092) and incubated at 37° C. for 24 h. The sowing medium consists of MEM alpha medium (supplemented with 5% FCS, 2% Glutamax). For the respective measurement, the medium is removed and the cells, after addition of 20 µl in each case of Fluo-8 buffer per 384-well, were incubated in an incubator at 37° C. for 1 h. After addition of 10 µl in each case per 384-well of the prediluted test substances, cell fluorescence was measured for a period of 5 min in 1 sec increments. The relative degree of maximum activation of the M2 receptor by the respective test substances is calculated by normalizing the test signal to the signal corresponding to the $E_{Max}$ concentration of acetylcholine (3 µM).

B-2.2. Determination of the Positive Allosteric Modulator Effect

In order to be able to determine the positive cooperativity of the test substances in relation to the acetylcholine-mediated M2 receptor activation, reference agonist (acetylcholine) is then added for a full dose-response analysis. For this purpose, acetylcholine is serially diluted in Fluo-8 buffer in steps of 1:3.16 beginning with a maximum final concentration of 1 µM. After addition of 10 µl in each case of agonist solution per 384-well, cell fluorescence is again measured for a period of 5 min in 1 sec increments. The same assay plate is used as immediately before for the M2 agonism assay. The shift in the acetylcholine dose-response curve in the presence of increasing concentrations of the test substance is analyzed and quantified by means of GraphPad PRISM (Allosteric $EC_{50}$ shift) (see above).

B-3. Selectivity Test with Respect to Human Muscarinic Acetylcholine Receptors

Any potentially agonistic effect, or else positive allosteric effect, of the test substances on other human muscarinic acetylcholine receptors can be determined in a functional $Ca^{2+}$ release test (Eurofins; GPCRProfiler® Services in agonistic and allosteric mode for Mx Receptors; cat#: HTS600GPCR).

The test cells used were the Chem-1 or Chem-4 cell lines transfected with the particular receptor (ChemiScreen™ M1 Calcium-Optimized FLIPR Cell Lines, Eurofins; M1: HTS044C; ChemiScreen™ Calcium-Optimized Stable Cell Line Human Recombinant M2 Muscarininc Acetylcholine Receptor, Eurofins; M2: HTS115C; ChemiScreen™ Human Recombinant M3 Muscarinic Acetylcholine Receptor Calcium-Optimized Stable Cell Line, Eurofins; M3: HTS116C; ChemiScreen™ Human Recombinant M4 Muscarinic Acetylcholine Receptor Calcium-Optimized Stable Cell Line, Eurofins; M4: HTS117C; ChemiScreen™ M5 Calcium-Optimized FLIPR Cell Lines, Eurofins; M5: HTS075C). The substance test is conducted with a FLIPR$^{TETRA}$ instrument (Molecular Devices).

B-3.1. Agonism Assay

In order to determine any potential agonistic effect of the test substances, the respective test substances were added with a final test concentration of 10 µM or 1 µM. $Ca^{2+}$ release or cell fluorescence is measured over a period of 180 sec. The positive control used for normalization of the substance effect to the receptor activation is a concentration of acetylcholine corresponding to the $E_{Max}$ value.

After the agonism assay has ended, the assay plate is incubated at 25° C. for 7 min. After the incubation period, the positive allosteric modulator assay is initialized.

B-3.2. Allosteric Modulator Assay

In order to examine any positive or negative allosteric effect of the test substances on other human muscarinic acetylcholine receptors and the M2 receptor itself, every substance concentration is combined with an acetylcholine 8-point dose-response curve. Addition of agonist solution is again followed in turn by the measurement of cell fluorescence for a period of 180 sec. The shift in the acetylcholine dose-response curve (maximum shift in the $EC_{50}$ of acetylcholine) is analyzed and quantified by means of GraphPad PRISM (Sigmoidal dose-response (variable slope)—$EC_{50}$). Finally, quotients of the allosteric shift for the M2 receptor and M4 receptor are formed, which function in turn as a measure of the respective selectivity.

B-4. In Vitro M2 PAM Gi Assay

For the characterization of the test substances on positive allosteric modulation of the human M2 receptor, the carbachol-induced inhibition of the rise in cAMP due to forskolin in recombinant M2 receptor-expressing CHO cells is measured, these additionally expressing a luciferase gene under the control of a cAMP-responsive element (CRE): 3000 cells in 25 µl of full medium (DMEM F12 PAN medium, 10% FCS, 1.35 mM Na pyruvate, 20 mM Hepes, 4 mM Glutamax, 2% sodium bicarbonate, 1% Pen/Strep, 1% 100× non-essential amino acids) are sown per well of a 384 multititre plate (Greiner, TC Platte, black with clear base) and incubated at 37° C., 5% $CO_2$ for 24 hours. Before the measurement, the medium is replaced by 30 µl of test medium (Optimem) and incubated at 37° C., 5% $CO_2$ for 10 minutes. The test substance is prepared in DMSO in various concentrations (starting concentration 10 mM, dilution factor 3.16) as a dose-response curve and pre-diluted 1:50 with calcium-free Tyrode, 2 mM $CaCl_2$, 0.01% BSA. 10 µl of the prediluted substance solution are added to the cells and incubated at 37° C., 5% $CO_2$ for 10 minutes. The M2 receptor is activated by adding 10 µl of carbachol in various concentrations in calcium-free Tyrode, 2 mM $CaCl_2$ and incubated at 37° C., 5% $CO_2$ for 5 minutes. Adenylyl cyclase is activated by adding 10 µl of 1 µM (final concentration) forskolin in calcium-free Tyrode, 2 mM $CaCl_2$ and incubated at 37° C., 5% $CO_2$ for 5 hours. After removing the cell supernatant and adding 20 µl of Luci/Triton buffer (1:1), luminescence is determined in a luminometer for 60 seconds.

Calcium-free Tyrode: 130 mM NaCl, 5 mM KCl, 20 mM HEPES, 1 mM $MgCl_2$, 4.8 mM $NaHCO_3$, pH 7.4

Luci/Triton buffer (1:1): Luci buffer (20 mM tricine, pH 7.8, 2.67 mM magnesium sulfate, 0.1 mM EDTA, 4 mM DTT, 270 µM coenzyme A, 470 µM D-luciferin, 530 µM ATP) mixed 1:1 with triton buffer (25 mM Tris aqueous hydrochloric acid, pH 7.8, 25 mM $Na_2HPO_4$, 2 mM dithiothreitol, 3% Triton X-100, 10% glycerin).

The $EC_{50}$ value was determined with the aid of a 4-parameter logistic function (Hill function).

B-5. Competitive FRET Binding Test for Human M2 and M4 Receptors

The direct binding of the test substances to the M2 receptor and the boosting of the binding (increasing affinity) of the natural agonist acetylcholine to the M2 receptor in the presence of the test substances (positive allosteric effect) is determined by a FRET-based binding assay (HTRF Tag-lite® binding assay, Cisbio). For control of selectivity, the binding of the test substances to the structurally related M4 receptor is examined analogously. The HTRF Tag-lite® assay is a homogeneous binding assay and is based on the competitive binding of a fluorescent ligand (probe) and the unlabeled test substance to the receptor, which is expressed in living cells. The receptor in turn is derivatized with a fluorescent donor dye (terbium cryptate), such that excitation of the donor dye gives rise to a FRET signal between the receptor and probe (acceptor) when the probe is bound to the receptor. The acceptor probe used was a telenzepine derivative conjugated with an HTRF fluorescent dye (red ligand; L0040RED). The probe therefore binds in the conserved orthosteric binding site both of the M2 and of the M4 receptor. The allosteric binding site of the M2 receptor has been characterized by x-ray crystallography and is postulated as being directly above the orthosteric binding pocket (Kruse et al., Nature, 2013, 504, 101-106). Both the binding of unlabeled orthosteric agonists (acetylcholine) to the orthosteric binding site and the binding of allosteric modulators (test substances) to the allosteric binding site therefore leads to a concentration-dependent competitive displacement of the probe and hence to a decrease in the FRET-based fluorescence signal.

All binding tests are conducted on white 384 microtitre plates (small volume) in a total volume of 20 µl. The HTRF measurements are undertaken with a PHERAstar instrument (BMG Labtech). For the muscarinic M2 or M4 receptor binding test, SNAPed-M2-expressing cells (C1TT1M2) or SNAPed-M4-expressing cells (C1TT1M4) are used, which have been labeled with a donor fluorophore (Lumi4Tb; CELLCUST). The cells are incubated with the acceptor probe in Tag-lite binding buffer (LABMED) in the presence of test substance or acetylcholine. Subsequently, the fluorescence signal is measured at wavelengths of 665 nm and 620 nm and the HTRF quotient (signal at 665 nm/signal at 620 nm) is determined. The relative specific signal is determined by subtracting the HTRF quotient of negative control (Tag-lite buffer only without probe).

B-5.1. Binding of the Test Substances

In order to determine the binding of the test substances to the M2 or M4 receptor in the absence of orthosteric agonist, a dose-response analysis of the test substances is undertaken in the competitive format of the M2-Tag-lite® or M4-Tag-lite® binding assay. The test substances are dissolved in DMSO at a concentration of 10 mM and serially diluted with DMSO in steps of 1:3.16 for a dose-response analysis. The maximum test concentration corresponds to 10 µM. The molar concentration of the test substance that brought about a half-maximum reduction in the HTRF signal in relation to the maximum and remaining HTRF signal at the highest substance concentration ($EC_{50}$ of the binding) is determined by means of GraphPad PRISM (Sigmoidal dose response). At the same time, the strength of the competition effect is determined by calculating the maximum decrease in the specific HTRF signal at the highest substance concentration (% max. competition).

B-5.2. Binding of the Test Substances in Allosteric Mode

To examine the allosteric modulation of the M2 receptor by the test compounds, firstly, a dose-response analysis of the test substances in the competitive format of the M2-Tag-lite® or M4-Tag-lite® binding assay in the presence of a concentration of acetylcholine corresponding to the $EC_{20}$ value is undertaken, the latter being determined in a separate 11-point acetylcholine dose-response analysis (3 µM). The test substances are dissolved in DMSO at a concentration of 10 mM and serially diluted with DMSO in steps of 1:3.16 for a 10-point dose/activity analysis. The maximum test concentration corresponds to 10 µM.

The molar concentration of the test substance that brought about a half-maximum reduction in the HTRF signal in relation to the maximum and remaining HTRF signal at the highest substance concentration in the presence of an acetylcholine concentration corresponding to the EC20 value ($EC_{50}$ of the binding) is determined by means of GraphPad PRISM (Sigmoidal dose response). At the same time, the strength of the competition effect is determined by calculating the maximum decrease in the specific HTRF signal at the highest substance concentration (% max. competition).

In order to examine the boosting of the binding of acetylcholine to the M2 or M4 receptor, in addition, secondly, an 11-point dose-response analysis of acetylcholine in the competitive format of the M2-Tag-lite® or M4-Tag-lite® binding assay was undertaken in the absence or in the presence of 1 µM or 10 µM test substance. The shift in the acetylcholine dose-response curve (maximum shift in the $EC_{50}$ value of acetylcholine) was analyzed and quantified by means of GraphPad PRISM (Sigmoidal dose-response).

B-6. Radioligand Binding Assay for Human M2 Receptors

The allosteric mechanism of action of the test substances can be further investigated in detail and be quantified by various radioligand binding assays. The binding of the allostere to the allosteric binding site of the M2 receptor results in an increase in the binding affinity of the orthosteric ligand for the M2 receptor in the case of positive cooperativity. The increase in the binding affinity of the orthosteric ligand by the allostere in the ternary complex consisting of orthostere, allostere and M2 receptor is in turn due to modulation of the binding kinetics of the orthostere. The allostere can alter the association and/or dissociation rate of the orthostere at the M2 receptor. A lowering of the dissociation rate reflects in this case a stabilization of the ternary complex and accompanies therefore a lowering of the dissociation constant of the orthosteric ligand under equilibrium conditions (Lazareno, Determination of Allosteric Interactions Using Radioligand-Binding Techniques in *Methods in Molecular Biology*, vol. 259, Receptor Signal Transduction Protocols, 2nd ed.; Kostenis and Mohr, *Trends Pharmacol. Sci.* 1996, 17(8), 280-283).

B-6.1. $^3$H-Oxotremorine M Radioligand Binding Assay Under Equilibrium Conditions In order to check and to quantify the influence of the test substances on the binding affinity of orthosteric agonists for the M2 receptor, a radioligand binding assay under equilibrium conditions can be conducted. In this case, the binding of the radiolabeled M2 receptor agonist $^3$H-oxotremorine M to the M2 receptor is investigated at different concentrations of $^3$H-oxotremorine M in the binding equilibrium (Croy et al., *Mol. Pharmacol.* 2014, 86, 106-115). Based on the amount of radioactive agonist specifically bound to the M2 receptor as a function of the agonist concentration (graphically represented as the so-called Langmuir isotherm), firstly the equilibrium dissociation constant $K_d$ of the agonist can be calculated as a quantitative measure of its binding affinity for the M2 receptor and secondly the concentration or number of specific binding sites of the radioligand (agonist) $B_{max}$ in the absence or presence of different concentrations of the test substances (positive allosteric modulators) (Hulme and Trevethick, *Brit. J. Pharmacol.* 2010, 161, 1219-1237).

The radioligand binding assay for the M2 receptor (Euroscreen, FAST-0261B) is carried out by means of $^3$H-labeled oxotremorine M (NET671) as agonist. The agonist binding to the M2 receptor is carried out in triplicate on 96-well microlitre plates (Master Block, Greiner, 786201) in binding buffer (sodium/potassium phosphate buffer, pH 7.4). For this purpose, each assay of M2 membrane extracts (20 µg of protein/96 well) are incubated with various concentrations of radiolabeled agonists (0.2-100 nM) alone or in the presence of 1 µM or 10 µM test substance or binding buffer alone in a total volume of 0.1 mL at 37° C. for 60 min. The non-specific binding of $^3$H-labeled oxotremorine M to the membrane is determined by co-incubating with N-methylscopolamine (NMS), an orthosteric antagonist of the M2 receptor, in a 200-fold excess. In order to stop the binding reaction, the samples are then filtered via GF/C filter (Perkin Elmer, 6005174), which had previously been wetted with 0.5% polyethylenimine (PEI) solution, for 2 h at room temperature. The filters are washed six times each with 0.5 mL of ice-cold wash buffer (10 mM sodium/potassium phosphate buffer, pH 7.4) and 50 µL of Microscint 20 scintillation solution (Packard) is added per assay. The samples are then incubated for 15 min on an orbital shaker before the radioactivity is measured by means of a Top-Count™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $K_d$ and $B_{max}$ of $^3$H-oxotremorine M for the M2 receptor are determined with the aid of a "one-site" specific binding model (Croy et al., *Mol. Pharmacol.* 2014, 86, 106-115).

B-6.2. $^3$H-NMS Competitive Radioligand Binding Assay Under Equilibrium Conditions In order to check and to quantify further the influence of the test substances on the binding affinity of orthosteric agonists for the M2 receptor, a competitive radioligand binding assay under equilibrium conditions is also conducted. In this case, the binding of the antagonistic radioligand $^3$H-N-methylscopolamine ($^3$H-NMS) to the M2 receptor is determined in the absence or presence of various concentrations of non-radiolabeled agonist oxotremorine M (Croy et al., *Mol. Pharmacol.* 2014, 86, 106-115; Schober et al., *Mol. Pharmacol.* 2014, 86, 116-123). The radiolabeled probe (antagonist) and the non-labeled agonist compete for the binding to the orthosteric binding site of the M2 receptor. The ability to displace the radiolabeled probe therefore serves as a measure of the binding affinity of the agonist for the receptor and can be quantified in accordance with the Cheng-Prusoff equation as an equilibrium inhibition constant ($K_i$) (Cheng and Prusoff, *Biochem. Pharmacol.* 1973, 22(23), 3099-3108). In order to further investigate the allosteric effect of the test substances, the influence of the test substances on the $K_i$ of oxotremorine M is determined.

The antagonist inhibition binding assay for the M2 receptor (Euroscreen, FAST-0261B) is carried out on 96-well microtitre plates (Master Block, Greiner, 786201) in binding buffer (50 mM Tris buffer pH 7.4, 1 mM EDTA, 10 µg/ml saponin) using $^3$H-NMS as M2 receptor antagonist. To adjust the binding equilibrium, each assay of M2 membrane extracts (20 µg of protein/96 well) are incubated with a defined concentration of radiolabeled antagonist (0.5 nM) alone or in the presence of various concentrations of non-labeled agonists (oxotremorine M; 0.001 nM to 1 mM) with or without 1 µM or 10 µM test substance or binding buffer alone in a total volume of 0.1 mL at 25° C. for 2 h. The non-specific binding of $^3$H-labeled NMS to the membrane is determined by co-incubating with non-radiolabeled acetylcholine in a 200-fold excess. In order to stop the binding reaction, the samples are then filtered over GF/C filters (Perkin Elmer, 6005174), which had previously been wetted with 0.5% PEI solution, for 2 h at room temperature. The filters are washed six times each with 0.5 mL of ice-cold wash buffer (10 mM sodium/potassium phosphate buffer, pH 7.4) and 50 µL of Microscint 20 scintillation solution (Packard) is added per assay. The samples were then incubated for 15 min on an orbital shaker before the radioactivity is measured by means of a TopCount™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $K_i$ values in the presence or absence of test substance are quantified with the aid of the Cheng-Prusoff equation (Cheng and Prusoff, *Biochem. Pharmacol.* 1973, 22(23), 3099-3108). In this case, the $IC_{50}$ values of the substances are determined according to a four parameter logistic equation and the $K_d$ of NMS determined in a radioligand binding assay under equilibrium conditions (Schober et al., *Mol. Pharmacol.* 2014, 86, 116-123).

B-6.3. $^3$H-Oxotremorine M Dissociation Kinetics Test

By means of a kinetic radioligand binding assay, the kinetics of the dissociation of the radiolabeled agonist $^3$H-oxotremorine M for the M2 receptor in the presence or absence of test substance can be investigated. By these means, the influence of the allosteric activity of the test substances on the dissociation constant ($k_{off}$ rate) of the M2 agonist can be determined and thus the allosteric mechanism of the test substances can be further characterized (Lazareno, Determination of Allosteric Interactions Using Radioligand-Binding Techniques in *Methods in Molecular Biology*, vol. 259, Receptor Signal Transduction Protocols, 2nd ed.; Schrage et al., *Biochem. Pharmacol.*, 2014, 90, 307-319).

The radioligand dissociation binding assay for the M2 receptor (Euroscreen, FAST-0261B) is carried out with $^3$H-labeled oxotremorine M (NET671) as agonist. The binding reaction is carried out in binding buffer (sodium/potassium phosphate buffer, pH 7.4) on 96-well microtitre plates (Master Block, Greiner, 786201). For this purpose, each assay of M2 membrane extracts (20 μg of protein/96 well) are pre-incubated with a defined concentration of radiolabeled agonist (9.65 nM) alone or in the presence of 1 μM or 10 μM test substance or binding buffer alone at 37° C. for 60 min. NMS is then added in 200-fold excess at various time points (one time point per assay) and the mixtures incubated in a total volume of 0.1 mL at 37° C. In order to stop the binding reaction, the samples are then filtered over GF/C filters (Perkin Elmer, 6005174), which had previously been wetted with 0.5% PEI solution, for 2 h at room temperature. The filters are washed six times each with 0.5 mL of ice-cold wash buffer (10 mM sodium/potassium phosphate buffer, pH 7.4) and 50 μL of Microscint 20 scintillation solution (Packard) is added per assay. The samples are then incubated for 15 min on an orbital shaker before the radioactivity is measured by a TopCount™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $k_{off}$ was determined with the aid of a "one phase" exponential decay model of the dissociation (Hulme and Trevethick, *Brit. J. Pharmacol.* 2010, 161, 1219-1237; Kostenis and Mohr, *Trends Pharmacol. Sci.* 1996, 17(8), 280-283).

B-6.4. $^3$H-M2-PAM Binding Test

Binding affinity of the test substances for the human M2 receptor can be determined directly using a radiolabeled test substance as probe. To this end, a positive allosteric test substance was radiolabeled by tritiation ($^3$H-M2-PAM).

Using a radioligand binding test under equilibrium conditions, it is possible, firstly, to determine the equilibrium dissociation constant $K_d$ of the positive allosteric test substance ($^3$H-M2-PAM) as a quantitative measure of its binding affinity for the M2 receptor and, secondly, to determine the number of specific binding sites of the radioligand $B_{max}$ in the absence or presence of an orthosteric agonist (acetylcholine) (Hulme and Trevethick, *Brit. J. Pharmacol.* 2010, 161, 1219-1237; Schober et al., *Mol. Pharmacol.* 2014, 86, 116-123). For the $^3$H-M2-PAM equilibrium binding test, M2 receptor cell membrane preparations (CHO-S/hM2, 200 μg) in incubation buffer (10 mM Tris/HCl pH 7.4, 2 mM MgCl2, 120 mM NaCl, protease inhibitors, 0.3% BSA) were incubated together with different concentrations of the allosteric radioligand $^3$H-M2-PAM (0.5-4000 nM) in the absence or presence of acetylcholine (100 μM) at 4° C. for 1 h. Unspecific binding is determined by addition of an excess of non-radiolabeled allosteric ligand (M2-PAM) (10 μM). To terminate the binding reaction, the samples are filtered through a Brandel filter system and washed with stop buffer (50 mM Tris/HCl pH 7.4, 500 mM NaCl, 0.3% BSA). Beforehand, the filters were wetted with 0.3% strength PEI solution. Kd and Bmax value of the allosteric radioligand are determined based on a "one-site" specific binding model (GraphPad Prism).

Using a competitive $^3$H-M2-PAM binding test, it is possible to determine the affinity of unlabeled allosteric test substances for the binding site of the radioligand $^3$H-M2-PAM at the M2 receptor. (Croy et al., *Mol. Pharmacol.* 2014, 86, 106-115; Schober et al., *Mol. Pharmacol.* 2014, 86, 116-123). The radiolabeled probe $^3$H-M2-PAM) and the non-labeled allosteric test substance compete for binding to the allosteric binding site of the M2 receptor. The ability to displace the radiolabeled probe therefore serves as a measure of the allosteric binding affinity of the test sunstances for the receptor and can be quantified in accordance with the Cheng-Prusoff equation as an equilibrium inhibition constant ($K_i$) (Cheng and Prusoff, *Biochem. Pharmacol.* 1973, 22(23), 3099-3108). Here, displacement of the radiolabeled allosteric probe is determined in the presence or absence of orthosteric agonists (acetylcholine). Analogously to the above-described $^3$H-M2-PAM binding test, the $^3$H-M2-PAM competition binding test is carried out under equilibrium conditions. Here, the membrane preparations comprising M2 receptor are incubated with 1 nM $^3$H-M2-PAM and various concentrations of unlabeled test substance in the absence or presence of acetylcholine (100 μM). The $K_i$ values in the presence or absence of acetylcholine are determined with the aid of the Cheng-Prusoff equation (Cheng and Prusoff, *Biochem. Pharmacol.* 1973, 22(23), 3099-3108).

B-7. Effects of the Test Substances on Acetylcholine-mediated GIRK1/4 Channel Currents in Primary Atrial Rat Cardiomyocytes The substance testing is carried out in accordance with a patch clamp protocol described in the literature for the electrophysiological measurement of acetylcholine-induced GIRK1/4 membrane currents in native rat atrial myocytes (Cheng and Prusoff, *Biochem. Pharmacol.* 1973, 22(23), 3099-3108, see e.g. Beckmann and Rinne et al., *Cell. Physiol. Biochem.* 2008, 21, 259-268).

An acetylcholine dose-response curve for GIRK1/4 activity is initially determined in the absence of test substance (DMSO control) by perfusing test solutions with increasing acetylcholine concentration and measuring the resulting membrane currents. The membrane currents or change in the membrane currents are measured for a given ACh concentration for approx. 10 to 20 seconds. After application of the maximum ACh concentration within a DRC series, a solution of atropine (10 μM) is perfused followed by washing out of the substance solutions in order to ensure the M2 selectivity and reversibility of M2 activation. Changes of the membrane currents are appropriately recorded. Here, each acetylcholine concentration of the membrane current measured is in each case normalized to the maximum acetylcholine-induced membrane current (I/IMax). An acetylcholine dose-response curve comprises in this case five different concentrations (1 nM, 10 nM, 100 nM, 1 μM, 10 μM). The $EC_{50}$ value is determined with the aid of a 4-parameter logistic function (Hill function).

In order to determine the allosteric effect of the test substances on the M2 receptor, the acetylcholine dose-response curve is determined for the GIRK1/4 membrane current in the presence of a constant concentration of the respective test substance (e.g. 1 μM). For this purpose, after pre-incubation of the cell with the test substance for approx. 20 seconds and measurement of the membrane currents, a test solution comprising the same substance concentration and a defined ACh concentration is perfused for approx. 10 to 20 seconds and the membrane currents are measured. After application of the maximum acetylcholine concentration within a measurement series, the perfusion of a solution with atropine (10 μM) is in turn carried out in order to check the M2 selectivity of the substance effect. The $EC_{50}$ value in the presence of test substance is determined analogously with the aid of a 4-parameter logistic function (Hill function) (see above).

The shift in the acetylcholine dose-response curve is determined and quantified by the change in the $EC_{50}$ value for acetylcholine in the absence or presence of the test substance.

B-8. Effects of the Test Substances on Isolated Perfused Rat Heart

Male Wistar rats (strain: (HsdCpb:WU) with a body weight of 200-250 g are anesthetized with Narcoren (100 mg/kg). The thorax is opened and the heart is then exposed, excised and connected to a Langendorff apparatus by placing a cannula into the aorta. The heart is perfused retrogradely at 9 ml/min at constant flow with a Krebs-Henseleit buffer solution (gassed with 95% $O_2$ and 5% $CO_2$, pH 7.4, 35° C.; with the following composition in mmol/l: NaCl 118; KCl 3; $NaHCO_3$ 22; $KH_2PO_4$ 1.2; magnesium sulfate 1.2; $CaCl_2$ 1.8; glucose 10; Na pyruvate 2). To measure the contractility of the heart, a balloon, made of thin plastic film, which is attached to a PE tube and filled with water is introduced via an opening in the left auricle of the heart into the left ventricle. The balloon is connected to a pressure transducer. The end-diastolic pressure is adjusted to 5-10 mmHg via the balloon volume. The data are enhanced by a bridge amplifier and registered on a computer using the LabChart software (ADInstruments).

To investigate the allosteric effect of the test substances, the hearts are perfused with addition of 300 nmol/l of the test substance. After 15 min, carbachol is added cumulatively to the perfusion solution in increasing concentrations. Lowering of the heart rate resulting therefrom is compared, as dose-response curve, with effects on hearts which had been treated with solvent in place of test substance. The shift in the carbachol dose-response curve is analyzed and quantified by GraphPad PRISM (sigmoidal dose-response).

B-9. Effects of the Test Substances on the Heart Rate in Anesthetized Rats

Male rats of the strain (WI) WU Br from the breeder Charles River are anesthetized initially with a 4-5% isoflurane inhalation for approx. 3 min. Subsequently, anesthesia is maintained using a 1.5% isoflurane inhalation For this purpose, the anesthetized animals are fixed on a heated operating plate. By means of visual inspection and between toe reflex, the depth of anesthesia is checked.

For the application of the test substance, an i.v. route into the jugular vein is used. A caudal to cranial skin incision is then made longitudinally and both the cervical musculature and the salivary glands are severed. The right common carotid artery is exposed and blood supply is arrested both proximally and distally. Using microinstrumentation, a TIP catheter (1.2F) is introduced into the vessel in order to measure the arterial pressure and the heart rate.

Initially, both parameters are monitored for 10 min in the basal state without substance addition. The substances to be investigated are dissolved in suitable solvent mixtures and subsequently administered at various dosages to a group of animals in each case via the jugular vein by an infusion pump over 5 min. A solvent-treated group is used as control under the same experimental conditions. The arterial blood pressure and heart rate with substance addition is determined for 20 min. The data are registered with the PowerLab system (ADinstruments) and evaluated using the LabChart program (ADinstruments).

B-10. Radiotelemetric Measurement of Blood Pressure and Heart Rate of Conscious Rats A commercially available telemetry system from Data Sciences International DSI, USA, is employed for the measurements on conscious rats described below. The system consists of 3 main components: (1) implantable transmitters (PhysioTel® telemetry transmitter), (2) receivers (PhysioTel® receiver), which are linked via a multiplexer (DSI Data Exchange Matrix) to a (3) data acquisition computer. The telemetry system makes it possible to continuously record blood pressure, heart rate and body motion of conscious animals in their usual habitat.

The studies are conducted on adult female rats (Wistar Unilever/WU or Spontaneous Hypertensive Rat/SHR) with a body weight of >200 g. After transmitter implantation, the experimental animals are housed singly in type III Makrolon® cages. They have free access to standard feed and water. The day/night rhythm in the test laboratory is set by changing the illumination of the room.

Transmitter Implantation:

The telemetry transmitters used (e.g. PA-C40 HD-S10, DSI) are surgically implanted under aseptic conditions in the experimental animals at least 14 days before the first experimental use. For the implantation, the fasted animals are anesthetized with isoflurane (IsoFlo®, Abbott, initiation 5%, maintenance 2%) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vetbond™, 3M). The transmitter housing is fixed intraperitoneally to the abdominal wall muscle, and the wound is closed layer by layer. Post-operatively, an antibiotic (Ursocyclin® 10%, 60 mg/kg s.c., 0.06 ml/100 g body weight, Serumwerk Bernburg AG, Germany) for infection prophylaxis and an analgesic (Rimadyl®, 4 mg/kg s.c., Pfizer, Germany) are administered.

Substances and Solutions:

Unless stated otherwise, the substances to be studied are administered orally to a group of animals in each case (M=6). In accordance with an administration volume of 2 ml/kg of body weight, the test substances are dissolved in suitable solvent mixtures. A solvent-treated group of animals is used as control.

Experimental Outline:

The telemetry measuring system is configured for 24 animals. Each of the instrumented rats living in the system is assigned a separate receiving antenna (RPC-1 Receiver, DSI). The implanted transmitters can be activated externally via an installed magnetic switch and are switched to transmission during the pre-run of the experiment. The signals emitted can be detected online by a data acquisition system (Dataquest™ A.R.T. for Windows, DSI or Ponemah, DSI) and processed accordingly. In the standard procedure, the following are measured for 10-second periods in each case: (1) systolic blood pressure (SBP), (2) diastolic blood pressure (DBP), (3) mean arterial pressure (MAP), (4) heart rate (HR) and (5) activity (ACT). These parameters are measured over 24 hours after administration. The acquisition of measurements is repeated under computer control at 5-minute intervals. The source data obtained as absolute values are corrected in the diagram with the currently measured barometric pressure (Ambient Pressure Reference Monitor, APR-1, DSI).

Evaluation:

After the end of the experiment, the acquired individual data are sorted using the analysis software (Dataquest™A.R.T. 4.1 Analysis or Ponemah, DSI). The 2 hour time point before substance administration is assumed as the blank value. The data are smoothed over a presettable period by determination of the means (30 minute mean).

B-11. Effects of the Test Substances on the Heart Rate in Anesthetized Dogs

Male or female cross-breeds (Mongrels, Marshall BioResources, USA) with a body weight between 20 and 30 kg are anesthetized with pentobarbital (30 mg/kg iv, Narcoren®, Merial, Germany). Pancuronium chloride (Pancuronium-Actavis®, Actavis, Germany, 1 mg/animal iv) serves here additionally as muscle relaxant. The dogs are intubated and ventilated with an oxygen-air mixture (40/60%) (approximately 5-6L/min). The ventilation is conducted using a ventilation device from GE Healthcare (Avance), which also serves as anesthesia monitor (CO2 analyser). The anesthesia is maintained by a constant infusion of pentobarbital (50 µg/kg/min); fentanyl (10 µg/kg/h) serves as analgesic. An alternative to pentobarbital consists of using isoflurane (1-2% by volume).

The dog is provided with the following:
- bladder catheter for bladder emptying or measurement of urine flow
- ECG leads to the extremities (for ECG measurement)
- insertion of an NaCl-filled Fluidmedic-PE-300 loop into the A. femoralis. This is linked to a pressure sensor (Braun Melsungen, Melsungen, Germany) for measuring the systemic blood pressure
- insertion of a NaCl-filled venous catheter (Vygon, Germany) into the V. femoralis for infusing test substances or withdrawing blood.
- insertion of a Millar Tip catheter (Typ 350 PC, Millar Instruments, Houston, USA) via the left atrium or via a sluice for measuring the heart hemodynamics incorporated into the A. carotis
- insertion of a Swan-Ganz catheter (CCOmbo 7.5F, Edwards, Irvine, USA) via the V. jugularis into the A. pulmonalis for measuring cardiac output, oxygen saturation, pulmonary arterial pressures and central venous pressure.
- provision of an ultrasound flowmeter probe (Transsonic Systems, Ithaka, USA) to the Aorta descendens for measuring aorta flow
- provision of an ultrasound flowmeter probe (Transsonic Systems, Ithaka, USA) to the left Aorta coronaria for measuring coronary flow
- placement of a Brauntile into the Venae cephalicae for infusing pentobarbital, liquid substitution and for withdrawing blood (determination of the substance plasma levels or other clinical blood values)
- placement of a Brauntile into the Venae saphenae for infusing fentanyl and substance application The primary signals are possibly amplified (Gould Amplifier, Gould Instrument Systems, Valley View, USA) or Edwards Vigilance Monitor (Edwards, Irvine, USA) and subsequently fed into the Ponemah system (DataSciences Inc, Minneapolis, USA) for evaluation. The signals are recorded continuously over the whole experimental time course, further processed digitally by this software and averaged over 30 s.

B-12. Effects of the Test Substances on the Heart Rate and Heart Rate Variability in Healthy, Conscious Dogs To characterize test substances with regard to their effect on heart rate, heart rate variability (HRV) and blood pressure, telemetric measurements are conducted in healthy, male Beagle dogs. Under isoflurane anesthesia, a telemetry transmitter (model L21, from Data Sciences International, USA) is firstly implanted in the animals After left-sided thoracotomy, pressure sensors are then placed in the aorta and in the left ventricle. To record an electrocardiogram (ECG), further electrodes are placed on the heart. For wound healing, the animals are then placed back in the pen under antiobiotic (clindamycin, Zoetis, Germany) and analgesic (fentanyl, Janssen, Germany) aftercare. By means of the antennae installed in the animal pen, the blood pressure and ECG signals are forwarded to a data acquistion computer and evaluated by analysis software (Ponemah, Data Sciences International, USA). The telemetry system makes it possible to continuously monitor blood pressures and ECG signals in conscious animals Technical details can be found in the documentation from the manufacturing company (Data Sciences International, USA).

The substances to be investigated are administered orally to the healthy dogs in suitable solvent mixtures by a gelatine capsule. A vehicle-treated group of animals is employed as control. The telemetry measurement is started before substance administration and recorded for a time period of several hours. The time course is displayed graphically by data smoothed by determination of means with the aid of the GraphPadPrism software (GraphPad, USA). To analyse the HRV, the ECG data are subjected to a frequency-domain heart rate variability analysis. For this purpose, the R-R intervals of the recorded ECGs are used. Data outside the previously defined range of 0.2 s-1.5 s are excluded from the analysis. The excluded data are replaced by values which had been obtained by linear interpolation. These data are converted by spline interpolation into equally-spaced supporting points. To analyse the heart rate variability, the data are further subdivided in 30 s steps to packets of 300 s length. For each data packet, a Fourier transformation is calculated. The power is further calculated in three frequency bands (vlf=0.0033-0.04 1/s; lf=0.04-0.15 1/s; hf=0.15-0.5 1/s). To characterize the test substance, the total power (sum total of all three frequency bands) of the HRV analysis is used.

The invention claimed is:

1. A compound of the formula (I)

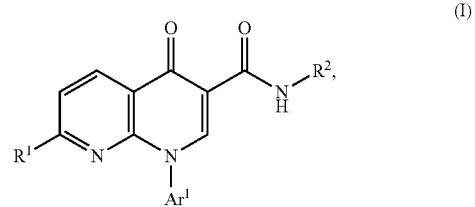

in which
$R^1$ represents $NR^3R^4$,
in which
$R^3$ represents hydrogen, methyl, $(C_2-C_4)$-alkyl or $(C_3-C_6)$-cycloalkyl, where $(C_2-C_4)$-alkyl may be substituted by hydroxy or up to trisubstituted by fluorine
and
$R^4$ represents $(C_1-C_6)$-alkyl, $(C_3-C_6)$-cycloalkyl, 3-to 6-membered saturated heterocyclyl or $(C_1-C_4)$-alkylsulfonyl,
where $(C_1-C_6)$-alkyl, $(C_3-C_6)$-cycloalkyl and 3-to 6-membered saturated heterocyclyl may be up to trisubstituted by identical or different substituents from the group consisting of methyl, difluoromethyl, trifluoromethyl, hydroxy, hydroxycarbonyl, oxo, methoxy, difluoromethoxy, trifluoromethoxy and cyano and furthermore up to tetrasubstituted by fluorine,
or
$R^3$ and $R^4$ together with the nitrogen atom to which they are attached form a saturated or partially unsaturated 3-to 6-membered monocyclic or 6-to 10-membered bicyclic heterocycle which may contain one or two further identical or different heteroatoms from the group consisting of N, O, S, SO and $SO_2$ as ring members,
where the 3-to 6-membered monocyclic and the 6-to 10-membered bicyclic heterocycle may each be substituted by 1 to 5 substituents independently selected from the group of $(C_1-C_4)$-alkyl, difluoromethyl, trifluoromethyl, hydroxy, hydroxycarbonyl, oxo, $(C_1-C_3)$-alkoxy, difluoromethoxy, trifluoromethoxy, cyano, $(C_1-C_3)$-alkoxycarbonyl, aminocarbonyl, mono-$(C_1-C_3)$-alkylaminocarbonyloxy, —NHC(=O)$R^{14A}$ and —CH$_2$NHC(=O)$R^{14B}$, and additionally up to tetrasubstituted by fluorine, in which
$R^{14A}$ and $R^{14B}$ independently represent $(C_1-C_3)$-alkyl or cyclopropyl, and
where $(C_1-C_4)$-alkyl may be mono-or disubstituted by identical or different substituents from the group consisting of hydroxy and $(C_1-C_3)$-alkoxy, and up to tetrasubstituted by fluorine,
$R^2$ represents a group of the formula

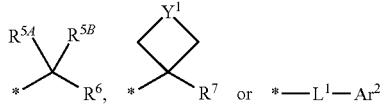

in which
* marks the point of attachment to the nitrogen atom of the amide moiety,
$R^{5A}$ represents hydrogen or $(C_1-C_4)$-alkyl,
$R^{5B}$ represents hydrogen, $(C_1-C_4)$-alkyl, cyclopropyl, monofluoromethyl, difluoromethyl, trifluoromethyl, pentafluoroethyl, methoxymethyl or trifluoromethoxymethyl,
$R^6$ represents $(C_1-C_4)$-alkyl which is up to pentasubstituted by fluorine, or $(C_3-C_5)$-cycloalkyl which is up to tetrasubstituted by fluorine,
$Y^1$ is —(CH$_2$)$_k$—, —CF$_2$—, —O—CH$_2$—, —CH$_2$—O— or —CH$_2$—O—CH$_2$—,
in which
k represents 0, 1, 2 or 3,
$R^7$ represents hydrogen, $(C_1-C_2)$-alkyl which is up to pentasubstituted by fluorine, or trifluoromethoxymethyl, $L^1$ represents a bond or a group of the formula —C($R^{8A}R^{8B}$)—(C($R^{9A}R^{9B}$))$_m$—,
in which
m represents 0 or 1,
$R^{8A}$ represents hydrogen or methyl,
$R^{8B}$ represents hydrogen, methyl, trifluoromethyl, pentafluoroethyl or trifluoromethoxymethyl,
$R^{9A}$ and $R^{9B}$ independently represent hydrogen or methyl,
$Ar^2$ represents phenyl,
where phenyl may be mono-to trisubstituted by identical or different substituents from the group consisting of fluorine, chlorine, $(C_1-C_3)$-alkyl, difluoromethoxymethyl, trifluoromethoxymethyl and trifluoromethyl,
or
represents a 5-to 10-membered bicyclic or tricyclic carbocycle,
where the 5-to 10-membered bicyclic or tricyclic carbocycle may be up to trisubstituted, identically or differently, by $(C_1-C_3)$-alkyl and trifluoromethyl, and additionally up to tetrasubstituted by fluorine,
$Ar^1$ represents a pyridine ring which is attached via a ring carbon atom,
where the pyridine ring may be mono-or disubstituted by fluorine, chlorine, cyano, methyl or trifluoromethyl,
and the N-oxides, salts, solvates, salts of the N-oxides and solvates of the N-oxides and salts thereof.

2. The compound accordingly to claim 1,
in which
$R^1$ represents NR$^3$R$^4$,
in which
$R^3$ represents hydrogen, methyl or $(C_2-C_4)$-alkyl, and
$R^4$ represents $(C_1-C_6)$-alkyl which is up to tetrasubstituted by fluorine,
where $(C_1-C_6)$-alkyl may be substituted by oxo,
or
$R^3$ and $R^4$ together with the nitrogen atom to which they are attached form a saturated 4-to 6-membered monocyclic or 6-to 9-membered bicyclic heterocycle which may contain one or two further identical or different heteroatoms from the group consisting of N and O as ring members,
where the 4-to 6-membered monocyclic and 6-to 9-membered bicyclic heterocycle may each be substituted by 1 to 5 substituents independently selected from the group of $(C_1-C_4)$-alkyl, difluoromethyl, trifluoromethyl, hydroxy, oxo, $(C_1-C_3)$-alkoxy, difluoromethoxy, trifluoromethoxy, and furthermore up to tetrasubstituted by fluorine,
where $(C_1-C_4)$-alkyl may be mono-or disubstituted by identical or different substituents from the group consisting of hydroxy and $(C_1-C_3)$-alkoxy, and up to tetrasubstituted by fluorine,
$R^2$ represents a group of the formula

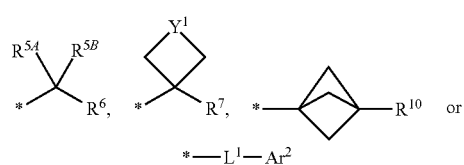

in which
* marks the point of attachment to the nitrogen atom of the amide moiety, $R^{5A}$ represents hydrogen or $(C_1-C_4)$-alkyl,
$R^{5B}$ represents methyl, monofluoromethyl, difluoromethyl, trifluoromethyl, pentafluoroethyl or trifluoromethoxymethyl, and
$R^6$ represents $(C_1-C_4)$-alkyl which is up to pentasubstituted by fluorine, or $(C_3-C_5)$-cycloalkyl which is up to tetrasubstituted by fluorine,
$Y^1$ represents —$(CH_2)_k$—,
  in which
  k represents 1 or 2,
$R^7$ represents $(C_1-C_2)$-alkyl which is up to pentasubstituted by fluorine,
$R^{10}$ represents hydrogen, fluorine or trifluoromethyl,
$L^1$ represents a bond or a group of the formula —$CR^{8A}R^{8B}$—,
  in which
  $R^{8A}$ represents hydrogen,
  $R^{8B}$ represents methyl, trifluoromethyl, pentafluoroethyl or trifluoromethoxymethyl,
$Ar^2$ represents phenyl,
  where phenyl may be mono-to trisubstituted by identical or different substituents from the group consisting of fluorine, chlorine, $(C_1-C_3)$-alkyl and trifluoromethyl,
$Ar^1$ represents a pyridine ring which is attached via a ring carbon atom,
  where the pyridine ring may be mono-or disubstituted by fluorine, chlorine, cyano, methyl or trifluoromethyl,
and the N-oxides, salts, solvates, salts of the N-oxides and solvates of the N-oxides and salts thereof.

3. The compound accordingly to claim 1,
in which
$R^1$ represents $NR^3R^4$,
  in which
  $R^3$ represents hydrogen or methyl, and
  $R^4$ represents methyl or 2-fluoroethyl,
  or
  represents a heterocycle, attached via a nitrogen atom, of the formula

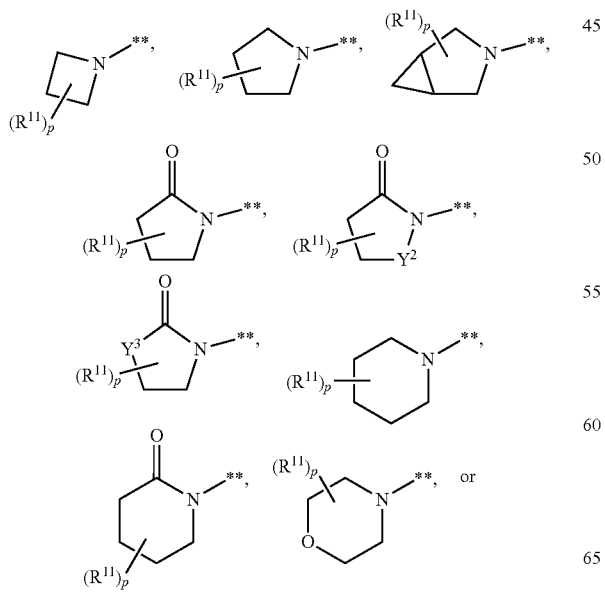

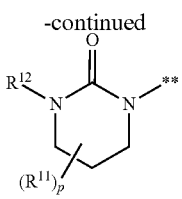

in which
** marks the point of attachment to the remainder of the molecule,
$Y^2$ represents a group of the formula

in which
$\#^1$ marks the point of attachment to the nitrogen atom of the pyrrolidinone ring, and
$\#^2$ marks the point of attachment to the carbon atom of the pyrrolidinone ring, and
$Y^3$ represents —$N(R^{12})$— or a group of the formula

in which
$\#^1$ and $\#^2$ each mark the point of attachment to the carbon atom of the pyrrolidinone ring,
$R^{11}$ represents fluorine, $(C_1-C_4)$-alkyl, difluoromethyl, trifluoromethyl, hydroxy, hydroxymethyl, methoxy, difluoromethoxy or trifluoromethoxy,
p represents the number 0, 1, 2, 3 or 4,
  where, in the case that the substituents $R^{11}$ occur more than once, their meanings may in each case be identical or different,
$R^{12}$ represents hydrogen or 2-hydroxyethyl,
$R^2$ represents a group of the formula

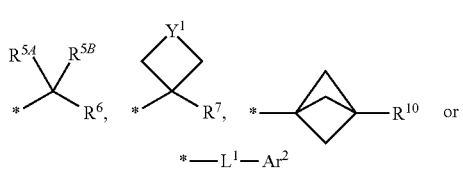

in which
* marks the point of attachment to the nitrogen atom of the amide moiety,
$R^{5A}$ is hydrogen or methyl,
$R^{5B}$ represents methyl, monofluoromethyl, difluoromethyl, trifluoromethyl, pentafluoroethyl or trifluoromethoxymethyl, and
$R^6$ represents methyl, ethyl, trifluoromethyl, 2,2,2-trifluoroethyl, tert-butyl, isobutyl or cyclopropyl,
$Y^1$ represents —$(CH_2)_k$—,
  in which
  k represents 1 or 2,
$R^7$ represents trifluoromethyl,
$R^{10}$ represents hydrogen, fluorine or trifluoromethyl, L¹ represents a bond or a group of the formula —CR⁸ᴬR⁸ᴮ—,
in which
R⁸ᴬ represents hydrogen,
R⁸ᴮ represents trifluoromethyl,
Ar² represents phenyl,
where phenyl may be mono-or disubstituted by identical or different substituents from the group consisting of fluorine and chlorine,
Ar¹ represents a group of the formula

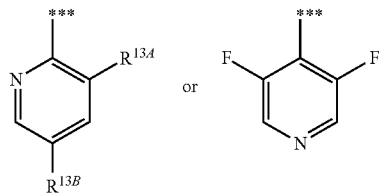

in which
\* \* \* marks the point of attachment to the nitrogen atom,
R¹³ᴬ represents fluorine or chlorine,
R¹³ᴮ represents fluorine or hydrogen,
and the salts, solvates and solvates of the salts thereof.

4. The compound accordingly to claim 1,
in which
R¹ represents a heterocycle, attached via a nitrogen atom, of the formula

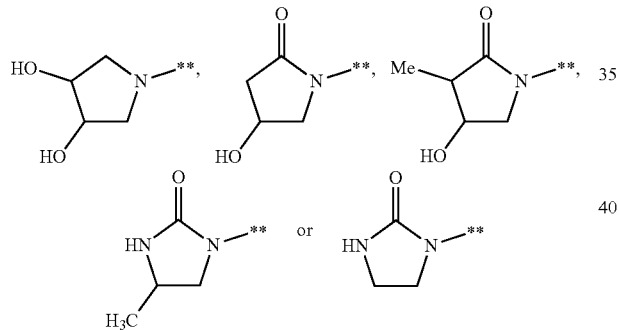

in which
\*\* marks the point of attachment to the remainder of the molecule,
R² represents a group of the formula

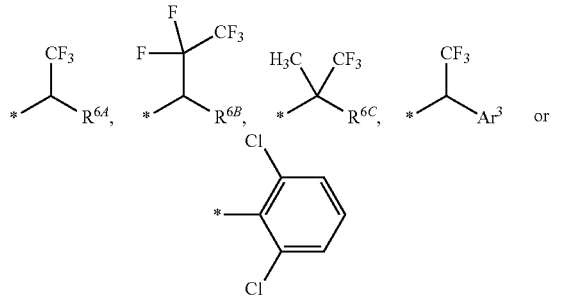

in which
\* marks the point of attachment to the nitrogen atom of the amide moiety, R⁶ᴬ represents trifluoromethyl, ethyl, tert-butyl, isobutyl or cyclopropyl,
R⁶ᴮ represents methyl or ethyl,
R⁶ᶜ represents trifluoromethyl or cyclopropyl,
Ar² represents a group of the formula

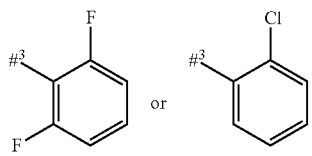

in which
³ in each case marks the bonding site
Ar¹ represents a group of the formula

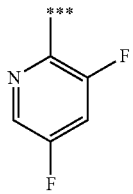

in which
\* \* \* marks the point of attachment to the nitrogen atom,
and the salts, solvates and solvates of the salts thereof.

5. The compound accordingly to claim 1,
R¹ represents a heterocycle, attached via a nitrogen atom, of the formula

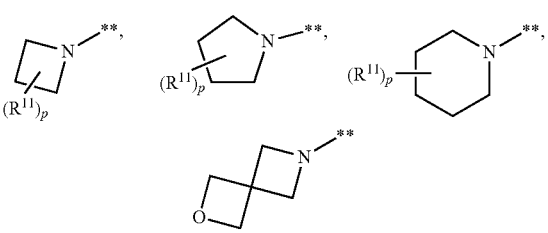

in which
\*\* marks the point of attachment to the remainder of the molecule,
R¹¹ represents fluorine, (C₁-C₄)-alkyl, difluoromethyl, trifluoromethyl, hydroxy, hydroxymethyl, methoxy, difluoromethoxy or trifluoromethoxy,
p represents the number 0, 1, 2, 3 or 4,
where, in the case that the substituents R¹¹ occur more than once, their meanings may in each case be identical or different,
R² represents a group of the formula

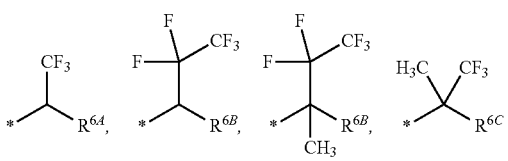

in which
\* marks the point of attachment to the nitrogen atom of the amide moiety, $R^{6A}$ represents trifluoromethyl, ethyl, tert-butyl, isobutyl or cyclopropyl, $R^{6B}$ represents methyl, ethyl, tert-butyl or cyclopropyl, $R^{6C}$ represents trifluoromethyl or cyclopropyl, $Ar^1$ represents a group of the formula

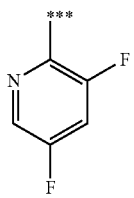

in which

\*\*\* marks the point of attachment to the nitrogen atom, and the salts, solvates and solvates of the salts thereof.

6. The compound accordingly to claim 5, $R^1$ represents a heterocycle, attached via a nitrogen atom, of the formula

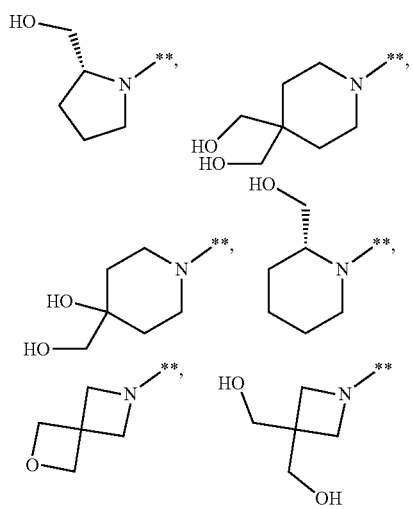

in which

\*\* marks the point of attachment to the remainder of the molecule, $R^2$ represents a group of the formula

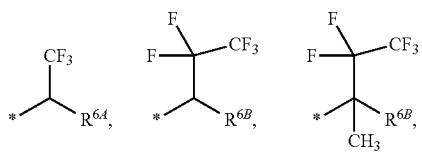

in which

\* marks the point of attachment to the nitrogen atom of the amide moiety, $R^{6A}$ represents trifluoromethyl, $R^{6B}$ represents methyl, $Ar^1$ represents a group of the formula

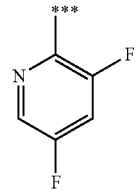

in which

\*\*\* marks the point of attachment to the nitrogen atom, and the salts, solvates and solvates of the salts thereof.

7. A process for preparing compounds accordingly to claim 1, characterized in that

[A] a compound of the formula (II)

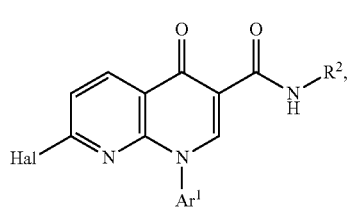

in which $R^2$ and $Ar^1$ have the meanings given in claim 1 and

Hal represents fluorine, chlorine, bromine or iodine, preferably chlorine, is reacted with a compound of the formula (III)

in which $R^1$ has the meaning given above, to give the carboxamide of the formula (I)

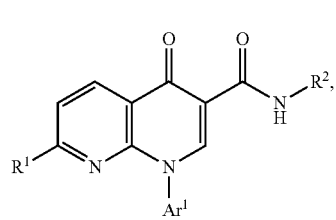

in which $R^1$, $R^2$ and $Ar^1$ have the meanings given in claim 1, or

[B] a compound of the formula (IV)

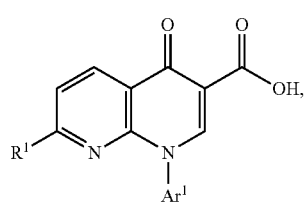

in which $R^1$ and $Ar^1$ have the meanings given in claim 1 is reacted with a compound of the formula (V)

in which $R^2$ has the meaning given above, to give the carboxamide of the formula (I)

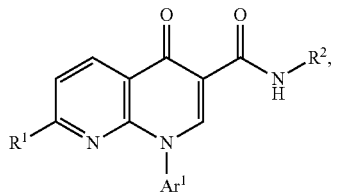

(I)

in which R¹, R² and Ar¹ have the meanings given in claim 1,
and, if appropriate, the compounds of the formula (I) thus obtained are separated into their enantiomers and/or diastereomers and/or converted with the appropriate (i) solvents and/or (ii) bases or acids to their solvates, salts and/or solvates of the salts.

8. A compound of the formula (II)

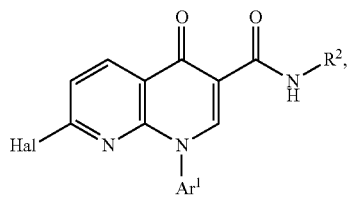

(II)

wherein R² represents a group of the formula

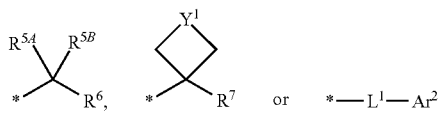

in which
* marks the point of attachment to the nitrogen atom of the amide moiety,
$R^{5A}$ represents hydrogen or $(C_1-C_4)$-alkyl,
$R^{5B}$ represents hydrogen, $(C_1-C_4)$-alkyl, cyclopropyl, monofluoromethyl, difluoromethyl, trifluoromethyl, pentafluoroethyl, methoxymethyl or trifluoromethoxymethyl,
$R^6$ represents $(C_1-C_4)$-alkyl which is up to pentasubstituted by fluorine, or $(C_3-C_5)$-cycloalkyl which is up to tetrasubstituted by fluorine,
$Y^1$ is $—(CH_2)_k—$, $—CF_2—$, $—O—CH_2—$, $—CH_2—O—$ or $—CH_2—O—CH_2—$,
in which
k represents 0, 1, 2 or 3,
$R^7$ represents hydrogen, $(C_1-C_2)$-alkyl which is up to pentasubstituted by fluorine, or trifluoromethoxymethyl,
$L^1$ represents a bond or a group of the formula $—C(R^{8A}R^{8B})—(C(R^{9A}R^{9B}))_m—$,
in which
m represents 0 or 1,
$R^{8A}$ represents hydrogen or methyl,
$R^{8B}$ represents hydrogen, methyl, trifluoromethyl, pentafluoroethyl or trifluoromethoxymethyl,
$R^{9A}$ and $R^{9B}$ independently represent hydrogen or methyl,
Ar² represents phenyl,
where phenyl may be mono-to trisubstituted by identical or different substituents from the group consisting of fluorine, chlorine, $(C_1-C_3)$-alkyl, difluoromethoxymethyl, trifluoromethoxymethyl and trifluoromethyl, or
represents a 5-to 10-membered bicyclic or tricyclic carbocycle,
where the 5-to 10-membered bicyclic or tricyclic carbocycle may be up to trisubstituted, identically or differently, by $(C_1-C_3)$-alkyl and trifluoromethyl, and additionally up to tetrasubstituted by fluorine,
Ar¹ represents a pyridine ring which is attached via a ring carbon atom,
where the pyridine ring may be mono-or disubstituted by fluorine, chlorine, cyano, methyl or trifluoromethyl, and
Hal represents fluorine, chlorine, bromine or iodine, preferably chlorine.

9. A compound of the formula (IV)

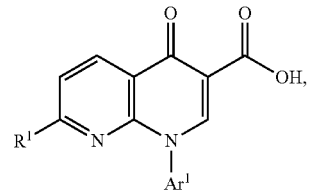

(IV)

R¹ represents $NR^3R^4$,
in which
R³ represents hydrogen, methyl, $(C_2-C_4)$-alkyl or $(C_3-C_6)$-cycloalkyl,
where $(C_2-C_4)$-alkyl may be substituted by hydroxy or up to trisubstituted by fluorine and
R⁴ represents $(C_1-C_6)$-alkyl, $(C_3-C_6)$-cycloalkyl, 3-to 6-membered saturated heterocyclyl or $(C_1-C_4)$-alkylsulfonyl,
where $(C_1-C_6)$-alkyl, $(C_3-C_6)$-cycloalkyl and 3-to 6-membered saturated heterocyclyl may be up to trisubstituted by identical or different substituents from the group consisting of methyl, difluoromethyl, trifluoromethyl, hydroxy, hydroxycarbonyl, oxo, methoxy, difluoromethoxy, trifluoromethoxy and cyano and furthermore up to tetrasubstituted by fluorine,
or
R³ and R⁴ together with the nitrogen atom to which they are attached form a saturated or partially unsaturated 3-to 6-membered monocyclic or 6-to 10-membered bicyclic heterocycle which may contain one or two further identical or different heteroatoms from the group consisting of N, O, S, SO and $SO_2$ as ring members,
where the 3-to 6-membered monocyclic and the 6-to 10-membered bicyclic heterocycle may each be substituted by 1 to 5 substituents independently selected from the group of $(C_1-C_4)$-alkyl, difluoromethyl, trifluoromethyl, hydroxy, hydroxycarbonyl, oxo, $(C_1-C_3)$-alkoxy, difluoromethoxy, trifluoromethoxy, cyano, $(C_1-C_3)$-alkoxycarbonyl, aminocarbonyl, mono-$(C_1-C_3)$-alkylaminocarbonyloxy, $—NHC(=O)R^{14A}$ and $—CH_2NHC(=O)R^{14B}$, and additionally up to tetrasubstituted by fluorine, in which
$R^{14A}$ and $R^{14B}$ independently represent $(C_1-C_3)$-alkyl or cyclopropyl, and
where $(C_1-C_4)$-alkyl may be mono-or disubstituted by identical or different substituents from the group consisting of hydroxy and $(C_1-C_3)$-alkoxy, and up to tetrasubstituted by fluorine,
Ar¹ represents a pyridine ring which is attached via a ring carbon atom, where the pyridine ring may be mono-or disubstituted by fluorine, chlorine, cyano, methyl or trifluoromethyl.

10. The use of a compound of the formula (II)

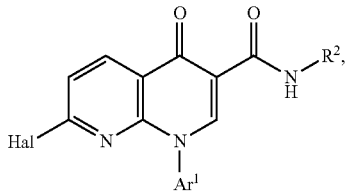
(II)

in which $R^2$ and $Ar^1$ have the meanings given in claim 1 for compounds of the formula (I) and
Hal represents fluorine, chlorine, bromine or iodine, preferably chlorine
or
of a compound of the formula (IV)

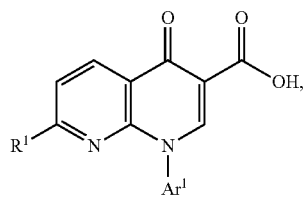
(IV)

in which $R^1$ and $Ar^1$ have the meanings given in claim 1 for compounds of the formula (I), for preparation of a compound of the formula (I) according to claim 1.

11. A method of treatment of heart failure, coronary heart disease, atrial and ventricular arrhythmia, renal failure and nephropathy in a human or an animal, comprising administering an effective amount of a compound according to claim 1.

12. A medicament comprising a compound accordingly to claim 1 in combination with one or more further active ingredients selected from the group consisting of active hypotensive ingredients, active antiarrhythmic ingredients, vasopressin receptor antagonists, PDE 5 inhibitors, platelet aggregation inhibitors, sGC activators and sGC stimulators.

13. A medicament comprising a compound accordingly to claim 1 in combination with an inert, non-toxic, pharmaceutically suitable excipient.

14. The medicament accordingly to claim 12 for use in the treatment of heart failure, coronary heart disease, atrial and ventricular arrhythmia, renal failure and nephropathy.

* * * * *